US011119093B2

(12) United States Patent
Ingber et al.

(10) Patent No.: US 11,119,093 B2
(45) Date of Patent: Sep. 14, 2021

(54) LOW SHEAR MICROFLUIDIC DEVICES AND METHODS OF USE AND MANUFACTURING THEREOF

(71) Applicant: President and Fellows of Harvard College, Cambridge, MA (US)

(72) Inventors: Donald E. Ingber, Boston, MA (US); Kambez Hajipouran Benam, Cambridge, MA (US); Remi Villenave, Boston, MA (US); Geraldine A. Hamilton, Cambridge, MA (US); Bryan Hassell, Cambridge, MA (US); Christopher D. Hinojosa, Cambridge, MA (US); Carolina Lucchesi, Westwood, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 46 days.

(21) Appl. No.: 15/105,962

(22) PCT Filed: Dec. 19, 2014

(86) PCT No.: PCT/US2014/071611
§ 371 (c)(1),
(2) Date: Jun. 17, 2016

(87) PCT Pub. No.: WO2015/138034
PCT Pub. Date: Sep. 17, 2015

(65) Prior Publication Data
US 2016/0313306 A1 Oct. 27, 2016

Related U.S. Application Data

(60) Provisional application No. 61/919,193, filed on Dec. 20, 2013.

(51) Int. Cl.
G01N 33/50 (2006.01)
C12M 3/06 (2006.01)
C12M 1/12 (2006.01)
C12M 1/42 (2006.01)
C12M 3/00 (2006.01)
C12M 1/34 (2006.01)

(52) U.S. Cl.
CPC ......... G01N 33/5044 (2013.01); C12M 21/08 (2013.01); C12M 23/16 (2013.01); C12M 25/02 (2013.01); C12M 35/04 (2013.01); C12M 41/46 (2013.01); G01N 2800/122 (2013.01)

(58) Field of Classification Search
CPC ..... B01L 3/5027; C12M 21/08; C12M 23/16; C12M 25/02; C12M 35/04; C12M 41/46; G01N 2800/122; G01N 33/5044
See application file for complete search history.

(56) References Cited

U.S. PATENT DOCUMENTS

| | | | |
|---|---|---|---|
| 3,300,386 A | 1/1967 | Aron-Brunetiere |
| 3,313,290 A | 4/1967 | Chance |
| 3,722,504 A | 3/1973 | Sawyer |
| 3,941,662 A | 3/1976 | Munder |
| 3,948,732 A | 4/1976 | Haddad |
| 4,225,671 A | 9/1980 | Puchinger |
| 4,436,824 A | 3/1984 | Bishop |
| 4,446,229 A | 5/1984 | Indech |
| 4,537,860 A | 8/1985 | Tolbert |
| 4,610,878 A | 9/1986 | Wilson |
| 4,629,686 A | 12/1986 | Gruenberg |
| 4,650,766 A | 3/1987 | Harm |
| 4,673,650 A | 6/1987 | Braden |
| 4,720,462 A | 1/1988 | Rosenson |
| 4,734,372 A | 3/1988 | Rotman |
| 4,737,455 A | 4/1988 | De Baetselier |
| 4,749,654 A | 6/1988 | Karrer |
| 4,835,102 A | 5/1989 | Bell |
| 4,839,280 A | 6/1989 | Banes |
| 4,851,354 A | 7/1989 | Winston |

(Continued)

FOREIGN PATENT DOCUMENTS

WO   WO 2010/009307 A2   1/2010
WO   WO 2012/118799 A2   9/2012

(Continued)

OTHER PUBLICATIONS

US 6,465,252 B1, 10/2002, Toner (withdrawn)
International Search Report, PCT/US2014/071611, dated Oct. 13, 2015 (4 pages).
Written Opinion of the International Searching Authority, PCT/US2014/071611, dated Oct. 13, 2015 (7 pages).
Extended European Search Report, Application No. 14885765.9, dated Jul. 21, 2017 (9 pages).
Huh et al., "Reconstituting Organ-Level Lung Functions on a Chip," Science, June 25, 2010, vol. 328, pp. 1662-1668 (8 pages).

(Continued)

Primary Examiner — Blaine Lankford
(74) Attorney, Agent, or Firm — Nixon Peabody LLP

(57) ABSTRACT

Provided herein relates to systems and methods for producing and using a body having a central channel separated by one or more membranes. The membrane(s) are configured to divide the central channel into at least one mesochannel and at least one microchannel. The height of the mesochannel is substantially greater than the height of the microchannel. A gaseous fluid can be applied through the mesochannel while a liquid fluid flowing through the microchannel. The systems and methods described herein can be used for various applications, including, e.g., growth and differentiation of primary cells such as human lung cells, as well as any other cells requiring low shear and/also stratified structures, or simulation of a microenvironment in living tissues and/or organs (to model physiology or disease states, and/or to identify therapeutic agents and/or vaccines). The systems and methods can also permit co-culture with one or more different cell types.

14 Claims, 58 Drawing Sheets

(56) References Cited

U.S. PATENT DOCUMENTS

| | | |
|---|---|---|
| 4,929,542 A | 5/1990 | Risley |
| 4,940,853 A | 7/1990 | Vandenburgh |
| 5,002,890 A | 3/1991 | Morrison |
| 5,043,260 A | 4/1991 | Jauregui |
| 5,108,926 A | 4/1992 | Klebe |
| 5,160,490 A | 11/1992 | Naughton |
| 5,197,575 A | 3/1993 | Mangum et al. |
| 5,217,899 A | 6/1993 | Shapiro |
| 5,290,684 A | 3/1994 | Kelly |
| 5,316,905 A | 5/1994 | Mori |
| 5,348,879 A | 9/1994 | Shapiro |
| 5,486,335 A | 1/1996 | Wilding |
| 5,496,697 A | 3/1996 | Parce |
| 5,498,392 A | 3/1996 | Wilding |
| 5,587,128 A | 12/1996 | Wilding |
| 5,612,188 A | 3/1997 | Shuler |
| 5,637,469 A | 6/1997 | Wilding |
| 5,645,432 A | 7/1997 | Jessop |
| 5,726,026 A | 3/1998 | Wilding |
| 5,744,366 A | 4/1998 | Kricka |
| 5,750,329 A | 5/1998 | Quinn |
| 5,820,769 A | 10/1998 | Chou |
| 5,900,160 A | 5/1999 | Whitesides |
| 5,906,828 A | 5/1999 | Cima |
| 6,048,723 A | 4/2000 | Banes |
| 6,054,277 A | 4/2000 | Furcht |
| 6,133,030 A | 10/2000 | Bhatia |
| 6,197,575 B1 | 3/2001 | Griffith |
| 6,255,106 B1 | 7/2001 | Marx |
| 6,306,644 B1 | 10/2001 | Marx |
| 6,329,195 B1 | 12/2001 | Pfaller |
| 6,454,924 B2 | 9/2002 | Jedrzejewski |
| 6,472,202 B1 | 10/2002 | Banes |
| 6,530,370 B1 | 3/2003 | Heinonen |
| 6,562,616 B1 | 5/2003 | Toner |
| 6,586,235 B1 | 7/2003 | Banes |
| 6,630,801 B2 | 10/2003 | Schuurmans |
| 6,645,759 B2 | 11/2003 | Banes |
| 6,653,124 B1 | 11/2003 | Freeman |
| 6,730,516 B2 | 5/2004 | Jedrzejewski |
| 6,921,253 B2 | 7/2005 | Shuler |
| 6,998,265 B2 | 2/2006 | Banes |
| 7,049,057 B2 | 5/2006 | Atala |
| 7,288,405 B2 | 10/2007 | Shuler |
| 7,314,718 B1 | 1/2008 | Dasgupta |
| 7,438,856 B2 | 10/2008 | Jedrzejewski |
| 7,745,209 B2 | 6/2010 | Martin |
| 7,763,456 B2 | 7/2010 | Li |
| 7,790,028 B1 | 9/2010 | Weinberg |
| 7,960,166 B2 | 6/2011 | Vacanti |
| 7,964,078 B2 | 6/2011 | Lee |
| 7,976,795 B2 | 7/2011 | Zhou |
| 7,977,089 B2 | 7/2011 | Wikswo |
| 7,985,336 B2 | 7/2011 | Weinberg |
| 8,030,061 B2 | 10/2011 | Shuler |
| 8,147,562 B2 | 4/2012 | Vacanti |
| 8,187,863 B2 | 5/2012 | Sim |
| 8,268,152 B2 | 9/2012 | Stelzle |
| 8,273,572 B2 | 9/2012 | Martin |
| 8,318,479 B2 | 11/2012 | Domansky |
| 8,343,740 B2 | 1/2013 | Gonda |
| 8,357,528 B2 | 1/2013 | Vacanti |
| 8,460,546 B2 | 6/2013 | Weinberg |
| 8,470,589 B2 | 6/2013 | Martin |
| 8,647,861 B2 | 2/2014 | Ingber |
| 2002/0129813 A1 | 9/2002 | Litherland |
| 2002/0173033 A1 | 11/2002 | Hammerick |
| 2003/0021792 A1 | 1/2003 | Roben |
| 2003/0082795 A1 | 5/2003 | Shuler |
| 2003/0096405 A1 | 5/2003 | Takayama |
| 2003/0175824 A1 | 9/2003 | Pishko |
| 2004/0034435 A1 | 2/2004 | Atala |
| 2004/0132166 A1 | 7/2004 | Miller |
| 2005/0032205 A1 | 2/2005 | Smith |
| 2005/0169962 A1 | 8/2005 | Bhatia |
| 2005/0266393 A1 | 12/2005 | Baxter |
| 2005/0273995 A1 | 12/2005 | Kanagasabapathi |
| 2006/0019326 A1 | 1/2006 | Vacanti |
| 2006/0099116 A1 | 5/2006 | Manger |
| 2006/0154361 A1 | 7/2006 | Wikswo |
| 2006/0263336 A1 | 11/2006 | Caplan |
| 2006/0270023 A1 | 11/2006 | LeDuc |
| 2007/0015273 A1 | 1/2007 | Shuler |
| 2007/0015274 A1 | 1/2007 | Shuler |
| 2007/0015275 A1 | 1/2007 | Shuler |
| 2007/0020693 A1 | 1/2007 | Shuler |
| 2007/0026519 A1 | 2/2007 | Shuler |
| 2007/0037273 A1 | 2/2007 | Shuler |
| 2007/0037275 A1 | 2/2007 | Shuler |
| 2007/0037277 A1 | 2/2007 | Shuler |
| 2007/0048727 A1 | 3/2007 | Shuler |
| 2007/0122794 A1 | 5/2007 | Shuler |
| 2007/0122896 A1 | 5/2007 | Shuler |
| 2007/0144514 A1 | 6/2007 | Yeates |
| 2007/0172943 A1 | 7/2007 | Freedman |
| 2007/0207194 A1 | 9/2007 | Grayburn |
| 2007/0224677 A1 | 9/2007 | Neumann |
| 2007/0243627 A1 | 10/2007 | Takayama |
| 2007/0275435 A1 | 11/2007 | Kim |
| 2007/0275455 A1 | 11/2007 | Hung |
| 2007/0275882 A1 | 11/2007 | Meijer |
| 2007/0281353 A1 | 12/2007 | Vacanti |
| 2008/0032380 A1 | 2/2008 | Kleis |
| 2008/0064088 A1 | 3/2008 | Shuler |
| 2008/0166794 A1 | 7/2008 | Shuler |
| 2008/0166795 A1 | 7/2008 | Shuler |
| 2008/0233607 A1 | 9/2008 | Yu |
| 2008/0318334 A1 | 12/2008 | Robotti |
| 2009/0028755 A1 | 1/2009 | Jedrzejewski |
| 2009/0074623 A1 | 3/2009 | Park |
| 2009/0075282 A1 | 3/2009 | Mahmood |
| 2009/0078614 A1 | 3/2009 | Varghese |
| 2009/0131858 A1 | 5/2009 | Fissell |
| 2009/0134235 A1 | 5/2009 | Ivri |
| 2009/0220932 A1 | 9/2009 | Ingber |
| 2010/0041128 A1 | 2/2010 | Banes |
| 2010/0043494 A1 | 2/2010 | Gascon |
| 2010/0267136 A1 | 10/2010 | Vacanti |
| 2010/0279277 A1 | 11/2010 | Warren |
| 2010/0294986 A1 | 11/2010 | Sultana |
| 2010/0304355 A1 | 12/2010 | Shuler |
| 2010/0323439 A1 | 12/2010 | Takayama |
| 2011/0000482 A1 | 1/2011 | Gumaste |
| 2011/0027804 A1 | 2/2011 | Yarmush |
| 2011/0053207 A1 | 3/2011 | Hoganson |
| 2011/0086382 A1 | 4/2011 | Marx |
| 2011/0183312 A1 | 7/2011 | Huang |
| 2011/0269226 A1 | 11/2011 | Van Noort |
| 2011/0287469 A1 | 11/2011 | Guenther |
| 2012/0003732 A1 | 1/2012 | Hung |
| 2012/0088693 A1 | 4/2012 | Lee |
| 2012/0135446 A1 | 5/2012 | Collins |
| 2012/0135452 A1 | 5/2012 | Shuler |
| 2012/0199487 A1 | 8/2012 | Stelzle |
| 2012/0214189 A1 | 8/2012 | Shuler |
| 2012/0318726 A1 | 12/2012 | Charest |
| 2012/0322097 A1 | 12/2012 | Charest |
| 2013/0059322 A1 | 3/2013 | Hung |
| 2013/0109594 A1 | 5/2013 | Gonda |
| 2013/0230911 A1 | 9/2013 | Charest |
| 2013/0295601 A1 | 11/2013 | Park |
| 2014/0038279 A1 | 2/2014 | Ingber |
| 2014/0158233 A1 | 6/2014 | Leslie |
| 2014/0186414 A1 | 7/2014 | Ingber |
| 2014/0199764 A1 | 7/2014 | Domansky |
| 2014/0342445 A1 | 11/2014 | Ingber |
| 2015/0004077 A1 | 1/2015 | Wikswo |
| 2015/0079670 A1 | 3/2015 | Domansky |

(56) References Cited

U.S. PATENT DOCUMENTS

2015/0209783 A1    7/2015  Ingber
2015/0306596 A1   10/2015  Thompson

FOREIGN PATENT DOCUMENTS

| WO | WO 2013/085909 A1 | 6/2013 |
| WO | WO 2013/148232 A1 | 10/2013 |
| WO | WO 2014/210364 A2 | 12/2014 |
| WO | WO 2015/006751 A1 | 1/2015 |
| WO | WO 2015/013332 A1 | 1/2015 |
| WO | WO 2015/138032 A2 | 9/2015 |
| WO | WO 2015/138034 A2 | 9/2015 |

OTHER PUBLICATIONS

Dongeun Huh et al., "A Human Disease Model of Drug Toxicity-Induced Pulmonary Edema in a Lung-on-a-Chip Microdevcie," Science Translational Medicine, Nov. 7, 2012, vol. 4, Issue 159, pp. 1-8 (10 pgs).

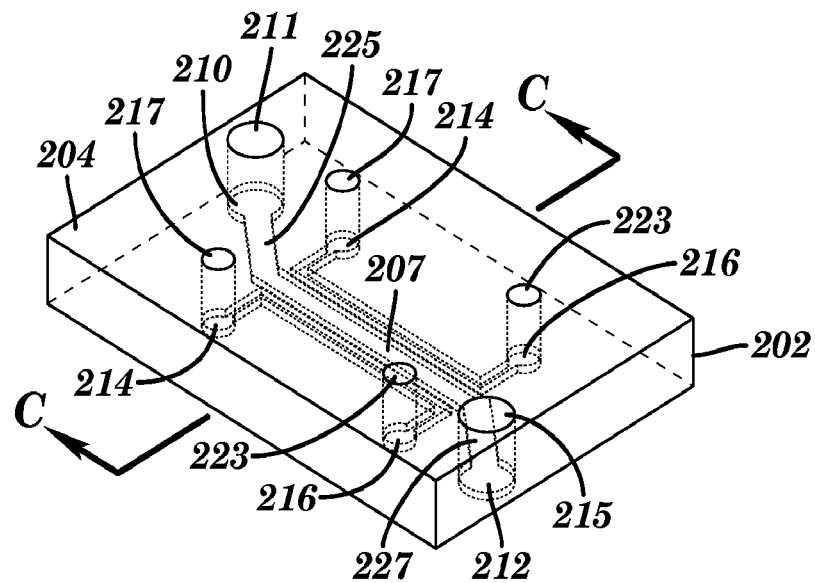
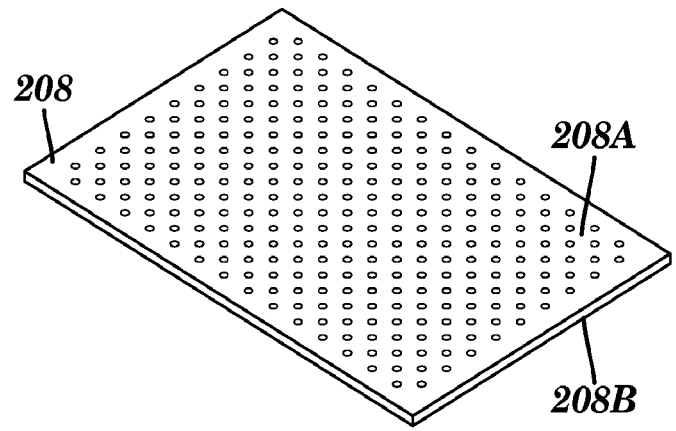
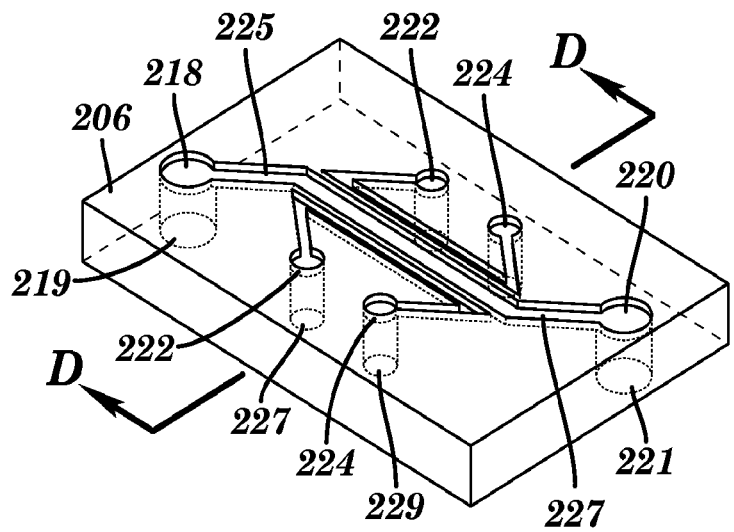
FIG. 2B

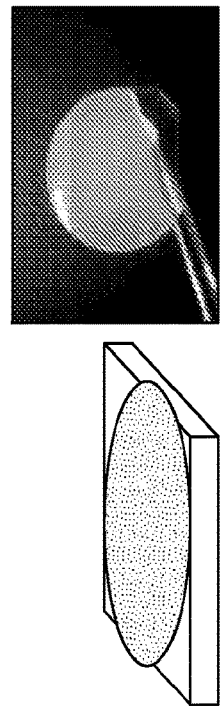
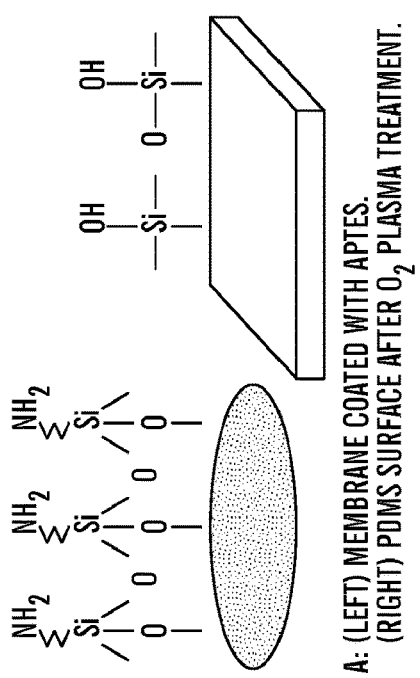
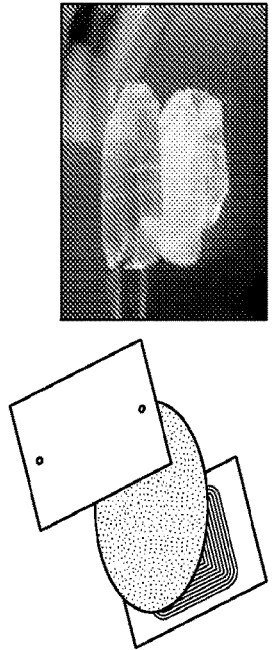
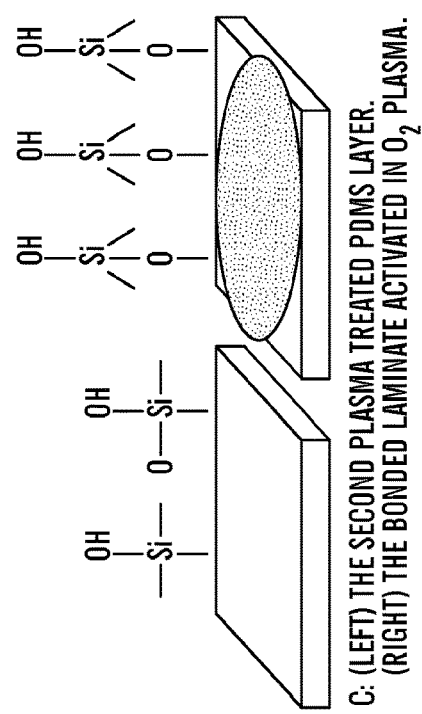

FIG. 4A

A: (LEFT) MEMBRANE COATED WITH APTES. (RIGHT) PDMS SURFACE AFTER $O_2$ PLASMA TREATMENT.

B: (LEFT) THE FUNCTIONALIZED MEMBRANE AND ACTIVATED PDMS MICRODEVICE ARE BROUGHT INTO CONTACT. (RIGHT) A PICTURE OF THE BONDED LAMINATE.

C: (LEFT) THE SECOND PLASMA TREATED PDMS LAYER. (RIGHT) THE BONDED LAMINATE ACTIVATED IN $O_2$ PLASMA.

D: (LEFT) SCHEMATIC OF THE TWO COMPARTMENT MICRODEVICE. (RIGHT) A PICTURE OF A SANDWICH STRUCTURE.

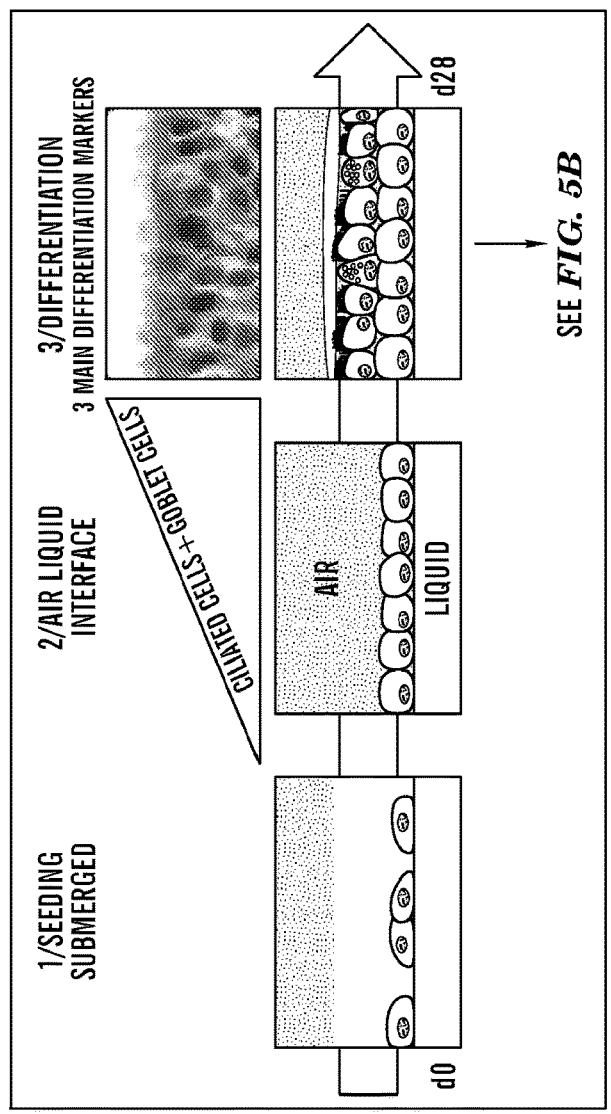
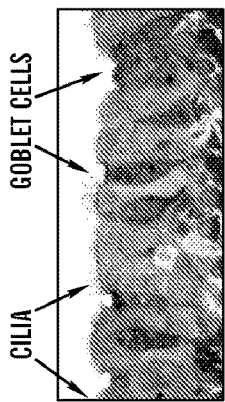
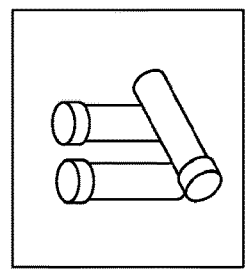
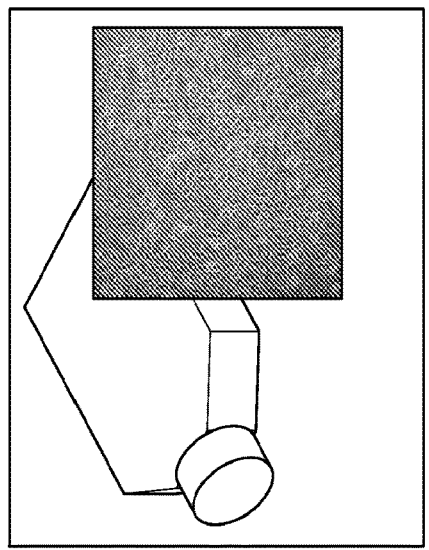
FIG. 5A

CHARACTERIZATION OF BRONCHI-ON-A-CHIP: BARRIER FUNCTION

INULIN-FITC PROVIDES A MORE ROBUST NON-INVASIVE BARRIER MEASUREMENT

ID005, 10d POST-ALI, 10μL OF INULIN-FITC, 50μL/h FOR 2 HOURS

AFTER 10d OF ALI, THE DIFFERENTIATED EPITHELIUM PREVENT INULIN TO CROSS, CONFIRMING THE BARRIER FUNCTION OF THE EPITHELIUM.

QUANTIFICATION OF NEUTROPHIL ATTACHMENT TO DIFFERENTIATED EPITHELIAL CELLS
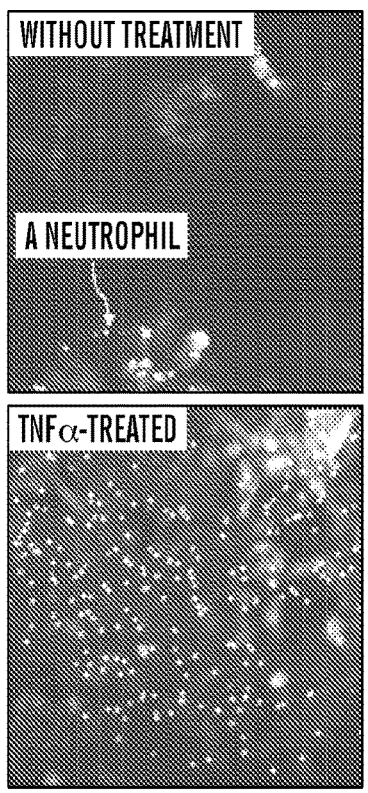
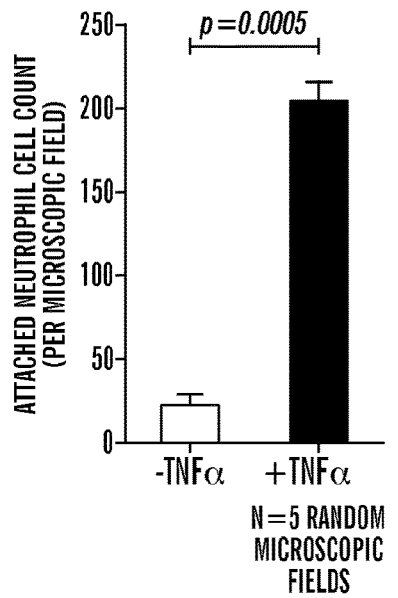
FIG. 10B
NEUTROPHIL FLOW THROUGH THE BLOOD VESSEL CHANNEL
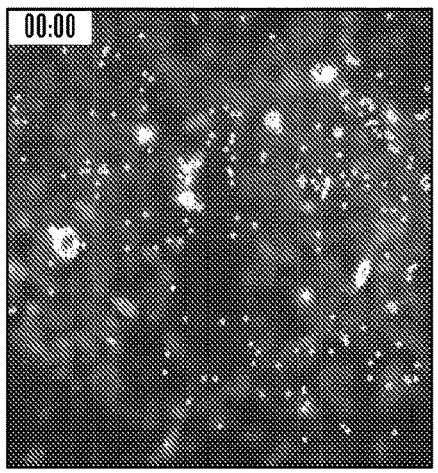
FIG. 10C

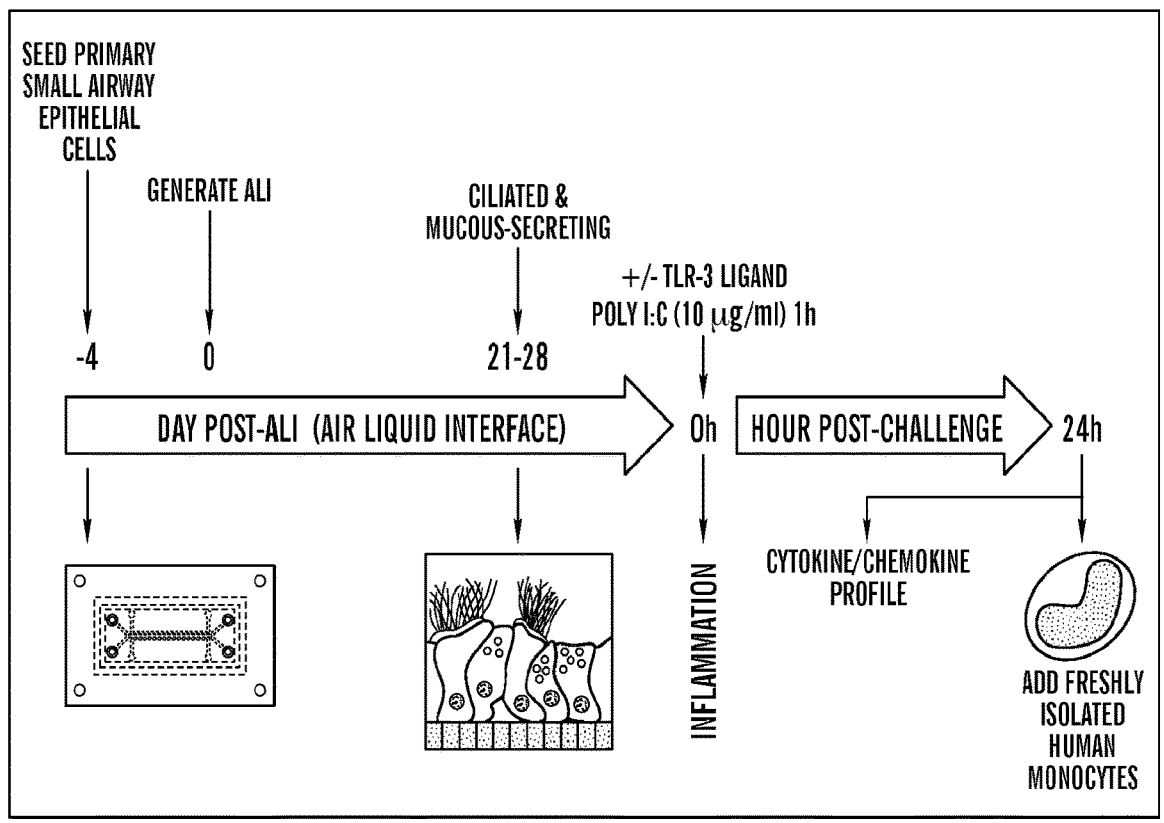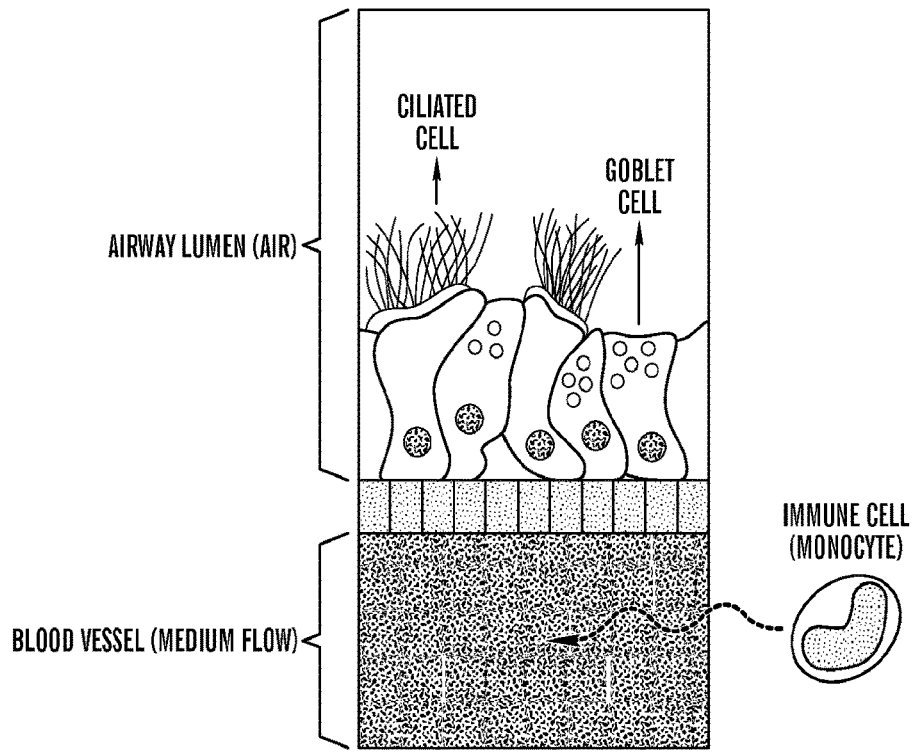
FIG. 11A

| | | SECRETED CYTOKINE/CHEMOKINE IN THE "BLOOD VESSEL" CHANNEL | | | |
|---|---|---|---|---|---|
| | | CONTROL (DMSO) | STEROID | COMPOUND 1 | COMPOUND 2 |
| MONOCYTE CHEMOATTRACTANT | MCP-1 (CCL2) | ++ | ++++ | -/+ | -/+ |
| NEUTROPHIL CHEMOATTRACTANT | GRO (CXCL1) | ++ | +++ | + | -/+ |
| | IL-8 (CXCL8) | ++ | ++ | + | -/+ |
| T CELL/MONOCYTE CHEMOATTRACTANT | IP-10 (CXCL10) | ++ | + | -/+ | -/+ |
| PRO-INFLAMMATORY CYTOKINE | IL-1α | ++ | + | + | + |
| EPITHELIAL ANTI-VIRAL CYTOKINE | IL-29 (IFN-λ1) | ++ | ++ | ++ | ++ |
| MYELOID DIFFERENTIATING CYTOKINES | GM-CSF | ++ | + | + | -/+ |
| | M-CSF | ++ | ++++ | ++ | ++ |
| ACUTE PHASE CYTOKINE | IL-6 | ++ | ++ | -/+ | - |

FIG. 12C

| | | SECRETED CYTOKINE/CHEMOKINE IN THE "AIRWAY LUMEN" CHANNEL | | | |
|---|---|---|---|---|---|
| | | CONTROL (DMSO) | STEROID | COMPOUND 1 | COMPOUND 2 |
| MONOCYTE CHEMOATTRACTANT | MCP-1 (CCL2) | ++ | +++ | ++ | - |
| NEUTROPHIL CHEMOATTRACTANT | GRO (CXCL1) | ++ | ++ | +++ | ++ |
| | IL-8 (CXCL8) | ++ | ++ | ++ | -/+ |
| T CELL/MONOCYTE CHEMOATTRACTANT | IP-10 (CXCL10) | ++ | + | -/+ | -/+ |
| PRO-INFLAMMATORY CYTOKINE | IL-1α | ++ | ++ | +++ | ++++ |
| EPITHELIAL ANTI-VIRAL CYTOKINE | IL-29 (IFN-λ1) | ++ | ++ | ++ | ++ |
| MYELOID DIFFERENTIATING CYTOKINES | GM-CSF | ++ | + | ++ | -/+ |
| | M-CSF | ++ | ++ | ++++ | + |
| ACUTE PHASE CYTOKINE | IL-6 | ++ | + | + | - |

*FIG. 12D*

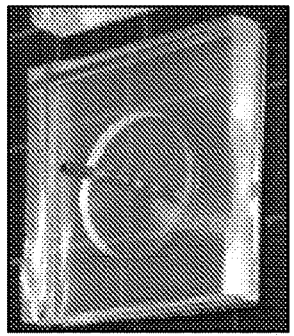
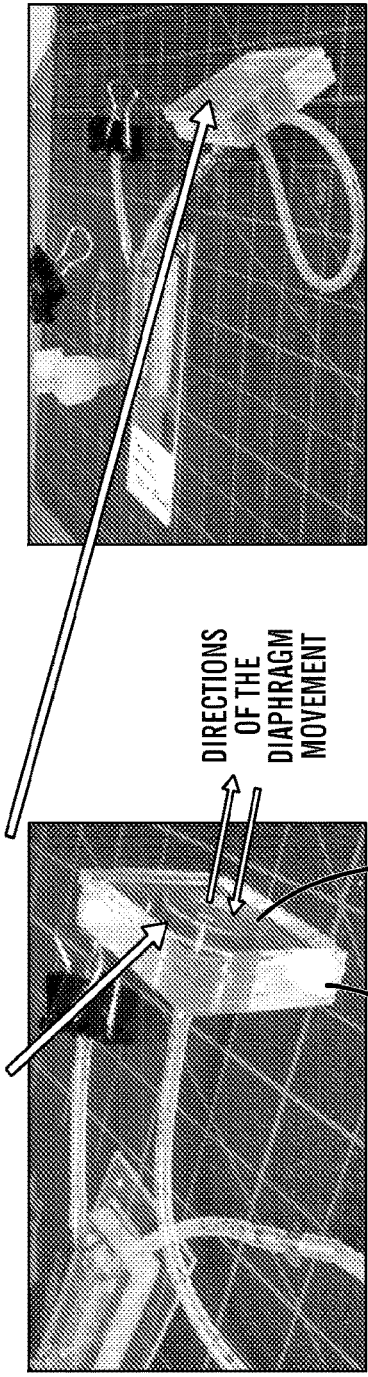
FIG. 13D

FIG. 15

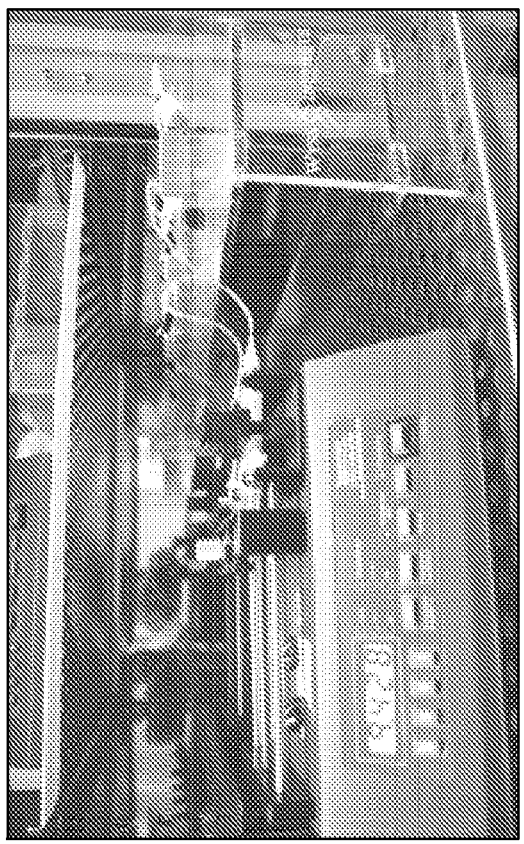
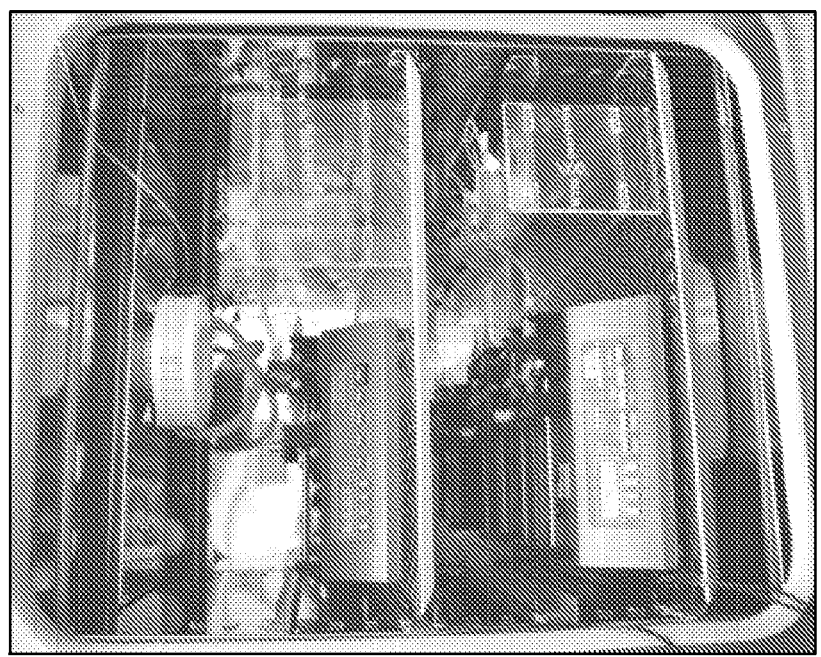
CHIP FARM
FROM 8 TO 16 CHIPS IN AN INCUBATOR
FIG. 19

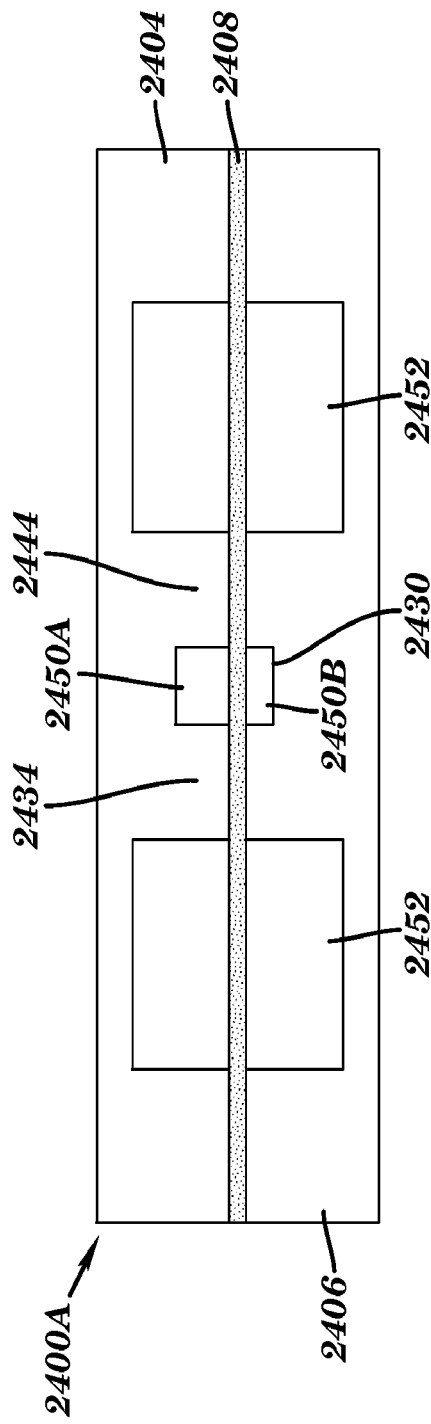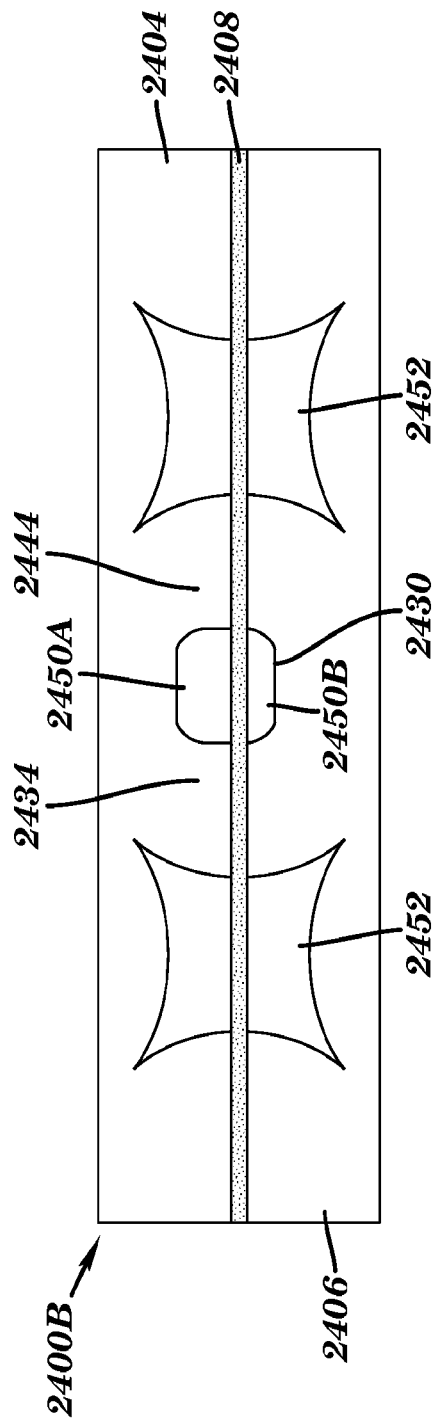

LOW SHEAR MICROFLUIDIC DEVICES AND METHODS OF USE AND MANUFACTURING THEREOF

CROSS-REFERENCE TO RELATED APPLICATIONS

This Application is the U.S. national stage of International Application No. PCT/US2014/071611, filed on Dec. 19, 2014, which claims the benefit under 35 U.S.C. § 119(e) of and priority to U.S. Provisional Application No. 61/919,193, filed on Dec. 20, 2013, each of which is incorporated herein by reference in its entirety.

GOVERNMENT SUPPORT

This invention was made with government support under Grant No. W911NF-12-2-0036 awarded by the DARPA. The government has certain rights in the invention.

TECHNICAL FIELD

The present disclosure relates generally to microfluidic devices and methods of use and manufacturing thereof. In some embodiments, the microfluidic devices can be used for culture and/or support of living cells such as mammalian cells, insect cells, plant cells, and microbial cells.

BACKGROUND

Mechanical forces—pushes, pulls, tensions, compressions—are important regulators of cell development and behavior. Tensegrity provides the structure that determines how these physical forces are distributed inside a cell or tissue, and how and where they exert their influence.

In the human body, most cells are constantly subjected to mechanical forces, such as tension or compression. Application of mechanical strain to cells in culture simulates the in vivo environment, causing dramatic morphologic changes and biomechanical responses in the cells. Both long and short term changes occur when cells are mechanically loaded in culture, such as alterations in the rate and amount of DNA or RNA synthesis or degradation, protein expression and secretion, the rate of cell division and alignment, changes in energy metabolism, changes in rates of macromolecular synthesis or degradation, and other changes in biochemistry and bioenergetics.

Every cell has an internal scaffolding, or cytoskeleton, a lattice formed from molecular "struts and wires". The "wires" are a crisscrossing network of fine cables, known as microfilaments, which stretch from the cell membrane to the nucleus, exerting an inward pull. Opposing the pull are microtubules, the thicker compression-bearing "struts" of the cytoskeleton, and specialized receptor molecules on the cell's outer membrane that anchor the cell to the extracellular matrix, the fibrous substance that holds groups of cells together. This balance of forces is the hallmark of tensegrity.

Tissues are built from groups of cells, like eggs sitting on the "egg carton" of the extracellular matrix. The receptor molecules anchoring cells to the matrix, known as integrins, connect the cells to the wider world. Mechanical force on a tissue is felt first by integrins at these anchoring points, and then is carried by the cytoskeleton to regions deep inside each cell. Inside the cell, the force might vibrate or change the shape of a protein molecule, triggering a biochemical reaction, or tug on a chromosome in the nucleus, activating a gene.

Cells also can be said to have "tone," just like muscles, because of the constant pull of the cytoskeletal filaments. Much like a stretched violin string produces different sounds when force is applied at different points along its length, the cell processes chemical signals differently depending on how much it is distorted.

A growth factor will have different effects depending on how much the cell is stretched. Cells that are stretched and flattened, like those in the surfaces of wounds, tend to grow and multiply, whereas rounded cells, cramped by overly crowded conditions, switch on a "suicide" program and die. In contrast, cells that are neither stretched nor retracted carry on with their intended functions.

Another tenet of cellular tensegrity is that physical location matters. When regulatory molecules float around loose inside the cell, their activities are little affected by mechanical forces that act on the cell as a whole. But when the regulatory molecules are attached to the cytoskeleton, they become part of the larger network, and are in a position to influence cellular decision-making. Many regulatory and signaling molecules are anchored on the cytoskeleton at the cell's surface membrane, in spots known as adhesion sites, where integrins cluster. These prime locations are key signal-processing centers, like nodes on a computer network, where neighboring molecules can receive mechanical information from the outside world and exchange signals.

Thus, assessing the full effects of drugs, drug delivery vehicles, nanodiagnostics or therapies or environmental stressors, such as particles, gases, and toxins, in a physiological environment requires not only a study of the cell-cell and cell-chemical interactions, but also a study of how these interactions are affected by physiological mechanical forces in both healthy tissues and tissues affected with diseases.

Methods of altering the mechanical environment or response of cells in culture have included wounding cells by scraping a monolayer, applying magnetic or electric fields, or by applying static or cyclic tension or compression with a screw device, hydraulic pressure, or weights directly to the cultured cells. Shear stress has also been induced by subjecting the cells to fluid flow. However, few of these procedures have allowed for quantitation of the applied strains or provided regulation to achieve a broad reproducible range of cyclic deformations within a culture microenvironment that maintains physiologically relevant tissue-tissue interactions.

Living organs are three-dimensional vascularized structures composed of two or more closely apposed tissues that function collectively and transport materials, cells and information across tissue-tissue interfaces in the presence of dynamic mechanical forces, such as fluid shear and mechanical strain. Creation of microdevices containing living cells that recreate these physiological tissue-tissue interfaces and permit fluid flow and dynamic mechanical distortion would have great value for study of complex organ functions, e.g., immune cell trafficking, nutrient absorption, infection, oxygen and carbon dioxide exchange, etc., and for drug screening, toxicology, diagnostics and therapeutics.

A major challenge lies in the lack of experimental tools that can promote assembly of multi-cellular and multi-tissue organ-like structures that exhibit the key structural organization, physiological functions, and physiological or pathological mechanical activity of the lung alveolar-capillary unit, which normally undergoes repeated expansion and contraction during each respiratory cycle. This limitation could be overcome if it were possible to regenerate this organ-level structure and recreate its physiological mechanical microenvironment in vitro. However, this has not been fully accomplished.

What is needed is a organ mimic device capable of being used in vitro or in vivo which performs tissue-tissue related functions and which also allows cells to naturally organize in the device in response to not only chemical but also mechanical forces and allows the study of cell behavior through a membrane which mimics tissue-tissue physiology.

SUMMARY

The existing transwell technology has been widely used to grow and differentiate human cells. The invention is directed to, inter alia, a platform and method for growth and differentiation of human cells in a microfluidic environment. Previously developed organ-on-chip devices are described in the International Patent Application Nos. PCT/US2009/050830 and PCT/US2012/026934, which are incorporated herein by reference in their entireties. In accordance with one embodiment of the invention, a microfluidic device can include a top mesochannel with a channel height of about 1 mm and a bottom microchannel with a channel height of about 100 µm. By increasing the height of at least a length portion of the top channel within the device (e.g., the length portion where cells are desired to grow to form a stratified/pseudostratified or 3-dimensional structure), the device can provide at least a length portion of the top channel with a reduced stress environment and increased overhead space for growth of cells that require low shear and/or more space to form a stratified, pseudostratified, or three-dimensional tissue structure. In one embodiment, airway epithelial cells (e.g., small airway and/or large airway epithelial cells) can be cultured on the surface of the membrane facing the mesochannel and can differentiate into terminally differentiated ciliated and mucous-secreting (goblet) cells. Other cells that are desired to be cultured in a higher top channel include, but are not limited to, heart cells, gut cells/intestinal cells, liver cells, skin cells, and kidney cells (e.g., glomerular cells). For example, intestinal epithelial cells can be cultured on the surface of the membrane facing the mesochannel and form three-dimensional intestinal villi. In some embodiments, animal cells, insect cells, and plant cells can also be used in the devices described herein.

System and method comprises a body having a central channel separated by one or more membranes. The membranes divide the central channel into two or more closely apposed parallel central sub-channels (mesochannels and microchannels), wherein one or more first fluids (e.g., gaseous or liquid fluid) can be applied through at least one mesochannel and one or more second fluids (e.g., liquid fluid) can be applied through one or more microchannels. The surfaces of each membrane can be treated or otherwise coated with cell adhesive molecules to support the attachment of cells and/or promote their organization into tissues on the upper and/or lower surface of each membrane, thereby creating one or more tissue-tissue interfaces separated by one or more membranes between the adjacent parallel fluid channels. The membrane can be porous (e.g., permeable or selectively permeable), non-porous (e.g., non-permeable), rigid, flexible, elastic, or any combination thereof. In some embodiments, the membrane can be porous, e.g., allowing exchange/transport of fluids (e.g., gas and/or liquids), passage of molecules such as nutrients, cytokines and/or chemokines, cell transmigration, or any combinations thereof. In some embodiments, the membrane can be non-porous. Fluid pressure, flow characteristics and channel geometry can be varied to apply a desired fluid (e.g., air and/or liquid) shear stress to one or both tissue layers.

In some embodiments, an air-liquid interface can be established in the devices described herein to mimic a physiological microenvironment, e.g., an airway, thus permitting cells to behave more like cells in vivo, e.g., differentiation of airway epithelial cells to ciliated and/or mucus-secreting cells to form a stratified structure. In some embodiments, a unidirectional or a bidirectional flow of gas (e.g., air) can be induced in the mesochannel by adapting one end of the mesochannel to engage to a gas-flow modulation device.

In some embodiments, the membrane of the device can be modulated or actuated to deform in a manner (e.g., stretching, retracting, compressing, twisting and/or waving) that simulates a physiological strain experienced by the cells in its native microenvironment, e.g., during breathing, peristalsis, and/or heart beating. In some embodiments where operating channels are adjacent to the central channel, a positive or negative pressure can be applied to the operating channels, which can in turn create a pressure differential that causes the membrane to, for example, selectively stretch and retract in response to the pressure differential, thereby further physiologically simulating mechanical force of a living tissue-tissue interface. For example, in some embodiments, a combination of culturing intestinal cells in a taller mesochannel for increased overhead space and lower liquid shear stress, and exposure of the cells to physiological peristalsis-like motions induced by cyclically stretching and retracting the membrane can induce human intestinal cells to form a three-dimensional villus structure.

In some embodiments, the devices described herein can permit two or more different cell types cultured in the same channel (e.g., mesochannel or microchannel), and/or in different channels (e.g., at least one cell type in the mesochannel and at least one cell type in the microchannel; or a first cell type in a first mesochannel and a second cell type in a second mesochannel). For example, tissue-specific epithelial cells can be cultured on one side of the membrane facing the mesochannel, while blood vessel-associated cells can be cultured on the other side facing the microchannel. By way of example only, in some embodiments, microbial cells, e.g., healthy or diseased microbial flora, can be cultured with the intestinal epithelial cells in the mesochannel to mimic the physiological microenvironment of a normal or diseased intestine in vivo.

In some embodiments, immune cells can be added to a liquid fluid present in the microchannel. The liquid fluid in the microchannel can be static or flowing through the microchannel continuously, cyclically, and/or intermittently. Recruitment of immune cells to the membrane and/or tissue-specific cells can be determined to provide a measure of immune response when the simulated physiological microenvironment is stimulated with an agent or a cytokine described herein. The ability to introduce immune cells in the device described herein and measure response of the immune cells (e.g., immune cell recruitment, maturation, activation, cell killing, and/or drainage) permits development of a more accurate tissue-specific disease model that takes into account of immune response as is typically activated in vivo when a subject is afflicted with a disease (except in a subject who is immunocompromised).

The ability of the devices described herein to recapitulate a physiological microenvironment and/or function can provide an in vitro model versatile for various applications, e.g., but not limited to, generation of cells corresponding to a physiological endpoint as described herein; modeling a tissue-specific physiological condition (e.g., but not limited to normal and disease states); determination of transmissibility of airborne pathogens, development of mucosal immunity platform; identification of therapeutic agents and vaccines; and any combinations thereof.

BRIEF DESCRIPTION OF THE DRAWINGS

FIG. 2B illustrates an exploded view of the organ mimic device in accordance with an embodiment.

FIGS. 4A-4C illustrate different methods of forming a fluidic seal between the membrane and the top and bottom body portions of the device in accordance with an embodiment. FIG. 4A illustrates 3-aminopropyl-triethoxysilane (APTES) bonding procedure adopted from Aran et al. (2010). FIG. 4B shows membrane clamping between the PDMS slabs utilizing the membrane-PDMS surface area. FIG. 4C illustrates a membrane sealed between the two pieces of PDMS slabs by plasma bond between the PDMS slabs to form a seal.

FIGS. 5A-5G illustrate an exemplary method of differentiating human primary airway (or bronchial) epithelial cells in a device in accordance with an embodiment, and experimental data resulting therefrom. FIG. 5A is a schematic diagram illustrating an example method to differentiate human bronchial epithelial cells in a device according to an embodiment. Primary small airway or bronchial epithelial cells were seeded on the membrane in the upper mesochannel (an "airway lumen" channel). The cells were then cultured in a submerged condition by introducing a static or flowing culture medium into both the mesochannel and the microchannel until the cells reached full confluence. Then, an air-liquid interface was established by removing the culture medium from the mesochannel through its outlet. The primary airway epithelial cells differentiated after about 3-4 weeks of culture in the device at the air-liquid interface. FIG. 5B is a diagrammatic view of human differentiated bronchial epithelium grown in a mesochannel separated from the bottom microchannel (a "blood vessel" channel) by a porous membrane. FIG. 5C illustrates morphology of the cells post-seeding and at the time when the air-liquid interface (ALI) was set up. FIG. 5D is a set of immunofluorescence images showing formation of a primary small airway epithelium on the membrane. Tight junction proteins (e.g., TJP-1 and/or ZO-1) were detected to indicate a functional tight junction barrier formed by the formed epithelium. FIG. 5E is a set of immunofluorescence and SEM images showing differentiation of the airway epithelial cells to ciliated cells. FIG. 5F shows a 3D view of differentiated epithelial primary cells (cilia: detected by beta-tubulin IV; and mucus secretion: detected by Muc5AC) in the device described herein. FIG. 5G shows representative images of ciliated cells along the length of the mesochannel of the device described herein. A uniform distribution of abundant cilia beating after about 3 weeks of culturing at an air-liquid interface is a hallmark of epithelial differentiation in vivo.

FIG. 6A is a bar graph comparing the cytotoxicity data (based on LDH release from the cells) of culturing primary human small airway epithelial cells in a microfluidic device (to mimic a small airway) with the cells cultured in a transwell. FIG. 6B is a microscopic image showing the healthy small airway epithelial cells forming an intact epithelium in the device described herein.

FIG. 7A is a set of florescent images showing that human bronchial epithelial cells grown in the mesochannel for about 4 weeks exhibited typical differentiation markers of an human bronchial epithelium in vivo. Beta-tubulin can be used as a marker to detect ciliated cells (upper left panel). The orthogonal section (lower panel) shows that cilia are localized on the apical side of the cultures as observed in vivo. The right panel is an image showing a 3D reconstruction of the epithelium. FIG. 7B is a set of fluorescent (left panel) and SEM (right panel) images showing that human bronchial epithelial cell cultures in a mesochannel of a device described herein display ciliated and goblet cells after about 3 weeks of culturing at an air-liquid interface. The SEM image shows fully formed cilia. FIG. 7C is a set of fluorescent images showing presence of tight junctions, as indicated by ZO-1 and phalloidin staining, formed between the differentiated human bronchial cells cultured in a mesochannel of a device according to an embodiment. FIG. 7D is a graph showing the barrier function of the differentiated epithelium formed in the mesochannel of a device described herein. The barrier function was evaluated by adding fluorescently-labeled large molecules (e.g., inulin-FITC) into the fluid introduced into the mesochannel. The differentiated epithelium prevents inulin to cross from the mesochannel to the microchannel, indicating that the epithelium forms a functional barrier.

FIGS. 10A-10C illustrate an exemplary method of evaluating neutrophil recruitment in response to inflammation induced by challenging the differentiated human primary airway (or bronchial) epithelial cells in a device with a pro-inflammatory factor, e.g., TNFα, and experimental data resulting therefrom. FIG. 10A is a schematic diagram illustrating an example method to evaluate neutrophil recruitment in response to a stimulus using a device according to an embodiment. Primary small airway epithelial cells were seeded on the membrane in the mesochannel (an "airway lumen" channel) for differentiation into ciliated and/or mucus-secreting cells following the differentiation method as described in FIG. 5A. Upon differentiation of the airway epithelial cells, another surface of the membrane (facing the microchannel, the "blood vessel" channel) could be seeded with or without endothelial cells. The differentiated cells in the mesochannel were then challenged with a pro-inflammatory factor, e.g., TNF-α. A fluid comprising human neutrophils was then flowed through the "blood vessel" channel to determine effects of TNF-α-induced inflammation on neutrophil recruitment. FIG. 10B includes a data graph showing quantification of neutrophils attached to differentiated epithelial cells cultured in the mesochannel with or without the treatment of TNFα (right panel). The quantification is based on counting the number of attached neutrophil in the fluorescent images (left panel) taken by microscopy imaging. FIG. 10C is a snapshot image showing neutrophil flowing through the "blood vessel" channel at a specific time point.

FIGS. 11A-11D illustrate an exemplary method of evaluating an infection response of differentiated small airway epithelial cells and optionally immune cells in a device in accordance with an embodiment, and experimental data resulting therefrom. FIG. 11A is a schematic diagram illustrating an example method to evaluate an infection response in the device. Primary small airway epithelial cells were seeded on the membrane in the mesochannel (an "airway lumen" channel) for differentiation into ciliated and/or mucus-secreting cells following the differentiation method as described in FIG. 5A. Upon differentiation of the airway epithelial cells, another surface of the membrane (facing the microchannel, the "blood vessel" channel) could be seeded with or without endothelial cells. The differentiated cells in the mesochannel were then challenged with a toll-like receptor 3 (TLR-3) ligand poly I:C to induce inflammation. A fluid comprising immune cells (e.g., human monocytes) was introduced into the "blood vessel" channel, either with a static fluid or a flowing fluid, to determine effects of TLR-3-induced inflammation on cytokine/chemokine profiles of the differentiated cells and/or recruitment of immune cells (e.g., monocytes and/or neutrophils). FIG. 11B is a set of bar graphs showing that TLR-3 activation (flu-like situation) stimulates release of chemokines (e.g., monocyte chemoattractants and neutrophil chemoattractants) by the differentiated airway epithelial cells in the device. FIG. 11C is a set of data showing quantification of monocytes attached to the TLR-3 activated differentiated epithelial cells in the device and the associated fluorescent images. FIG. 11D is a graph showing gene expression of differentiated epithelial cells after treatment with or without a TLR-3 ligand poly I:C.

FIGS. 12A-12F illustrate an exemplary method of evaluating an effect of different agents on differentiated small airway epithelial cells and optionally immune cells during an infection in a device in accordance with an embodiment, and experimental data resulting therefrom. FIG. 12A is a schematic diagram illustrating an example method to evaluate an effect of different agents during an infection simulated in the device. Primary human epithelial cells from chronic obstructive pulmonary disease (COPD) patients (obtained from a commercial vendor) were seeded on the membrane in the mesochannel (an "airway lumen" channel) for differentiation into ciliated and/or mucus-secreting cells following the differentiation method as described in FIG. 5A. Upon differentiation of the COPD epithelial cells, another surface of the membrane (facing the microchannel, the "blood vessel" channel) could be seeded with or without endothelial cells. The cells in the device were then starved using basal medium, followed by treatment with different agents (e.g., DMSO as a control, budesonide, and BRD4 inhibitor compounds 1 and 2 obtained from a pharmaceutical company). The agents were delivered to the differentiated epithelial cells via diffusion from the "blood vessel" channel. The pre-treated differentiated COPD epithelial cells were then challenged with TLR-3 ligand poly I:C (e.g., about 10 μg/mL delivered as an aerosol flowing into the mesochannel) to stimulate TLR-3 and mimic viral infection. Secreted cytokines and chemokines from the differentiated COPD epithelial cells were quantified in the flow-through of the "blood vessel" channel and/or from the apical wash of the "airway lumen" channel. In some embodiments, a fluid comprising immune cells (e.g., human monocytes) was introduced into the "blood vessel" channel, either with a static fluid or a flowing fluid, to determine effects of TLR-3-induced inflammation on recruitment of immune cells (e.g., monocytes and/or neutrophils). FIG. 12B is a set of graphs showing production of representative cytokines and chemokines (e.g., monocyte chemoattractants and neutrophil chemoattractants) by the differentiated COPD epithelial cells (pretreated with different agents prior to exposure to a TLR-3 ligand poly I:C) and released into the "blood vessel" channel. It indicates that compound 2 is more potent than compound 1 in reducing cytokine/chemokine secretion in response to the simulated viral infection. FIG. 12C is a table summarizing effects of different agents on release of some of the cytokines/chemokines from the differentiated COPD epithelial cells into the "blood vessel" channel. FIG. 12D is a table summarizing effects of different agents on secretion of some of the cytokines/chemokines by the differentiated COPD epithelial cells into the "airway lumen" channel. FIG. 12E is a graph showing gene expression of differentiated COPD epithelial cells pretreated with different agents prior to exposure to a TLR-3 ligand poly I:C. FIG. 12F is a graph showing quantification of neutrophil attachment to TLR-3 stimulated differentiated COPD epithelial cells in the device described herein. The graph shows that compound 2 is more potent in reducing neutrophil adhesion, whereas compound 1 did not have such effect, and such result is consistent with and validates the pharmaceutical company's in-house data on potency of compound 2 in reducing inflammation.

FIGS. 13A-13D are photographs of an example experimental set-up or gas-flow modulation device to simulate respiration/breathing in a device described herein. FIG. 13A is a photograph showing an overview of a system for simulating respiration/breathing through an airway of a lung. The system comprises a device according to one embodiment, wherein the mesochannel of the device is adaptably connected to a ventilator (for air-flow generation); and optionally an optical device (e.g., a microscope) for monitoring the cells. The breathing dynamics inside the device can be controlled and/or monitored using a pre-programmed computer. FIG. 13B shows an example method to provide a bi-directional flow of air through the mesochannel of the device described herein. The top panel is a diagrammatic top view of a small airway-on-a-chip indicating the inlet and outlet of the mesochannel (the "airway lumen" channel). The bottom panel shows that using a small animal ventilator and other equipment, rhythmic airflow can be introduced into the mesochannel (e.g., 15 breaths per min; tidal volume of about 100 µL/breath). In addition, the outlet of the mesochannel is adaptably connected to a gas-flow modulation device (e.g., an inflatable chamber such as a balloon) to facilitate expiration of air out of the device (due to the chamber material's elasticity and compliance). FIG. 13C is a photograph showing a balloon-located at the outlet of the mesochannel (the "airway lumen" channel)—expands due to accumulation of air flown into the device through the inlet of the mesochannel and contracts to push the air back due to its elasticity and compliance. FIG. 13D is a set of photographs showing an alternative embodiment of a gas-flow modulation device, which is a drum comprising a flexible diaphragm. As the ventilator pushes the air in (inspiratory flow) through the inlet of the mesochannel, the drum diaphragm moves outward (inflates) and inward (deflates) to accumulate and expel the air, respectively.

FIG. 14A is a set of snapshot images showing the movement of the fluorescent beads within the "airway lumen" channel of the device at a specific time point. The left panel is directed to a control device that did not receive airflow and shows partially polarized bead movements—i.e. some beads in one direction, a few in the opposite direction. The right panel is directed to a device that received airflow for about 24 hrs and shows more polarized bead movement towards the "mouth end. " FIG. 14B is a bar graph showing a higher ciliary clearance rate (determined by movement of the fluorescent beads) in the device that received airflow (breathing chip) than in the control device without airflow (the non-breathing chip).

FIG. 15 is a schematic diagram showing an example system to evaluate transmissibility of airborne pathogens. The system comprises a "pathogen-infected" small airway-on-a-chip and a "uninfected" small airway-on-a-chip, wherein the mesochannel of the "pathogen-infected" small airway-on-a-chip is fluidically connected to the mesochannel of the "uninfected" small airway-on-a-chip. An inspiratory airflow is introduced into the mesochannel of the pathogen-infected" small airway-on-a-chip, and the output airflow is directed to the "uninfected" small airway-on-a-chip to determine airborne transmissibility.

FIG. 19 is a photograph showing a system in which more than one devices described herein (e.g., 8-16 devices) can be fluidically connected to each other and/or to fluid sources. The system can comprise an incubator to provide a temperature-controlled environment for the devices.

FIG. 22A illustrates a device comprising at least one mesochannel separated from at least two microchannels by a membrane. FIG. 22B illustrates a device comprising at least two mesochannels separated from at least one microchannel by a membrane.

FIGS. 24A-24B show transverse cross sectional views of a device with operating channels according to some embodiments described herein. In these embodiments, the height of the operating channels is greater than the height of the mesochannel and/or the height of the microchannel. As shown in the figures, the membrane is constructed to include a central region, wherein the central region includes the portion of the membrane separating the mesochannel from the microchannel. In some embodiments, the membrane can be extended into the operating channel(s) and separating the operating channel(s) into two or more compartments (as shown in the figures). In alternative embodiments, the operating channel(s) does not/do not contain any membrane separating the operating channel(s) into two or more compartments.

(FIG. 25A) Top panel shows primary healthy donor-derived epithelium. Bottom panel is an orthogonal section showing apical cilia coverage in pseudostratified columnar epithelia Note the apical localization of the cilia. (FIG. 25B) Top panel shows epithelial cells obtained from a COPD patient. Bottom panel is an orthogonal section showing apical cilia coverage in pseudostratified columnar epithelia (nucleic were counterstained with DAPI). In FIGS. 25A-25B, ciliated cells were labeled fro β-tublin IV and mucous-producing goblet cells were stained with anti-MUC5AC antibody. Nucleic were counterstained with DAPI. Note the apical localization of the cilia. (Top panels) Scale bar, 20 µm. (Bottom panels) Scale bar, 20 µm.

FIG. 26A shows the mRNA levels of TLR 4 (left) and TLR3 (right) expression between healthy and COPD-derived epithelial cells that were grown in the device (4 COPD donors and 6 healthy subjects). FIG. 26B compares IL-8 secretion between COPD and healthy epithelia after LPS (lipopolysaccharides) stimulation. FIG. 26C compares M-CSF secretion between COPD and healthy epithelia after poly (I:C) (polyinosinic:polycytidylic acid) stimulation. FIGS. 26D-26E show the expression of cytokines IP-10 (FIG. 26D) and RANTES (FIG. 26E) induced in both healthy donor and COPD epithelial cells upon stimulation with poly(I:C) (4 donors for both groups per condition used).

(FIG. 27A) Left panel: a 3D cross-sectional diagram of one embodiment of the devices described herein used to re-create post-capillary venules (major sites of leukocyte recruitment and adhesion in vivo). Middle panel: a schematic diagram showing a 3-cell type co-culture of epithelium, endothelium and neutrophils (all primary cells). Right panel: vertical immunofluorescence cross-section of ciliated epithelium and endothelium bilayer on-device. Ciliated cells were labeled for β-tubulin IV and endothelial cells were stained with anti-CD31/PECAM-1 antibody. Nuclei were counterstained with DAPI. Scale bar, 20 µm. (FIG. 27B) A series of time-lapse microscopic images showed capture of a flowing neutrophil (not visible in the first panel from left but appears in the second panel; shown by the arrow head) to endothelium adjacent to a pre-adhered neutrophil (circles). Following initial attachment the neutrophil crawled over apical surface of activated endothelium and then firmly adhered (times indicated in seconds). Neutrophils and endothelial cells had been live stained with CellTracker Red and Calcein AM, respectively. (FIG. 27C) Bar graphs showing E-selectin and VCAM1 mRNA levels in endothelia cells upon treatment of differentiated epithelial cells with or without poly (I:C). (3 devices per condition were used)

(FIG. 28A) Representative immunofluorescence images showing adhesion of recruited neutrophils under three different conditions: (left) no drug; (middle) budesonide; (right) PFI-2. Neutrophils were stained with Hoechst immediately prior to experiment to allow visualization and quantification. (FIG. 28B) Bar graph showing percentage change in neutrophil adhesion to activated endothelium as imaged in FIG. 28A. (n=3 different donors per condition; 7-8 devices per condition from 4 independent experiments; 4-5 distinct fields per chip). (FIG. 28C) A set of bar graphs showing levels of different cytokine secretion modulated by the indicated drug or under no treatment. Cytokines measured include: neutrophil-attractant IL-8, GROα, and GM-CSF, monocyte-chemoattractant MCP-1, and acute inflammation associated cytokine IL-6. (n=3 donors per condition).

(FIG. 29A) Confocal microscopic top view image of Clara cells stained for CC10 and ciliated cells labeled with β-tubulin IV following well-differentiation of bronchiolar cells in the device. Scale bar, 10 µm. (FIG. 29B) Representative scanning electron micrograph of differentiated bronchiolar cells grown in the device, showing the extensive ciliated cells coverage ("1" arrow), microvilli ("2" arrow) that normally indicates apical membrane of mucous-producing goblet cells, and some dome-shaped structures that indicate Clara cells ("3" arrow). Scale bar, 10 µm.

FIG. 30A is a set of fluorescent images showing airway chips stimulated with IL-13 exhibit a higher number of goblet cells (cells that produce mucus). FIG. 30B is a bar graph showing quantification of globet cell coverage based on the fluorescent images (representative images shown in FIG. 30A). FIG. 30C is a set of bar graphs showing secretion of G-CSF and GM-CSF by IL-13 stimulated cells, as compared to cells without IL-13 stimulation. FIG. 30D is a bar graph showing cilia beating frequency under indicated conditions. In FIGS. 30B-30D, the "airway" devices were also used to assess the drug efficacy of Tofacitinib, a JAK inhibitor, by treating the IL-13 stimulated cells with Tofacitinib, and measuring each phenotype as described above accordingly.

DETAILED DESCRIPTION OF THE INVENTION

Figure 1:
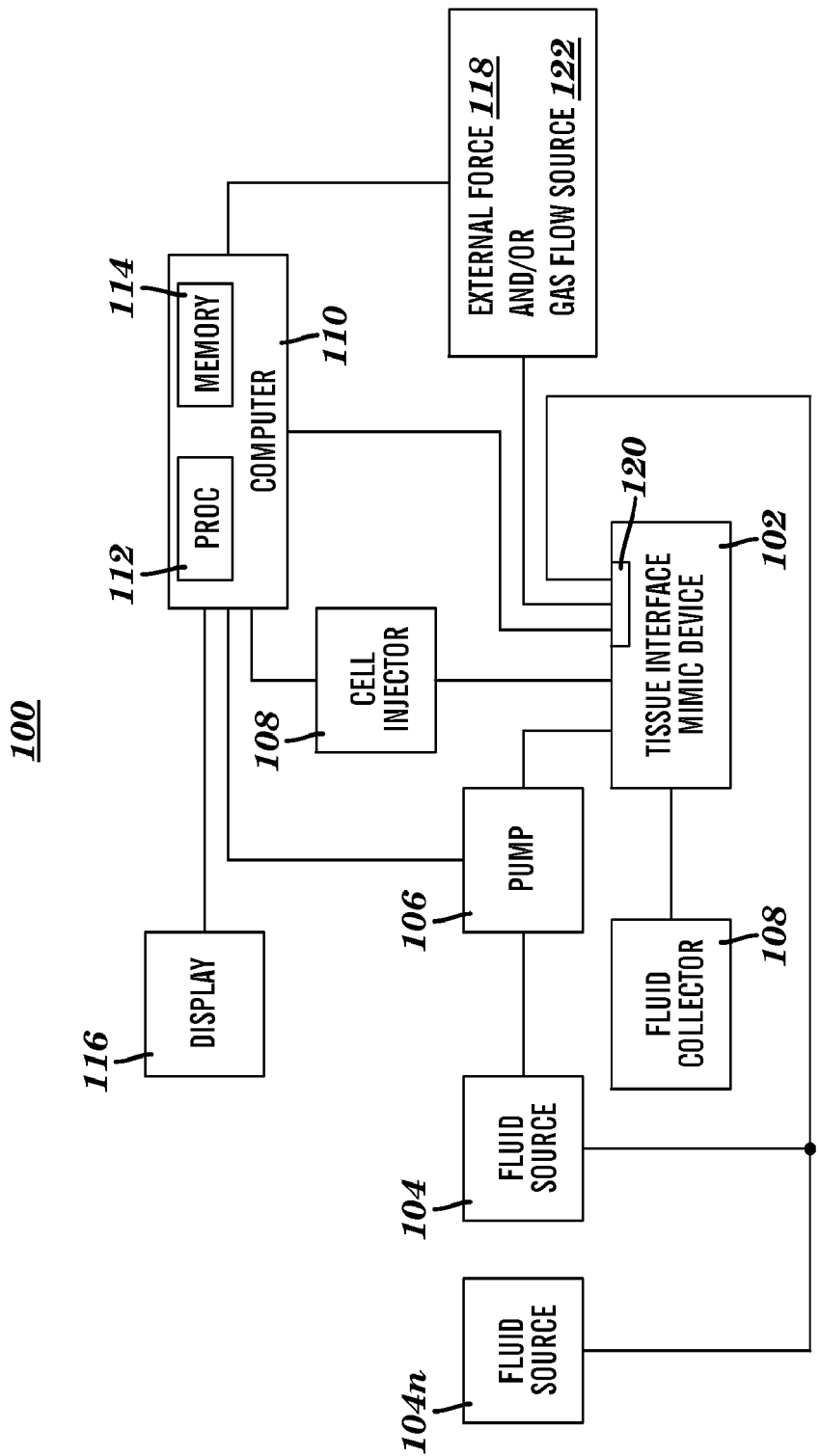
FIG. 1 illustrates a block diagram of a system employing an example organ mimic device in accordance with an embodiment.

Example embodiments of various aspects are described herein in the context of an organ simulating device and methods of use and manufacturing thereof. In particular, one embodiment of the invention is directed to, inter alia, an organ simulating device and methods of uses thereof for growth and differentiation of cells (e.g., cells that require low shear and/or form a stratified structure or a 3-dimensional tissue). In accordance with various aspects described herein, an organ simulating device comprises a first channel and a second channel separated by a membrane, wherein the first channel (termed a "mesochannel" described herein) has a height sufficient to allow cells to form a pseudostratified or stratified structure, or a three-dimensional tissue structure. In one embodiment, the height of the mesochannel can be substantially greater than the height of the second channel (also referred to as the microchannel). In another embodiment, the height of the mesochannel can be substantially same as the height of the second channel.

For example, the inventors have demonstrated in one embodiment of the device described herein well-differentiation of primary human airway epithelial cells (e.g., small airway epithelial cells) into ciliated cells, mucous-secreting goblet cells, and Clara cells in a pseudostratified structure, by culturing the airway epithelial cells at an air-liquid interface established within the device. In this embodiment, the device comprises a mesochannel and a microchannel, wherein the mesochannel has a height (e.g., ~1000 µm) that is substantially higher than that of the microchannel (e.g., ~100 µm). The mesochannel can be adapted to mimic an "airway lumen" channel and the microchannel can be adapted to mimic a "blood vessel" channel. For example, to form an "airway lumen" channel, airway or bronchial epithelial cells are seeded on the membrane facing the upper mesochannel (the "airway lumen" channel) and the epithelial cells differentiate after about 3-4 weeks of culture in the device at the air-liquid interface.

In addition, unlike the existing open-top transwell system that has been previously used to grow and differentiate human cells, but does not allow delivery of air (with a given volume, direction, and speed) on top of epithelial cells, the mesochannel (or an "airway lumen" channel) can be adapted to form a closed top system, which allows airflow over differentiated epithelial cells to mimic breathing pattern and/or rhythm. For example, one end of the mesochannel can be adapted to connect to a gas-flow modulation device (e.g., a reversibly expandable or inflatable chamber) that is adapted to provide a unidirectional and/or a bi-directional flow of air in the mesochannel. Thus, air can be delivered through the mesochannel (at a predefined volume, rate and/or speed) into and out of the device to mimic respiration and/or permit aerosol delivery of compounds, chemicals and/or biologics. Further, the directionality of airflow in the mesochannel can also facilitate directional and rhythmic beating of the differentiated ciliated cells grown in the mesochannel, which can be in turn used to determine mucociliary clearance of a particle (e.g., debris, pathogens and/or particulates) over the length of the mesochannel from one end to another.

Additionally, the device can be used to determine recruitment of immune cells (e.g., but not limited to, CD8+ T cells, lymphocytes, monocytes, and/or neutrophils) from a static or flowing medium in the bottom microchannel (or the "blood vessel" channel) to the membrane, or to blood vessel-associated cells (e.g., endothelial cells, fibroblasts, pericytes and/or smooth muscle cells) grown on another surface of the membrane facing the microchannel (or the "blood vessel" channel), both of which can represent or model an inflammatory response (e.g., involved in a respiratory disease or an infection). Thus, various embodiments of the devices described herein can be used to model and study respiratory diseases (e.g., asthma, chronic obstructive pulmonary disease (COPD), pulmonary hypertension, cystic fibrosis, and any disease associated with a respiratory system including, e.g., nasal, trachea, bronchus, and/or airway), radiation-induced injury, and/or infectious disease (e.g., viral or bacterial infection). These disease models can be in turn used, e.g., for drug screening, and/or study of pathophysiology of various diseases or disorders.

While in one embodiment, the device described herein is suitable for growth and differentiation of human lung cells including alveolar, airway, bronchial, tracheal and nasal epithelia, the device described herein can also be used for other organs-on-a-chip requiring taller channel height to support optimal cell culture and/or formation of multiple cell layers or a three-dimensional tissue structure, for example, including but not limited to Skin-on-a-Chip, Liver-on-a-Chip, Gut-on-a-Chip, Heart-on-a-Chip, Eye-on-a-Chip, and others. Accordingly, in some embodiments, the devices described herein can be used to model diseases other than respiratory diseases, e.g., but not limited to, skin disease, liver diseases, gastrointestinal diseases, heart diseases, and ocular diseases.

Those of ordinary skill in the art will realize that the following description is illustrative only and is not intended to be in any way limiting. Other embodiments will readily suggest themselves to such skilled persons having the benefit of this disclosure. Reference will now be made in detail to implementations of the example embodiments as illustrated in the accompanying drawings. The same reference indicators will be used throughout the drawings and the following description to refer to the same or like items. It is understood that the phrase "an embodiment" encompasses more than one embodiment and is thus not limited to only one embodiment for brevity's sake.

In accordance with this disclosure, the organ mimic device (also referred to as "present device") is preferably utilized in an overall system incorporating sensors, computers, displays and other computing equipment utilizing software, data components, process steps and/or data structures. The components, process steps, and/or data structures described herein with respect to the computer system with which the organ mimic device is employed can be implemented using various types of operating systems (e.g., Windows™, LINUX, UNIX, etc.) computing platforms (e.g., Intel, AMD, ARM, etc.), computer programs, and/or general purpose machines. In addition, those of ordinary skill in the art will recognize that devices of a less general purpose nature, such as hardwired devices, field programmable gate arrays (FPGAs), digital signal processors (DSPs), or application specific integrated circuits (ASICs), can also be used without departing from the scope and spirit of the inventive concepts disclosed herein.

Where a method comprising a series of process steps is implemented by a computer or a machine with use with the organ mimic device described below and those process steps can be stored as a series of instructions readable by the machine, they can be stored on a tangible medium such as a computer memory device (e.g., ROM (Read Only Memory), PROM (Programmable Read Only Memory), EEPROM (Electrically Erasable Programmable Read Only Memory), FLASH Memory, Jump Drive, and the like), magnetic storage medium (e.g., tape, magnetic disk drive, and the like), optical storage medium (e.g., CD-ROM, DVD-ROM, paper card, paper tape and the like) and other types of program memory.

Embodiments of the present device can be applied in numerous fields including basic biological science, life science research, drug discovery and development, drug safety testing, chemical and biological assays, as well as tissue and organ engineering. In an embodiment, the organ mimic device can be used as microvascular network structures for basic research in cardiovascular, cancer, and organ-specific disease biology. Furthermore, one or more embodiments of the device find application in organ assist devices for liver, kidney, lung, intestine, bone marrow, and other organs and tissues, as well as in organ replacement structures.

The cellular responses to the various environmental cues can be monitored using various systems that can be combined with the present device. One can monitor changes in pH using well known sensors. One can integrate force sensors into the membrane to measure changes in the mechanical properties of the cells. One can also sample cells, continuously or periodically for measurement of changes in gene transcription or changes in cellular biochemistry or structural organization. For example, one can measure reactive oxygen species (ROSs) that are a sign of cellular stress. One can also subject the "tissue" grown on the membrane to microscopic analysis, immunohistochemical analysis, in situ hybridization analysis, or typical pathological analysis using staining, such as hematoxylin and eosin staining. Samples for these analysis can be carried out in real-time, or taken after an experiment or by taking small biopsies at different stages during a study or an experiment.

One can subject the cells grown on the membrane to other cells, such as immune system cells or bacterial cells, to antibodies or antibody-directed cells, for example to target specific cellular receptors. One can expose the cells to viruses or other particles. To assist in detection of movement of externally supplied substances, such as cells, viruses, particles or proteins, one can naturally label them using typical means such as radioactive or fluorescent labels.

Cells can be grown, differentiated, cultured, supported or sustained, and/or analyzed using the present device for at least about 1 week, at least about 2 weeks, at least about 3 weeks, at least about 4 weeks, at least about 5 weeks, at least about 6 weeks, at least about 7 weeks, at least about 8 weeks or longer. For example, as discussed below, it has been shown that the cells can be maintained viable and differentiated on a membrane in an embodiment of the described device for at least about 1 month or longer. In some embodiments, cells can be cultured in the device to induce cell growth. In some embodiments, cells (e.g., some primary cells) can be sustained, rather than continue proliferating, in the device.

The organ mimic device described herein has many different applications including, but not limited to, cell differentiation, formation of a stratified and/or three-dimensional tissue structure, development of a disease model in a tissue of interest, development of a mucosal immunity platform; studies on ciliary clearance of a particle; studies on airborne transmissibility of pathogens; studies on immune cell response (e.g., trans-epithelial migration, maturation, activation, cell killing, and/or drainage); studies on various tissue-specific diseases such as respiratory, intestinal, digestive, skin, cardiac, and/or ocular diseases; studies of mechanism of action of drugs, target identification and/or validation, identification of markers of disease; assessing pharmacokinetics and/or pharmacodynamics of various chemical or biological agents; assessing efficacy of therapeutics and/or vaccines; testing gene therapy vectors; drug and/or vaccine development; molecule or drug screening or drug discovery; determination of an appropriate treatment or drug for a specific patient population or individual patient; identification of a risk population to a disease or disorder; identification of a new drug target for a patient population that is non-responsive to a previously-administered treatment; studies of cell behavior in a physiologically-relevant model (including, e.g., stem cells and bone marrow cells); studies on biotransformation, absorption, clearance, metabolism, and activation of xenobiotics; studies on bioavailability and transport of chemical or biological agents across epithelial or endothelial layers; studies on transport of biological or chemical agents across the blood-brain barrier; studies on transport of biological or chemical agents across the intestinal epithelial barrier; studies on acute basal toxicity of chemical agents; studies on acute local or acute organ-specific toxicity of chemical agents; studies on chronic basal toxicity of chemical agents; studies on chronic local or chronic organ-specific toxicity of chemical agents; studies on teratogenicity of chemical agents; studies on genotoxicity, carcinogenicity, and/or mutagenicity of chemical agents; detection of infectious biological agents and/or biological weapons; detection of harmful chemical agents and chemical weapons; studies on infectious diseases (e.g., bacterial, viral and/or fungal infections); assessing infectivity and/or virulence of a new strain; studies on the optimal dose range of a chemical and/or biological agent to treat a disease; prediction of the response of an organ in vivo exposed to a biological and/or chemical agent; studies concerning the impact of genetic content on response to agents; studies on gene transcription in response to chemical or biological agents; studies on protein expression in response to chemical or biological agents; studies on changes in metabolism in response to chemical or biological agents; as well as example uses described below. The organ mimic device can also be used to screen on the cells, for an effect of the cells on the materials (for example, in a manner equivalent to tissue metabolism of a drug).

In some embodiments, the present device can be used to simulate the mechanical load environment of walking, running, breathing, peristalsis, flow of flow or urine, or the beat of a heart, to cells cultured from mechanically active tissues, such as heart, lung, skeletal muscle, bone, ligament, tendon, cartilage, smooth muscle cells, intestine, kidney, endothelial cells and cells from other tissues. Rather than test the biological or biochemical responses of a cell in a static environment, the investigator can apply a range of frequencies, amplitudes and duration of mechanical stresses, including tension, compression and shear, to cultured cells. For example, one can mechanically modulate the membrane within the device to simulate the mechanical load environment of walking, running, breathing/respiration, and peristalsis.

A skilled artisan can place various types of cells on the surface(s) of the membrane. Cells include any cell type from a multicellular structure, including nematodes, amoebas, up to mammals such as humans. Cell types implanted on the device depend on the type of organ or organ function one wishes to mimic, and the tissues that comprise those organs. More details of the various types of cells implantable on the membrane of the devices described herein are discussed below.

One can also co-culture various stem cells, such as bone marrow cells, induced adult stem cells, embryonic stem cells, induced pluripotent stem cells, or stem cells isolated from adult tissues on either one or both sides of the membrane. Using different culture media in the chambers feeding each layer of cells, one can allow different differentiation cues to reach the stem cell layers thereby differentiating the cells to different cell types. One can also mix cell types on the same side of the membrane to create co-cultures of different cells without membrane separation.

Exemplary Microfluidic Devices and Methods of Uses Thereof

In general, the present disclosure is directed to device and method of use in which the device includes a body having a central channel separated by one or more membranes. The membrane(s) are configured to divide the central channel into two or more closely apposed parallel channels of substantially different heights, wherein one or more first fluids are applied through at least one mesochannel and one or more second fluids are applied through at least one microchannel. The height ratio of the mesochannel(s) to the microchannel(s) is greater than 1:1. The surfaces of each membrane can be treated or coated with cell adhesion molecules to support the attachment of cells and promote their organization into tissues on the upper and lower surface of the membrane, thereby creating a tissue-tissue interface separated by a membrane between the adjacent parallel fluid channels. The membrane can be porous (e.g., permeable or selectively permeable), non-porous (e.g., non-permeable), rigid, flexible, elastic, or any combination thereof. In some embodiments, the membrane can be porous, e.g., allowing exchange/transport of fluids (e.g., gas and/or liquids), passage of molecules such as nutrients, cytokines and/or chemokines, cell transmigration, or any combinations thereof. In some embodiments, the membrane can be non-porous. Fluid pressure, flow and channel geometry can be varied to apply a desired fluid shear stress to one or both cell or tissue layers. The larger mesochannel(s) provides a lower shear, more spacious environment for the cell or tissue layer cultured therein, as compared to the cell or tissue layer cultured in the smaller microchannel(s).

In a non-limiting example embodiment, the device can be configured to mimic operation of an airway or a bronchus, whereby cells that prefer lower shear and/or a stratified structure, e.g., airway epithelial cells, are present on one surface of the membrane facing the mesochannel, while lung capillary endothelial cells, fibroblasts, smooth muscle cells are present on the opposite face of the same membrane facing the microchannel. The device thereby allows simulation of the structure and function of a functional airway or bronchus unit that can be exposed to physiological mechanical strain to simulate breathing or to both air-borne and blood-borne chemical, molecular, particulate and cellular stimuli to investigate the exchange of chemicals, molecules, and cells across this tissue-tissue interface through the pores of the membrane. The device impacts the development of in vitro airway or bronchus models that mimic organ-level responses which are able to be analyzed under physiological and pathological conditions. This system can be used in several applications including, but not limited to, disease models, drug screening, drug delivery, vaccine delivery, biodetection, toxicology, physiology and organ/tissue engineering applications.

In other embodiments, the device can be adapted for other organ mimetic devices requiring taller channel height to support optimal cell culture including, but not limited to, skin-on-a-chip, heart-on-a-chip, liver-on-a-chip, gut-on-a-chip, and eye-on-a-chip. For example, the organ mimetic devices described in the International Patent Application Nos. PCT/US12/68725 and PCT/US12/68766, the content of which are incorporated herein by reference, can be modified to have one of the microchannels with a taller channel height.

FIG. 1 illustrates a block diagram of the overall system employing the inventive device in accordance with an embodiment. As shown in FIG. 1, the system 100 includes an organ mimic device 102, one or more fluid sources 104, $104_N$ coupled to the device 102, one or more optional pumps 106 coupled to the fluid source 104 and device 102. One or more central processing units (CPUs) 110 can be coupled to the pump 106 and preferably control the flow of fluid in and out of the device 102. The CPU 110 preferably includes one or processors 112 and one or more local/remote storage memories 114. A display 116 can be coupled to the CPU 110, and one or more pressure sources 118 can be coupled to the CPU 110 and the device 102. The CPU 110 preferably controls the flow and rate of pressurized fluid to the device. It should be noted that although one interface device 102 is shown and described herein, a plurality of interface devices 102 can be tested and analyzed within the system 100 as discussed below.

As will be discussed in more detail, the organ mimic device 102 preferably includes two or more ports which place the mesochannels and microchannels of the device 102 in communication with the external components of the system, such as the fluid and pressure sources. In particular, the device 102 can be coupled to the one or more fluid sources $104_N$ in which the fluid source can contain air, culture medium, blood, water, cells, compounds, particulates, and/or any other media which are to be delivered to the device 102. In one embodiment, the fluid source 104 provides fluid to one or more mesochannels and microchannels of the device 102 and also preferably receives the fluid which exits the device 102. In some embodiments, the fluid exiting the device 102 can additionally or alternatively be collected in a fluid collector or reservoir 108 separate from the fluid source 104. Thus, it is possible that separate fluid sources 104, $104_N$ respectively provide fluid to and remove fluid from the device 102.

In an embodiment, fluid exiting the device 102 can be reused and reintroduced into the same or different input port through which it previously entered. For example, the device 102 can be set up such that fluid passed through a particular central sub-channel (e.g., mesochannel or microchannel) is recirculated back to the device and is again run through the same channel. This could be used, for instance, to increase the concentration of an analyte in the fluid as it is recirculated the device. In another example, the device 102 can be set up such that fluid passed through the device and is recirculated back into the device and then subsequently run through another channel (e.g., mesochannel or microchannel). This could be used to change the concentration or makeup of the fluid as it is circulated through another channel (e.g., mesochannel or microchannel).

One or more pumps 106 are preferably utilized to pump the fluid into the device 102, although pumps in general are optional to the system. Fluid pumps are well known in the art and are not discussed in detail herein. As will be discussed in more detail below, each microchannel portion is preferably in communication with its respective inlet and/or outlet port, whereby each microchannel portion of allow fluid to flow therethrough.

Each mesochannel and microchannel in the device preferably has dedicated inlet and outlet ports which are connected to respective dedicated fluid sources and/or fluid collectors to allow the flow rates, flow contents, pressures, temperatures and other characteristics of the media to be independently controlled through each channel. Thus, one can also monitor the effects of various stimuli to each of the cell or tissue layers separately by sampling the separate fluid channels for the desired cellular marker, such as changes in gene expression at RNA or protein level.

The cell injector/remover 108 component is shown in communication with the device 102, whereby the injector/remover 108 is configured to inject, remove and/or manipulate cells, such as but not limited to epithelial, endothelial cells, fibroblasts, smooth muscle cells, basal cells, ciliated cells, columnar cells, goblet cells, muscle cells, immune cells, neural cells, hematopoietic cells, lung cells (e.g., alveolar epithelial cells, airway cells, bronchial cells, tracheal cells, and nasal epithelial cells), gut cells, brain cells, stem cells, skin cells, liver cells, heart cells, spleen cells, kidney cells, pancreatic cells, reproductive cells, and any combinations thereof, on one or more surfaces of the interface membrane within the device 102 independent of cells introduced into the device via the inlet port(s) 210, 218. For example, blood containing magnetic particles which pull pathogenic cells can be cultured in a separate device whereby the mixture can be later introduced into the system via the injector at a desired time without having to run the mixture through the fluid source 104. In an embodiment, the cell injector/remover 108 is independently controlled, although the injector/remover 108 can be controlled by the CPU 110 as shown in FIG. 1. The cell injector/remover 108 is an optional component and is not necessary.

Although not required, the membrane of the device 102 can be adapted, e.g., by pneumatic means, to cause mechanical movements within the device 102. In these embodiments, an external force (e.g., mechanical force or pressure)

can be applied from the one or more external force sources 118 to cause mechanical movements of the membrane within the device 102. In an embodiment in which mechanical energy is used with the device, the external force source (e.g., stretching) 118 is controlled by the CPU 110 to stretch or release one or more membranes within the device to stretch and/or retract in response to the applied force. In an embodiment in which pressures are used with the device, the external force source (e.g., pressure source) 118 is controlled by the CPU 110 to apply a pressure differential within the device to effectively cause one or more membranes within the device to stretch and/or retract in response to the applied pressure differential. In an embodiment, the pressure applied to the device 102 by the external force source (e.g., pressure source) 118 is a positive pressure, depending on the configuration or application of the device. Additionally or alternatively, the pressure applied by the external force source (e.g., pressure source) 118 is a negative pressure, such as vacuum or suction, depending on the configuration or application of the device. The external force source 118 is preferably controlled by the CPU 110 to apply an external force (e.g., mechanical force or pressure) at set timed intervals or frequencies to the device 102, whereby the timing intervals can be set to be uniform or non-uniform. The external force source 118 can be controlled to apply uniform force (e.g., mechanical force or pressure) in the timing intervals or can apply different force (e.g., mechanical forces or pressures) at different intervals. For instance, the pressure applied by the pressure source 118 can have a large magnitude and/or be set at a desired frequency to mimic a person running or undergoing exertion. The external force source 118 can also apply slow and/or irregular patterns, such as simulating a person sleeping or having a respiratory problem. In an embodiment, the CPU 110 operates the external force source 118 to randomly vary intervals of applying an external force (e.g., mechanical force or pressure) to cause cyclic stretching patterns to simulate irregularity in breath rate and tidal volumes during natural breathing.

In some embodiments, a gas-flow source generator 122 can be coupled to the device 102 to introduce a gas inflow (e.g., an air inflow) to at least one channel of the device (e.g., the mesochannel of the device to mimic respiration).

One or more sensors 120 can be coupled to the device 102 to monitor one or more areas within the device 102, whereby the sensors 120 provide monitoring data to the CPU 110. One type of sensor 120 is preferably a force sensor which provides data regarding the amount of force, stress, and/or strain applied to a membrane or pressure in one or more operating channels within the device 102. In one embodiment in which pressure is used within the device, pressure data from opposing sides of the channel walls can be used to calculate real-time pressure differential information between the operating and central sub-channels (e.g., mesochannels and microchannels). The monitoring data would be used by the CPU 110 to provide information on the device's operational conditions as well as how the cells are behaving within the device 102 in particular environments in real time. The sensor 120 can be an electrode, have infrared, optical (e.g. camera, LED), or magnetic capabilities or utilize any other appropriate type of technology to provide the monitoring data. For instance, the sensor can be one or more microelectrodes which analyze electrical characteristics across the membrane (e.g. potential difference, resistance, and short circuit current) to confirm the formation of an organized barrier, as well as its fluid/ion transport function across the membrane. It should be noted that the sensor 120 can be external to the device 102 or be integrated within the device 102. In some embodiments, the CPU 110 controls operation of the sensor 120, although it is not necessary. The data is preferably shown on the display 116.

Figure 2A:
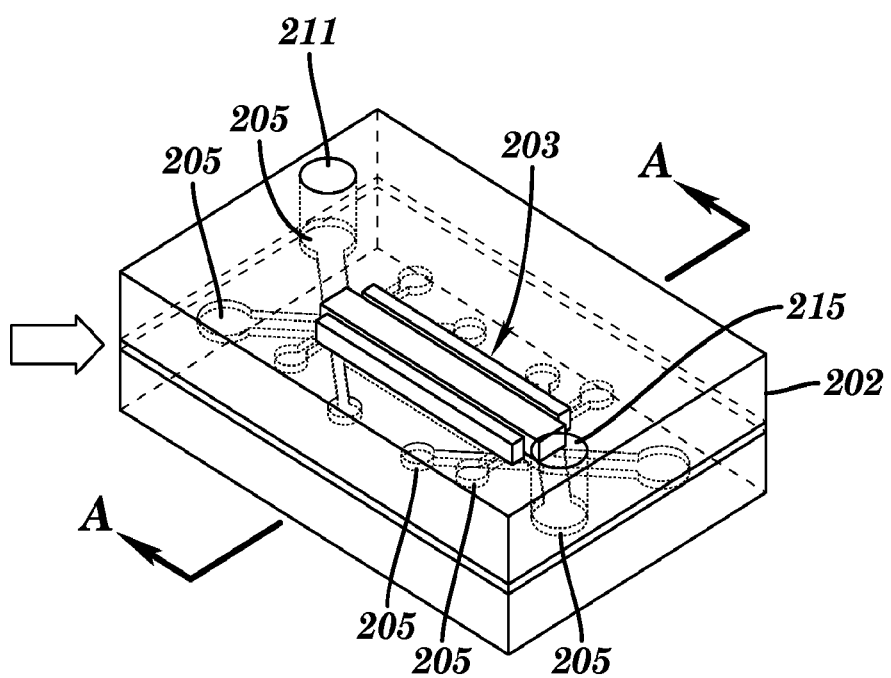
FIG. 2A illustrates a perspective view of an organ mimic device in accordance with an embodiment.

FIG. 2A illustrates a perspective view of the microfluidic device in accordance with an embodiment. In particular, as shown in FIG. 2A, the device 200 (also referred to reference numeral 102) preferably includes a body 202 having a branched microchannel design 203 in accordance with an embodiment. The body 202 can be made of an elastomeric material, although the body can be alternatively made of a non-elastomeric material, or a combination of elastomeric and non-elastomeric materials. It should be noted that the microchannel design 203 is only exemplary and not limited to the configuration shown in FIG. 2A.

The body 202 can be fabricated from a rigid material, an elastomeric material, or a combination thereof. As used herein, the term "rigid" refers to a material that is stiff and does not bend easily, or maintains very close to its original form after pressure has been applied to it. The term "elastomeric" as used herein refers to a material or a composite material that is not rigid as defined herein. An elastomeric material is generally moldable and curable, and has an elastic property that enables the material to at least partially deform (e.g., stretching, expanding, contracting, retracting, compressing, twisting, and/or bending) when subjected to a mechanical force or pressure and partially or completely resume its original form or position in the absence of the mechanical force or pressure. In some embodiments, the term "elastomeric" can also refer to a material that is flexible/stretchable but does not resume its original form or position after pressure has been applied to it and removed thereafter. The terms "elastomeric" and "flexible" are interchangeably used herein.

In some embodiments, the material used to make the body 202 or at least the portion of the body 202 that is in contact with a gaseous and/or liquid fluid is preferably made of a biocompatible polymer or polymer blend, including but not limited to, polydimethylsiloxane (PDMS), polyurethane, polyimide, styrene-ethylene-butylene-styrene (SEBS), polypropylene, or any combinations thereof. As used herein, the term "biocompatible" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood.

In some embodiments, the body 202 can comprise an elastomeric portion fabricated from a styrenic block copolymer-comprising composition, e.g., as described in the U.S. Provisional Application No. 61/919,181 filed Dec. 20, 2013 and the corresponding PCT International Application No. PCT/US2014/071611, entitled "Organomimetic devices and methods of use and manufacturing thereof" filed concurrently with the current application on Dec. 19, 2014, can be adopted in the devices described herein, the content of which is incorporated herein by reference. In some embodiments, the styrenic block copolymer-comprising composition can comprise SEBS and polypropylene.

Additionally or alternatively, at least a portion of the body 202 can be made of non-flexible or rigid materials like glass, silicon, hard plastic, metal, or any combinations thereof.

The membrane 208 can be made of the same material as the body 202 or a material that is different from the body 202 of the device. In some embodiments, the membrane 208 can be made of a rigid material. In some embodiments, the membrane is a thermoplastic rigid material. Examples of rigid materials that can be used for fabrication of the membrane include, but are not limited to, polyester, polycarbonate or a combination thereof. In some embodiments, the membrane 208 can comprise a flexible material, e.g., but not limited to PDMS.

In some embodiments, the body of the device and/or the membrane can comprise or is composed of an extracellular matrix polymer, gel, and/or scaffold. Any extracellular matrix can be used herein, including, but not limited to, silk, chitosan, elastin, collagen, proteoglycans, hyaluronic acid, collagen, fibrin, and any combinations thereof.

The device in FIG. 2A includes a plurality of access ports 205 which will be described in more detail below. In addition, the branched configuration 203 includes a tissue-tissue interface simulation region (membrane 208 in FIG. 2B) where cell behavior and/or passage of gases, chemicals, molecules, particulates and cells are monitored. FIG. 2B illustrates an exploded view of the organ mimic device in accordance with an embodiment. In particular, the outer body 202 of the device 200 is preferably comprised of a first outer body portion 204, a second outer body portion 206 and an intermediary membrane 208 configured to be mounted between the first and second outer body portions 204, 206 when the portions 204, 206 are mounted to one another to form the overall body.

The first outer body portion 204 can have a thickness of any dimension, depending, in part, on the height of the mesochannel 250A. In some embodiments, the thickness of the first outer body portion 204 can be about 1 mm to about 100 mm, or about 2 mm to about 75 mm, or about 3 mm to about 50 mm, or about 3 mm to about 25 mm. In one embodiment, the thickness of the first outer body portion 204 can be about 4.8 mm. In some embodiments, the first outer body portion 204 can have a thickness that is more than the height of the mesochannel by no more than 500 microns, no more than 400 microns, no more than 300 microns, no more than 200 microns, no more than 100 microns, no more than 70 microns or less. In some embodiments, it is desirable to keep the first outer body portion 204 as thin as possible such that cells on the membrane can be visualized or detected by microscopic, spectroscopic, and/or electrical sensing methods.

The second outer body portion 206 can have a thickness of any dimension, depending, in part, on the height of the microchannel 250B. In some embodiments, the thickness of the second outer body portion 206 can be about 50 µm to about 10 mm, or about 75 µm to about 8 mm, or about 100 µm to about 5 mm, or about 200 µm to about 2.5 mm. In one embodiment, the thickness of the second outer body portion 206 can be about 1 mm to about 1.5 mm. In one embodiment, the thickness of the second outer body portion 206 can be about 0.2 mm to about 0.5 mm. In some embodiments, the second outer body portion 206 can have a thickness that is more than the height of the microchannel by no more than 500 microns, no more than 400 microns, no more than 300 microns, no more than 200 microns, no more than 100 microns, no more than 70 microns or less. In some embodiments, it is desirable to keep the second outer body portion 206 as thin as possible such that cells on the membrane can be visualized or detected by microscopic, spectroscopic, and/or electrical sensing methods.

FIG. 2B illustrates an exploded view of the device in accordance with an embodiment. As shown in FIG. 2B, the first outer body portion 204 includes one or more inlet fluid ports 210 in communication with one or more corresponding inlet apertures 211 located on an outer surface of the body 202. The device 100 is preferably connected to the fluid source 104 via the inlet aperture 211 in which fluid travels from the fluid source 104 into the device 100 through the inlet fluid port 210.

Additionally, the first outer body portion 204 includes one or more outlet fluid ports 212 in communication with one or more corresponding outlet apertures 215 on the outer surface of the body 202. In particular, fluid passing through the device 100 exits the device 100 to a fluid collector 108 or other appropriate component via the corresponding outlet aperture 215. It should be noted that the device 200 can be set up such that the fluid port 210 is an outlet and fluid port 212 is an inlet.

Figure 2C:
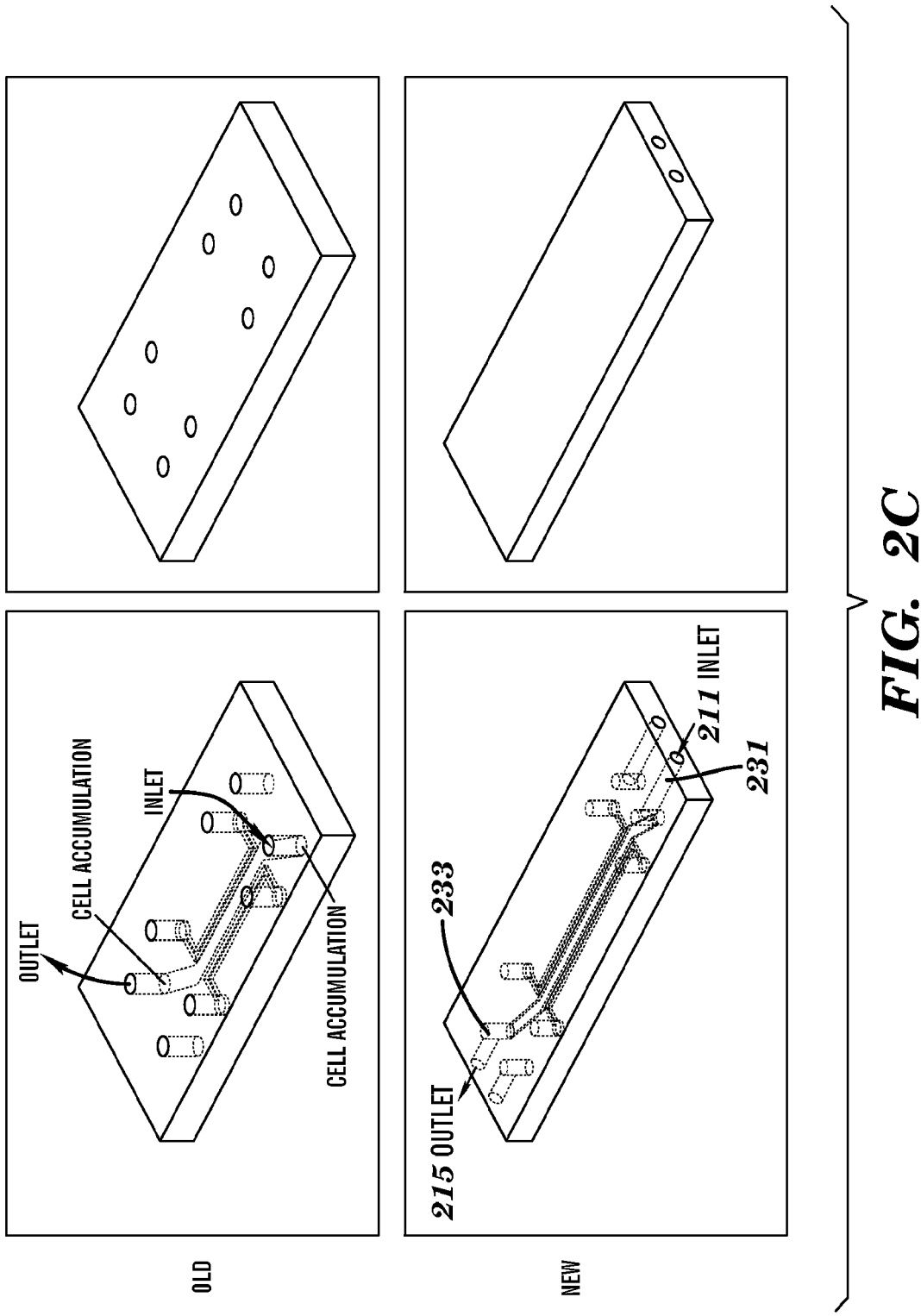
FIG. 2C illustrative perspective views of organ mimic devices with different positions of inlet and outlet ports. The top panel illustrates that the inlet and outlet ports are positioned on a top surface of a portion of the device described herein. The bottom panel illustrates that the inlet and outlet ports are positioned on the lateral side of a portion of the device described herein.
Figure 2D:
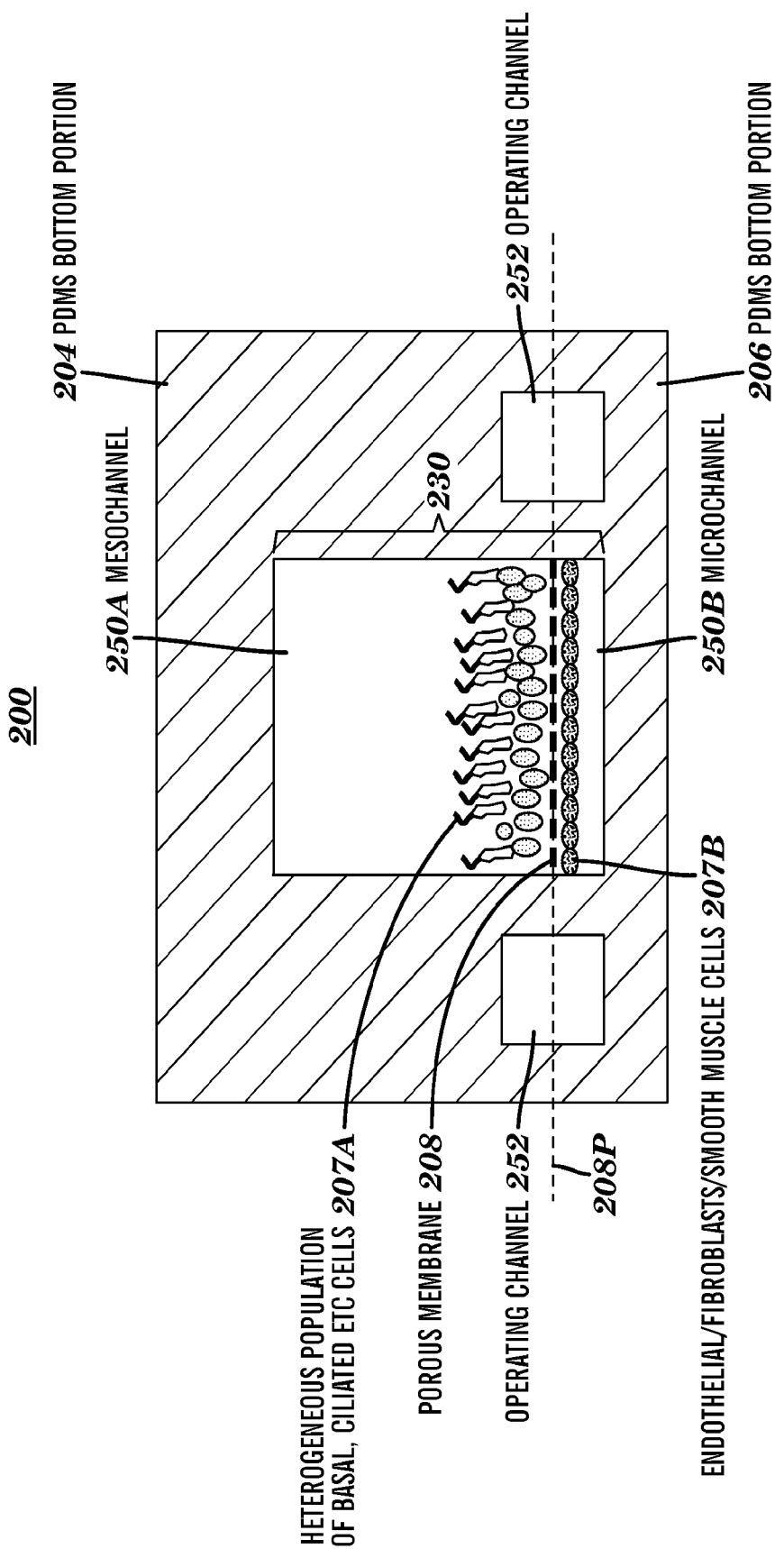
FIG. 2D illustrates a diagrammatic view of a cell-cell interface region of the device in accordance with an embodiment.
Figure 2E:
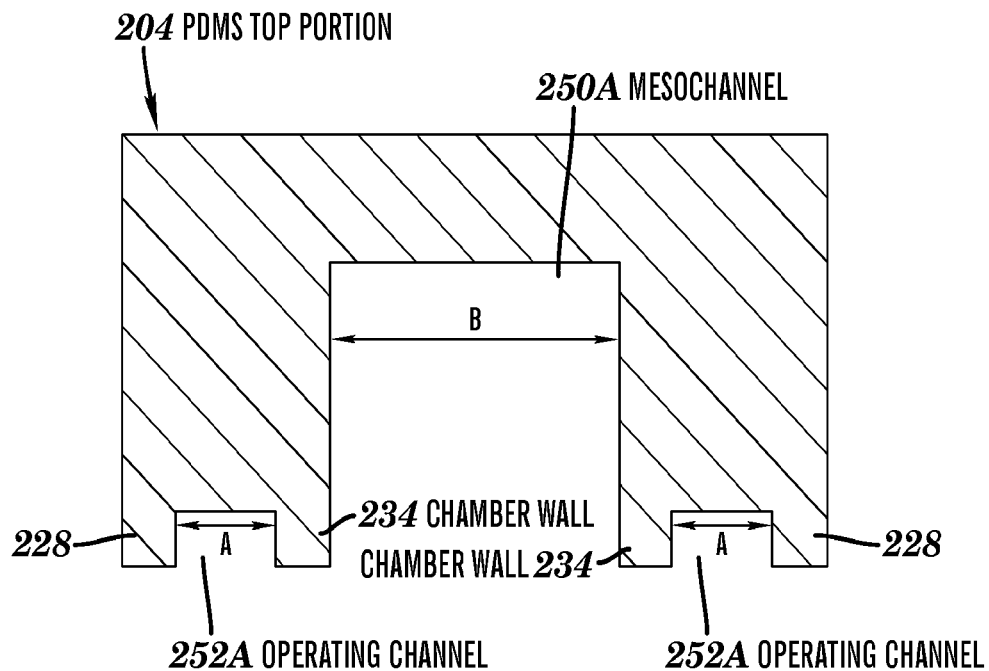
FIGS. 2E-2F illustrate cross sectional views of a top body portion and a bottom body portion of the device in accordance with an embodiment, respectively.
Figure 2F:
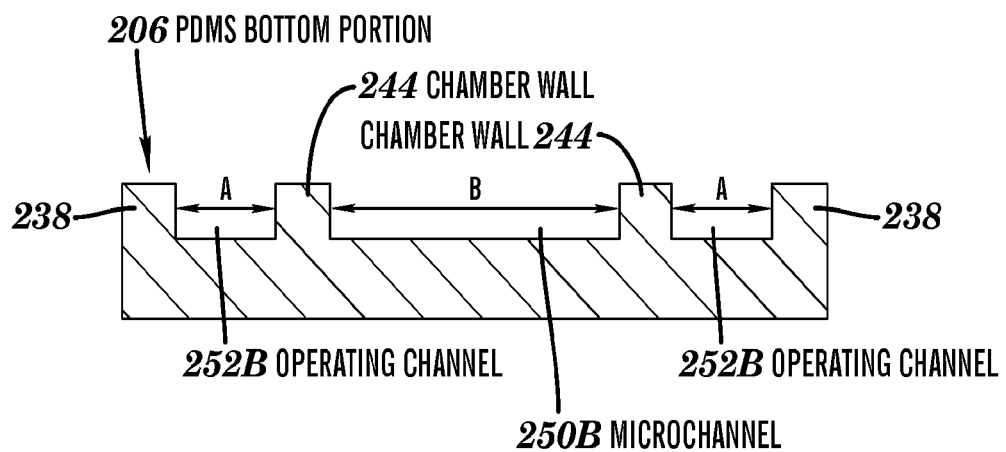
Figure 2G:
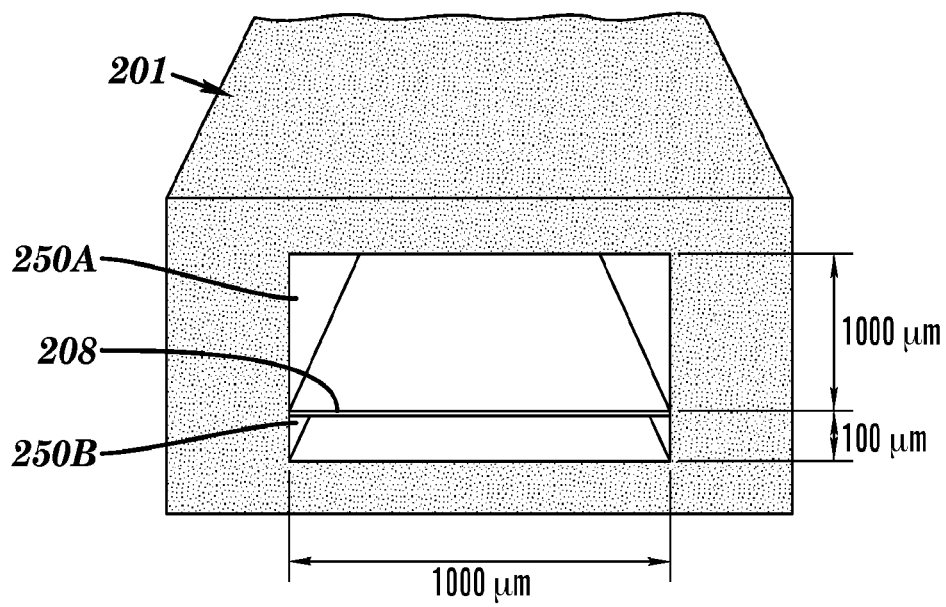
FIG. 2G illustrates a cross-sectional view of a device in accordance with an embodiment.
Figure 2H:
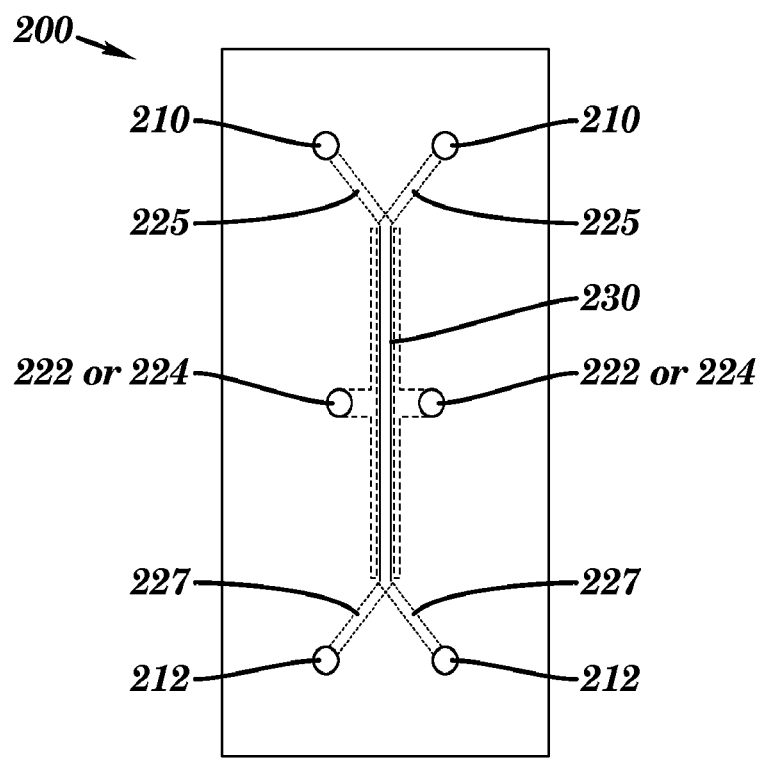
FIG. 2H illustrate a top view of a device in accordance with the embodiment described in FIG. 2D.

In some embodiments, as shown in FIGS. 2B and 2H, the device 200 can comprise an inlet channel 225 connecting an inlet fluid port 210 to the central channel 230. The inlet channels and inlet ports can be used to introduce cells, agents (e.g., but not limited to, stimulants, drug candidate, particulates), air flow, and/or cell culture media into the mesochannel 250A and microchannel 250B.

The central and operating channels described herein are shown generally as linear. It is to be understood, however, that the channels can be substantially linear or they can be non-linear. Thus, the present inventive concepts are not limited to straight or linear channels and can comprise curved, angled, or otherwise non-linear channels, e.g., central channel and/or operating channel(s). It is to be further understood that a first portion of a channel (e.g., central channel and/or operating channel(s)) can be straight, and a second portion of the same channel can be curved, angled, or otherwise non-linear. Generally, the non-linear channel comprises at least one (e.g., one, two, three, four, five, six, seven, eight, nine, ten or more) curved or angled sections. A non-linear channel can also comprise at least one (e.g., one, two, three, four, five, six, seven, eight, nine, ten or more) substantially linear sections.

Generally, non-linear section has curve or angle in the range from about 5° to about 175°. In some embodiments, the non-linear section comprises a curve or angle of about 80° to about 100°. In some embodiments, a non-linear section joins two substantially linear sections that are substantially parallel to each other. In some embodiments, a non-linear section joins two substantially linear sections that are substantially perpendicular to each other. In some embodiments, a non-linear section joins two substantially linear sections that are positioned at an angle less than perpendicular to each other. In some embodiments, a non-linear section joins two substantially linear sections that are positioned at an angle higher than perpendicular to each other.

Figure 23:
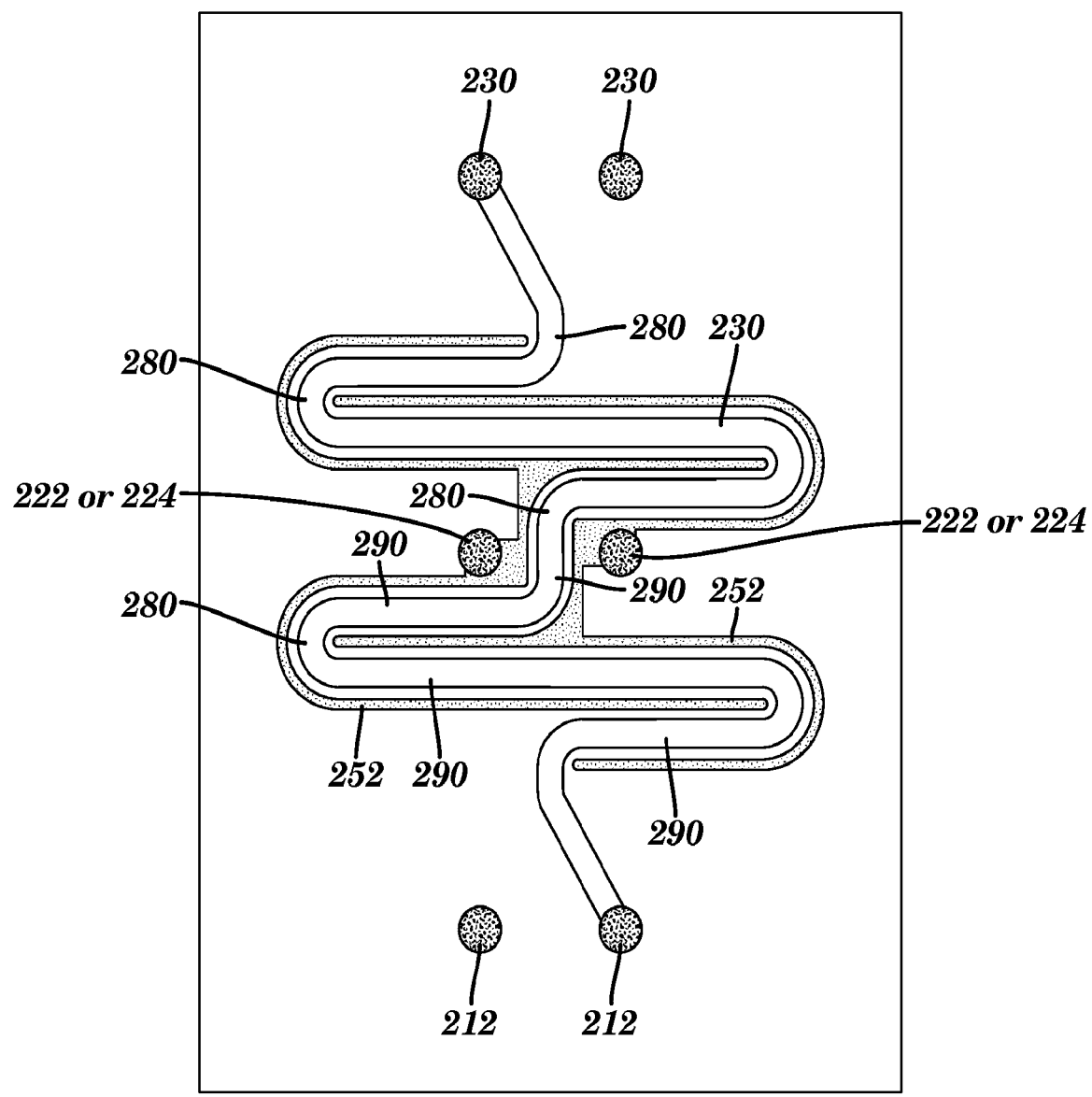
FIG. 23 illustrates a top view of a device in accordance with the embodiment described in FIG. 2D.

FIG. 23 illustrates an embodiment of device 200 that comprises a non-linear central channel (230) and operating channels 252. The central channel 200 comprises one or more non-linear sections (280) that join together two linear sections (290) of the central channel. Without wishing to be bound by a theory, a non-linear central channel can increase the ratio of culture area to chip area, thereby providing a larger surface area for cells to grow. This can also allow for a higher amount or density of cells in the central channel.

In some embodiments, the device comprises a non-linear central channel, wherein height of the mesochannel is about 1 mm and height of the microchannel is about 200 µm. In some further embodiments of this device, the height of the operating channels is about 500 µm. In some embodiments, the height of the operating channels can be greater than the height of the mesochannel or microchannel, or the combined height of the mesochannel and the microchannel.

The device 200 can also comprise an outlet channel 227 connecting an outlet fluid port 212 to the central channel 230. The outlet channels and outlet ports can also be used to introduce cells, agents (e.g., but not limited to, stimulants, drug candidate, particulates), air flow, and/or cell culture media into the mesochannel 250A and microchannel 250B.

Although the inlet and outlet apertures 211, 215 are shown on the top surface of the body 202 and are located perpendicular to the inlet and outlet channels 225, 227, one or more of the apertures 211, 215 can be located on one or more lateral surfaces of the body such that at least one of the inlet and outlet apertures 211, 215 can be in-plane with the inlet and/or outlet channels 225, 227, respectively, and/or be oriented at an angle from the plane of the inlet and/or outlet channels 225, 227. For example, FIG. 2C shows a perspective view of the device with the inlet and outlet apertures configured on the lateral surfaces of the body in accordance with one embodiment. By placing the inlet and outlet apertures on the lateral surfaces of the body, the inlet channels 231 and outlet channels 233 can form an angle of less than 90 degrees (e.g., ranging between 10 degrees and 50 degrees) with the mesochannel 250A and/or microchannel 250B. In one embodiment, the inlet channels 231 and outlet channels 233 can form an angle of about 25 degrees with the mesochannel 250A and/or microchannel 250B. In one embodiment, the inlet channels 231 and outlet channels 233 can form an angle of about 45 degrees with the mesochannel 250A and/or microchannel 250B. These angled configurations can reduce or prevent accumulation of cells upon cell seeding process at the ports and/or formation of cell plugs. In addition, the design of the inlet and outlet apertures 211, 215 on the lateral surfaces of the body can allow access to both the mesochannel and microchannel, which can be used, e.g., to remove bubbles with microinjection tips in the bottom channel, access the cells, wound the cells, and/or inject new cell type into the device.

In an embodiment, the inlet fluid port 210 and the outlet fluid port 212 are in communication with the mesochannel 250A (see FIG. 2D) such that fluid can dynamically travel from the inlet fluid port 210 to the outlet fluid port 212 via the mesochannel 250A, independently of the microchannel 250B (see FIG. 2D).

In another embodiment, the fluid passing between the inlet and outlet fluid ports can be shared between the mesochannel 250A and microchannel 250B. In either embodiment, characteristics of the fluid flow, such as flow rate, fluid type and/or composition, and the like, passing through the mesochannel 250A can be controllable independently of fluid flow characteristics through the microchannel 250B and vice versa.

In one embodiment, the first portion 204 includes one or more pressure inlet ports 214 and one or more pressure outlet ports 216 in which the inlet ports 214 are in communication with corresponding apertures 217 located on the outer surface of the device 100. Although the inlet and outlet apertures are shown on the top surface of the body 202, one or more of the apertures can alternatively be located on one or more lateral sides of the body. In operation, one or more pressure tubes (not shown) connected to the external force source (e.g., pressure source) 118 (FIG. 1) provides positive or negative pressure to the device via the apertures 217. Additionally, pressure tubes (not shown) are connected to the device 100 to remove the pressurized fluid from the outlet port 216 via the apertures 223. It should be noted that the device 200 can be set up such that the pressure port 214 is an outlet and pressure port 216 is an inlet. It should be noted that although the pressure apertures 217, 223 are shown on the top surface of the body 202, one or more of the pressure apertures 217, 223 can be located on one or more side surfaces of the body 202.

Referring to FIG. 2B, the second portion 206 includes one or more inlet fluid ports 218 and one or more outlet fluid ports 220. As shown in FIG. 2B, the inlet fluid port 218 is in communication with aperture 219 and outlet fluid port 220 is in communication with aperture 221, whereby the apertures 219 and 221 are located on the outer surface of the second outer body portion 206. Although the inlet and outlet apertures are shown on the surface of the body 202, one or more of the apertures can be alternatively located on one or more lateral sides of the body, e.g., as shown in FIG. 2C.

As with the first outer body portion 204 described above, one or more fluid tubes connected to the fluid source 104 (FIG. 1) are preferably coupled to the aperture 219 to provide fluid to the device 100 via port 218. Additionally, fluid exits the device 100 via the outlet port 220 and out aperture 221 to a fluid reservoir/collector 108 or other component. It should be noted that the device 200 can be set up such that the fluid port 218 is an outlet and fluid port 220 is an inlet.

In one embodiment, the second outer body portion 206 includes one or more pressure inlet ports 222 and one or more pressure outlet ports 224. In particular, it is preferred that the pressure inlet ports 222 are in communication with apertures 227 and pressure outlet ports 224 are in communication with apertures 229, whereby apertures 227 and 229 are located on the outer surface of the second portion 206. Although the inlet and outlet apertures are shown on the bottom surface of the body 202, one or more of the apertures can be alternatively located on one or more lateral sides of the body. Pressure tubes connected to the external force source (e.g., pressure source) 118 (FIG. 1) can be engaged with ports 222 and 224 via corresponding apertures 227 and 229. It should be noted that the device 200 can be set up such that the pressure port 222 is an outlet and fluid port 224 is an inlet.

In some embodiments where the operating channels as described below (e.g., 252 shown in FIG. 2D) are not mandatory, the first portion 204 does not require any pressure inlet port 214, pressure outlet port 216. Similarly, the second portion 206 does not require any pressure inlet port 222 or pressure outlet port 224.

In an embodiment, the membrane 208 is mounted between the first portion 204 and the second portion 206, whereby the membrane 208 is located within the body 202 of the device 200 (see FIG. 2D). In an embodiment, the membrane 208 is a made of a material having a plurality of pores or apertures therethrough, whereby molecules, cells, fluid or any media is capable of passing through the membrane 208 via one or more pores in the membrane 208. As discussed in more detail below, the membrane 208 in one embodiment can be made of a material which allows the membrane 208 to undergo stress and/or strain in response to an external force (e.g., cyclic stretching or pressure). In one embodiment, the membrane 208 can be made of a material which allows the membrane 208 to undergo stress and/or strain in response to pressure differentials present between the mesochannel 250A, the microchannel 250B and the operating channels 252. Alternatively, the membrane 208 is relatively inelastic or rigid in which the membrane 208 undergoes minimal or no movement while media is passed through one or more of the central sub-channels 250A, 250B and/or cells organize and move between the central sub-channels 250A, 250B via the membrane.

Referring FIG. 2E illustrates a perspective view of the tissue-tissue interface region of the first outer portion 204 of the body taken at line C-C (from FIG. 2B). As shown in FIG. 2E, the top portion of the tissue-tissue interface region 207A is within the body of the first portion 204 and includes a top portion of a central channel 230 (mesochannel 250A) and one or more top portion side operating channels 252A located adjacent to the mesochannel 250A. Channel walls 234, 244 preferably separate the central channel 230 from the operating channels 252 such that fluid traveling through the central channel 230 does not pass into operating channels 252. Likewise, the channel walls 234, 244 prevent pressurized fluid passing along operating channels 252 from entering the mesochannel 250A. It should be noted that a pair of operating channels 252 are shown on opposing sides of central channel 230 in FIG. 2D, however the device can incorporate more than two operating channels 252. In some embodiments that the device 200 can include only one operating channel 252 adjacent to the central channel 230.

FIG. 2F illustrates a perspective view of the tissue interface region taken at line D-D of the second outer portion 206 of the body. As shown in FIG. 2F, the tissue interface region includes a bottom portion of the central channel 230 (microchannel 250B) and at least two bottom portions of operating channels 252B located adjacent to the microchannel 250B. A pair of channel walls 234, 244 preferably separate the central channel 230 from the operating channels 252 such that fluid traveling through the central channel 230 does not pass into operating channels 232. Likewise, the channel walls 234, 244 prevent pressurized fluid passing along operating channels 232 from entering the central channel 230.

The central channel 230 can have a length suited to the need of an application (e.g., a physiological system to be modeled), desirable size of the device, and/or desirable size of the view of field. In some embodiments, the central channel 230 can have a length of about 0.5 cm to about 10 cm. In one embodiment, the central channel 230 can have a length of about 1 cm to about 2 cm.

As shown in FIGS. 2E and 2F, the top and bottom portions of the central channel 230 each have a range of width dimension (shown as B) between 200 microns and 10 mm, or between 200 microns and 1500 microns, or between 400 microns and 1000 microns, or between 50 and 2000 microns. In some embodiments, the dimensions of the devices described herein can be configured to provide a low shear stress on epithelial cells while submerged in liquid culture (which can be subsequently subjected to an air-liquid interface (ALI) induction). For example, in some embodiments, the width of the channels (mesochannels and microchannels) can be at least or greater than 400 µm or more, including, e.g., at least or greater than 500 µm, at least or greater than 600 µm, at least or greater than 700 µm, at least or greater than 800 µm, at least or greater than 900 µm, at least or greater than 950 µm or more. In one embodiment, the top and bottom portions of the central channel (250A mesochannel and 250B microchannel) each have a width dimension of greater than 400 µm. In one embodiment, the top and bottom portions of the central channel (250A mesochannel and 250B microchannel) each have a width dimension of about 1 mm. It should be noted that other width dimensions (e.g., greater than 10 mm or smaller than 50 microns) can be used depending on the type of physiological system which is being mimicked in the device, and/or the number of mesochannel(s)/microchannel(s) formed in the central channel, which will be discussed further below. Thus, in some embodiments, the width of the central channel can be between 400 microns and 50 mm, or between 400 microns and 10 mm, or between 800 microns and 5 mm, or between 100 microns and 10 mm.

In some embodiments where the top portion of the central channel 230 forms a single mesochannel 250A, the width of the mesochannel 250A is essentially the same width of the central channel 230. Similarly, in some embodiments where the bottom portion of the central channel 230 forms a single microchannel 250B, the width of the microchannel 250B is essentially the same width of the central channel 230.

Figure 22A:
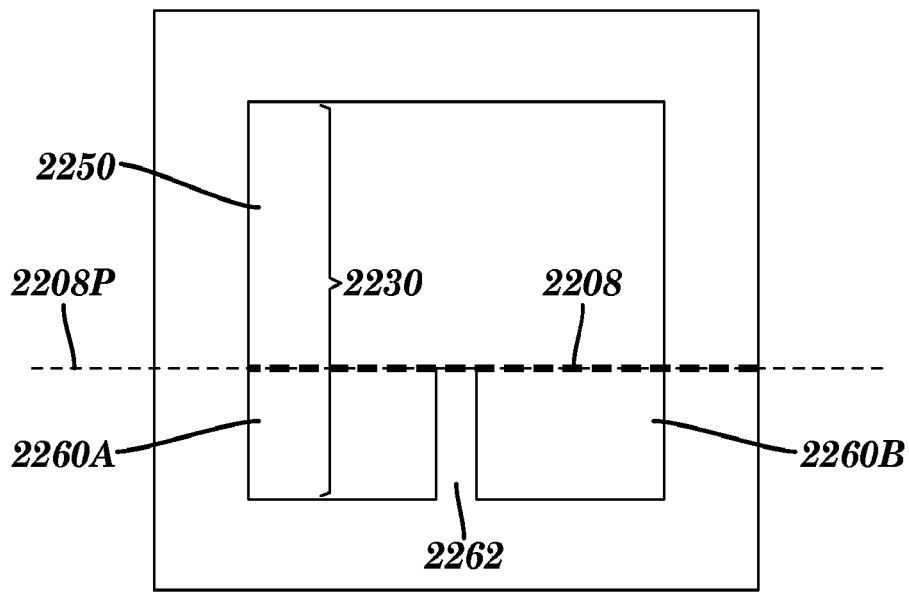
FIGS. 22A and 22B illustrate alternative embodiments of a device described herein.
Figure 22B:
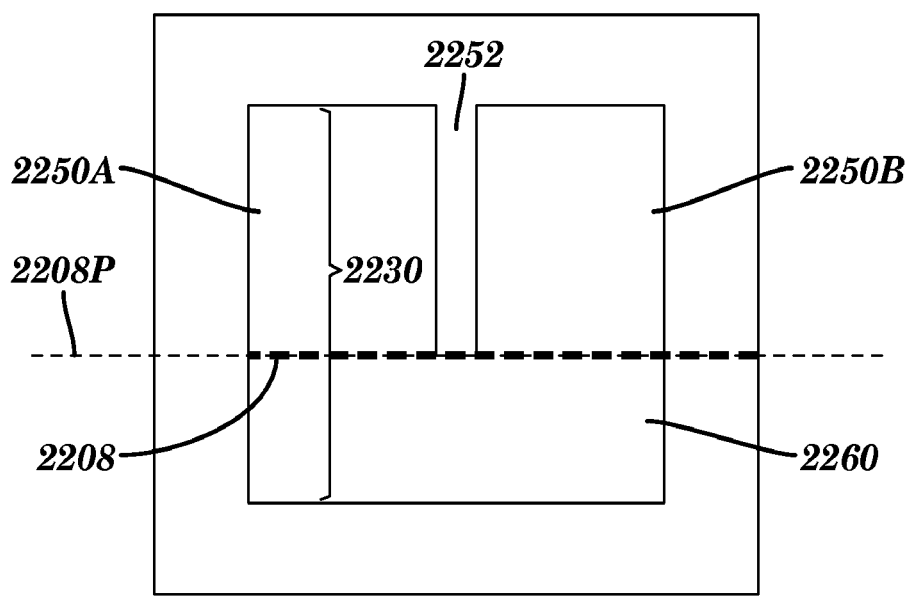

In some embodiments where the top portion of the central channel 230 forms at least two or more mesochannels, e.g., as shown in FIG. 22B, the width of the mesochannels 2250A and 2250B are smaller than the width of the central channel 230. In some embodiments where the bottom portion of the central channel 230 forms at least two or more microchannels, e.g., as shown in FIG. 22A, the width of the microchannels 2260A and 2260B are smaller than the width of the central channel 230. Multiple mesochannels and/or microchannels formed in a central channel are further described in detail below.

In some embodiments, the width of the two channels can be configured to be different, with the centers of the channels aligned or not aligned. In some embodiments, the channel heights, widths, and/or cross sections can vary along the length the devices described herein.

In accordance with some embodiments described herein, the height of at least a length portion of the mesochannel 250A (e.g., the length portion where the cells are desired to grow and form a stratified, pseudostratified or 3-dimensional tissue structure) is substantially greater than the height of the microchannel 250B within the same length portion. For example, the height ratio of the mesochannel to the microchannel is greater than 1:1, including, for example, greater than 1.1:1, 1.5:1, 2:1, 2.5:1, 3:1, 3.5:1, 4:1, 4.5:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1. In some embodiments, the height ratio of the mesochannel to the microchannel can range from 1.1:1 to about 50:1, or from about 2.5:1 to about 50:1, or from 2.5 to about 25:1, or from about 5:1 to about 25:1. In one embodiment, the height ratio of the mesochannel to the microchannel ranges from about 10:1 to about 20:1. The higher mesochannel can offer a reduced stress environment and increased overhead space for growth of cells that require low shear and more space to form a stratified structure and/or a three-dimensional tissue.

In some embodiments, the height of at least a length portion of the mesochannel 250A can be sufficient to accommodate the tallest cell (including any projections from the cell such as cilia) or the thickest cell present on the membrane facing the mesochannel.

Figure 5B:
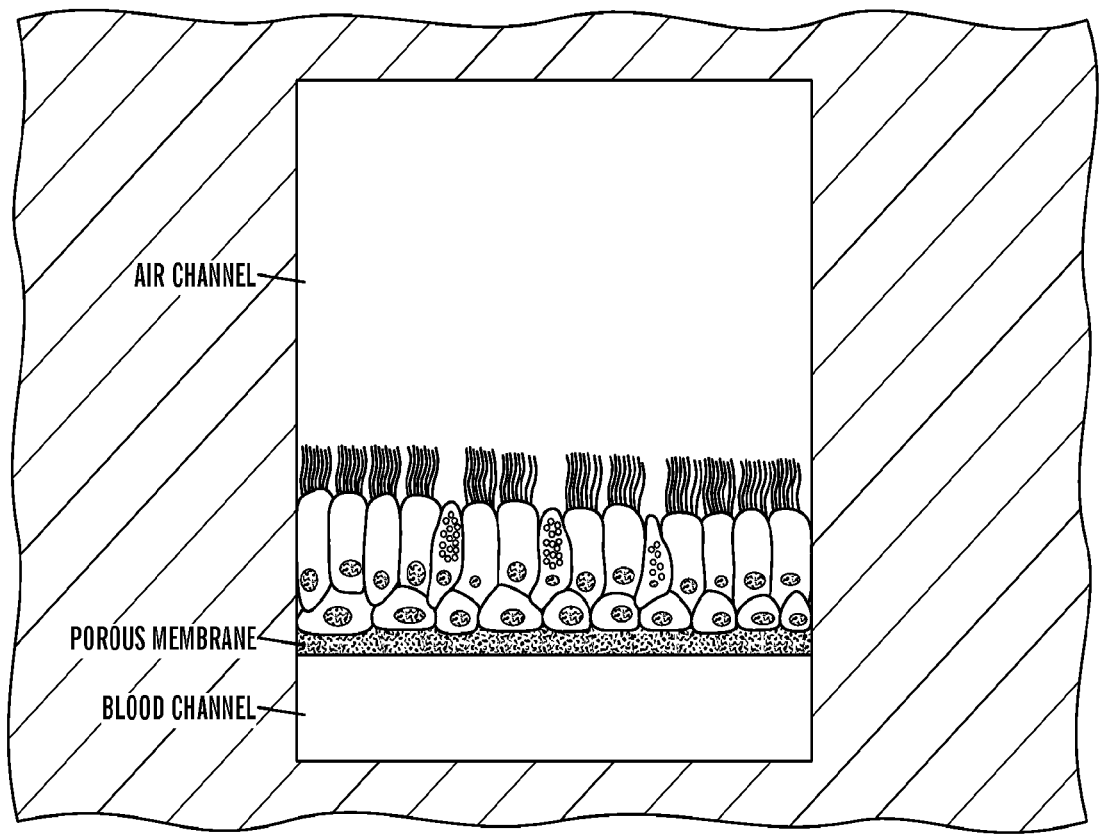
Figure 5C:
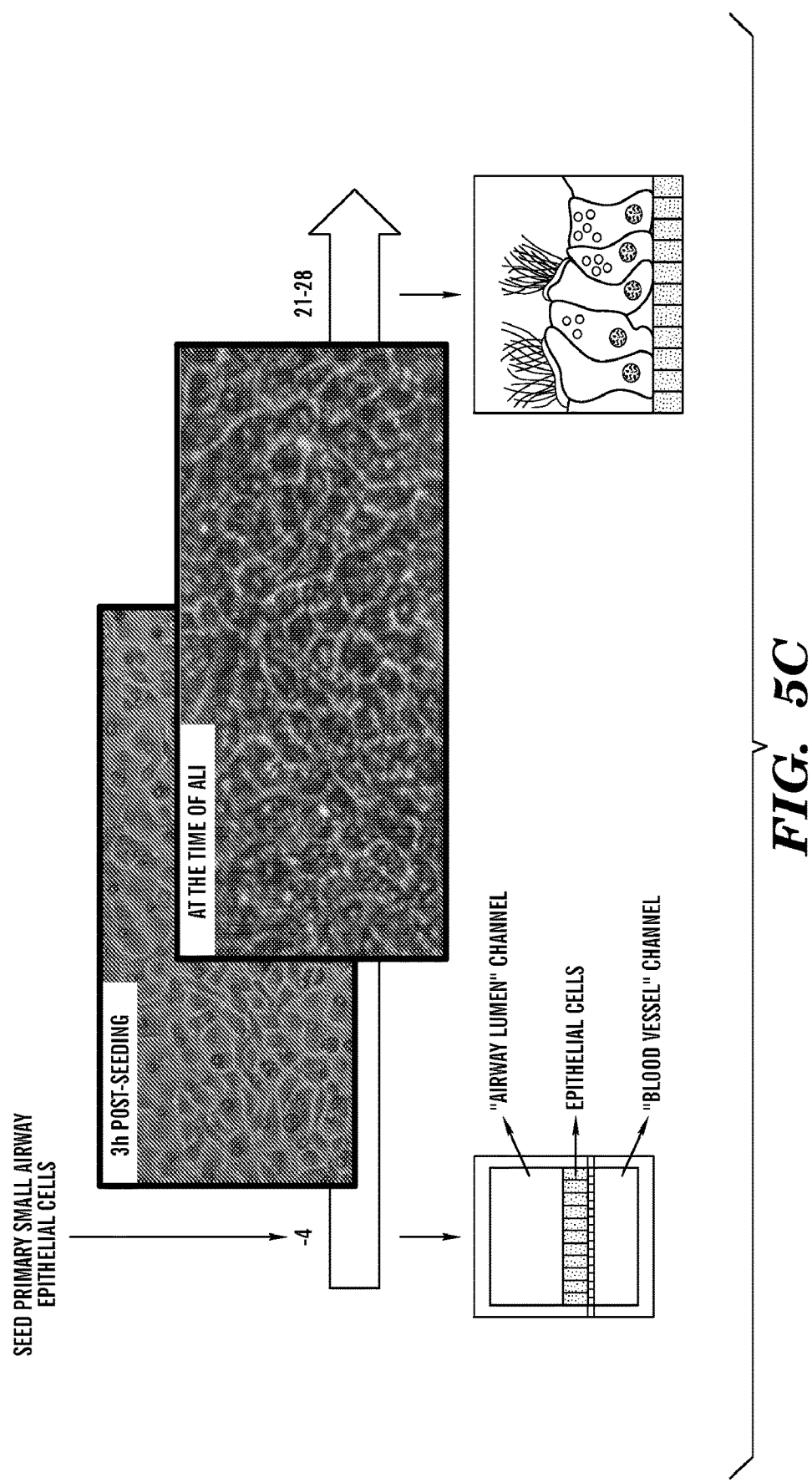

In some embodiments, the height of at least a length portion of the mesochannel 250A can have a dimension sufficient to permit growth of more than one cell layers, e.g., 2 cell layers, 3 cell layers, 4 cell layers, 5 cell layers, 6 cell layers, or more. The cell layers can each be functionally and/or morphologically the same or different. The height of the mesochannel can vary with the thickness of at least a portion of a biological tissue or organ to be modeled. For example, in some embodiments, the height of the mesochannel 250A can have a dimension sufficient to form a stratified structure (a structure comprising cells arranged in layers) of an airway epithelium comprising ciliated cells and mucus-secreting cells, e.g., as shown in FIG. 5B. In some embodiments, the height of the mesochannel 250A can have a dimension sufficient to form a stratified structure of a small airway epithelium. In some embodiments, the mesochannel 250A can have a height dimension configured to permit formation of a skin equivalent to model the skin (e.g., a mammalian or animal skin) as an organ.

In some embodiments, the height of the mesochannel 250A can be configured to provide sufficient overhead space above a stratified/pseudostratified or three-dimensional structure for an air flow such that air shear stress on the cells (e.g., airway or skin epithelial cells) can be maintained within a physiological range (e.g., between 0.01 dynes/cm$^2$ and 1700 dynes/cm$^2$). In one embodiment, the air flow can be maintained as a static flow.

In some embodiments, the height of the mesochannel 250A can have a dimension sufficient for formation of a three-dimensional tissue. For example, the height of the mesochannel 250A can have a dimension sufficient for formation of a three-dimensional gut or intestinal tissue, where the intestinal epithelial cells grow into folds that recapitulate the structure of intestinal villi. In some embodiments, the height of the mesochannel 250A can be configured to provide sufficient overhead space above the three dimensional structure for a liquid flow such that liquid shear stress on the cells (e.g., intestinal epithelial cells) can be maintained within a physiological range (e.g., between 0.01 dynes/cm$^2$ and 1700 dynes/cm$^2$).

In some embodiments, the height of the mesochannel 250A can depend on aspect ratio of the height of the mesochannel 250A to the width of the central channel 230. The aspect ratio of the height of the mesochannel 250A to the width of the central channel 230 can range from about 1:5 to about 50:1 or about 1:10 to about 20:1. In some embodiments, the height of the mesochannel 250A can range from about 100 µm to about 50 mm, about 150 µm to about 25 mm, or about 200 µm to about 10 mm. In some embodiments, the height of the mesochannel 250A can range from about 100 µm to about 5 mm, about 150 µm to about 2.5 mm, or about 200 µm to about 2 mm. In one embodiment, the height of the mesochannel 250A is about 220 µm to about 1 mm. In one embodiment, the height of the mesochannel 250A is about 100 µm to about 5 mm. In one embodiment, for a 1 mm wide channel, the height of the mesochannel can range from about 100 µm to about 20 mm.

The mesochannel can have a uniform height along the length of the mesochannel. Alternatively, the mesochannel can have a varying height along the length of the mesochannel. For example, a length portion of the mesochannel (e.g., where a stratified/pseudo-stratified or three-dimensional tissue structure is desired to be formed therein) can be substantially taller than the same length portion of the microchannel, while the rest of the mesochannel can have a height comparable to or even smaller than the height of the microchannel.

The height of the microchannel 250B can be of any dimension provided that the flow rate and/or shear stress of a medium flowing in the microchannel can be maintained within a physiological range, or does not cause any adverse effect to the cells, and/or there is sufficient space for the cell growth on the surface of the membrane facing the microchannel. For example, in some embodiments, the height of the microchannel 250B can be designed to mimic a blood vessel channel in which blood or cell culture medium flows at a physiological fluid pressure and/or flow rate.

Accordingly, in some embodiments, the height of the microchannel 250B can be substantially smaller than the height of the mesochannel 250A. For example, the height of the microchannel can be about 1% to about 80%, or about 5% to about 70%, or about 10% to about 50%, of the height of the mesochannel. In some embodiments, the height of the microchannel can be no more than 30%, no more than 20%, no more than 10%, of the height of the mesochannel. In some embodiments, the height of the microchannel is no more than 10% of the height of the mesochannel.

In alternative embodiments, the height of the microchannel 250B can be substantially the same as the height of the mesochannel 250A.

In some embodiments, the height of the microchannel 250B can range from about 1 µm to about 5 mm, about 10 µm to about 5 mm, about 25 µm to 2.5 mm, or about 50 µm to about 1 mm. In some embodiments, the height of the microchannel 250B can range from about 25 µm to about 1 mm, about 50 µm to about 750 µm, or about 75 µm to about 500 µm. In one embodiment, the height of the microchannel 250B is about 50 µm to about 150 µm. In one embodiment, the height of the microchannel 250B is about 100 µm to about 160 µm.

In some embodiments, the body of the device can be further adapted to provide mechanical modulation of the membrane within the central channel. Mechanical modulation of the membrane can include any movement of the membrane that is parallel to and/or perpendicular to the force/pressure applied to the membrane, including, but are not limited to, stretching, bending, compressing, vibrating, contracting, waving, or any combinations thereof. By way of example only, FIG. 2D illustrates a sectioned view of the cell culture interface region within the body in accordance with an embodiment where the membrane can be mechanically modulated by a pneumatic mechanism. In this embodiment where the pressure is applied within the device to mechanically modulate the membrane 208, the operating channel(s) 252 can be symmetrically arranged around the membrane 208. For example, the top half of the operating channel(s) 252A are formed in a bottom surface of the top body portion 204 and the bottom half of the operating channel(s) 252B are formed in a top surface of the bottom body portion 206 such that when the two body portions 204 and 206 are mated to each other with a membrane 208 positioned between the mesochannel 250A and the microchannel 250B whereby the side walls 228 and 238 as well as the channel walls 234, 244 form the overall central channel 230 and operating channels 252, the plane 208P along the membrane 208 can bisect the operating channel(s) 252 into the top half and bottom half of the operating channel(s) 252A and 252B.

The width of the operating channels 252 can be of any dimension provided that the aspect ratio of the height to width of the operating channels 252 allows a sufficient mechanical force to be applied to the membrane and/or yields sufficient mechanical strength to withstand application of cyclic pressures. In some embodiments, the width of the operating channels 252 can range from about 100 µm to about 5 mm or from about 200 µm to about 2 mm.

In some embodiments, e.g., as shown in FIG. 2D, the heights of the operating channels 252 can be smaller than the height of the central channel 230. In some embodiments, the heights of the operating channels 252 can be no more than 70% of the height of the central channel 230, including, e.g., no more than 60%, no more than 50%, no more than 40%, no more than 30%, no more than 20% or less, of the height of the central channel 230. In some embodiments, the heights of the operating channels 252 can be about 1.5 times to about 2.5 times the height of the microchannel 250B. In some embodiments, the heights of the operating channels 252 can range from about 20 µm to about 10 mm, about 50 µm to 5 mm, or about 100 µm to about 2 mm. In some embodiments, the height of the operating channels 252 can range from about 50 µm to about 2 mm, about 100 µm to about 1.5 mm, or about 150 µm to about 1000 µm. In one embodiment, the height of the operating channels 252 is about 100 µm to about 300 µm. In one embodiment, the height of the operating channels 252 is about 200 µm to about 800 µm.

In some embodiments, e.g., as shown in FIGS. 24A-24B, the heights of the operating channels 2452 can be greater than the height of the central channel 2430. In some embodiments, the heights of the operating channels 2452 can be greater than the height of the central channel 2430 by at least about 5%, including, e.g., at least about 10%, at least about 20%, at least about 30%, at least about 40%, at least about 50%, at least about 60%, at least about 70%, at least about 80%, at least about 90%, at least about 95%, or more. In some embodiments, the heights of the operating channels 2452 can be greater than the height of the central channel 2430 by at least about 1.1-fold, including, e.g., at least about 1.5-fold, at least about 2-fold, at least about 3-fold, at least about 4-fold, at least about 5-fold, at least about 6-fold or higher. In some embodiments, it can be desirable to have the heights of the operating channels larger than the height of the central channel. Without wishing to be bound by theory, increasing the heights of the operating channels generally provides a larger surface area of the channel wall between the operating channels and the central channel (e.g., 2434 and 2444 as shown in FIGS. 24A-24B), which can in turn allow a larger force acting on the channel wall to flex in response to a pressure differential between the operating channels and the central channel. In some embodiments, a thicker channel wall between the operating channels and the central channel can be used, when a larger force is acted on the channel wall.

In some embodiments, the heights of the operating channels can be substantially same as the height of the central channel.

Using FIGS. 2E and 2F as examples, in some embodiments, the top and bottom portions of the operating channels (252A and 252B) can each have a width dimension (shown as A) between 25 and 5000 microns, or between 200 microns and 2000 microns, although other width dimensions can be used, e.g., depending on the amount of the mechanical force applied to the membrane. While FIGS. 2E and 2F shows a uniform width dimension (shown as B) along at least a portion of the central channel height in the device, the central channel can also have a non-uniform width dimension B along at least a portion of its height in the device.

The channel walls 234, 244 can have any thickness that would permit the channel walls to flex in response to a pressure differential between the operating channels and the central channel 230. In some embodiments, the channel walls 234, 244 can have a thickness range between 5 microns to 500 microns, although other width dimensions can be used depending on the material used for the walls, application in which the device is used. In one embodiment, the channel walls 234, 244 can have a thickness range between 50 microns to 500 microns or between 70 microns and 300 microns.

The membrane 208 is oriented along a plane 208P parallel to the x-y plane within the central channel 230 shown in FIG. 2D. It should be noted that although one membrane 208 is shown in the central channel 230, more than one membrane 208 can be configured within the central channel 230, as discussed in more detail below. In addition to being positioned within the central channel 250, the membrane 208 is sandwiched in place by channel walls 234, 244 during formation of the device.

In some embodiments, the membrane 208 can separate the central channel 250 into two or more distinct central sub-channels 250A and 250B, of which at least one is a mesochannel 250A.

As will be discussed in further detail below, the membrane 208 can be non-porous or can have at least a portion which is sufficiently porous to allow cells and/or molecules to pass therethrough. The membrane 208 can be rigid or flexible. In some embodiments, the membrane 208 is a rigid porous membrane. In other embodiments, the membrane 208 is a flexible porous membrane. At least a portion of the membrane 208 can have elastic or ductile properties which allow the membrane 208 to be manipulated to stretch/retract along one or more planar axe. Thus, in some embodiments, one or more portions of the membrane 208 can be porous and elastic or porous, but inelastic. In some embodiments, the membrane 208 can be non-porous and elastic or non-porous but inelastic.

A pressure differential can be applied within the device to cause relative continuous expansion and contraction of the membrane 208 along the x-y plane. In particular, as stated above, one or more pressure sources can apply pressurized fluid (e.g., air) along the one or more operating channels 252, whereby the pressurized fluid in the operating channels 252 creates a pressure differential on the channel walls 234, 244.

In the embodiments shown in FIG. 2D, the pressurized fluid is a vacuum or suction force that is applied only through the operating channels 252. The difference in pressure caused by the suction force against the channel walls 234, 244 causes the walls 234, 244 to bend or bulge outward toward the sides of the device 228, 238 (see FIGS. 2E-2F). Considering that the membrane 208 is mounted to and sandwiched between the channel walls 234, 244, the relative movement of the walls 234, 244 thereby causes the opposing ends of the membrane to move along with the walls to stretch along the membrane's plane. This stretching mimics the mechanical forces experienced by a tissue-tissue interface, for example, in the airway or bronchus during breathing, and thus provides the relevant regulation for cellular self assembly into tissue structures and cell behavior.

When the negative pressure is no longer applied (and/or positive pressure is applied to the operating channels), the pressure differential between the operating channels 252 and the central channel 230 decreases and the channel walls 234, 244 retract toward their neutral position or their original position prior to the application of the negative pressure. During operation, the negative pressure is alternately applied in timed intervals to the device 200 to cause continuous expansion and contraction of the membrane 208 along its plane, thereby simulating within a controlled in vitro environment a physiological strain that is substantially the same as the stain produced by motion associated with operation of the tissue-tissue interface of the living organs, e.g., but not limited to breathing, peristalsis, or heart beating. As will be discussed, this mimicked organ operation within the controlled environment allows development of different corresponding organ-associated disease models. For example, the device described herein can be used to simulate breathing motion in an airway or bronchus and thus allows development of disease models associated with breathing and airway constriction, such as asthma, and chronic obstructive pulmonary disease (COPD). In some embodiments, the device can be used to simulate other diseases models such as pulmonary hypertension, radiation induced injury, cystic fibrosis or airborne diseases such as viral or bacterial infection, e.g., by culturing appropriate types of cells on at least one or both surfaces of the membrane 208 and inducing disease phenotypes in the cells, e.g., by using physical, chemical and/or biological agents. Cell behavior can be monitored within the device, as well as passage of molecules, chemicals, particulates and cells with respect to the membrane and the associated first and second microchannels 250A, 250B.

It should be noted that the term pressure differential in the present specification relates to a difference of pressure on opposing sides of a particular wall between the central channel and the outer operating channel. In some embodiments, the pressure differential can be created in a number of ways to achieve the goal of expansion and/or contraction of the membrane 208. As stated above, a negative pressure (i.e. suction or vacuum) can be applied to one or more of the operating channels 252. Alternatively, the membrane 208 can be pre-loaded or pre-stressed to be in a stretched state by default such that the channel walls 234, 244 are already in the bent configuration. In this embodiment, positive pressure applied to the operating channel 252 will create the pressure differential which causes the channel walls 234, 244 to move inward toward the central channel to contract the membrane 208.

In another embodiment, a combination of positive and negative pressure is applied to one or more operating channels 252 to cause movement of the membrane 208 along its plane in the central channel. In any of the above embodiments, it is desired that the pressure of the fluid in the one or more operating channels 252 be such that a pressure differential is in fact created with respect to the pressure of the fluid(s) in one or more of the central channel(s) 250A, 250B to cause relative expansion/contraction of the membrane 208. For example, fluid having a certain pressure can be applied within the top central channel 250A, whereby fluid in the bottom central channel 250B can have a different pressure. In this example, pressure applied to the one or more operating channels 252 must take into account the pressure of the fluid in either or both of the central channels 250A, 250B to ensure desired expansion/contraction of the membrane 208.

It is possible, in an embodiment, for a pressure differential to exist between the top and bottom microchannels 250A, 250B to cause at least a portion of the membrane 208 to stretch and/or retract vertically in the z-direction in addition to expansion/contraction along the x-y plane.

In an embodiment, the expansion and retraction of the membrane 208 in turn applies mechanical forces to the adherent cells and ECM that mimic physiological mechanical cues that can influence transport of chemicals, molecules particulates, and/or fluids or gas across the tissue-tissue interface, and alter cell physiology. It should be noted that although mechanical modulation of the membrane created by pressure differentials between the operating channels 252 and the central channel 230 is shown in FIG. 2D, in other embodiments, mechanical means, such as micromotors or actuators, or any means that can cause the movement of the membrane, including use of one or more magnetic forces, can be employed to assist or substitute for the pressure differential to provide mechanical modulation of the membrane within the central channel, e.g., to modulate cell physiology. The membrane can be mechanically modulated to move in any direction, e.g., within the plane 208P and/or transverse to the plane 208P. In some embodiments, the membrane can be mechanically modulated to move along a single axis within or transverse to the plane 208P. In alternative embodiments, the membrane can be mechanically modulated to move along at least two predefined axes, e.g., the axes that define the plane 208P. Other example means of mechanical modulation of the membrane, e.g., as described in the U.S. Provisional Application No. 61/919, 181 filed Dec. 20, 2013 and the corresponding PCT International Application No. PCT/US2014/071611, entitled "Organomimetic devices and methods of use and manufacturing thereof" filed concurrently with the current application on Dec. 19, 2014, the content of which is incorporated herein by reference, can be adopted in the devices described herein.

In some embodiments, one or more of the channels can be configured to change direction along the lengths of the channels, for example, using curved or sharp bends. This can provide a means to enable the direction of membrane modulation to vary along the length of the channel.

While FIGS. 2A-2F illustrate devices 200 comprising operating chambers 252 (for mechanical modulation of the membrane 208), the device 200 does not require the operating channels 252 where the mechanical modulation of the membrane is not mandatory, e.g., where respiration through an airway is to be simulated. For example, as shown in FIG. 2G, the device 201 comprises a mesochannel 250A and a microchannel 250B separated by a membrane 208, without operating chambers on the sides. In this embodiment, since the membrane 208 does not need to be mechanically modulated, the membrane can be rigid or at least partially flexible. In one embodiment, the membrane 208 is rigid.

By way of example only, some embodiments of the devices described herein, e.g., as shown in FIG. 2G, can be used to model at least a portion of a human airway (e.g., a human small airway or large airway). In order to mimic the tissue structure of an airway, anatomically-relevant dimensions should be used. As human lung small airway is anatomically defined as an airway with a radius of less than or equal to 1 mm, in one embodiment, the device to mimic at least a portion of a human small airway (small airway-on-a-chip) is designed such that the mesochannel (the "airway lumen" channel) has a height corresponding to the radius of small airway in vivo (e.g., less than or equal to about 1 mm). In one embodiment, the small airway-on-a-chip has a mesochannel with a height of about 1 mm.

It should be noted that although the central and operating channels 230, 252 are shown to have substantially square or rectangular cross sections, other cross-sectional shapes such as circular, oval, and hexagonal, can also be used. In some embodiments, the central channel 230 can have a polygonal cross-section (e.g., U-shaped, polygonal-shaped, or comb-shaped). By way of example only, as shown in FIGS. 22A-22B, the central channel 2230 can have a substantially U-shaped cross-section. The U-shaped cross-section can be formed, for example by having a partition wall 2252 or 2262 disposed in a wider mesochannel 2250 (2250A, 2250B) and microchannel 2260 (2260A, 2260B), respectively, wherein the partition wall is disposed traverse to the plane 2208P. Thus, the wider mesochannel 2250 can be divided into two or more smaller mesochannels (2250A, 2250B); and/or the wider microchannel 2260 can be divided into two or more smaller microchannels (2260A, 2260B). FIG. 22A illustrates a device 2200A comprising at least one mesochannel 2250 separated from at least two microchannels 2260A and 2260B by a membrane 2208. FIG. 22B illustrates a device 2200B comprising at least two mesochannels 2250A and 2250B separated from at least one microchannel 2260 by a membrane 2208. Accordingly, in some embodiments, at least one or more (e.g., 1, 2, 3, 4, or more) partition walls can be disposed in the wider mesochannel and/or the microchannel to form multiple sub-channels therein (i.e., to form smaller mesochannels and/or microchannels), wherein the partition walls are disposed transverse to the plane 2208P. The partitions walls can have substantially the same height as the mesochannel or microchannel, depending on where they are disposed. The partition wall can have any thickness as long as they are structurally stable. The partition walls can form a fluidic seal with the membrane 2208 such that there is no fluid communication between the sub-channels (e.g., 2250A and 2250B; 2260A and 2260B). In these embodiments, different cell types cultured in separate sub-channels on one surface of the membrane can interact with the same cell type(s) on the other surface of the membrane. The same or different fluids can be introduced into individual sub-channels.

In these embodiments where at least one partition wall is present, the width of the sub-channels (e.g., 2250A and 2250B; or 2260A and 2260B) is smaller than the width of the central channel as described earlier. In some embodiments, the width of the sub-channels can be in a range between 50 microns and 10 mm, or between 100 microns and 5 mm, or between 200 microns and 1500 microns, or between 400 microns and 1000 microns, or between 50 and 2000 microns. Each sub-channel can have the same or different width.

In some embodiments, the device 200 can have more or less than two operating channels 252 and/or more or less than two central channels 250A, 250B in accordance with an embodiment.

In accordance with some embodiments of the invention, the device can be placed in or secured to a cartridge. In accordance with some embodiments of the invention, the device can be integrated into a cartridge and form a monolithic part. Some examples of a cartridge are described in U.S. Application No. 61/856,876 filed Jul. 22, 2013; U.S. Provisional Application No. 61/696,997, filed on Sep. 5, 2012 and No. 61/735,215, filed on Dec. 10, 2012, contents of each application is incorporated herein by reference in its entirety. The cartridge can be placed into and removed from a cartridge holder that can establish fluidic connections upon or after placement and optionally seal the fluidic connections upon removal. In accordance with some embodiments of the invention, the cartridge can be incorporated or integrated with at least one sensor, which can be placed in direct or indirect contact with a fluid flowing through a specific portion of the cartridge during operation. In accordance with some embodiments of the invention, the cartridge can be incorporated or integrated with at least one electric or electronic circuit, for example, in the form of a printed circuit board or flexible circuit. In accordance with some embodiments of the invention, the cartridge can comprise a gasketing embossment to provide fluidic routing.

In accordance with some embodiments of the invention, the cartridge and/or the device described herein can comprise a barcode. The barcode can be unique to types and/or status of the cells present on the membrane. Thus, the barcode can be used as an identifier of each device adapted to mimic function of at least a portion of a specific tissue and/or a specific tissue-specific condition. Prior to operation, the barcode of the cartridge can be read by an instrument so that the cartridge can be placed and/or aligned in a cartridge holder for proper fluidic connections and/or proper association of the data obtained during operation of each device. In accordance with some embodiments of the invention, data obtained from each device include, but are not limited to, cell response, immune cell recruitment, intracellular protein expression, gene expression, cytokine/chemokine expression, cell morphology, functional data such as effectiveness of an endothelium as a barrier, concentration change of an agent that is introduced into the device, or any combinations thereof.

In accordance with some embodiments of the invention, the device can be connected to the cartridge by an interconnect adapter that connects some or all of the inlet and outlet ports of the device to microfluidic channels or ports on the cartridge. Some examples interconnect adapters are disclosed in U.S. Provisional Application No. 61/839,702, filed on Jun. 26, 2013, and the International Patent Application No. PCT/US2014/044417 filed Jun. 26, 2014, the contents of each of which are hereby incorporated by reference in their entirety. The interconnect adapter can include one or more nozzles having fluidic channels that can be received by ports of the device described herein. The interconnect adapter can also include nozzles having fluidic channels that can be received by ports of the cartridge.

In accordance with some embodiments described herein, the interconnect adaptor can comprise a septum interconnector that can permit the ports of the device to establish transient fluidic connection during operation, and provide a sealing of the fluidic connections when not in use, thus minimizing contamination of the cells and the device. Some examples of a septum interconnector are described in U.S. Provisional Application No. 61/810,944 filed Apr. 11, 2013, the content of which is incorporated herein by reference in its entirety.

Membrane:

The membrane can be porous (e.g., permeable or selectively permeable), non-porous (e.g., non-permeable), rigid, flexible, elastic or any combinations thereof. Accordingly, the membrane 208 can have a porosity of about 0% to about 99%. As used herein, the term "porosity" is a measure of total void space (e.g., through-holes, openings, interstitial spaces, and/or hollow conduits) in a material, and is a fraction of volume of total voids over the total volume, as a percentage between 0 and 100% (or between 0 and 1). A membrane with substantially zero porosity is non-porous or non-permeable.

As used interchangeably herein, the terms "non-porous" and "non-permeable" refer to a material that does not allow any molecule or substance to pass through.

In some embodiments, the membrane can be porous and thus allow molecules, cells, particulates, chemicals and/or media to migrate or transfer between the mesochannel 250A and the microchannel 250B via the membrane 208 from the mesochannel 250A to the microchannel 250B or vice versa.

As used herein, the term "porous" generally refers to a material that is permeable or selectively permeable. The term "permeable" as used herein means a material that permits passage of a fluid (e.g., liquid or gas), a molecule, a whole living cell and/or at least a portion of a whole living cell, e.g., for formation of cell-cell contacts. The term "selectively permeable" as used herein refers to a material that permits passage of one or more target group or species, but act as a barrier to non-target groups or species. For example, a selectively-permeable membrane can allow passage of a fluid (e.g., liquid and/or gas), nutrients, wastes, cytokines, and/or chemokines from one side of the membrane to another side of the membrane, but does not allow whole living cells to pass therethrough. In some embodiments, a selectively-permeable membrane can allow certain cell types to pass therethrough but not other cell types.

The permeability of the membrane to individual matter/species can be determined based on a number of factors, including, e.g., material property of the membrane (e.g., pore size, and/or porosity), interaction and/or affinity between the membrane material and individual species/ matter, individual species size, concentration gradient of individual species between both sides of the membrane, elasticity of individual species, and/or any combinations thereof.

A porous membrane can have through-holes or pore apertures extending vertically and/or laterally between two surfaces of the membrane (FIG. 2B), and/or a connected network of pores or void spaces (which can, for example, be openings, interstitial spaces or hollow conduits) throughout its volume. The porous nature of the membrane can be contributed by an inherent physical property of the selected membrane material, and/or introduction of conduits, apertures and/or holes into the membrane material.

In some embodiments, a membrane can be a porous scaffold or a mesh. In some embodiments, the porous scaffold or mesh can be made from at least one extracellular matrix polymer (e.g., but not limited to collagen, alginate, gelatin, fibrin, laminin, hydroxyapatite, hyaluronic acid, fibroin, and/or chitosan), and/or a biopolymer or biocompatible material (e.g., but not limited to, polydimethylsiloxane (PDMS), polyurethane, styrene-ethylene-butylene-styrene (SEBS), poly(hydroxyethylmethacrylate) (pHEMA), polyethylene glycol, polyvinyl alcohol and/or any biocompatible material described herein for fabrication of the device body) by any methods known in the art, including, e.g., but not limited to, electrospinning, cryogelation, evaporative casting, and/or 3D printing. See, e.g., Sun et al. (2012) "Direct-Write Assembly of 3D Silk/ Hydroxyapatite Scaffolds for Bone Co-Cultures." Advanced Healthcare Materials, no. 1: 729-735; Shepherd et al. (2011) "3D Microperiodic Hydrogel Scaffolds for Robust Neuronal Cultures." Advanced Functional Materials 21: 47-54; and Barry III et al. (2009) "Direct-Write Assembly of 3D Hydrogel Scaffolds for Guided Cell Growth." Advanced Materials 21: 1-4, for examples of a 3D biopolymer scaffold or mesh that can be used as a membrane in the device described herein.

In some embodiments, a membrane can comprise an elastomeric portion fabricated from a styrenic block copolymer-comprising composition, e.g., as described in the U.S. Provisional Application No. 61/919,181 filed Dec. 20, 2013 and the corresponding PCT International Application No. PCT/US2014/071611, entitled "Organomimetic devices and methods of use and manufacturing thereof" filed concurrently with the current application on Dec. 19, 2014, can be adopted in the devices described herein, the contents of each of which are incorporated herein by reference. In some embodiments, the styrenic block copolymer-comprising composition can comprise SEBS and polypropylene.

In some embodiments, a membrane can be a hydrogel or a gel comprising an extracellular matrix polymer, and/or a biopolymer or biocompatible material. In some embodiments, the hydrogel or gel can be embedded with a conduit network, e.g., to promote fluid and/or molecule transport. See, e.g., Wu et al. (2011) "Omnidirectional Printing of 3D Microvascular Networks." Advanced Materials 23: H178-H183; and Wu et al. (2010) "Direct-write assembly of biomimetic microvascular networks for efficient fluid transport." Soft Matter 6: 739-742, for example methods of introducing a conduit network into a gel material.

In some embodiments, a porous membrane can be a solid biocompatible material or polymer that is inherently permeable to at least one matter/species (e.g., gas molecules) and/or permits formation of cell-cell contacts. In some embodiments, through-holes or apertures can be introduced into the solid biocompatible material or polymer, e.g., to enhance fluid/molecule transport and/or cell migration. In one embodiment, through-holes or apertures can be cut or etched through the solid biocompatible material such that the through-holes or apertures extend vertically and/or laterally between the two surfaces of the membrane 208A and 208B. It should also be noted that the pores can additionally or alternatively incorporate slits or other shaped apertures along at least a portion of the membrane 208 which allow cells, particulates, chemicals and/or fluids to pass through the membrane 208 from one section of the central channel to the other.

The pores of the membrane (including pore apertures extending through the membrane 208 from the top 208A to bottom 208B surfaces thereof and/or a connected network of void space within the membrane 208) can have a cross-section of any size and/or shape. For example, the pores can have a pentagonal, circular, hexagonal, square, elliptical, oval, diamond, and/or triangular shape.

The cross-section of the pores can have any width dimension provided that they permit desired molecules and/or cells to pass through the membrane. In some embodiments, the pore size can be selected to permit passage of cells (e.g., immune cells and/or cancer cells) from one side of the membrane to the other. In some embodiments, the pore size can be selected to permit passage of nutrient molecules. When cells are cultured on the membrane at an air-liquid interface, the pore size of the membrane should be big enough to provide the cells sufficient access to nutrients present in the "liquid" channel (or the microchannel). In some embodiments, the width dimension of the pores can be selected to permit molecules, particulates and/or fluids to pass through the membrane 208 but prevent cells from passing through the membrane 208. In some embodiments, the width dimension of the pores can be selected to permit cells, molecules, particulates and/or fluids to pass through the membrane 208. Thus, the width dimension of the pores can be selected, in part, based on the sizes of the cells, molecules, and/or particulates of interest. In some embodiments, the width dimension of the pores (e.g., diameter of circular pores) can be in the range of 0.01 microns and 20 microns, or in one embodiment, approximately 0.1-10 microns, or approximately 7-10 microns. However, in some embodiments, the width dimension can be outside of the range provided above. In some embodiments, the membrane 208 has pores or apertures larger than traditional molecular/ chemical filtration devices, which allow cells as well as molecules to migrate across the membrane 208 from one channel section (e.g. 250A) to the other channel section (e.g. 250B) or vice versa. In one embodiment, the width dimension of the pores can be selected such that a selected type of cells, but not all different types of the cells present on the membrane, can migrate through the pores.

In some embodiments where the porous membrane comprise through-holes or pore apertures, the pore apertures can be randomly or uniformly distributed (e.g., in an array or in a specific pattern, or in a gradient of pore sizes) on the membrane. In one embodiment, the pore apertures are hexagonally arranged on the membrane. In one embodiment, at least some or all of the pore apertures are equidistant to each neighboring pore aperture. In this embodiment, at least some or all of the pore apertures can have a center-to-center pore spacing of about 1 µm to about 1000 µm, or about 10 µm to about 500 µm, or about 20 µm to about 100 µm. In one embodiment, at least some or all of the pore aperture can have a center-to-center pore spacing of about 20 µm to about 50 µm. The spacing between pores can vary, e.g., with cell sizes. Without wishing to be bound by theory, larger pore spacing can be used for bigger cells, e.g., epithelial cells, and similarly, smaller pore spacing can be used for smaller cells.

In an embodiment, the porous membrane 208 can be designed or surface patterned to include micro and/or nanoscopic patterns therein such as grooves and ridges, whereby any parameter or characteristic of the patterns can be designed to desired sizes, shapes, thicknesses, filling materials, and the like.

The surface area of the membrane exposed to the mesochannel 250A and the microchannel 250B can vary, e.g., depending on the physiological ratio(s) of the surface area to the volume of an organ or a tissue to be modeled, volume of the mesochannel and/or microchannel, cell analysis and/or detection methods, and any combinations thereof. A proper ratio(s) of the surface area of the membrane exposed to the mesochannel and/or microchannel to the volume of the mesochannel and/or microchannel can ensure that the device can function more like an in vivo organ or tissue, which can in turn allow for in vitro results to be extrapolated to an in vivo system. In some embodiments, the surface area of the membrane exposed to the mesochannel 250A and the microchannel 250B can be configured to satisfy the physiological ratio(s) of the surface area to the volume of an organ or tissue to be modeled. In some embodiments, the surface area of the membrane can be configured to provide a sufficient space for cell culture, e.g., such that a sufficient amount of cellular materials (e.g., protein, RNA, secreted cytokines and/or chemokines) can be collected for analysis, e.g., using quantitative PCR, ELISA, sequencing and/or mass spectroscopy. In some embodiments, the surface area of the membrane can be configured to provide a sufficient space for examination and/or monitoring of cell behavior, e.g., but not limited to, immune cell recruitment and/or extravasation.

The membrane 208 can have any thickness provided that the selected thickness does not significantly affect cell behavior and/or response. For example, in some embodiments, the thickness of the membrane can be selected such that it does not significantly slow down or inhibit transmigration of cells (e.g., immune cells and/or cancer cells) from one side of the membrane to the other; and/or it does not affect access of cells growing in the "airway lumen" channel" to nutrients in the "blood vessel" channel. In some embodiments, the thickness of the membrane 208 can range between 70 nanometers and 100 microns, or between 1 microns and 100 microns, or between 10 and 100 microns. In one embodiment, the thickness of the membrane 208 can range between 10 microns and 50 microns. While the membrane 208 generally have a uniform thickness across the entire length or width, in some embodiments, the membrane 208 can be designed to include regions which have lesser or greater thicknesses than other regions in the membrane 208. The decreased thickness area(s) 209 can run along the entire length or width of the membrane 208 or can alternatively be located at only certain locations of the membrane 208. The decreased thickness area can be present along the bottom surface of the membrane 208 (i.e. facing microchannel 250B), or additionally/alternatively be on the opposing surface of the membrane 208 (i.e. facing microchannel 250A). It should also be noted that at least portions of the membrane 208 can have one or more larger thickness areas relative to the rest of the membrane, and capable of having the same alternatives as the decreased thickness areas described above.

The membrane 208 can be rigid or flexible. In some embodiments, the membrane can be made of a rigid material, e.g., but not limited to polycarbonate. In some embodiments, the membrane can be made of flexible material, e.g., a polydimethylsiloxane (PDMS) or any other polymeric compound or material. For instance, the membrane 208 can be made of polyimide, polyester, polycarbonate, cyclicolefin copolymer, polymethylmethacrylate, nylon, polyisoprene, polybutadiene, polychlorophene, polyisobutylene, poly(styrene-butadiene-styrene), nitriles, the polyurethanes and the polysilicones. GE RTV 615, a vinyl-silane crosslinked (type) silicone elastomer (family) can be used. Polydimethysiloxane (PDMS) membranes are available HT-6135 and HT-6240 membranes from Bisco Silicons (Elk Grove, Ill.) and are useful in selected applications. The choice of materials typically depends upon the particular material properties (e.g., solvent resistance, stiffness, fluid permeability, and/or temperature stability) required for the application being conducted. Additional elastomeric materials that can be used in the manufacture of the components of the microfluidic devices described in Unger et al. (2000 Science 288:113-116). Some elastomers of the present devices are used as diaphragms and in addition to their stretch and relax properties, are also selected for their porosity, permeability, chemical resistance, and their wetting and passivating characteristics. Other elastomers are selected for their thermal conductivity. Micronics Parker Chomerics Thermagap material 61-02-0404-F574 (0.020" thick) is a soft elastomer (<5Shore A) needing only a pressure of 5 to 10 psi to provide a thermal conductivity of 1.6 W/m-° K. Deformable films, lacking elasticity, can also be used in the microfluidic device. One can also use silk, ECM gels with or without crosslinking as other such suitable materials to make the devices and membranes as described herein.

The device 200 described herein can be used for various applications ranging from studying different cell processes, e.g., but not limited to, ciliary clearance of particulates, epithelial differentiation and cytokine production, inflammatory response to developing relevant disease models, e.g., but not limited to, asthma, COPD, pulmonary hypertension, radiation induced injury, cystic fibrosis, and airborne diseases such as viral infection or bacterial infection. The device 200 or 201 can be used with or without underlying endothelium, different immune cell types or white blood cell types, smooth muscle cells, fibroblasts, etc. For example, in one application, the inventors have for the first time demonstrated differentiation of human primary airway epithelial cells in a microfluidic platform using one embodiment of the device described herein, e.g., as shown in FIG. 2D or FIG. 2G.

In one embodiment, the membrane 208 can be subjected to physiological mechanical strain generated by cyclic stretching of the membrane 208 and/or the flow of biological fluids (e.g. air, mucus, blood, culture medium) in either one or both of the mesochannel and microchannel to recapitulate the native microenvironment of the airway and optional underlying capillaries. In an embodiment, the culture conditions of cells upon the membrane 208 can be optimized under extracellular matrix (ECM) coating, media perfusion, or cyclic mechanical strain to maintain morphological and functional characteristics of the co-cultured cells and to permit their direct cellular interaction across the membrane 208. The device 200 would thus permit long-term cell culture and optional dynamic mechanical stretching of adjacent monolayers of airway epithelial or endothelial cells grown on the membrane at the same time.

The cells on the membrane 208 can display at least one characteristic corresponding to a pre-determined physiological endpoint. As used herein, the term "physiological endpoint" refers to a pre-determined state of cells desired to be reach at a certain time point. The cells can be maintained at the same physiological endpoint in the devices over time, or they can reach a different physiological endpoint in the devices at a later time point. Examples of the pre-determined physiological endpoint can include, but are not limited to, a mature state, a differentiated state, a precursor state, a stratified state, a pseudo-stratified state, a confluency state, an inflamed state, an infected state, a stimulated state, an activated state, an inhibitory state, a normal healthy state, a disease-specific state, a pre-disease state, a distressed state, a growth state, a migratory state, a three-dimensional state, or any combinations thereof.

As used herein, the term "precursor state" refers to a cell having a capability to differentiate into a mature cell. Thus, a precursor state refers to a cell which is partially or fully undifferentiated. In some embodiments, a cell at a precursor state can include a partially-undifferentiated cell that is capable of de-differentiating to a more primitive state. In some embodiments, the term "precursor state" can refer to a progenitor cell or a stem cell.

As used herein, the term "mature state" refers to a fully differentiated cell of a specific tissue. A mature cell is neither a fetal cell nor an embryonic cell, and is not of the gamete lineage.

As used herein, the term "differentiated state" refers to a cell that is partially or fully differentiated to a tissue-specific cell. A fully-differentiated cell can be considered as a cell in a mature state as defined herein. In some embodiments, the differentiated cells can form a stratified structure. In some embodiments, the differentiated cells can form a 3-D structure.

As used herein, the term "stratified state" refers to cells substantially arranged in more than one layer, e.g., 2 layers, 3 layers, 4 layers, or more.

As used herein, the term "pseudo-stratified state" refers to cells present in a single layer, but when they are visualized by immunostaining they appear as if they form multiple layers. For example, a pseudostratified epithelium is a type of epithelium that, though comprising only a single layer of cells, has its cell nuclei positioned at different levels, thus creating an illusion of cellular stratification.

As used herein, the term "confluency state" refers to a state where complete or almost complete (at least approximately 50-60% coverage) coverage of a surface area by the cells (e.g., available membrane surface area allowed for cell proliferation).

As used herein, the term "inflamed state" refers to cells showing at least one phenotype associated with inflammation. Exemplary phenotypes associated with inflammation include, but are not limited to, attachment and recruitment of immune cells (e.g., but not limited to neutrophils, monocytes, lymphocytes, dendritic cells and immature macrophages), presence or increased expression of inflammation-associated secreted cytokines/chemokines and/or intracellular molecules, decreased number of ciliated cells, abnormal cilia morphology, increased proportion of goblet cells, increased mucus secretion, abnormal cilia beating frequency, and any combinations thereof.

As used herein, the term "infected state" refers to cells showing at least one phenotype associated with microbial infection, e.g., but not limited to, viral infection, bacterial infection, fungus infection, parasitic infection, and/or any combinations thereof. Exemplary phenotypes associated with microbial infection, include, but are not limited to, presence of microbial proteins (e.g., viral/bacterial proteins) in an infected cell, damage to an infected cell's epithelium, elevated levels of cytokines/chemokines such as CXCL10 or IL8 secreted by an infected cell, presence of a cellular antimicrobial protein (e.g., antiviral protein such as MX proteins), microbial replication in effluents from the mesochannel/microchannel, and any combinations thereof.

As used herein, the term "activated state" refers to cells having at least one cellular process (e.g., but not limited to, migration potential, cell proliferation, protein synthesis and/or cytokine secretion) in an active state. The cellular process can be effected, for example, by a change in at least one gene expression and/or phosphorylation/dephosphorylation of at least one protein.

As used herein, the term "inhibitory state" refers to cells having at least one cellular process (e.g., but not limited to, migration potential, cell proliferation, protein synthesis and/or cytokine secretion) in an inhibitory state. The cellular process can be effected, for example, by a change in at least one gene expression and/or phosphorylation/dephosphorylation of at least one protein.

As used herein, the term "stimulated state" refers to a state of cells that are responsive to a condition-inducing agent exposed to them. As used herein, the term "condition-inducing agent" refers to any agent that can cause a cell to display a phenotype that is deviated from a basal state (without exposure to the condition-inducing agent). The condition-inducing agent can provoke a beneficial or adverse effect such as cytotoxic effect on the cells. In some embodiments Examples of a condition-inducing agent can include, but are not limited to, environmental agents such as radiation (e.g., gamma radiation) and mechanical stress (e.g., fluid shear stress); proteins, peptides, nucleic acids, antigens, cytokines, growth factors, toxins, cells (including prokaryotic and eukaryotic cells such as virus, bacteria, fungus, parasites, and mammalian cells), particulates (e.g., smoke particles or asbestos), particles (e.g., nanoparticles or microparticles, magnetic particles), small molecules, biologics, and any combinations thereof. Thus, a stimulated state can encompass a mature state, a differentiated state, a precursor state, a stratified state, a pseudo-stratified state, an inflamed state, an infected state, an activated state, a disease-specific state, and any combinations thereof.

As used herein, the term "normal healthy state" refers to a state without any symptoms of any diseases or disorders, or not identified with any diseases or disorders, or not on any physical, chemical and/or biological treatment, or a state that is identified as healthy by skilled practitioners based on microscopic examinations.

As used herein, the term "disease-specific state" refers to a state of cells that recapitulates at least one characteristic associated with a disease, disorder or an injury, or different stages thereof. In some embodiments, the term "disease-specific state" can refer to a specific stage or grade of a disease, disorder or an injury. Examples of diseases, disorders, or injuries can be related to any organ or tissue, e.g., but not limited to, lung, brain, nerve network, blood-brain-barrier, vascular, kidney, liver, heart, spleen, pancreas, ovary, testis, prostate, skin, eye, ear, skeletal muscle, colon, intestine, and esophagus. In some embodiments, the disease-specific state can be associated with a lung disease, e.g., but not limited to, asthma, chronic obstructive pulmonary disease (COPD), pulmonary hypertension, radiation induced injury, cystic fibrosis, or any combinations thereof. In some embodiments, the disease-specific state can be associated with an intestinal disease, e.g., but not limited to, inflammatory bowel disease, Crohn's disease, ulcerative colitis, celiac disease, angiodysplasia, appendicitis, bowel twist, chronic functional abdominal pain, coeliac disease, colorectal cancer, diverticular disease, endometriosis, enteroviruses, gastroenteritis, Hirschsprung's disease, ileitis, irritable bowel syndrome, polyp, pseudomembranous colitis, or any combinations thereof. In some embodiments, the disease-specific state can include a specific stage of a cancer.

The cell in a disease-specific state can be obtained either from a biopsy of a patient carrying the disease, disorder or an injury, or by inducing a normal healthy cell with a condition-inducing agent (e.g., an environmental agent such as radiation; a chemical or biological agent, e.g., but not limited to, cytokines described herein and/or pathogens) that is known to induce the cell to acquire at least one characteristic associated with the disease, disorder, or injury.

As used herein, the term "growth state" refers to a state at which cells are growing in size and/or in numbers. In some embodiments, the cells at a growth state are undergoing an exponential growth.

As used herein, the term "migratory state" refers to cells having or adopting at least one or more migratory phenotypes, e.g., but not limited to, disruption of cadherens junctions (e.g., E-cadherin junctions); increased metalloproteinase expression; loss of an apico-basal polarity, a spindle-shaped morphology, cell-cell interaction through focal points, and any combinations thereof. In some embodiments, the migratory state can include an epithelial-mesenchymal transition or transformation (EMT), which is a process by which epithelial cells lose their cell polarity and cell-cell adhesion, and gain migratory properties to become mesenchymal cells. EMT occurs in various developmental processes including mesoderm formation and neural tube formation. EMT also occurs in wound healing, in organ fibrosis and in the initiation of metastasis for cancer progression. In some embodiments, the devices described herein can be used to model metastasis, wherein at least some cancer cells undergo EMT and become migratory and migrate from one side of the membrane (where the tumor cells reside) to the other, which is the "blood vessel" channel.

As used herein, the term "metamorphosing state" refers to a tissue (e.g., a group of cells) being readily capable of or undergoing metamorphosis or a developmental transition. In some embodiments, a metamorphosing state refers to an embryonic tissue undergoing induction (e.g., epithelial-mesenchyme interface transforming into a fully or partially-developed specific tissue, e.g., tooth, bone or epithelial gland). In some embodiments, a metamorphosing state refers to an insect tissue undergoing metamorphosis or any whole tissue undergoing a whole developmental transition.

As used herein, the term "three-dimensional state" refers to arrangement of cells in a three-dimensional structure. By way of example only, intestinal epithelial cells grow into folds and form villi in form of tubular projections.

The device described herein can be utilized to grow and culture cells to reach a pre-determined physiological endpoint by optimizing cell culture conditions. Cell culture conditions that can be optimized include, but are not limited to, seeding density, cell source and/or type, supporting cells, composition of the media, flow rate of air and/or media, presence or absence of an air-liquid interface, requirement of mechanical stimulation (e.g., induced by the membrane movement), membrane surface properties, dimensions of the mesochannel and/or microchannel, or any combinations thereof. The pre-determined physiological endpoint can be detected by cell morphology and/or the presence of at least one marker associated with the pre-determined physiological endpoint, which is further illustrated in the example below.

Optimization of Cell Culture Conditions to Reach a Pre-Determined Physiological Endpoint:

As discussed above, a number of cell culture condition parameters can be optimized in a device described herein for different pre-determined physiological endpoints. Exemplary cell culture condition parameters include, but are not limited to, cell-related parameters (e.g., cell sources, cell types, supporting cells, seeding density, and degree of confluency); culture medium-related parameters (e.g., composition or formulation of culture media); microenvironment-related parameters (e.g., flow rates of air and/or media, presence or absence of an air-liquid interface, mechanical stimulation requirement, membrane surface properties, and dimensions of the mesochannel and/or microchannel), and any combinations thereof.

Cell-Related Parameters:

Cells used in the device can be primary cells (e.g., any cells obtained directly from a living tissue, e.g., a biopsy material, of a human or an animal, which include, but are not limited to normal healthy cells, and disease-specific cells), immortalized or established cell lines, stem cells (e.g., embryonic stem cells, fetal stem cells, adult stem cells, stem cells derived from bone marrow, cord blood, and/or an amniotic fluid, induced pluripotent stem cells, and patient-specific stem cells), and/or modified cells.

In some embodiments, the cells used in the device described herein can comprise primary cells. For example, normal healthy cells can be obtained from one or more healthy donors. Disease-specific cells can be obtained from one or more patients diagnosed with the specific disease. For example, asthmatic, chronic obstructive pulmonary disease (COPD) and cystic fibrosis (CF)-associated airway cells can be obtained from one or more asthmatic, COPD and CF patients, respectively.

In some embodiments, the phenotype and/or behavior of the cells can be modified with a condition-inducing agent described herein. For example, normal healthy cells can be transformed to behave like disease-specific cells phenotypically and/or morphologically by stimulating the normal healthy cells with an agent known to induce symptom(s) of a specific disease in the cells. In one embodiment, cigarette smoke can be used to stimulate normal healthy cells for inducing chronic obstructive pulmonary disease (COPD) phenotype. In another embodiment, asthmatic-like cells can be derived from normal healthy cells by inducing inflammation in the normal healthy cells, e.g., by exposure to a pro-inflammatory factor described herein, e.g., but not limited to, TNF-alpha; by stimulation of normal cells with an allergen (e.g., house dust mite); and/or by stimulation with TH2 cytokines such as IL-13.

In some embodiments, the cells used in the device described herein can be genetically modified, e.g., by silencing one or more genes, or over-expressing one or more genes. Exemplary methods of gene silencing include, but are not limited to, RNA interference (e.g., but not limited to small interfering RNA (siRNA), microRNA (miRNA), and/or short hairpin RNA (shRNA)), antisense oligonucleotides, ribozymes, triplex forming oligonucleotides, and the like. Alternatively or additionally, the cells can be labeled with a detectable reporter (e.g., an optical reporter such as a fluorescent molecule, and/or a protein tag). By way of example only, CF-associated airway cells can be derived from normal healthy cells by a knock-out or silencing of the cystic fibrosis transmembrane conductance regulator (CFTR) gene, in which the presence of at least one or more mutations is known to cause CF. Methods of gene silencing is known in the art. For example, a CFTR-targeting shRNA, siRNA, antisense oligonucleotide, ribozyme, and/or triplex forming oligonucleotide can be introduced into normal healthy airway cells (e.g., primary cells), e.g., by a lentivirus system, in order to silence the CFTR gene, which can in turn result in a CF phenotype in the normal healthy cells.

Different cell types can be appropriately selected in accordance with a tissue and/or its function to be mimicked. By way of example only, lung alveolar cells can be selected for use in a device described herein to simulate a microenvironment in a portion of a lung air sac during breathing; while airway or bronchial epithelial cells can be used to simulate a microenvironment in an airway (e.g., a small airway) or bronchus during breathing. Other tissue-specific cells such as heart cells (e.g., but not limited to, cardiac muscle cells, connective tissue cells, aorta cells, atrial cells, ventricular cells, and heart valve interstitial cells), gut cells (e.g., but not limited to, esophagus cells, stomach cells, intestine cells, and colon cells), liver cells (e.g., but not limited to, karat parenchymal cells, and non-parenchymal cells such as sinusoidal hepatic endothelial cells, Kupffer cells and hepatic stellate cells), and skin cells (e.g., but not limited to, keratinocytes, fibroblasts, adipocytes, connective tissue cells, dermal cells, epidermal cells, and/or gland cells) can be used in the devices described herein to simulate a portion of a corresponding tissue. Additional cell types of various tissues that can be used in the devices described herein are described in the section "Cells" below. In some embodiments, stem cells can be used to differentiate into different cell types.

In some embodiments, supporting cells can be cultured together with subject cells of interest. As used herein, the term "supporting cells" refers to cells that provide protection, support, chemical signals (e.g., factors secreted by the supporting cells) and/or physical signals (e.g., direct physical contact between the subject cells and the supporting cells) that can be essential for proper phenotypes and/or functions of the subject cells of interest. For example, interstitial cells (e.g., but not limited to fibroblasts and/or smooth muscle cells) can be used as supporting cells for epithelial cells and act as a "feeder" layer for the epithelium. In one embodiment, lung interstitial cells (e.g., fibroblasts and/or smooth muscle cells) can be used as supporting cells for airway epithelial cells.

Seeding density and/or degree of cell confluency can influence cell morphology and/or their behavior (e.g., but not limited to, proliferation, viability, migration, protein synthesis, and/or differentiation). The cell seeding density and/or degree of cell confluency can be optimized for individual cell types (e.g., cell size, and/or modes of cell signaling such as direct contact, paracrine signaling, and/or endocrine signaling. For example, cells that require at least a part of the cell body to be in direct contact with neighboring cells in order to proliferate and remain viable generally need to be seeded at a higher cell density, as compared to cells that can also rely on paracrine signaling. Accordingly, the seeding density of cells can range from about 0.01 cell/$\mu m^2$ to about 1 cell/$\mu m^2$, or from about 0.05 cell/$\mu m^2$ to about 0.5 cell/$\mu m^2$. Similarly, some cells can be grown a in a sparsely-populated environment, while other cell types can require a denser population. Thus, degree of cell confluency can range from about 30% to 100% or about 50% to 100%. In one embodiment, airway cells can be seeded in the device described herein with a seeding density of about 0.1 cell/$\mu m^2$, which can provide about 90-100% confluence.

Culture Medium-Related Parameters:

The formulation of cell culture media can vary with individual cell types and/or their stages within a cell cycle as different cell types can require a unique combination and concentrations of nutrients and/or supplements (e.g., growth factors and/or small molecules such as amino acids and minerals) during different stages of a cell cycle (e.g., proliferation vs. differentiation). For example, as shown in Example 1, higher concentration of retinoic acid is used in the culture medium to induce differentiation of airway cells to ciliated and mucus-secreting cells after the cells have proliferated to reach confluency. Accordingly, one or more cell culture media (or a mix of at least two cell culture media) can be used in the devices described herein to achieve any of the physiological endpoints described herein. In some embodiments, a mix of at least two cell culture media can be used in the devices described herein to accommodate at least two or more cell types in a co-culture condition. By way of example only, in a co-culture condition, epithelial cells (optionally with supporting cells such as fibroblasts and/or smooth muscle cells) can be cultured in the mesochannel, while endothelial cells (optionally with supporting cells) can be cultured in the microchannel. Alternatively or additionally, immune cells can be introduced into the microchannel, either with a static fluid or a flowing fluid.

Cell culture media can comprise amino acids (e.g., but not limited to, alanine, arginine, asparagine, aspartic acid, cystine, cysteine, glutamic acid, glutamine, glycine, histidine, isoleucine, leucine, lysine, L-methionine, phenylalanine, proline, serine, threonine, tryptophan, tyrosine and valine); vitamins (e.g., but not limited to, folic acid, i-inositol, ascorbic acid, biotin, choline chloride, $Ca^{++}$-pantothenate, menadione, niacinamide, nicotinic acid, paraaminobenzoic acid (PABA), pyridoxal, pyridoxine, riboflavin, thiamine-HCl, vitamin A acetate, vitamin B12 and vitamin D2); inorganic salts (e.g., sodium salts, magnesium salts and calcium salts); transition metals, lipids, peptides, carbohydrates (e.g., glucose), sodium pyruvate, a buffered solution (e.g., N-{2-hydroxyethyl}piperazine-N'-[2-ethanesulfonic acid] (HEPES) or one or more other zwitterion buffers), a pH indicator (e.g., phenol red), antibiotics (e.g., penicillin and/or streptomycin), cytokines, hormones (e.g., epinephrine, hydrocortisone and/or insulin), serum, serum albumin, transferrin, retinoic acid (vitamin A), adenine sulfate, ATP, trace elements (e.g., but not limited to, ions of barium, bromine, cobalt, iodine, manganese, chromium, copper, nickel, selenium, vanadium, titanium, germanium, molybdenum, silicon, iron, fluorine, silver, rubidium, tin, zirconium, cadmium, zinc and aluminum), deoxyribose, ethanolamine, glutathione, hypoxanthine, linoleic acid, lipoic acid, phosphoethanolamine, putrescine, thymidine, uracil, xanthine, any art-recognized culture supplements, and any combinations thereof. Each of these ingredients can be obtained commercially, for example from Sigma (Saint Louis, Mo.).

Cytokines which can be used in the cell culture media include growth factors such as epidermal growth factor (EGF), acidic fibroblast growth factor (aFGF), basic fibroblast growth factor (bFGF), hepatocyte growth factor (HGF), insulin-like growth factor 1 (IGF-1), insulin-like growth factor 2 (IGF-2), keratinocyte growth factor (KGF), nerve growth factor (NGF), platelet-derived growth factor (PDGF), transforming growth factor beta (TGF-β), vascular endothelial cell growth factor (VEGF), transferrin, various interleukins (such as IL-1 through IL-18), various colony-stimulating factors (such as granulocyte/macrophage colony-stimulating factor (GM-CSF)), various interferons (such as IFN-γ) and other cytokines having effects upon hematopoietic stem cells such as stem cell factor (SCF) and erythropoietin (Epo). These cytokines can be obtained commercially, for example from Life Technologies, Inc. (Rockville, Md.) or R&D Systems (Minneapolis, Minn.), of from Peprotech (Rocky Hill, N.J.) and can be either natural or recombinant. In some embodiments, for culture of a wide variety of mammalian cells, the basal media can contain EGF at a concentration of about 0.1-100 nanograms/milliliter. In some embodiments, the basal media can contain EGF at a concentration of about 1-10 nanograms/milliliter. In some embodiments, the basal media can contain EGF at a concentration of about 5-10 nanograms per milliliter. Other cytokines, if used, can be added at concentrations that are determined empirically or as guided by the established cytokine art. See the section "Additional examples of cytokines" for other cytokines that can be added in the cell culture media.

Concentrations of each component of the culture media can be optimized for different cell types and physiological endpoints to be achieved. In general, the components of the culture media can each be independently present in an amount in a range of about $1\times10^{-10}$ mg/L to about $1\times10^4$ mg/L. For example, the concentration of amino acids can be in a range of about 0.05 mg/L to about 750 mg/L; vitamins in a range of about 0.0005 mg/L to about 500 mg/L; inorganic salts in a range of about 1 mg/L to about 10000 mg/L; trace elements in a range of about $1\times10^{-10}$ mg/L to about 0.5 mg/L.

In some embodiments, the cell culture media for use in the device described herein can comprise one or more ingredients of cell culture media described in the International Application Publication Nos.: WO 2003/048313; WO 2006/004728; WO 2005/065341; WO 2002/077202; WO 2010/096588; WO 2005/095582; and WO 1998015614, the contents of which are incorporated herein by reference.

In some embodiments, the cell culture medium can comprise blood (e.g., whole blood, plasma, serum, or any combinations thereof). In one embodiment, the cell culture medium can comprise blood or blood components derived from a patient for culturing patient-specific cells.

The media can comprise one or more differentiation agents. As used herein, the term "differentiation agent" refers to molecule(s) and/or composition(s) that can induce differentiation of a stem cell or an undifferentiated or partially differentiated cell to a desired state. This can be useful when stem cells or undifferentiated or partially differentiated cells are used.

Microenvironment-Related Parameters:

In addition to the cell-related and culture medium-related parameters, one or more microenvironment-related parameters (e.g., flow rates of air and/or cell culture media, presence or absence of an air-liquid interface, mechanical cue, membrane surface properties, and dimensions of the mesochannel and/or microchannel) can be regulated to achieve any of the physiological endpoints described herein.

A device having a mesochannel and/or microchannel of physiologically-relevant dimensions can be used to provide a simulated tissue microenvironment, which can, at least in part, regulate cell development to various physiological endpoints defined herein. For example, the higher mesochannel can offer a reduced stress environment and increased overhead space for growth and/or differentiation of cells that require low shear and/or more space to form a stratified structure. In one embodiment, the higher mesochannel can be used to permit sufficient overhead space for growth and differentiation of airway epithelial cells to ciliated and mucus-secreting cells.

In some embodiments, an air-liquid interface can be established in the devices described herein to mimic the native tissue microenvironment of tissue-specific cells and/or induce differentiation and/or maturation of the tissue-specific cells. As used herein, the term "air-liquid interface" refers to one of the mesochannel and microchannel having air therein while the remaining channel has a liquid fluid, e.g., cell culture medium and/or blood. There can be substantially no liquid fluid present in the "air" channel. However, cells present on the membrane facing the "air" channel can secrete a liquid-like substance, such as mucus, and/or a small amount of a liquid fluid can permeate through the membrane from the "liquid" channel to the "air" channel. In some embodiments, the term "air-liquid interface" refers to substantially no liquid fluid being introduced into one of the mesochannel and microchannel, while a liquid fluid is introduced into the remaining channel. In one embodiment, an air-liquid interface refers to the mesochannel having air therein while the microchannel has a liquid fluid, e.g., cell culture medium and/or blood. State another way, substantially no liquid fluid is introduced into the mesochannel, while a liquid fluid is introduced into the microchannel. For example, an air-liquid interface can be established in the devices described herein to induce differentiation or maturation of airway epithelial cells (as described below) or skin cells. In other embodiments, the native microenvironment of some tissue-specific cells (e.g., heart cells, liver cells and/or gut cells) may not require an air-liquid interface. In these embodiments, a liquid fluid, e.g., cell culture medium, can be present in both the mesochannel and the microchannel.

Air and/or culture media can be introduced into the appropriate channels in the devices (e.g., mesochannel and microchannel) as a static fluid (which can be periodically replaced) or a continuous (dynamic) flow. Flow rates of air and/or culture media in the mesochannel and/or microchannel can be adjusted independently to reflect the physiological values specific to a tissue-specific condition or state (e.g., a resting state vs. an active state, e.g., during exercise; or a normal healthy state vs. a disease-specific state). For example, air flow can be controlled at a volumetric rate to provide a fluid shear stress of about 0 dynes/cm² to about 2000 dynes/cm², or 0.1 dynes/cm² to about 2000 dynes/cm². In some embodiments where the device is used to mimic breathing through an airway and/or a lung, the air flow through the mesochannel can be adjusted to have a rate of about 1 µL per breath to about 50 mL per breath, or about 5 µL per breath to about 25 mL per breath, or about 10 µL per breath to about 10 mL per breath, or about 25 µL per breath to about 1 mL per breath. As used herein in reference to the device, the term "breath" refers to air flow induced in the mesochannel to mimic inspiration and expiration of air in a lung. The air flow volume and/or rhythm can vary depending on the state of a lung to be mimicked. For example, when stimulating air flow in a lung during exercise, e.g., running, the volume of air getting into and out of the lungs can increase per breath and unit time.

Culture medium flow rates can be controlled to simulate the flow rate of blood corresponding to a tissue-specific condition or state (e.g., a resting state vs. an active state, e.g., during exercise; or a normal healthy state vs. a disease-specific state). In some embodiments, the culture medium flow rates can be provided in a range of about 0 µL/hr to about 50 mL/hr.

In some embodiments where the cells are exposed to a mechanical stress or strain in their native tissue microenvironment such as a strain produced by motion associated with breathing, peristalsis or heart beating, the cells present on the membrane can be subjected to a simulated mechanical strain for development of a pre-determined physiological endpoint. The simulated mechanical strain can be produced by modulating the movement of the membrane, which can be parallel to and/or perpendicular to a force/pressure applied to the membrane, including, but are not limited to, stretching, bending, compressing, vibrating, contracting, waving, or any combinations thereof. By way of example only, in a pulmonary alveolus, alveolar cells experience stretching when the alveolus is filled with air during inhalation but restore to an original state or relaxed state during exhalation in order to expel carbon-dioxide-rich air. Another example is that esophagus cells or intestinal cells are subjected to a mechanical stress or strain produced by peristaltic waves occurring in the esophagus, or intestines, respectively. In a heart, the atria and ventricles work together, alternately contracting and relaxing to pump blood through the heart. In order to simulate a physiological strain produced by motion associated with breathing, peristalsis, or heart beating, the membrane can be, in one embodiment, modulated to stretch and release along the plane, e.g., by a pneumatic mechanism based on application of a pressure differential between the central channel 230 and the operating channel(s) 252 as shown in FIG. 2D, thereby providing the cells (e.g., alveolar cells, esophagus cells, intestinal cells, atrial myocardial cells, and ventricular myocardial cells) with a simulated mechanical cue as they reside in the native tissue microenvironment.

In some embodiments, the membrane can be treated or coated with cell adhesion molecules and/or extracellular matrix molecules to facilitate development of a pre-determined physiological endpoint. Examples of cell adhesion molecules, and/or extracellular matrix molecules include, without limitations, fibronectin, laminin, various collagen types, glycoproteins, vitronectin, elastins, fibrin, proteoglycans, heparin sulfate, chondroitin sulfate, keratin sulfate, hyaluronic acid, integrin-binding peptides such as Arg-Gly-Asp (RGD) peptides, or any combinations thereof.

By way of example only, utilizing the device described herein to reach a differentiated or mature state of human epithelial cells, e.g., human primary airway epithelial cells, one method (e.g., as shown in FIG. 5A) comprises seeding human cells or human primary cells (e.g., human primary airway or bronchial epithelial cells) on the membrane in the upper mesochannel (or an "airway lumen" channel). The cells are cultured in a submerged condition by flowing a culture medium through both the mesochannel and the microchannel. In some embodiments, the cells are cultured in a submerged condition until the cells reach a full confluence. Then, an air-liquid interface is optionally established by removing the culture medium from the mesochannel through its outlet. As the air-liquid interface can induce differentiation of certain cell-types, e.g., airway epithelial cells, the cells can differentiate after about 3-4 weeks or longer of culture in the device at the air-liquid interface. A static air flow is generally sufficient to induce cell differentiation. While not necessary, in some embodiments, a dynamic air flow can be induced in the mesochannel during cell differentiation to improve the cellular function(s) of the differentiated epithelial cells (e.g., differentiated airway epithelial cells). For example, a dynamic air flow can improve cilia beating frequency, mucous secretion, monolayer barrier function (e.g., permeability of epithelial layer) and/or surface protein expression of differentiated airway epithelial cells.

However, it should be noted that depending on cell types, an air-liquid interface is not always necessary for cell differentiation. In these embodiments, a liquid flow can be maintained in the mesochannel during cell differentiation. For example, intestinal epithelial cells do not require an air-liquid interface to undergo villus differentiation.

In some embodiments, a liquid fluid, e.g., cell growth media, flowing through the microchannel can comprise at least one differentiation-inducing agent, including, e.g., at least two, at least three, at least four, at least five differentiation-inducing agents.

In some embodiments, the cells can require exposure to a mechanical strain in order to reach a differentiated or mature state. For example, the cells in the mesochannel can be exposed to a mechanical cyclic strain (e.g., about 0.1% to about 50%, or about 1% to about 30%, or about 10% to about 25% at a frequency of about 0 Hz to about 1 Hz, or about 0.01 Hz to about 1 Hz) by stretching and/or retracting the membrane. In one embodiment, intestinal epithelial cells in the mesochannel can be exposed to a cyclic stain (e.g., about 10% at ~0.15 Hz).

In one embodiment, differentiation of airway epithelial cells in a device described herein comprises fully confluent of epithelial cells, an air-liquid interface induction and a cell-growth medium that supports cell differentiation.

Figure 5D:
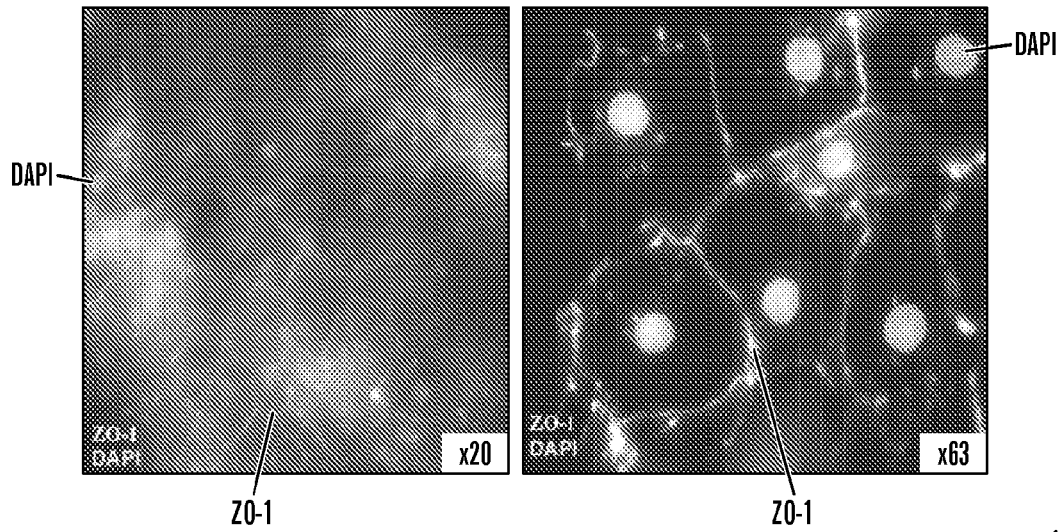
Figure 7A:
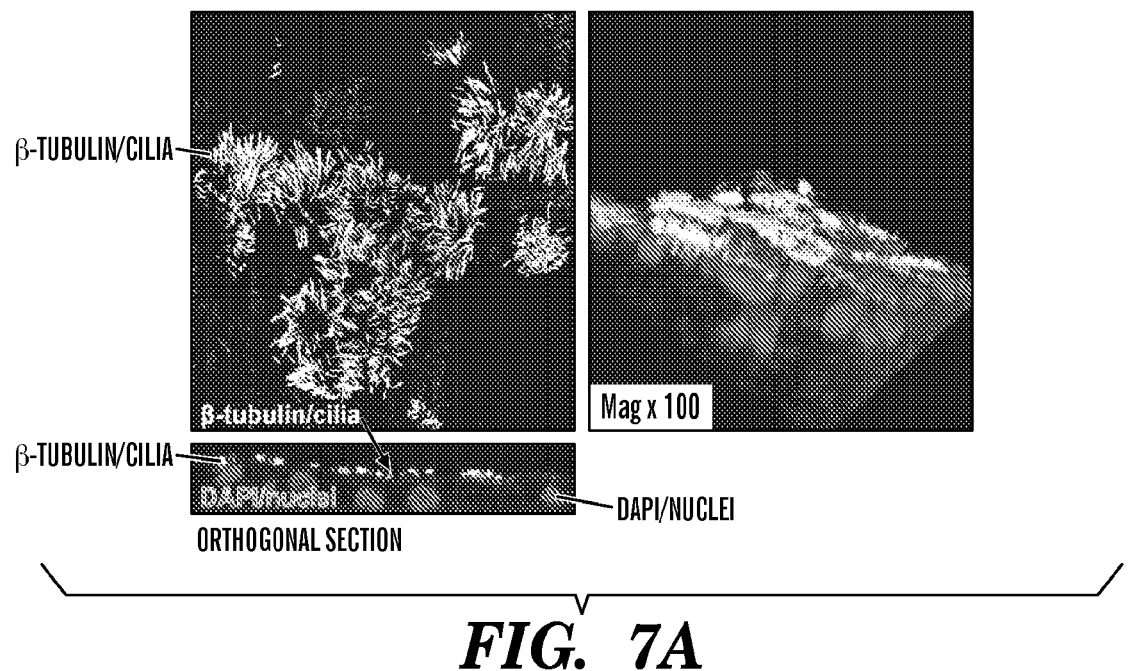
FIGS. 7A-7D show experimental data indicating differentiation of human bronchial epithelial cells in a mesochannel of a device in accordance with an embodiment.
Figure 7B:
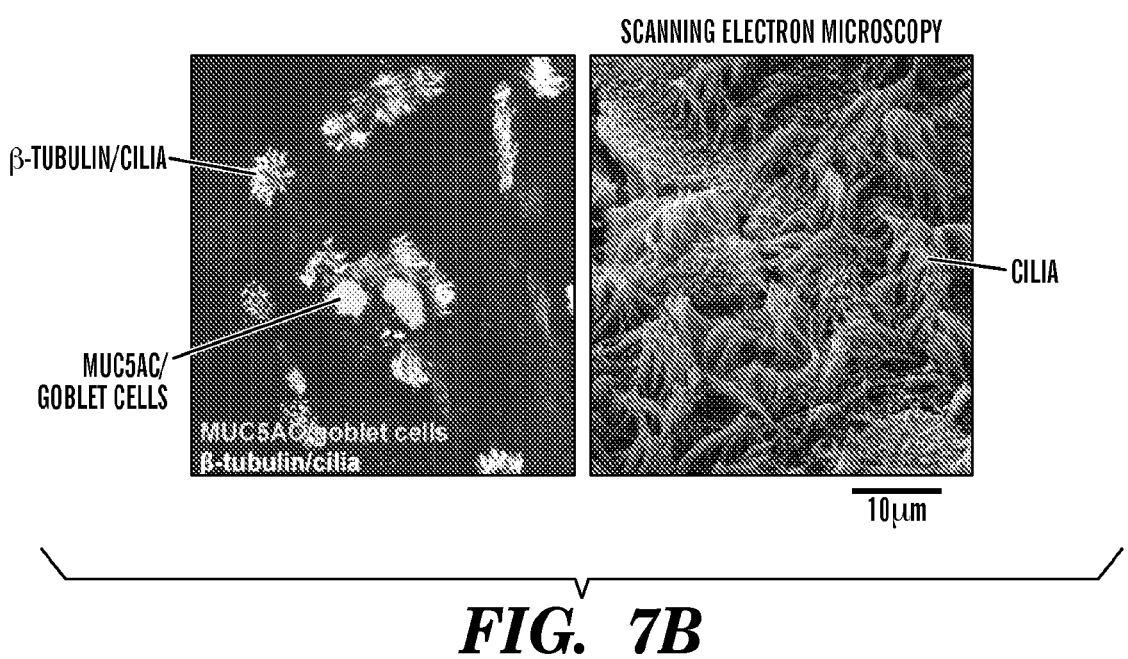
Figure 7C:
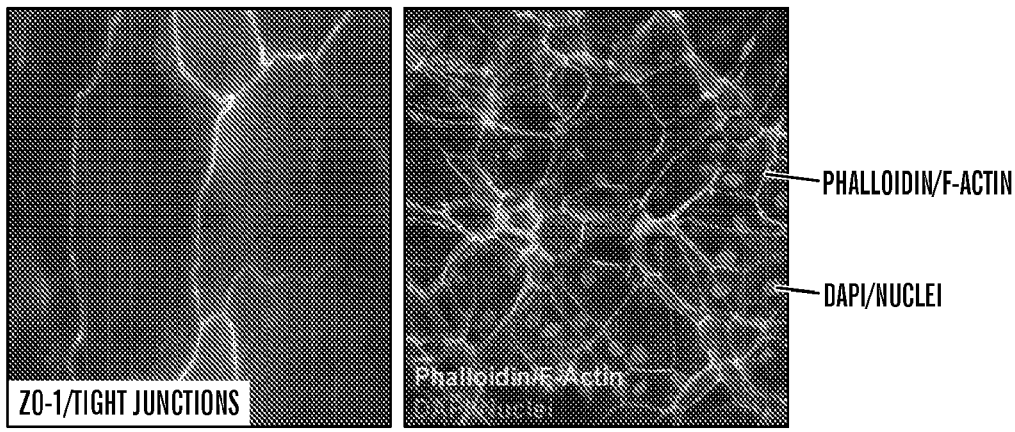
Figure 17A:
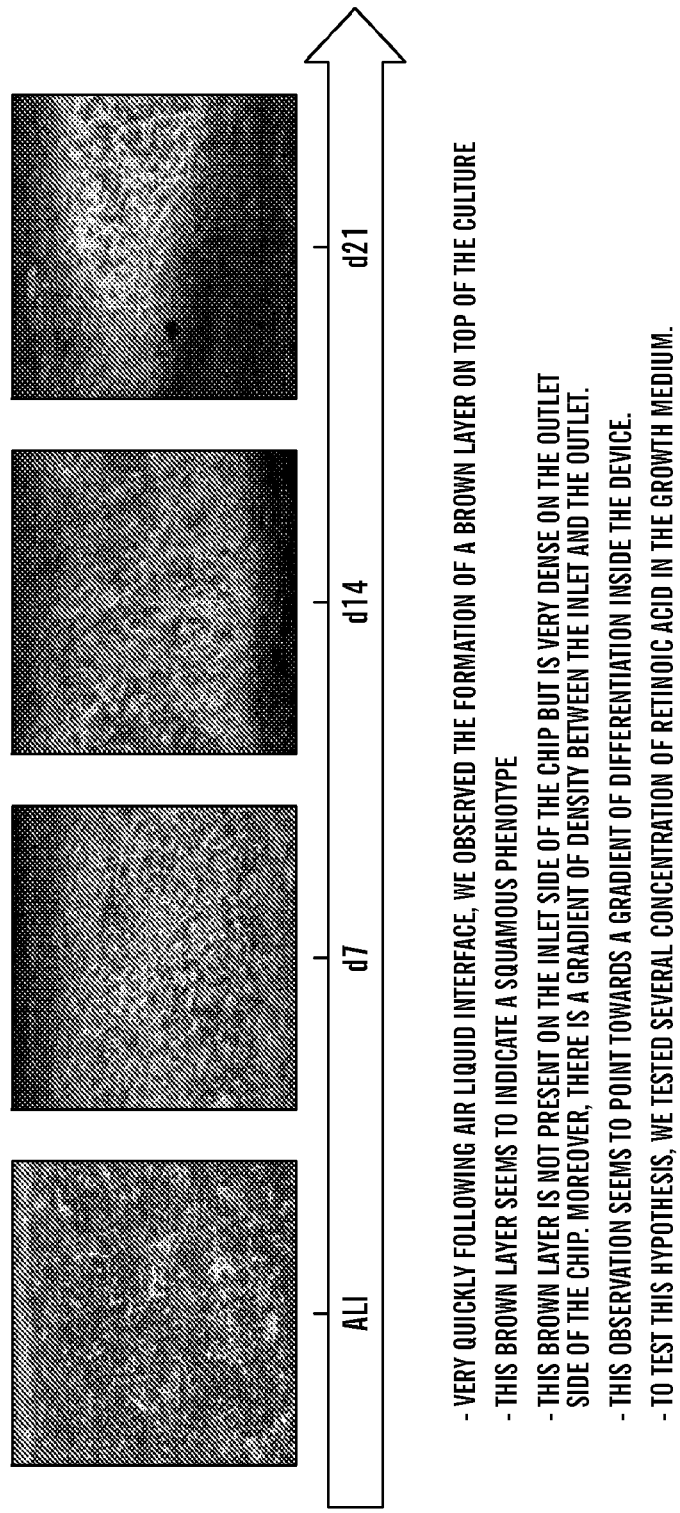
FIGS. 17A-17B are images showing squamous phenotype of bronchial cell culture in a device in accordance with an embodiment (FIG. 17A), and reversal of the squamous phenotype by addition of retinoic acid (FIG. 17B).
Figure 17B:
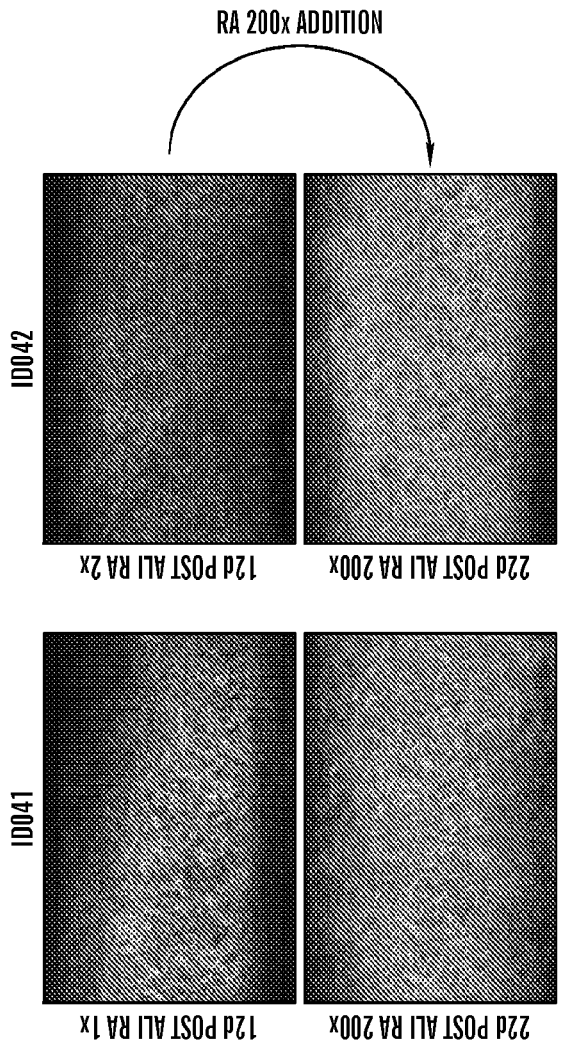
Figure 18:
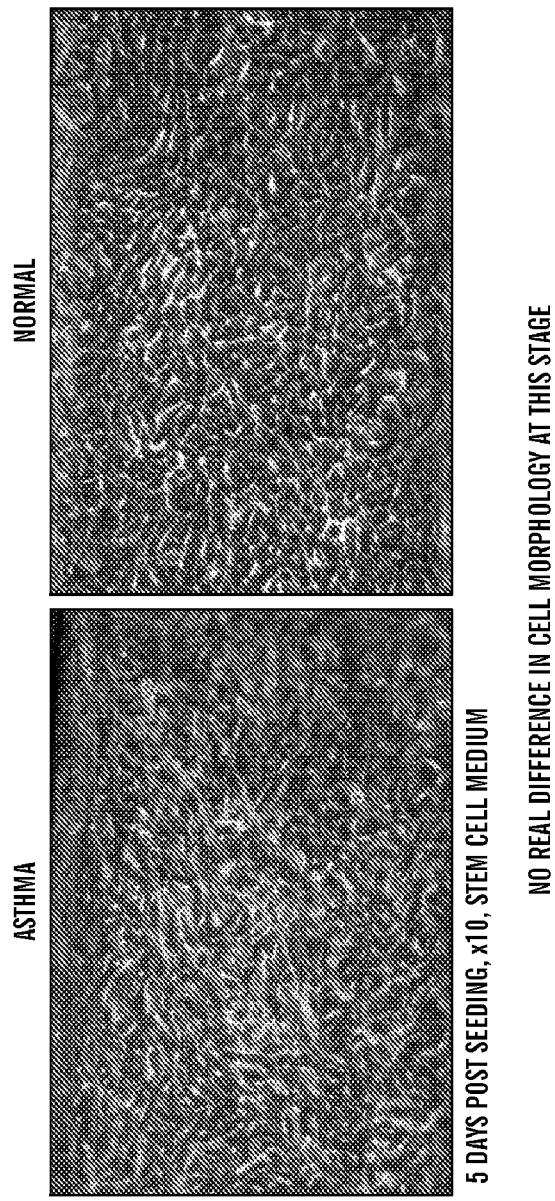
FIG. 18 is a set of images showing morphology of human airway epithelial cells from asthmatic donors and normal donors cultured in a device in accordance with one embodiment.

While methods of differentiating airway epithelial cells in transwell systems has been previously reported, technologies and techniques for differentiating primary human airway epithelial cells (e.g., human small airway epithelial cells) in microfluidic setting have not existed yet. For example, simply transposing the composition of growth medium from transwell culture is not sufficient. For example, small airway epithelial cells cultured in a microfluidic setting with a normal growth medium as used in the transwell culture exhibit a squamous phenotype (FIG. 17B), which is not same as in vivo morphology. To this end, the inventors surprisingly discovered that increasing retinoic acid concentration in the growth medium can reverse the squamous phenotype and restore a normal phenotype as observed in vivo. In one embodiment, the inventors discovered that a physiological airway unit (e.g., small airway unit) can be formed on the membrane 208 of the device, e.g., using the device and the method described herein. After exposing the airway epithelial cells (e.g., small airway epithelial cells) to an air-liquid interface in the device described herein, the cells are differentiated into a 3-D structure of terminally differentiated ciliated and mucous-secreting (goblet) cells, e.g., as detected by immunofluorescence microscopy and/or scanning electron microscopy (FIGS. 5E-5G and 7A-7B). Differentiated cells exhibit cilia beating and mucus secretion (FIGS. 5E-5G and 7A-7B), and tight barrier function (FIGS. 5D and 7C). Typical junctional structures can form between the differentiated airway epithelial cells (e.g., small airway epithelial cells) on the membrane 208 and fluids as well as ions be transported across the membrane 208 between the mesochannel and microchannel 250A, 250B. The formation of tight junctions between the differentiated airway epithelial cells on the membrane 208 can be evaluated using immunohistochemical detection of tight junction proteins such as ZO-1, TJP-1 (see FIGS. 5D and 7C).

Depending on the nature and/or properties of the selected body material (at least a portion of the device body that is in contact with the fluid), the composition of the cell-growth medium needs to be optimized accordingly. For example, in the case of using PDMS to fabricate the device body, concentrations of certain hydrophobic components or factors in the cell growth medium needs to be increased because they likely get absorbed on the PDMS surface. In one embodiment, retinoic acid in the cell growth medium is increased, e.g., up to 200 times as compared to other material used, to allow sufficient availability of the retinoic acid for the epithelial cells.

Validation/Quality Control Tests of the Physiological Endpoints:

Cells with different physiological endpoints defined herein (e.g., precursor cells or non-differentiated cells vs. differentiated or mature cells; or normal healthy cells vs. disease-specific cells) can be identified by methods and assays known to one of skill in the art. For example, a physiological endpoint can be identified based on, but not limited to, cell function, molecule release from cells, cell morphology, cell metabolism, expression level or presence/absence of a molecule known to be associated with the pre-determined physiological endpoint. Cells can be analyzed "on-device" (e.g., cells remain inside the mesochannel and/or microchannel during analysis) or some cells can be removed and analyzed "off-device" (e.g., cells are removed from the device for subsequent analysis that is not performed on the device).

In some embodiments, the membrane 208 can be removed from the devices for analysis, e.g., immunohistochemical detection, immunofluorescence microscopy and/or scanning electron microscopy. In other embodiments, the membrane 208 can be evaluated and analyzed using on-chip detection methods, e.g., immunohistochemical detection and/or microscopy. In some embodiments, the entire device including the membrane can be evaluated and analyzed, e.g., under a microscope.

Figure 7D:
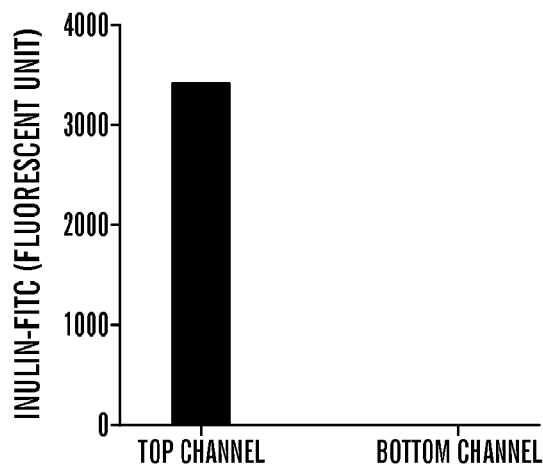

For example, as described earlier, in contrast to non-differentiated epithelial cells, differentiated airway cells typically form ciliated cells, globet cells (mucus-secreting cells) and a tight epithelial barrier, the phenotypes of each of which can be detected, e.g., by staining the cells for cilia-associated markers (e.g., but not limited to β-tubulin IV), goblet cell-associated markers (e.g., but not limited to MU5AC) and/or tight junction-associated markers (e.g., TJP-1 and ZO-1), followed by microscopy imaging (FIGS. 5D-5E, and FIGS. 7A-7C). Alternatively or additionally, cilia beating frequency can be determined by scanning electron microscopy. The barrier function of a differentiated epithelium can also be determined by a functional assay, e.g., adding fluorescently-labeled large molecules (e.g., inulin-FITC) into a fluid flowing through the mesochannel and then detecting the presence of the fluorescently-labeled large molecules in the microchannel, wherein the no detectable fluorescent signal from the microchannel is indicative of a functional barrier formed by the differentiated epithelium (FIG. 7D).

To determine an inflamed state, cell response to inflammation can be quantified by a functional assay and/or cytokine and/or chemokine expression analysis. For example, attachment and recruitment of immune cells (e.g., but not limited to neutrophils, monocytes, lymphocytes, dendritic cells and immature macrophages) from a static or flowing fluid in the microchannel ("blood vessel" channel) to the membrane and/or epithelium on the side of the mesochannel can be quantified by microscopy, histology, and/or by tracking movement of detectable markers (e.g., fluorescently-labeled immune cells) using, e.g., fluorescence activated cell sorter (FACS). Alternatively or additionally, cytokine and/or chemokine expression analysis (including secreted and/or intracellular molecules) can be performed by collecting effluents and/or cells from the mesochannel and/or microchannel and detecting inflammation-associated cytokines and/or chemokines, e.g., by microarray, ELISA, immunofluorescence, microscopy, and/or quantitative real-time polymerase chain reaction (PCR).

Other methods that can be used to determine inflammation include, but are not limited to, monitoring the frequency of cilia beating, e.g., by microscopy; measuring mucus clearing speed, e.g., by particle image velocimetry; evaluating cilia morphology, e.g., by scanning electron microscopy; and/or detecting the presence of mucus-producing cells (globet cells) by morphology through microscopic examination and/or apical secretions. To measure mucus clearing speed, for example, particle image velocimetry, can be used as follows: a fluid (e.g., cell culture media) comprising small detectable beads (e.g., fluorescent beads of ~1-~3 microns) can be introduced into the mesochannel where ciliated cells are growing. Under a microscope (e.g., a fluorescent microscope), the mucociliary transport (e.g., characterized by speed and/or direction) can be monitored and/or quantified (e.g., based on a series of recorded images or movies).

In order to distinguish normal healthy cells from disease-specific cells such as airway-associated diseases or disorders, one of skill in the art can compare and contrast phenotypes of the diseased cells with the normal healthy cells, thereby identifying distinct features between the normal healthy cells and the diseased cells. By way of example only, in an asthma disease model, asthmatic airway cells can display at least one (including at least two or more) of the following phenotypes, as compared to normal healthy airway cells: (i) higher mucus secretion by at least about 10% or more; (ii) higher proportion of globet cells (globet cells metaplasia) by at least about 10% or more; and (iii) decreased number of ciliated cells by at least about 5% or more. In some embodiments, an increase in nitric oxide can be detected in the device with asthmatic airway cells, as compared to normal healthy cells. Any art recognized methods, e.g., ELISA, microscopy, immunofluorescence, and/or PCR, can be used to determine cell morphology and its behavior/response. For example, mucus secretion by the airway cells can be determined by ELISA, immunofluorescence, and/or PCR.

In a chronic obstructive pulmonary disease (COPD) disease model, COPD-associated airway cells can display at least one (including at least two or more) of the following phenotypes, as compared to normal healthy airway cells: (i) higher basal secretion of pro-inflammatory cytokines/chemokines, e.g., IL-8, by at least about 10% or more; (ii) increased responsiveness to viral and/or bacterial challenges, which include, e.g., more rapid synthesis and/or secretion of at least one pro-inflammatory cytokine/chemokine by at least about 10% or more; (iii) higher mucin gene expression (e.g., measured by real time quantitative PCR) and/or mucin secretion (e.g., measured by ELISA) by at least about 10% or more; and (iv) lower ciliated cell count and/or cilia beating frequency by at least about 5%. In some embodiments, the COPD-associated airway cells can display higher adhesion of alveolar macrophages by at least about 10%, as compared to normal healthy cells. For example, one can flow a fluid comprising alveolar macrophages through the mesochannel and/or microchannel and then measure the number of the alveolar macrophages adhered to the COPD cells, e.g., by microscopy.

The cause of cystic fibrosis (CF) is at least in part related to the presence of at least one or more mutations in cystic fibrosis transmembrane conductance regulator (CFTR) protein, which can affect functioning of the chloride ion channels in the cell membranes. Mutation can include, but are not limited to replacements, duplications, deletions or shortenings in the CFTR gene. These mutations can result in dysfunction, faster degradation, and/or lower expression level of the CFTR protein. See, e.g., Rowe, S. M. et al., "Cystic Fibrosis" N Engl J Med 2005; 352:1992-2001. Some of the CFTR mutations can include, but are not limited to, (i) ΔF508, a deletion (Δ) of three nucleotides which results in a loss of the amino acid phenylalanine (F) at the 508th position on the protein, resulting in faster degradation of the protein; (ii) G542X; (iii) G551D; (iv) N1303K; and (v) W1282X. Accordingly, in a CF disease model, the CF-associated airway cells can display at least one (including at least two or more) of the following phenotypes, as compared to normal healthy airway cells: (i) at least one or more mutations in the cystic fibrosis transmembrane conductance regulator (CFTR) protein as described above. In one embodiment, the CFTR mutation can include ΔF508; (ii) increased mucus secretion and/or mucus thickness (where mucus thickness can be measured, in one embodiment, by transmission electron microscopy); and (iii) lower cilia beating frequency or in some cases, cilia stop beating (e.g., due to mucus getting thicker and heavier). The mutation in the CFTR protein can be determined, e.g., by sequencing to identify the single nucleotide polymorphisms (SNPs); by performing a gene and/or transcript expression analysis to determine a decreased expression of the CFTR protein; and/or by detecting a decreased functioning of the chloride ion channels in the cell membranes of the CF-associated airway cells.

Figure 13A:
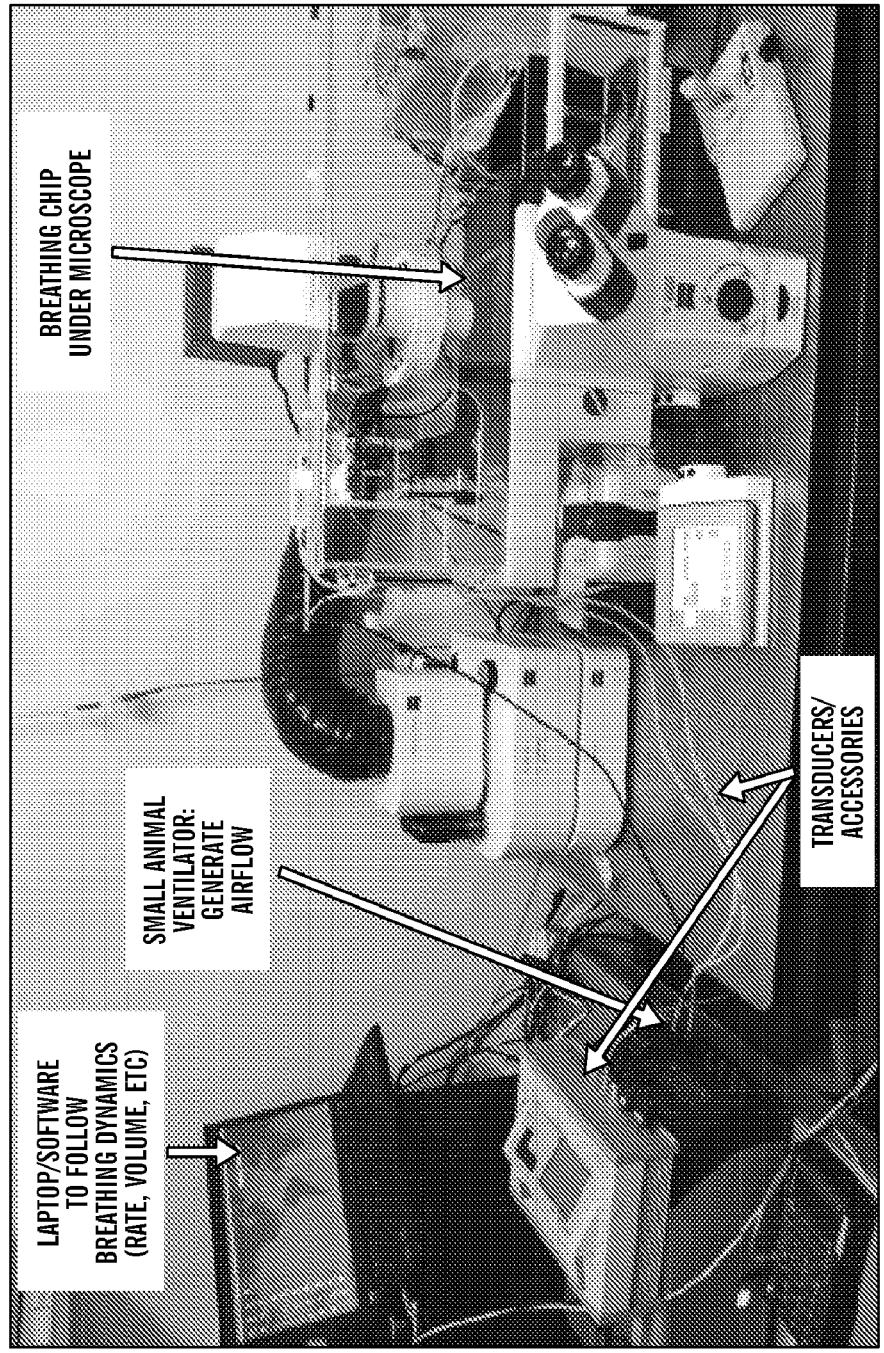
Figure 13B:
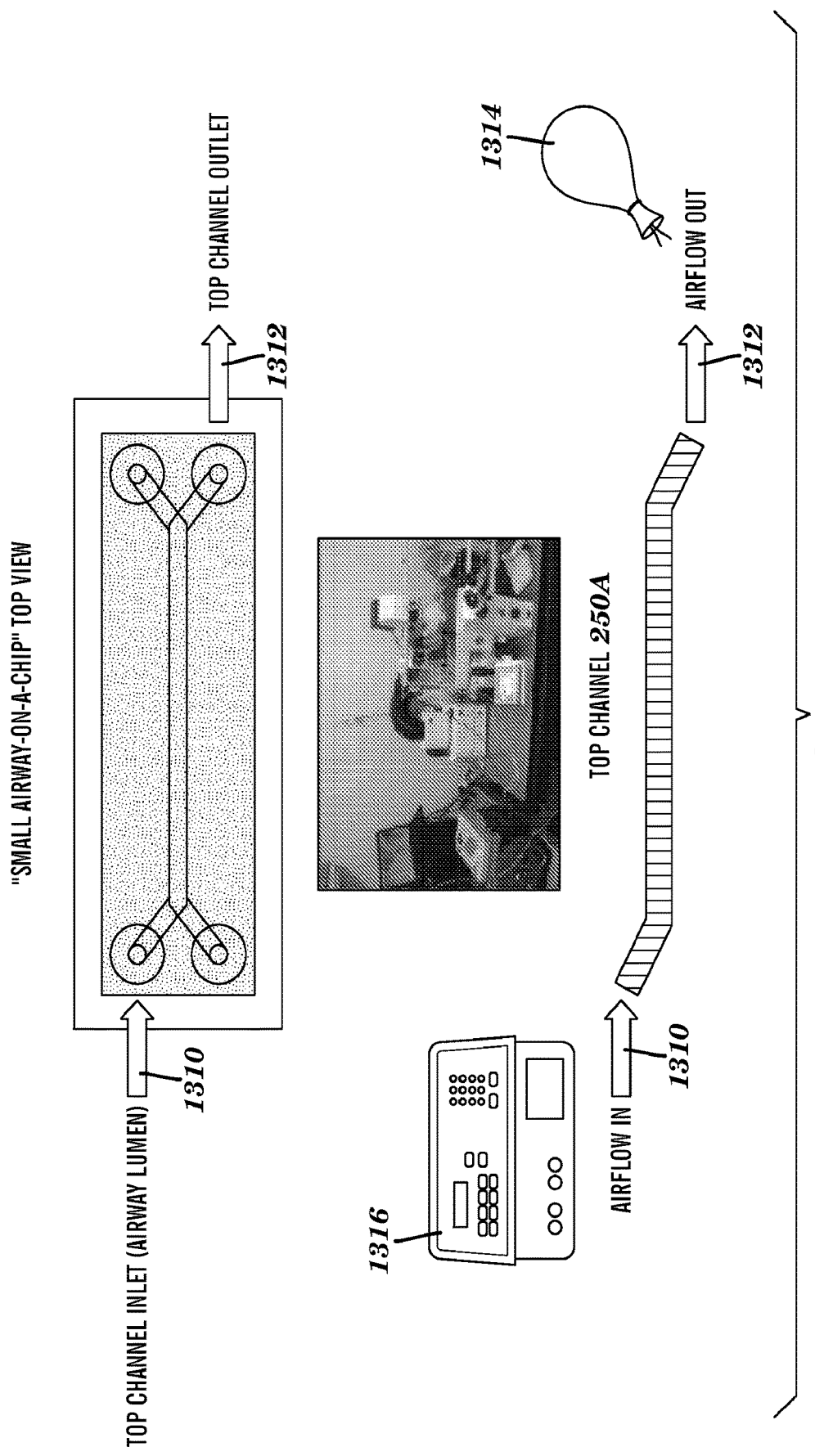
Figure 13C:
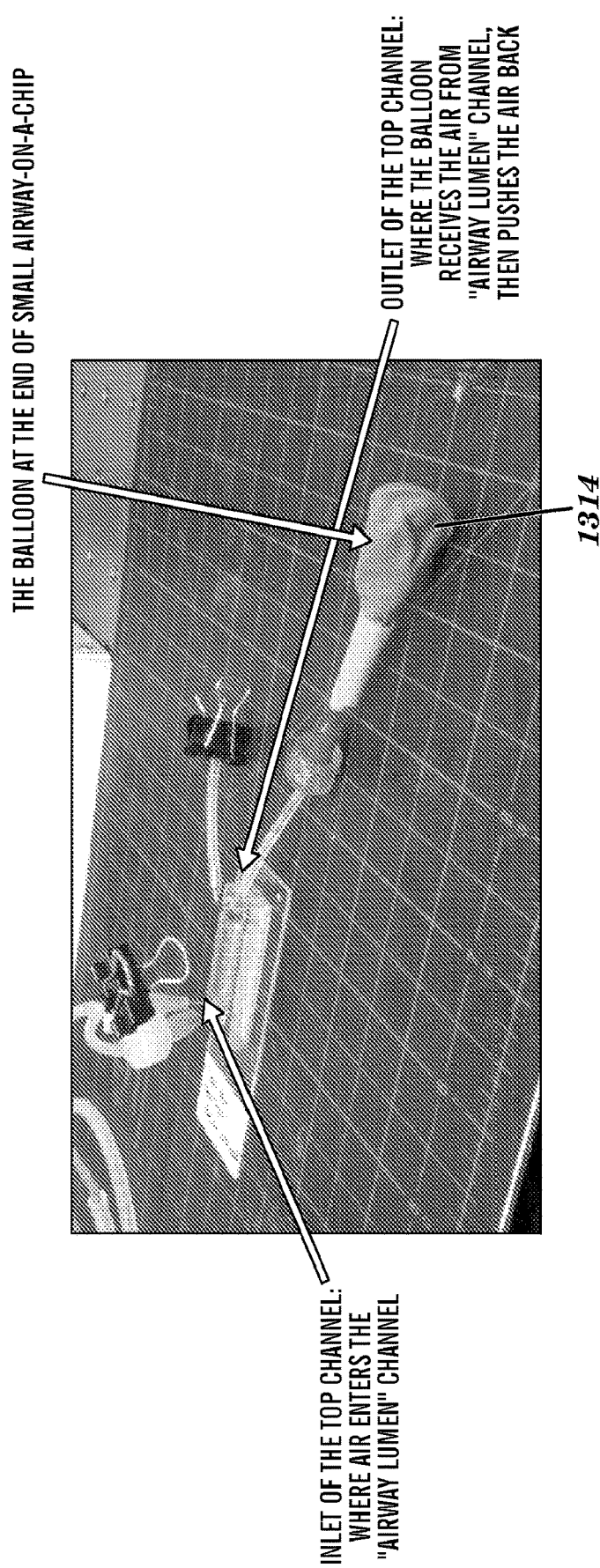

Introduction of a Gas Flow into the Mesochannel:

In some embodiments, one end of the mesochannel can be adapted to engage to a gas-flow modulation device, which can be used to control the flow of a gas through the mesochannel. In some embodiments, the gas-flow modulation device can be adapted to provide a directional flow of gas or an alternating flow of gas that can reverse its direction periodically. For example, as shown in FIGS. 13A-13D, at least one end or both ends (e.g., 1310 and/or 1312) of the mesochannel 250A can be adapted to engage to a gas-flow modulation device 1314. In some embodiments, the outlet 1312 of the mesochannel 250A is adapted to engage to a gas-flow modulation device 1314. The gas-flow modulation device 1314 can be in a form of any reversibly inflatable or reversibly expandable chamber, which can expand and contract to receive and expel a gaseous fluid (e.g., but not limited to air), respectively. The gas-flow modulation device can also allow introduction of a particular sample such as polluted air, cigarette smoke or air-borne viruses. By way of example only, the gas-flow modulation device 1314 can be in a form of a balloon (FIG. 13C), a drum (FIG. 13D), or a thin-walled tube. The drum as shown in FIG. 13D comprise a flexible diaphragm 1315, which can move outward (inflates—away from the inflow direction) and inward (deflates—toward the inflow direction) to accumulate and expel a gaseous fluid (e.g., air), respectively.

In some embodiments, the inlet 1310 of the mesochannel 250A can be adapted to engage to a gas-flow generator 1316, e.g., but not limited to, a ventilator.

In some embodiments, the devices described herein can be used to mimic alternating inspiratory and expiratory airflow during respiration and thus mimic breathing pattern and/or rhythm, e.g., during a resting state, exercise, stress, or illness, e.g., suffering from a respiratory disease or distress. For example, the gas-flow modulation device 1314 can be configured to create an alternating inspiratory and expiratory air flow with an average tidal volume ranging from about 10 μL to about 5000 μL, or from about 50 μL to about 2500 μL, or from about 75 μL to about 1000 μL, or from about 100 μL to about 500 μL. The term "tidal volume" as used herein refers to a volume of air displaced between inspiration and expiration when no external pressure is not applied (e.g., to mimic breathing during a resting state). The tidal volume can vary depending on the size of the lung to be mimicked, e.g., a newborn vs. an adult; or a human being vs. a large animal such as an elephant. In some embodiments, the gas-flow modulation device 1314 can be configured to create an alternating inspiratory and expiratory air flow where a volume of air displaced between inspiration and expiration is greater or smaller than the tidal volume as defined herein, for example, to mimic breathing during exercise or illness.

In some embodiments, the gas-flow modulation device 1314 can be configured to create an alternating inspiratory and expiratory air flow with a respiratory frequency or rate of about 5 breaths/min to about 100 breaths/min, or about 10 breaths/min to about 50 breaths/min.

Figure 14B:
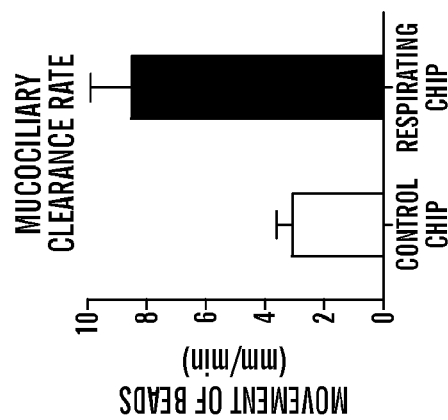
FIGS. 14A-14B are experimental data showing simulation of respiration in a device according to one embodiment. One end of the mesochannel (the "airway lumen" channel) of the device was adaptably connected to, e.g., a small animal ventilator and attached equipment that can adjust pressure and volume of air, in order to generate air flow. Air was flown from the one end of the "airway lumen" channel, namely "mouth end" into the device—that is "inspiratory flow." The other end of the "airway lumen" channel, known as "alveolar end" was adaptably connected to a rubber balloon structure with compliance and elasticity to help forcing the air out of the device—that is "expiratory airflow." The airflow/breathing was adjusted in a way to mimic breathing of a human subject in the resting state at a small airway level ~15×(inspiration+expiration) cycles with tidal volume average of 100 µl, and can be adjusted to accommodate different breathings patterns and/or tidal volumes. About 24 hrs after breathing, ~2 µm fluorescence (red) beads were added into the "airway lumen" channel, i.e., on top of epithelial cells, and the movement of the fluorescent beads was followed by microscope. This set-up can be used to determine ciliary clearance rate.
Figure 14A:
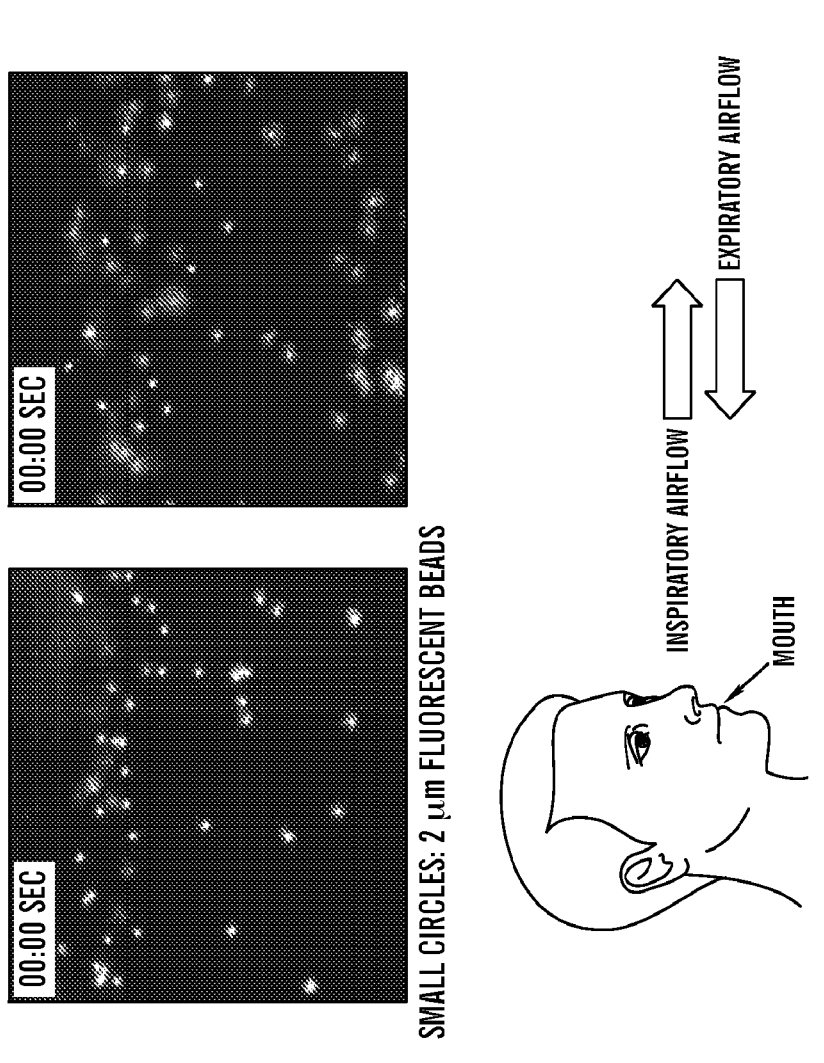

FIGS. 14A-14B are experimental data showing simulation of respiration using a gas-flow modulation device in a device according to one embodiment. One end of the mesochannel (the "airway lumen" channel) of the device was adaptably connected to, e.g., a small animal ventilator 1316 and attached equipment that can adjust pressure and volume of air, in order to generate air flow. Air was flown from the one end of the "airway lumen" channel, namely "mouth end 1310" into the device—that is "inspiratory flow." The other end of the "airway lumen" channel, known as "alveolar end 1312" was adaptably connected to a rubber balloon structure with compliance and elasticity to help forcing the air out of the device—that is "expiratory airflow." The airflow/breathing can be adjusted in a way to mimic breathing of a human subject in the resting state at a small airway level–15×(inspiration+expiration) cycles with tidal volume average of 100 μl, or can be adjusted to accommodate different breathings patterns and/or tidal volumes.

To visualize and measure the direction/rate of the gas flow or air flow, art-recognized techniques such as particle image velocimetry or micron-resolution particle image velocimetry can be employed. For example, fluorescence beads can be added into the "airway lumen" channel, i.e., on top of the differentiated epithelial cells (e.g., differentiated airway epithelial cells), and the movement of the fluorescent beads can be captured with a microscope. FIG. 14A is a set of snapshot images showing the movement of the fluorescent beads within the "airway lumen" channel of the device at a specific time point. The left panel is directed to a control device that did not receive airflow and shows partially polarized bead movements—i.e. some beads in one direction, a few in the opposite direction. The right panel is directed to a device that received airflow for about 24 hrs and shows more polarized bead movement towards the "mouth end." This set-up can be, for example, used to determine ciliary clearance rate of a particle. By way of example only, FIG. 14B is a bar graph showing a higher ciliary clearance rate of the fluorescent beads in the device that received airflow (breathing chip) than in the control device without airflow (the non-breathing chip). Similarly, ciliary clearance rate of pathogens, compounds, and/or particulates introduced into the mesochannel can also be determined using the device described herein. In some embodiments, the pathogens, compounds, and/or particulates can be labeled with a detection molecule (e.g., a fluorescent molecule) for ease of visualization and/or tracking.

Figure 8:
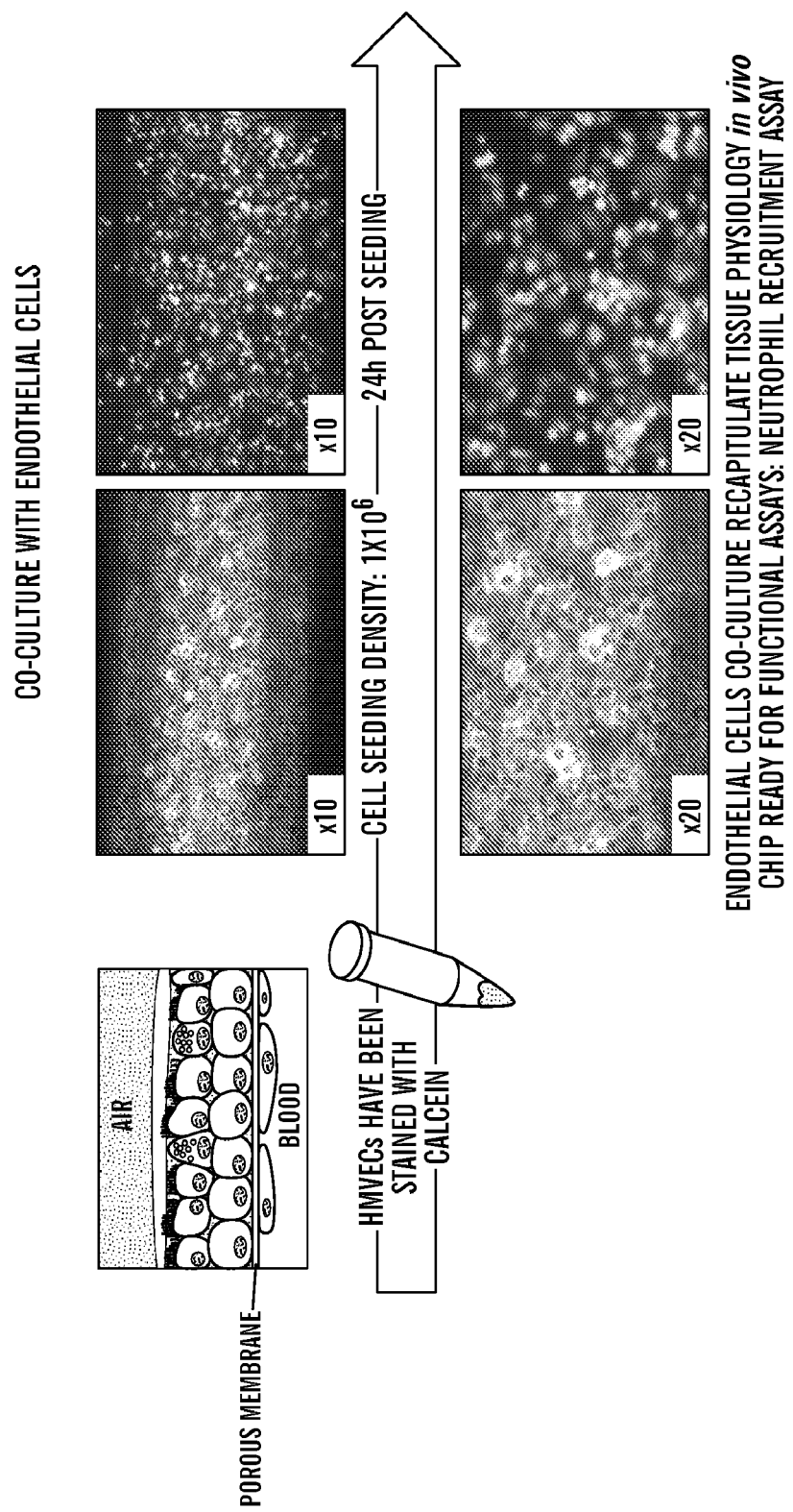
FIG. 8 is a set of images showing co-culture of human primary airway epithelial cells on one side of a porous membrane facing the mesochannel with the endothelial cells cultured on another side of the porous membrane facing the microchannel.
Figure 9:
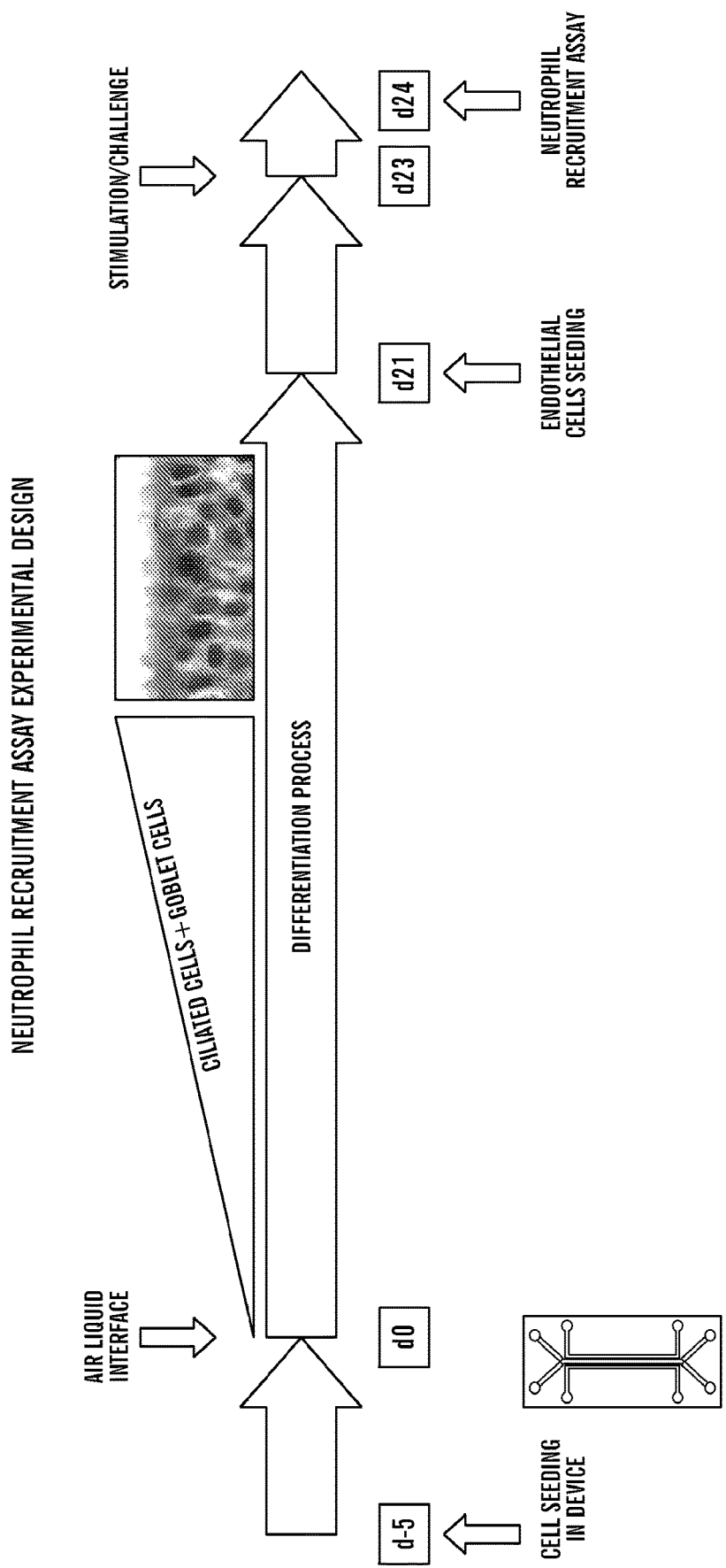
FIG. 9 is a schematic diagram illustrating an example experimental design for a neutrophil recruitment assay. Primary small airway epithelial cells were seeded on the membrane in the mesochannel (an "airway lumen" channel) for differentiation into ciliated and goblet cells following the differentiation method as described in FIG. 5A. Once the cells are differentiated, endothelial cells can be seeded on another surface of the porous membrane forming a coculture. The cells can then be contacted with an agent and neutrophil recruitment can be determined by measuring attachment of neutrophils to the endothelial monolayer.
Figure 10A:
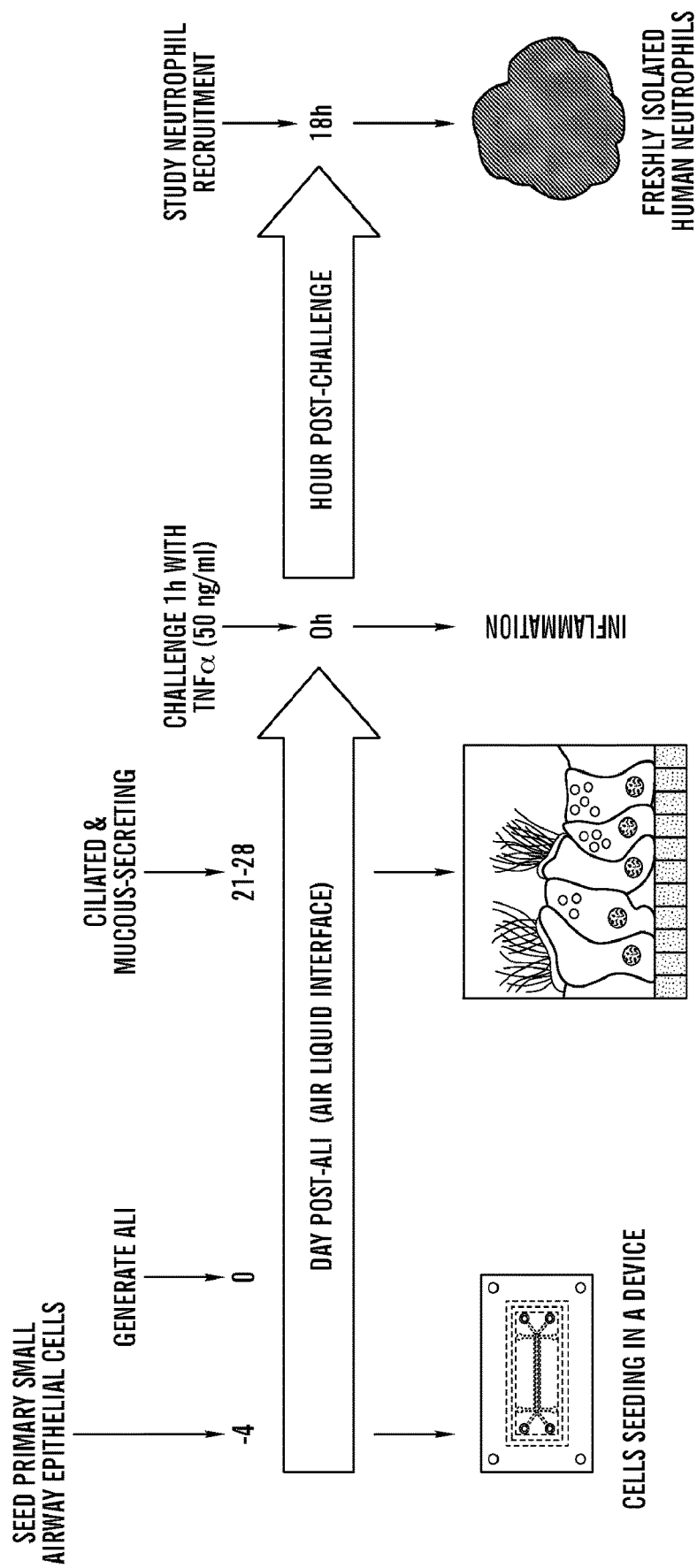

Co-Culture:

As used herein, the term "co-culture" refers to two or more different cell types being cultured in a device described herein. The different cell types can be cultured in the same channel (e.g., mesochannel or microchannel) and/or in different channels (e.g., one cell type in a mesochannel and another cell type in a microchannel). For example, in some embodiments, in order to recapitulate in vivo microenvironment, in some embodiments, another side of the membrane 208 facing the microchannel 250B can be cultured with blood vessel-associated cells, e.g., but not limited to, endothelial cells, fibroblasts, smooth muscle cells, pericytes, or any combinations thereof. In one embodiment, as shown in FIG. 8, the side of the membrane 208 facing the microchannel 250B is cultured with endothelial cells. As endothelial cells generally play a significant role in immune cell recruitment and/or extravasation, co-culture of tissue-specific epithelial cells (e.g., airway epithelial cells) on one surface of the membrane facing the mesochannel 250A with endothelial cells on another surface of the membrane facing the microchannel 250B can create a physiologically-relevant model to perform an immune cell recruitment assay, e.g., by introducing immune cells (e.g., but not limited to, CD8+ T cells, lymphocytes, monocytes, neutrophils) in the microchannel, followed by determination of the number of immune cells adhered onto the endothelial monolayer. In some embodiments, endothelial cells can also participate in cytokine/chemokine secretion during a virus infection.

In some embodiments, the side of membrane 208 facing the microchannel 250B can further comprise smooth muscle cells and/or fibroblasts. When there is more than one cell type in a channel, a culture medium supplied to the channel can comprise a mixture of culture media typically used to culture individual cell types.

In some embodiments, tumor cells can be co-cultured with normal epithelial cells in the mesochannel.

In some embodiments where the device models an intestine, the intestinal epithelial cells can be co-cultured with intestinal microbial flora in the mesochannel.

In some embodiments, the device described herein can be used to create an in vitro model that mimics a tissue-specific condition. As used herein, the term "tissue-specific condition" refers to any condition that can be diagnosed in a tissue of an organ in vivo. The condition can occur naturally in the tissue in vivo (including, e.g., a normal healthy condition, or a condition induced or caused by a congenital defect), or induced or caused by a condition-inducing agent or stimulant (e.g., including, but not limited to an environmental agent). Examples of a tissue-specific condition include, without limitations, a normal state, a disease-specific state, a pre-disease state, a disease remission state, a distressed state, an inflamed state, an infected state, and a stimulated state. In these embodiments, the tissue-specific cells placed on the surface of the membrane facing the mesochannel can be adapted to display at least one characteristic associated with the tissue-specific condition. For example, in some embodiments, patient- and disease-specific epithelial cells and optional structural cells can be cultured and differentiated on the surface of the membrane facing the mesochannel, for example, to model chronic organ disorders such as chronic lung disorders, e.g., but not limited to chronic obstructive pulmonary disease (COPD), asthma, cystic fibrosis (CF), and fibrotic conditions such as sarcoidosis, and idiopathic lung fibrosis, In some embodiments, disease-specific cells can be obtained from one or more patients diagnosed with the specific disease. For example, asthmatic, chronic obstructive pulmonary disease (COPD) and cystic fibrosis (CF)-associated airway cells can be obtained from one or more asthmatic, COPD and CF patients, respectively.

In other embodiments, the tissue-specific cells (e.g., normal tissue-specific cells) can be contacted with a condition-inducing agent described herein that is capable of inducing the tissue-specific cells to acquire at least one characteristic associated with the tissue-specific condition. For example, lung infections can be modeled by introducing a biological and/or chemical agent, e.g., pathogens such as influenza virus, and/or an immunostimulant (e.g., polyinosinic:polycytidylic acid (usually abbreviated as poly I:C) to model lung infections, including bacterial and/or viral infections. In one embodiment, cigarette smoke can be used to stimulate normal healthy cells for inducing chronic obstructive pulmonary disease (COPD) phenotype. In another embodiment, asthmatic-like cells can be derived from normal healthy cells by inducing inflammation in the normal healthy cells, e.g., by exposure to a pro-inflammatory agent described herein. Pro-inflammatory agents are described below in the section "Additional examples of cytokines". In some embodiments, the pro-inflammatory agent can be TNF-alpha. In some embodiments, it can be desirable to induce an asthma-like phenotype in normal cells (rather than using diseased cells collected from patients diagnosed with asthma), for example, to reduce or eliminate genetic variability/heterogeneity among different asthmatic donors.

Figure 21:
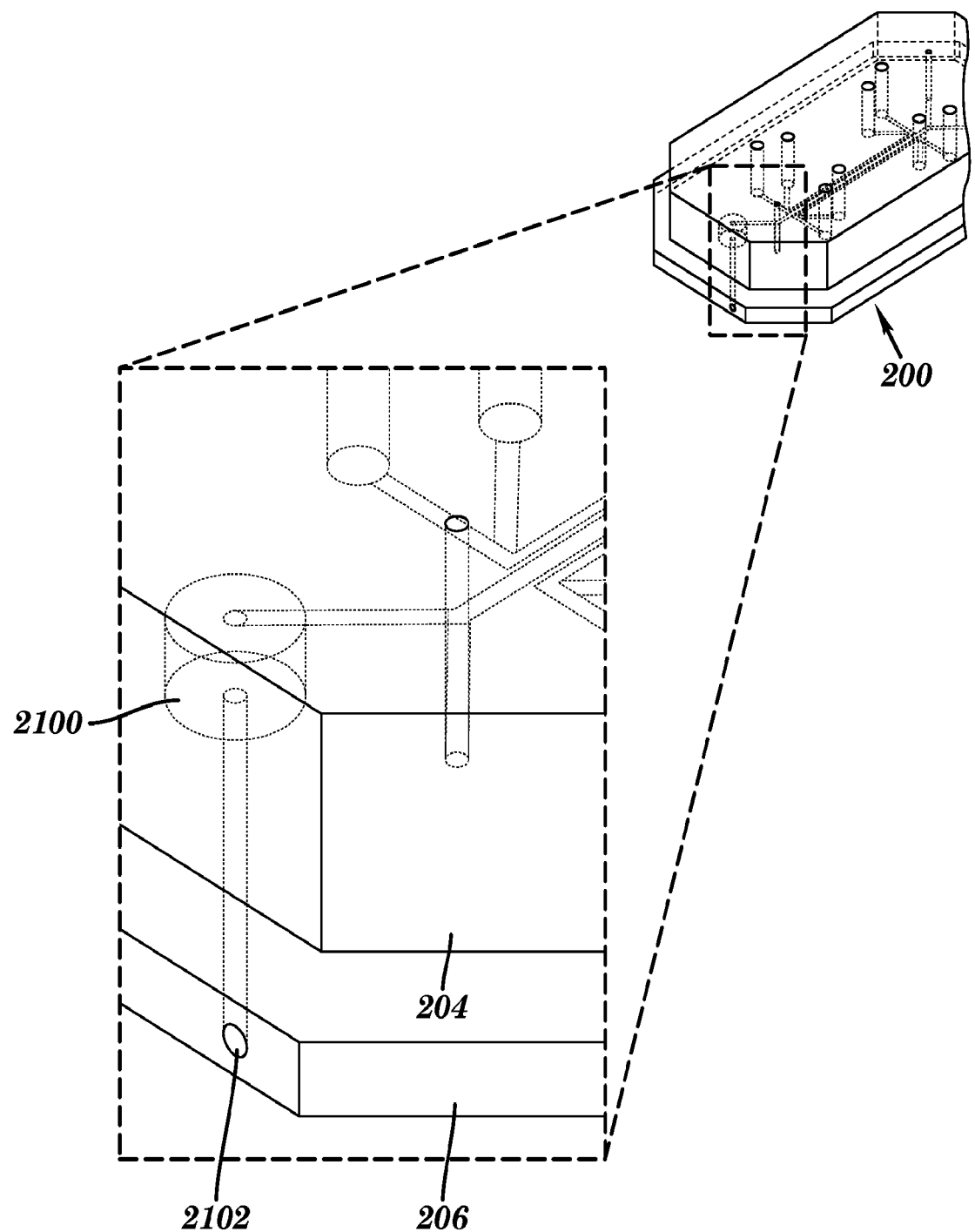
FIG. 21 illustrates integration of an inertial impactor into one embodiment of a device described herein for aerosol delivery of an agent.

The stimulants or condition-inducing agents as described herein (e.g., but not limited to, smoke particles, pathogens, cytokines such as pro-inflammatory agents, and/or drugs) can be delivered to the cells via diffusion from the microchannel, and/or as an aerosol or liquid through the mesochannel. The aerosol of molecules or pathogens can be generated on-chip, e.g., modifying the device described herein to integrate with an in vitro aerosol delivery device described in the PCT application serial nos. PCT/US12/37096 and PCT/US13/36569, the content of which are incorporated herein by reference. In one embodiment, as shown in FIG. 21, an inertial impactor 2100 as described in the PCT application serial no. PCT/US12/37096 can be placed in the bottom portion 206 of the device body and fluidically connects to the mesochannel in the top portion 204 of the device body. An access port 2102 can be placed on the lateral surface of the bottom portion of the device body and fluidically connects to the inertial impactor 2100. Thus, an aerosol produced from an aerosol-producing element can be introduced into the access port 2012, flowing through the inertial impactor 2100 where larger droplets of the aerosol are captured on the wall surface of the inertial impactor 2100 (e.g., to prevent blocking of the mesochannel), while smaller droplets of the aerosol continue to flow into the mesochannel.

As used herein, the term "immune cells" generally refer to resting and/or activated cells of the immune system involved in defending a subject against both infectious disease and foreign materials. Examples of immune cells include, without limitations, white blood cells including, e.g., neutrophils, eosinophils, basophils, lymphocytes (e.g., B-cells, T-cells, and natural killer cells), monocytes, macrophages (including, e.g., resident macrophages, resting macrophages, and activated macrophages); as well as Kupffer cells, histiocytes, dendritic cells, Langerhans cells, mast cells, microglia, and any combinations thereof. In some embodiment, immune cells include derived immune cells, for example, immune cells derived from lymphoid stem cells and/or myeloid stem cells.

In some embodiments, a tissue-specific condition, e.g., a disease-specific condition can be created by genetically modifying normal healthy cells, e.g., by silencing one or more genes, or over-expressing one or more genes. Methods of gene silencing include, but are not limited to, RNA interference (e.g., but not limited to small interfering RNA (siRNA), microRNA (miRNA), and/or short hairpin RNA (shRNA)), antisense oligonucleotides, ribozymes, triplex forming oligonucleotides, and the like. By way of example only, CF-associated airway cells can be derived from normal healthy cells by a knock-out or silencing of the cystic fibrosis transmembrane conductance regulator (CFTR) gene, in which the presence of at least one or more mutations is known to cause CF. For example, a CFTR-targeting shRNA, siRNA, antisense oligonucleotide, ribozyme, and/or triplex forming oligonucleotide can be introduced into normal healthy airway cells (e.g., primary cells), e.g., by a lentivirus system, in order to silence the CFTR gene, which can in turn result in a CF phenotype in the normal healthy cells.

In some embodiments, rhythm of airflow in the mesochannel of the device described herein can be adjusted, alone or in combination with a liquid medium flowing in the microchannel, for example, to model acute lung injuries—either physical or chemical, or with or without breathing, e.g., inhaled acids/alkali or ventilator-induced injuries.

In some embodiments where the devices described herein are used to create a disease-specific model, the devices can further comprise normal healthy cells (e.g., obtained from one or more healthy donors) cultured in a separate central channel, e.g., to create a baseline for comparison.

In some embodiments, the device can comprise both healthy and disease-specific cells. In some embodiments, the device can include only disease-specific cells.

Figure 11B:
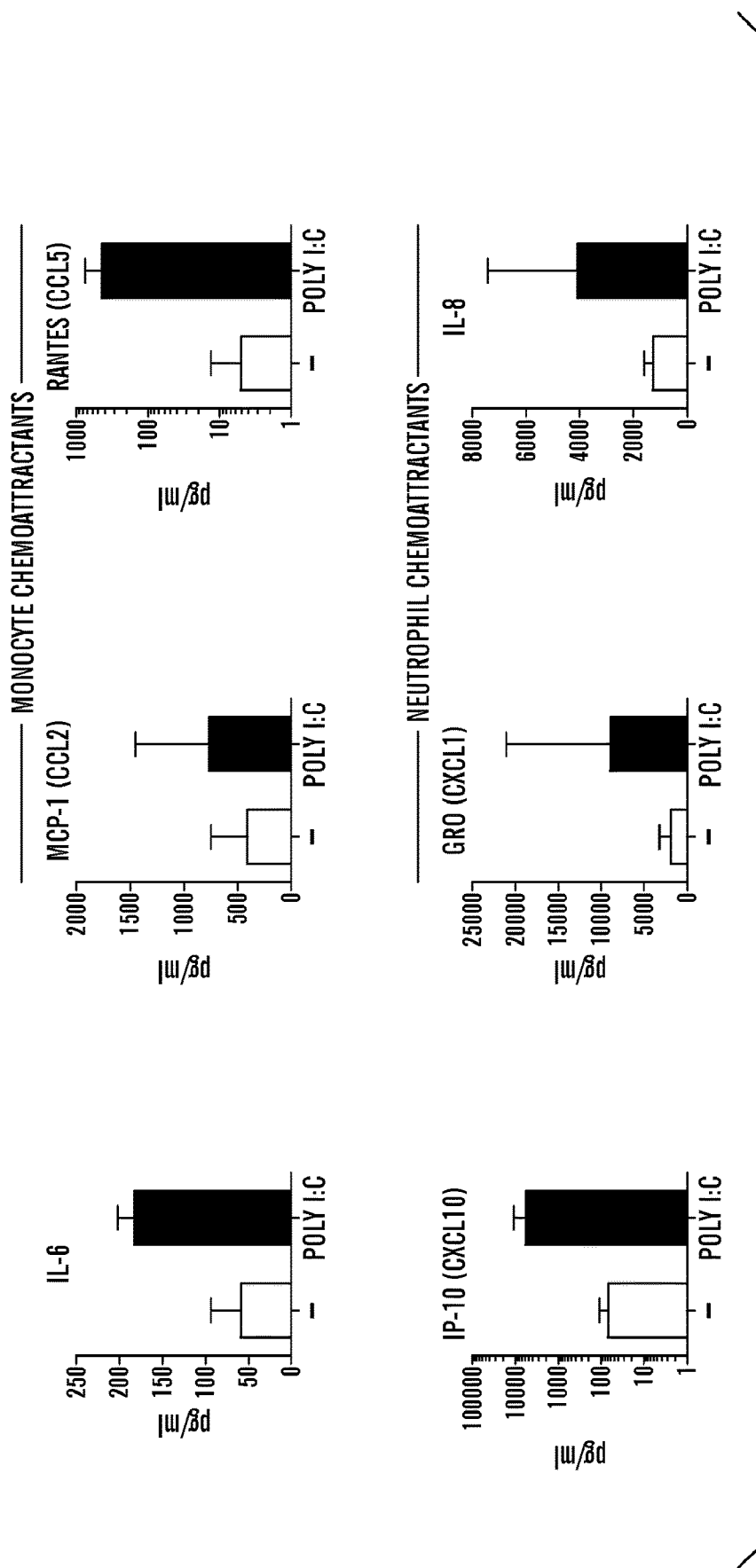
Figure 11C:
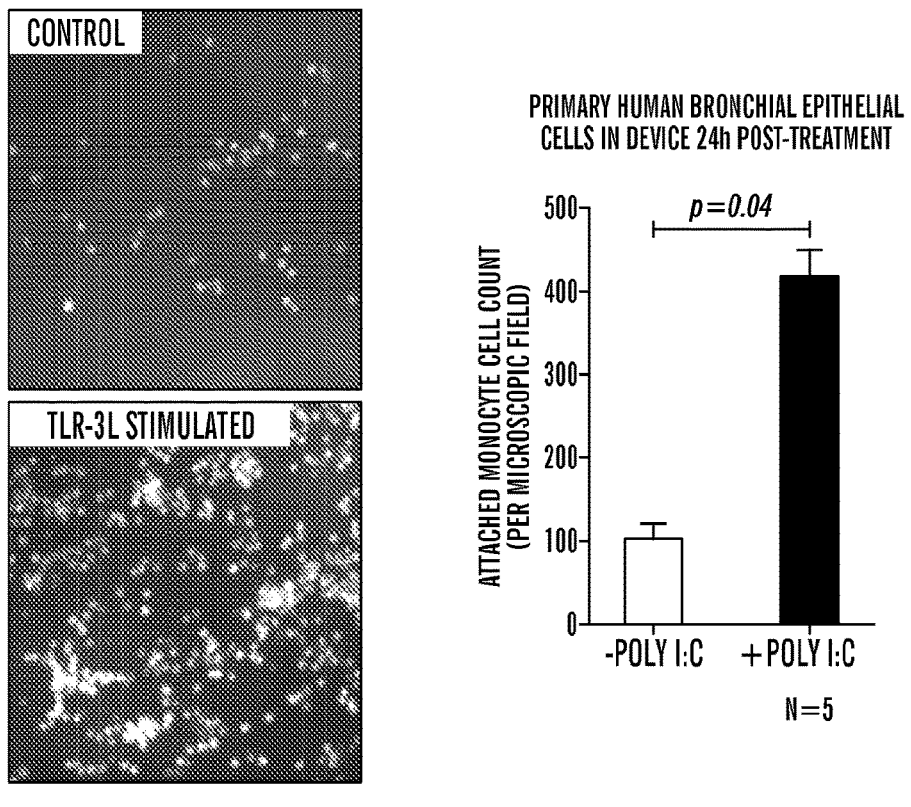
Figure 11D:
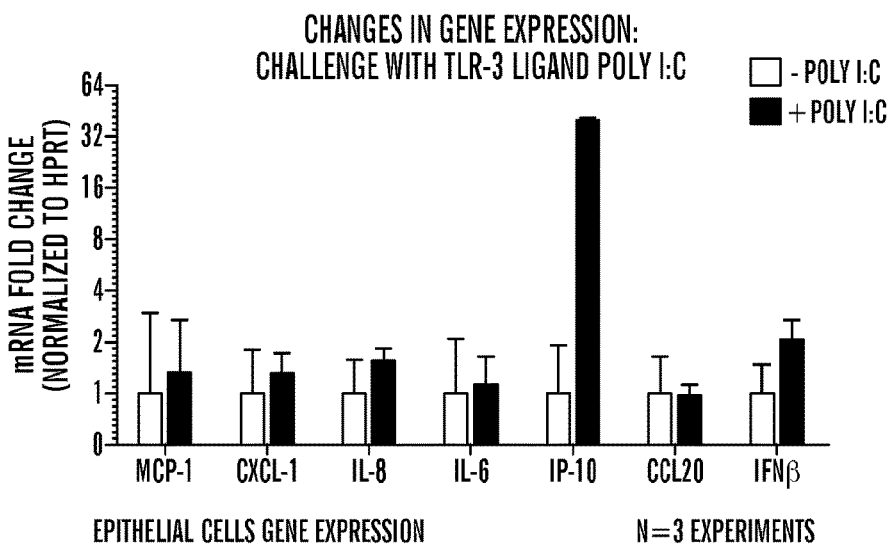

By way of example only, FIGS. 11A-11D illustrate the capability of using one embodiment of the device described herein to model a bacterial/viral infection. Upon differentiation of the airway epithelial cells into ciliated and mucous-secreting (goblet) cells, the differentiated cells can be challenged with pathogens (e.g., bacteria, fungus, and/or virus) and/or their associated stimuli (e.g., toll-like receptor 3 (TLR-3) ligand poly I:C, or pro-inflammatory agents, e.g., but not limited to TNF-α) in order to induce inflammation. A fluid comprising immune cells described herein (e.g., but not limited to, human monocytes) is introduced into the "blood vessel" channel, either with a static fluid or a flowing fluid, to determine effects of a pro-inflammatory agent-induced inflammation on cytokine/chemokine profiles of the differentiated cells and/or recruitment of immune cells described herein (e.g., but not limited to, monocytes and/or neutrophils). FIG. 11B shows that TLR-3 activation (flu-like situation) stimulates release of chemokines (e.g., monocyte chemoattractants and neutrophil chemoattractants) by the differentiated airway epithelial cells in the device. Cytokines or chemokines secreted into the fluid flowing in the mesochannel and/or microchannel can be measured by collecting from the outlet an aliquot of the fluid exiting the mesochannel and/or microchannel, which is then subjected to cytokine/chemokine expression analyses. FIG. 11C shows that TLR-3 stimulation enhances monocyte adhesion to differentiated epithelial cells. FIG. 11D shows that differentiated epithelial cells after stimulation with a TLR-3 ligand poly I:C significantly increases epithelial cells' gene expression of IP-10.

In some embodiments, tumor cells can be co-cultured with tissue-specific epithelial cells on the surface of the membrane facing the mesochannel, e.g., to study metastasis of a tissue-specific cancer. In one embodiment, lung cancer can be modeled by studying metastasis of tumor cells among the lung epithelial cells.

In some embodiments, a smoking lung-on-a-chip can be created by introducing a flow of smoke particles across the mesochannel to study effect of smoke on function and transformation of airway and/or lung epithelial cells cultured on one surface of the membrane facing the mesochannel, with or without endothelial cells lining another surface of the membrane facing the microchannel.

In some embodiments, the device described herein can be used to model at least a portion of an intestine or gut and induce intestinal cells to undergo morphogenesis of three-dimensional (3D) intestinal villi. For example, human intestinal epithelial cells (e.g., epithelial cells associated with an intestine such as duodenum, jejunum, ileum, cecum, colon and an appendix) can be cultured on the surface of the membrane facing the mesochannel, with or without endothelial cells lining another surface of the membrane facing the microchannel. By exposing the cultured cells to a physiological peristalsis-motion produced by stretching and retracting the membrane (e.g., about 5% to about 20% at a frequency of about 0.05 Hz to about 0.3 Hz) and flowing a liquid at low shear stress (e.g., 0.02 dyne cm$^{-2}$) in the mesochannel, the intestinal cells can grow into folds and form tubular projections (villi) projecting into the mesochannel (which is modeled as "intestinal lumen") to recapitulate the 3D structure. Formation of these intestinal villi-like structures can provide increased surface area that mimics the absorptive efficiency of human intestine, and/or enhanced cytochrome P450 3A4 isoform-based drug metabolizing activity (Kim et al., 2012 Lab Chip, 12: 2165-2174 and Kim et al., 2013 Integrative Biology, first published online 26 Jun. 2013; DOI: 10.1039/C3IB40126J). These functional features of human intestine recapitulated in a controlled microfluidic environment can be used for transport, absorption, and toxicity studies, drug testing as well as development of intestinal disease models and screening for therapeutic agents. Examples of intestinal diseases that can be modeled using the devices described herein include, but are not limited to, inflammatory bowel disease, Crohn's disease, ulcerative colitis, celiac disease, angiodysplasia, appendicitis, bowel twist, chronic functional abdominal pain, coeliac disease, colorectal cancer, diverticular disease, endometriosis, enteroviruses, gastroenteritis, Hirschsprung's disease, ileitis, irritable bowel syndrome, polyp, pseudomembranous colitis, or any combinations thereof.

Drugs intended for oral administration generally require good bioavailability in order to achieve therapeutic concentrations at the targeted site of action. Good bioavailability implies that an effective amount of drug is able to reach the systemic circulation. However, drug absorption via oral route can be affected by drug properties and/or the physiology of the gastrointestinal tract, including drug dissolution from the dosage form, the manner in which drug interacts with the aqueous environment and membrane, permeation across membrane, and irreversible removal by first-pass organs such as the intestine, liver, and lung (Martinez and Amidon, 2002 J Clin Pharmacol 42: 620-643). In particular, the majority of drug absorption generally occurs at the small intestine where the presence of villi and microvilli markedly increases the absorptive area. Thus, in some embodiments, the devices modeling the function of an intestinal villus structure as described above can be used to assess intestinal absorption, metabolism, and/or excretion of a test agent for the prediction of its bioavailability. In some embodiments, the devices modeling the function of the intestinal villus structure can be fluidically connected to another device mimicking a target tissue to be treated by the test agent.

In some embodiments, the devices described herein can be used to determine an effect of a test agent on the cells on one or both surface of the membrane. Effects of a test agent can include, but are not limited to, ciliary clearance, villi absorption, cell viability, permeability of a cell layer, cell morphology, protein expression, gene expression, cell adhesion, adhesiveness of immune cells, cell differentiation, cytokine or chemokine production, inflammation, or any combinations thereof.

In accordance with some embodiments of the invention, the devices described herein can be used to determine an efficacy of a test agent upon exposure of the cells on one or both surfaces of the membrane to the test agent. For example, the efficacy of a test agent can be determined by measuring response of the cells and/or at least one component present in a fluid (e.g., gaseous and/or liquid fluid) within the device or present in an output fluid (e.g., gaseous and/or liquid fluid) from the device after exposure to the test agent. As used herein, the term "efficacy" generally refers to ability of a test agent to produce a desired effect or outcome. Depending on the nature and/or type of the test agents, examples of desired effects or outcomes include, but are not limited to, therapeutic effect, cytotoxicity, cell growth, cell differentiation, improved or reduced cell function or phenotype (e.g., but not limited to, ciliary clearance, permeability of a cell layer, cell migration, expression and/or secretion of a protein or cytokine that can be affected by cell exposure to the test agent), and any combinations thereof. The term "therapeutic effect" as used herein refers to a consequence of treatment, the results of which are judged to be desirable and beneficial.

In accordance with some embodiments of the invention, the devices described herein can be used to determine toxicity of a test agent upon exposure of the cells on one or both surfaces of the membrane to the test agent. For example, the toxicity of a test agent can be determined by measuring response of the cells and/or at least one component present in a fluid (e.g., gaseous and/or liquid fluid) within the device or present in an output fluid (e.g., gaseous and/or liquid fluid) from the device after exposure to the test agent. As used herein, the term "toxicity" refers to ability of a test agent to induce or cause any adverse and/or side effect on a cell and/or even cell death. For example, the toxicity of a test agent can be characterized by its ability to induce or cause an adverse effect on cell function and/or phenotype, including, but not limited to, alteration in cell metabolism, mutagenicity, carcinogenicity, teratogenicity, DNA damage, protein or membrane damage, cell energy depletion, mitochondrial damage, genotoxicity, apoptosis, cell death, cell rupture, and any combinations thereof.

In accordance with some embodiments of the invention, the devices described herein can be used to determine a mechanism of action upon exposure of the cells on one or both surfaces of the membrane to the test agent. For example, the mechanism of action can be determined by measuring response of the cells and/or at least one or more components present in a fluid (e.g., gaseous and/or liquid fluid) within the device or present in an output fluid (e.g., gaseous and/or liquid fluid) from the device after exposure to the test agent. As used herein, the term "mechanism of action" refers generally to a cellular pathway or biological interaction through which an agent exerts its biological effect on a cell. For example, when an agent is a drug substance, mechanism of action can refer to the biochemical interaction through which a drug substance produces its pharmacological effect. Depending on the nature and/or type of test agents, the mechanism of action can be associated with any art-recognized cellular pathways or biological interaction, e.g., including, but not limited to, protein synthesis, cell migration, chromatin regulation/epigenetics or acetylation, MAPK signaling, apoptosis, autophagy, PI3K/Akt signaling, translation control, cell cycle/checkpoint, Jak/Stat Pathway, NF-B signaling, TGF-/Smad signaling, lymphocyte signaling, angiogenesis, cytoskeletal signaling, cell adhesion, cell metabolism, cell development and/or differentiation, tyrosine kinase/adaptors, protein stability, protein folding, nuclear receptor signaling, and any combinations thereof. Accordingly, in some embodiments, a mechanism of action can encompass a mechanism of efficacy and/or toxicity of a test agent.

In accordance with some embodiments of the invention, the tissue-specific epithelial cells on the surface of the membrane facing the mesochannel can be contacted with a test agent. The test agent can be delivered to the cells as an aerosol or liquid through the mesochannel or "airway lumen" channel and/or via diffusion from the microchannel or "blood vessel" channel. As described earlier, an aerosol (e.g., of the test agent) can be generated on-chip, e.g., modifying the device described herein to integrate with an in vitro aerosol delivery device described in the PCT application serial nos. PCT/US12/37096 and PCT/US13/36569, the content of which are incorporated herein by reference.

Any test agent can be introduced into the device described herein to determine its effect on the cells. Examples of the test agent can include, but are not limited to, proteins, peptides, antigens, nanoparticles, environmental toxins or pollutant, cigarette smoke, chemicals or particles used in cosmetic products, small molecules, drugs or drug candidates, vaccine or vaccine candidates, aerosols, inflammatory molecules, naturally occurring particles including pollen, chemical weapons, single or double-stranded nucleic acids, viruses, bacteria and unicellular organisms.

Effects of the test agent on the cells can be determined by measuring response of the cells on at least one side of the membrane to the test agent, the gaseous fluid exiting the first sub-channel, the liquid fluid exiting the second sub-channel, or any combinations thereof; and comparing the measured response with the cells not contacted with the test agent. Various methods to measure cell response are known in the art, including, but not limited to, cell labeling, immunostaining, optical or microscopic imaging (e.g., immunofluorescence microscopy and/or scanning electron microscopy), spectroscopy, gene expression analysis, cytokine/chemokine secretion analysis, metabolite analysis, polymerase chain reaction (PCR), immunoassays, ELISA, gene arrays, spectroscopy, immunostaining, electrochemical detection, polynucleotide detection, fluorescence anisotropy, fluorescence resonance energy transfer, electron transfer, enzyme assay, magnetism, electrical conductivity (e.g., trans-epithelial electrical resistance (TEER)), isoelectric focusing, chromatography, immunoprecipitation, immunoseparation, aptamer binding, filtration, electrophoresis, use of a CCD camera, mass spectroscopy, or any combination thereof. Detection, such as cell detection, can be carried out using light microscopy with phase contrast imaging and/or fluorescence microscopy based on the characteristic size, shape and refractile characteristics of specific cell types. Greater specificity can be obtained using optical imaging with fluorescent or cytochemical stains that are specific for individual cell types or microbes.

In some embodiments, adhesion of immune cells that are introduced through the "blood vessel" channel to the endothelium or membrane can be measured to determine effects of a test agent on immune response.

Figure 12A:
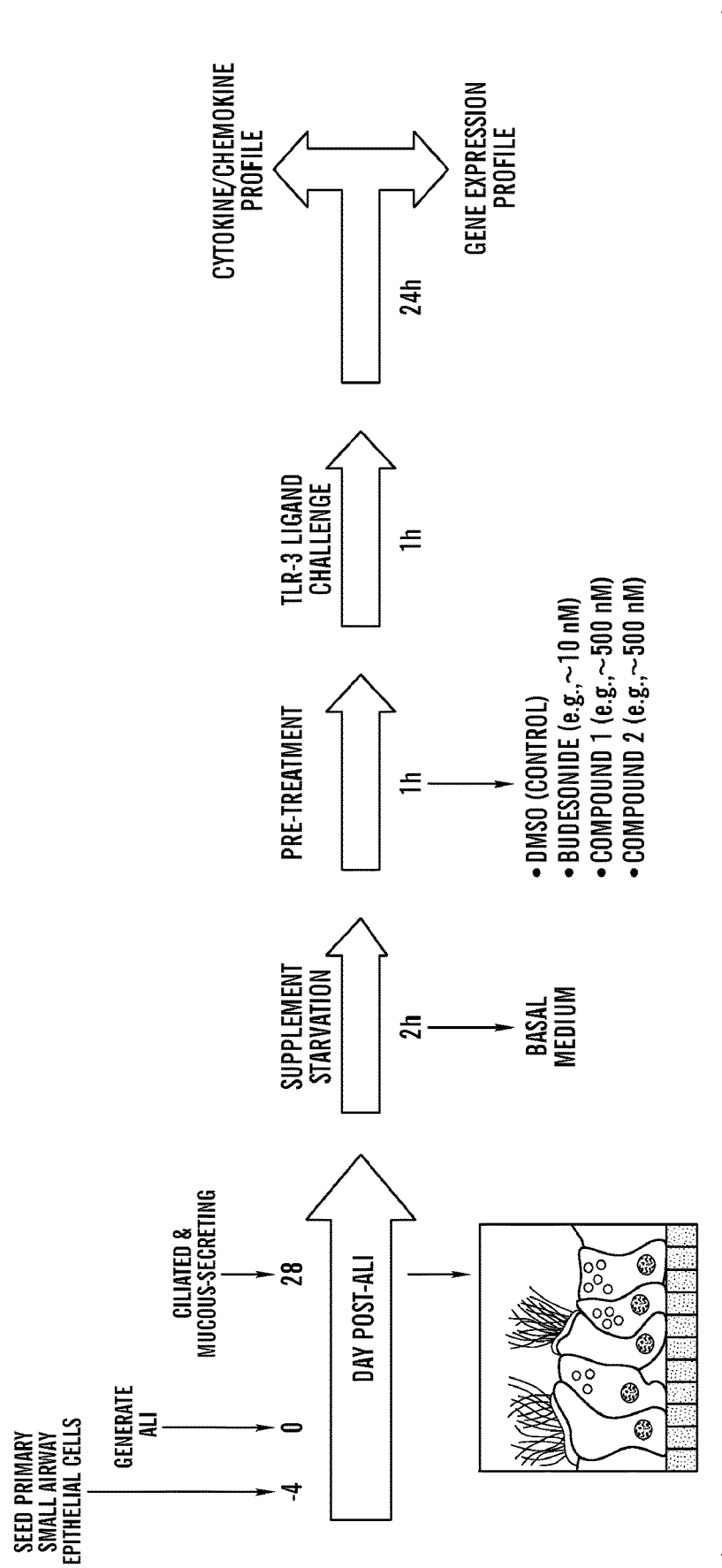
Figure 12B:
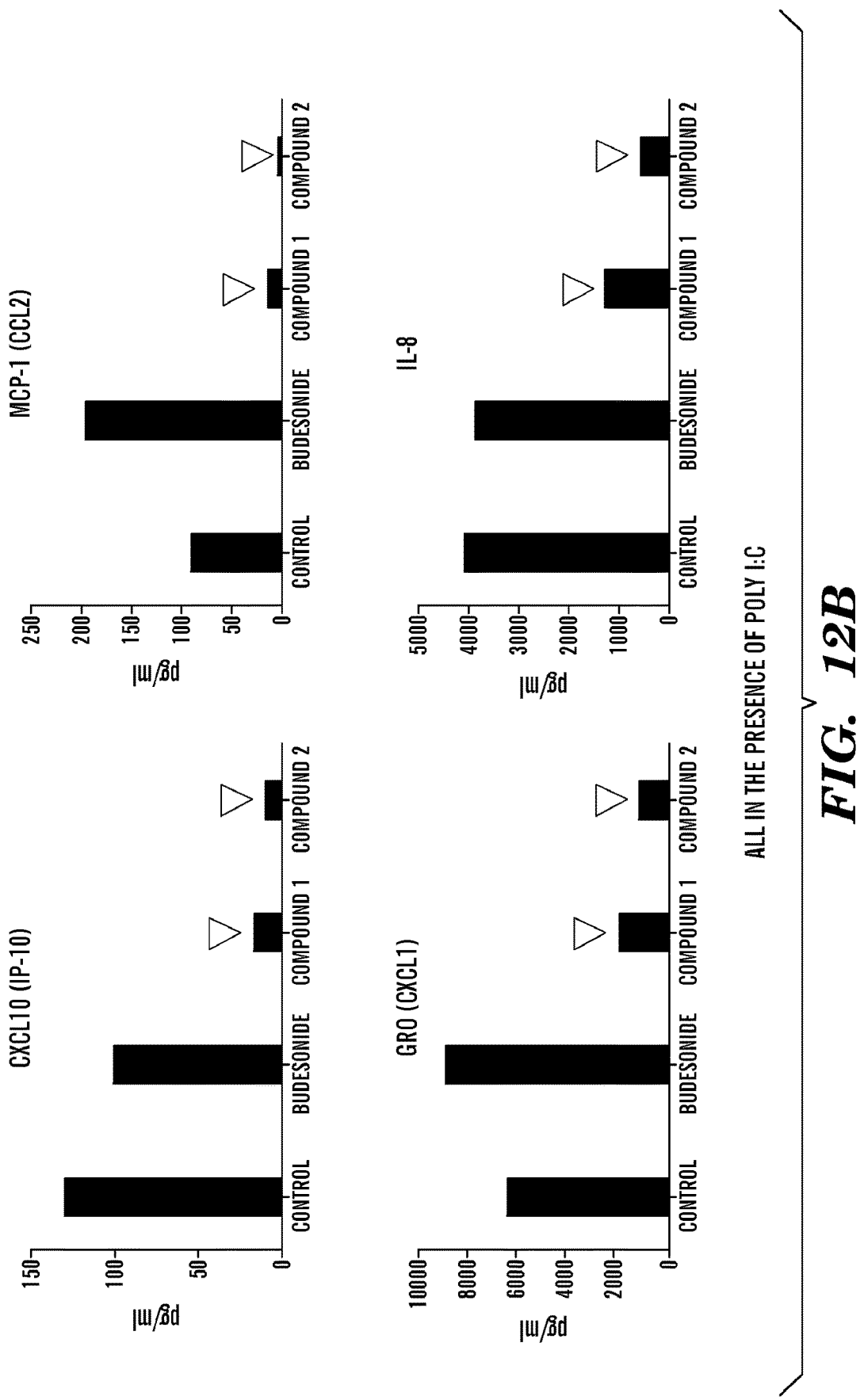
Figure 12E:
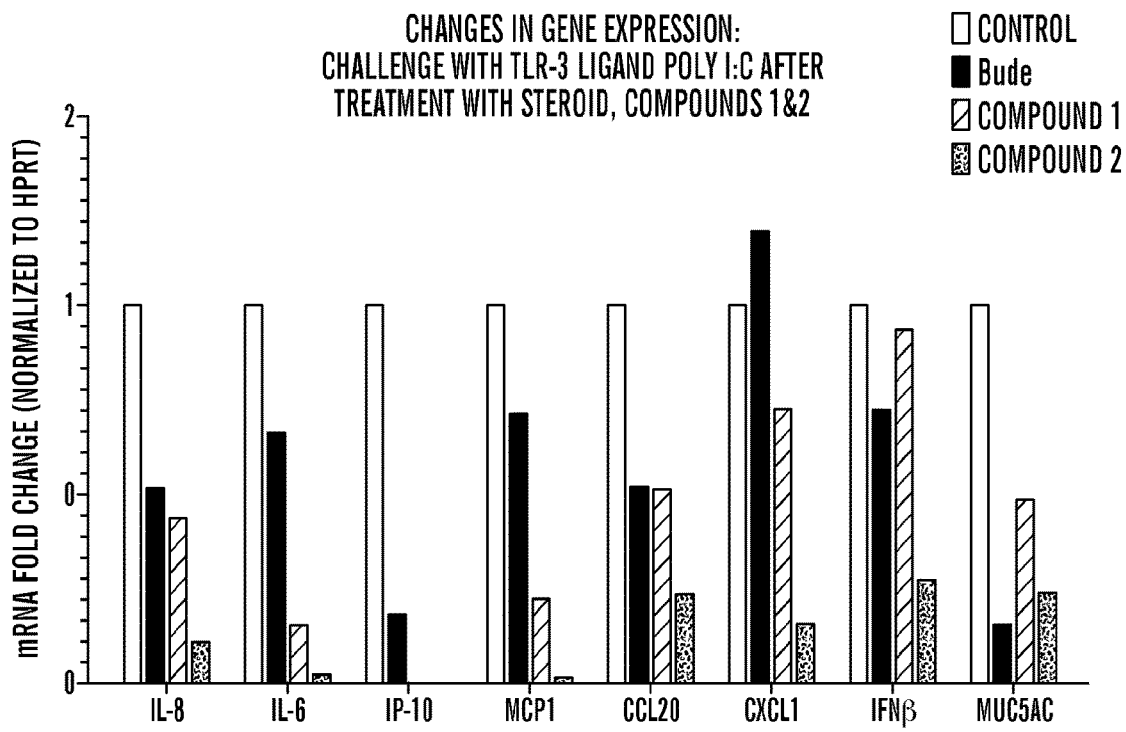
Figure 12F:
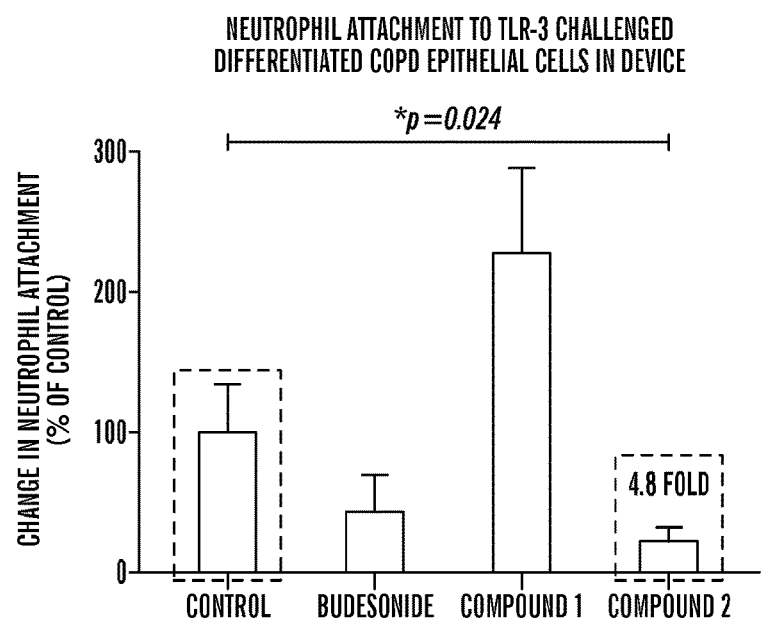

In some embodiments where the tissue-specific cells to be assayed are adapted to be condition-specific (e.g., disease-specific), exposure of the tissue-specific cells to a test agent followed by determination of the effect of the test agent on the cells can facilitate identification of a therapeutic agent for treatment of the condition. For example, FIGS. 12A-12D illustrate an exemplary method of evaluating an effect of different agents on differentiated airway epithelial cells and optionally immune cells during an infection in a device in accordance with an embodiment, and experimental data resulting therefrom. FIG. 12A is a schematic diagram illustrating an example method to evaluate an effect of different agents during an infection simulated in the device. Primary human epithelial cells from chronic obstructive pulmonary disease (COPD) patients are seeded on the membrane in the mesochannel (an "airway lumen" channel) for differentiation into ciliated and/or mucus-secreting cells following the differentiation method as described in FIG. 5A. Upon differentiation of the COPD epithelial cells, another surface of the membrane (facing the microchannel, the "blood vessel" channel) can be seeded with or without endothelial cells. The cells in the device can be optionally starved using basal medium, followed by treatment with different test agents (e.g., DMSO as a control, budesonide, and BRD4 inhibitor compounds 1 and 2 obtained from a pharmaceutical company). The agents can be delivered to the differentiated epithelial cells via diffusion from the "blood vessel" channel. The pre-treated differentiated COPD epithelial cells are then challenged with TLR-3 ligand poly I:C (e.g., about 10 µg/mL delivered as an aerosol or liquid flowing in the mesochannel) to stimulate TLR-3 and mimic viral infection. Secreted cytokines and chemokines from the differentiated COPD epithelial cells can be quantified in the flow-through of the "blood vessel" channel and/or from the apical wash of the "airway lumen" channel. In some embodiments, a fluid comprising immune cells (e.g., human monocytes) can be introduced into the "blood vessel" channel, either with a static fluid or a flowing fluid, to determine effects of TLR-3-induced inflammation on recruitment of immune cells (e.g., monocytes and/or neutrophils). FIG. 12B shows production of representative cytokines and chemokines (e.g., monocyte chemoattractants and neutrophil chemoattractants) by the differentiated COPD epithelial cells (pretreated with different agents prior to exposure to a TLR-3 ligand poly I:C) and released into the "blood vessel" channel, and indicates that compound 2 is more potent than compound 1 in reducing cytokine/chemokine secretion in response to the simulated viral infection. In addition, FIG. 12F shows that compound 2 is more potent in reducing neutrophil adhesion, whereas compound 1 did not have such effect, and such result is consistent with and validates the pharmaceutical company's in-house data on potency of compound 2 in reducing inflammation. Thus, the devices and methods described herein can be used to screen drugs.

In some embodiments where the tissue-specific cells are patient-specific, exposure of the patient-specific cells to a test agent, followed by determination of the effect of the test agent on the cells can facilitate identification of a personalized treatment for a subject.

In some embodiments where the tissue-specific cells are patient population-specific, exposure of the patient population-specific cells to a test agent, followed by determination of the effect of the test agent on the cells can facilitate identification of a treatment specified for that particular patient population. As used herein, the term "patient population-specific" refers to cells collected from a population of patients sharing at least one or more phenotypes and/or characteristics (e.g., but not limited to, specific gene mutation, ethnicity, gender, life styles, BMI, resistance to treatment, and any combinations thereof) other than the disease or disorder.

In some embodiments, one or more devices described herein can be used in combination with a pharmacokinetic (PK) model, a pharmacodynamic (PD) model, or a PK-PD model to quantitatively analyze the effect of an agent to be tested. For example, a series of devices, each modeling a tissue, e.g., one for gut, one for liver, and another one for heart, can be connected to provide a microphysiological system that can be used to determine the fate of an agent administered into the system. The term "pharmacokinetics" is used herein in accordance with the art, and refers to the study of the action of agents, e.g., drugs, in the body, for example, the effect and duration of drug action, the rate at which they are absorbed, distributed, metabolized, and eliminated by the body etc. (e.g. the study of a concentration of an agent, e.g., a drug, in the serum of a patient following its administration via a specific dose or therapeutic regimen). The term "pharmacodynamics" is used in accordance with the art, and refers to the study of the biochemical and physiological effects of an agent, e.g., a drug, on a subject's body or on microorganisms such as viruses within or on the body, and the mechanisms of drug action and the relationship between drug concentration and effect (e.g. the study of a pathogen, e.g., a virus, present in a patient's plasma following one or more therapeutic regimens). Methods for PK-PD modeling and analysis are known in the art. See, e.g., Bonate, P. L. (2006). Pharmacokinetic-Pharmacodynamic Modeling and Simulation. New York, Springer Science & Business Media; Gabrielsson, J. and D. Weiner (2000); and Pharmacokinetic and Pharmacodynamic Data Analysis: Concepts and Applications. Stockholm, Swedish Pharmaceutical Press. For example, a PK model can be developed to model a microphysiological system comprising a plurality of the devices described herein, wherein each device can model a different tissue that can produce an effect (e.g., absorption, metabolism, distribution and/or excretion) on an agent to be administered. To construct a PK model for a device described herein, mass balance equations describing the flow in, flow out, and metabolism of an agent can be set up for each mesochannel and microchannel. A PD model can be integrated into each device described herein, describing the kinetics of potential cell response (e.g., inflammation, cytokine release, ligand binding, cell membrane disruption, cell mutation and/or cell death) in each device that mimics a tissue or an organ. This in vitro/in silico system, combining one or more devices described herein with an integrated PK-PD modeling approach, can be used to predict drug toxicity in a more realistic manner than conventional in vitro systems. In some embodiments, one or more of the devices described herein can be used to quantify, estimate or gauge one or more physical-chemical, pharmacokinetic and/or pharmacodynamic parameters. Various physical-chemical, pharmacokinetic and pharmacodynamic parameters are known in the art, including, for example, the ones discussed in the aforementioned references. Exemplary physical-chemical, pharmacokinetic and pharmacodynamic parameters include, but are not limited to, permeability, log P, log D, volume of distribution, clearances (including intrinsic clearances), absorption rates, rates of metabolism, exchange rates, distribution rates and properties, excretion rates, IC50, binding coefficients, etc.

In some embodiments, the devices described herein can be used for target identification/validation. For example, the devices described herein can be used to mimic a tissue-specific condition as described herein (e.g., a disease or disorder) in order to elucidate the molecular mechanism underlying a disease or a condition, the identification of candidate target molecules and the evaluation of said target molecules. In some embodiments, use of genetically modified cells, e.g., by silencing or over-expressing a specific gene, in the devices described herein can be used to identify target molecules for a specific disease. Once such a validated target molecule, e.g., ligand, receptor, transcription factor, and/or enzyme, which is herein referred to also as target, is identified, drug candidates directed to the target (e.g., suppression or activation) can be tested. The drug candidate can be introduced to the disease-specific cells in the devices described herein and cell response to the drug candidate can be measured to validate the identified target. This can also promote drug discovery for a specific disease or condition. In many cases such drug candidates can be members of a compound library which can comprise synthetic and/or natural compounds. Combinatorial libraries can also be used.

Similarly, the devices described herein can be used to mimic a physiological environment under which a drug fails during a clinical trial. Thus, mechanism of action of the drug can be studied to facilitate identification of a new drug target.

In some embodiments, the devices described herein can be cultured with animal cells (e.g., but not limited to, pig cells, rabbit cells, dog cells, mouse cells, and/or rat cells) to determine response of the animal cells to an agent introduced into the devices described herein. The measured response of the animal cells in the devices can then be correlated with the actual response occurred in vivo when the agent is administered to a living animal (e.g., a pig, a rabbit, a dog, a mouse, and/or a rat). By identifying the correlation between the in vitro and in vivo responses in one or more animal models, one can extrapolate or predict effect of the agent on a human subject in vivo, based on the measured responses of the human cells to the agent in the devices. Additionally or alternatively, a therapeutic dose of an agent for a human subject can be determined accordingly.

Figure 15:
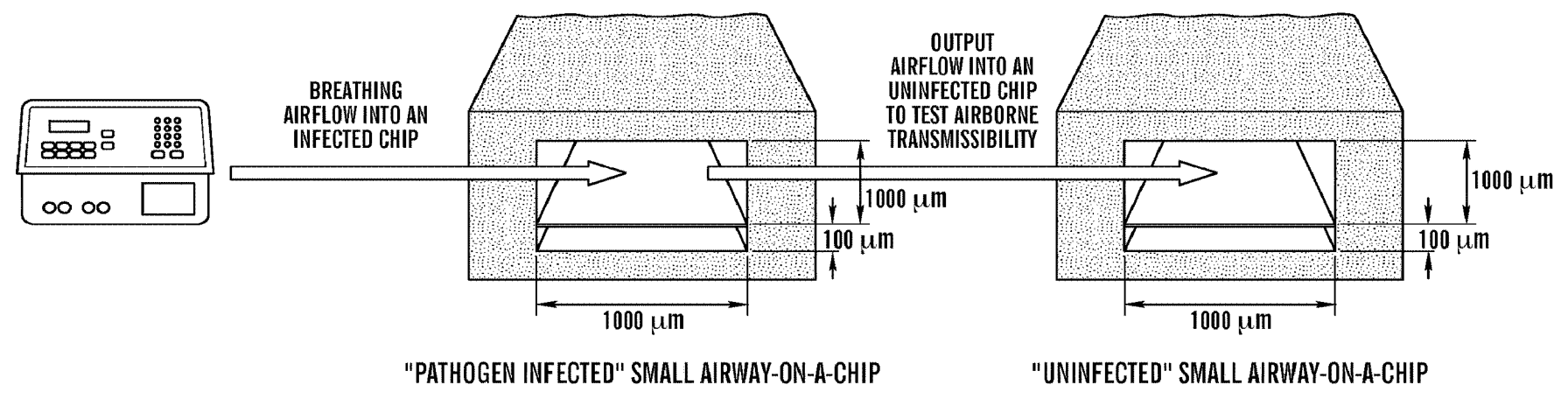

In some embodiments, the combination of simulated breathing through the "airway lumen" channel and ability to connect to two or more devices described herein (e.g., in series and/or in parallel) can allow studying how airborne pathogens, e.g., but not limited to virus, bacteria, respiratory syncytial virus, influenza virus, or Mycobacterium Tuberculosis (MTB), from a "pathogen-infected" device can infect one or more "non-infected" devices, as shown in FIG. 15. In these embodiments, a first device comprising pathogen-infected epithelial cells can be adapted to connect, e.g., in series and/or in parallel, to at least one a second device comprising non-infected cells. The distance between two devices can be adjusted to simulate closeness of contact between two subjects and/or control the rate of airborne pathogen transmission between two subjects.

In some embodiments, the pathogen-infected epithelial cells can be obtained from one or more infected subjects. In some embodiments, the non-infected cells can be obtained from one or more normal healthy subjects and/or subjects with a disease or disorder such as a respiratory disease. An air flow can then be directed from the "airway lumen" mesochannel of the first device to the "airway lumen" mesochannel of the second device. Response of the non-infected cells (including immune cells) upon exposure to the air flow from the first device as well as response of the infected cells (including immune cells) can be measured to determine transmissibility of airborne pathogens.

In some embodiments, the "airborne pathogen transmission" model as described above can be used to assess infectivity or virulence of a pathogenic strain such as a strain of virus. For example, at least two or more (e.g., 2, 3, 4, 5, 6, 7, 8, 9, 10 or more) "non-infected" devices can be connected in series and/or in parallel. In each "non-infected" device, one surface of the membrane facing the mesochannel can comprise lung-associated cells (e.g., lung cells, nasal cells, tracheal cells, airway cells, and/or bronchial cells) while the other surface of the membrane can comprise blood vessel-associated cells or not. Then, a pathogenic strain to be assessed can be introduced into the mesochannel of one of the connected devices. Recruitment and/or infiltration of immune cells can be measured in each device to determine infectivity or virulence of the introduced pathogenic strain. Typically, a viral infection can induce an immune response, which can include, e.g., increased immune cell recruitment and/or infiltration.

The lung-associated or other appropriate tissue-specific cells to be infected in each "non-infected" device can be collected from a different subject or subject population having distinct phenotypes (e.g., by age, sex, genotypes, life-style such as smoking, frequent exercises, and diets, diseases or disorders). For example, children and elderly are generally more prone to a viral infection, and subjects with a respiratory disease such as asthmatic patients can suffer from viral exacerbation of the respiratory disease when they are exposed to a virus. Accordingly, by measuring the response of immune cells from different subject populations in the individual connected devices, one can also identify risk populations for a pathogenic strain.

In some embodiments, the "airborne pathogen transmission" model as described herein can be used to assess risk of a novel (i.e., new in humans) virus strain acquiring the ability to spread easily and efficiently in humans. Ten evaluation criteria that Centers for Disease Control and Prevention (CDC) currently use to measure the potential pandemic risk posed by influenza A viruses (Influenza Risk Assessment Tool accessible at www.cdc.gov/flu/pandemic-resources/tools/risk-assessment.htm) can be used as guidelines to determine the potential pandemic risk associated with emergence of a novel virus strain using the devices described herein. For example, a novel influenza virus can be introduced to "non-infected human" devices comprising human cells to determine if human-to-human transmission can occur and/or how frequently and easily the transmission can occur after a direct and prolonged "contact" or connection between the devices. In addition or alternatively, a novel influenza virus can be introduced to "non-infected animal" devices comprising various animal cells to determine what kind of animals can be impacted by the influenza virus, because the likelihood of human contact with some animals can be higher (e.g., domestic birds vs. wild birds), which can influence the pandemic risk. Additionally or alternatively, a novel influenza virus can be introduced to "non-infected" devices comprising different tissue-specific cells to determine the types of tissues and/or cells the virus is more prone or susceptible to infection (e.g., nose tissue and cells vs. deep lung tissue and cells).

In some embodiments, the "airborne pathogen transmission" model as described above can also be used to determine prophylactic or therapeutic efficacy of an anti-pathogen agent (e.g., anti-viral agent) or a vaccine against an airborne pathogen. For example, for prophylactic agents or vaccines, the normal healthy cells can be pre-exposed to an agent or vaccine of interest and then exposed to an airflow contaminated with the airborne pathogens from the first device. By measuring the response of the non-infected cells and optional immune cells to the airborne pathogens, efficacy (e.g., immunogenicity) and/or safety of the agent or vaccine can be determined. Similarly, for therapeutic agents or vaccines (e.g., anti-viral vaccines), the pathogen-infected cells in the first device can be treated with an agent or vaccine of interest before directing an air flow from the first device to the second device comprising non-infected cells. A reduction or an inhibition of the transmissibility of the airborne pathogens is indicative of the efficacy of a therapeutic agent or vaccine.

Additional examples of using one or more embodiments of the devices described herein for development of a vaccine, e.g., a mucosal vaccine, are described in detail below.

Uses of the devices described herein to determine transmissibility of airborne pathogens, identify risk populations for airborne pathogens and/or to develop agents or vaccines against airborne pathogens are provided herein as illustrative examples. As one of skill in the art will appreciate, the "airborne pathogen transmission" model described herein can be readily adapted to mimic transmission of a body fluid-borne pathogen such as hepatitis B, hepatitis C, and/or HIV/AIDS between subjects. For example, a droplet of a liquid fluid from an "infected" device can be introduced to a liquid fluid in a "non-infected" device. Response of the non-infected cells (including immune cells) upon exposure to the infected liquid fluid as well as response of the infected cells (including immune cells) can be measured to determine transmissibility of body fluid-borne pathogens, e.g., pathogens that can be transmitted through blood, semen, vaginal secretions, cerebrospinal fluid, synovial fluid, pleural fluid, pericardial fluid, peritoneal fluid, amniotic fluid, saliva, or any combinations thereof.

In some embodiments, the exclusion of fluorescently labeled large molecules (e.g. dextrans of different weight or FITCs) can be quantitated to determine the permeability of the membrane and thus assess the barrier function of the epithelium, e.g., in a tissue-specific condition (e.g., but not limited to, COPD, asthma, and smoking). For example, flowing a fluid containing fluorescently labeled large molecules (e.g., but not limited to, inulin-FITC) into a mesochannel cultured with differentiated epithelium can provide a non-invasive barrier measurement. As a functional tight junction barrier will prevent large molecules from passing through the epithelium from the mesochannel to the microchannel, the absence of the detection of the fluorescently labeled large molecules in the microchannel is indicative of a functional barrier function of the epithelium.

Additionally, histological, biochemical, microfluorimetric and/or functional techniques can be employed to demonstrate formation of a functional airway-endothelial that reproduces the key structural organization of its in vivo counterpart on the membrane 208.

In an example, the gas exchange function of the tissue-tissue interface self assembled on membrane 208 can be determined by injecting different fluids, each having their own oxygen partial pressures and blood, into the respective mesochannel and microchannel 250A, 250B, whereby the mesochannel 250A acts as the "airway lumen" compartment and the microchannel 250B acts as the "microvascular" or "blood vessel" compartment. A blood-gas measurement device preferably within the device 200 is used to measure the level of oxygen in the blood in the respective sections 250A, 250B before and after the passing of the blood through the device. For example, blood can flow through the channel 250B while air is being injected into the upper channel 250A, whereby the exiting air is collected and measured to determine the oxygen level using an oximeter. Oximeters can be integrated with the existing system or as a separate unit connected to the outlet port of one or more central sub-channels. In an embodiment, air or another medium with aerosols containing drugs or particulates can flow through the device, whereby the transport of these drugs or particulates to the fluid flowing in the "microvascular" microchannel (e.g., blood, culture medium) via the membrane is then measured. In some embodiments, pathogens or cytokines can be added to the air or gaseous medium side and then the adhesion of immune cells introduced in the microvascular microchannel to nearby capillary endothelium and their passage along with edema fluid from the blood side to the airway side, as well as pathogen entry into blood, can be measured.

Since the functionality of an epithelium requires polarization of constituent cells, the structure of the membrane can be visualized using transmission electron microscopy, immunohistocytochemistry, confocal microscopy, or other appropriate means to monitor the polarization of the airway epithelial cell side of the membrane 208. In an airway mimic embodiment, a florescent dye can be applied to the mesochannel and microchannel 250A, 250B to determine pulmonary surfactant production by the airway epithelium at the membrane 208. In particular, airway epithelial cells on the membrane 208 can be monitored by measuring the fluorescence resulting from cellular uptake of the fluorescence dye that specifically labels intracellular storage of pulmonary surfactant (e.g. quinacrine) or using specific antibodies.

One of the unique capabilities of the device 200 allows development of in vitro models that simulate inflammatory responses of the airway or bronchus at the organ or tissue level to allow study of how immune cells migrate from the blood, through the endothelium and into the airway compartment. One way this is achieved can be by controlled and programmable microfluidic delivery of pro-inflammatory agents described herein (e.g. but not limited to, IL-1β, TNF-α, IL-8, silica micro- and nanoparticles, pathogens) to the differentiated airway epithelial cells in the mesochannel 250A as well as whole human blood flowing or culture medium containing circulating or static immune cells described herein (e.g., white blood cells such as neutrophils, and monocytes) in the microchannel 250B. Electrical resistance and short circuit current across the membrane can be monitored to study changes in the vascular permeability, extravasation of fluid and cell passage into the airway space during inflammatory responses. Microscopy imaging, e.g., fluorescence microscopy, can be used to visualize dynamic cell motile behavior during the extravasation response.

Figure 16:
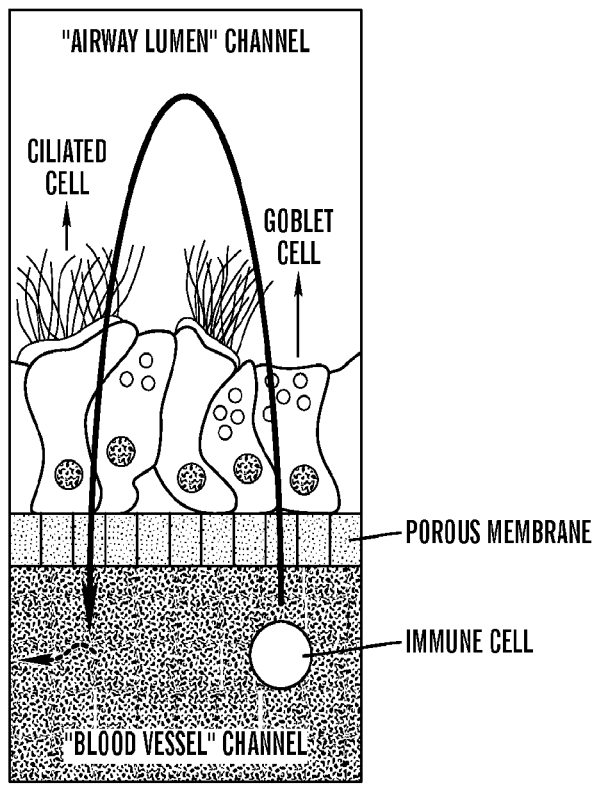
FIG. 16 is a schematic diagram showing a cross-sectional view of a device according to one embodiment that can be used to form a mucosal immunity platform to study immune cell recruitment, maturation and activation and drainage. Immune cells are introduced into the "blood vessel" channel, either with a static fluid or a flowing fluid, and their behavior (e.g., trans-epithelial migration, maturation, activation and/or drainage back to the "blood vessel" channel) are monitored. The platform can be used to study role of airway mucosal surface in innate and adaptive immunity.

In some embodiments, the device described herein can be used to develop a mucosal immunity platform, e.g., to study immune cell recruitment, maturation, and activation, cell killing, and drainage (e.g., as shown in FIG. 16). Mucosal immunity is a form of protective immunity that acts at mucosal surfaces of the gastrointestinal and/or respiratory tracts to prevent colonization by ingested and inhaled microbes. There are mucosa-associated lymphoid tissues (MALT), such as tonsils and Peyer's Patches, that act to prevent infection. The mucosal layers are usually lined or protected by epithelial barriers. This layer of epithelium serves as the first line of defense against microbes. If microbes breach the epithelial layer, mucosal tissues are the sites of immunological activity. When epithelial cells detect presence of dangerous microbial components such as pathogen-associated molecular patterns, they send cytokine and chemokine signals to underlying mucosal cells such as macrophages and dendritic cells to trigger an immune response. Epithelial cells are able to regulate these responses so that undesirable responses are not activated by normal flora that could lead to mucosal inflammation. Accordingly, in some embodiments, to develop a mucosal immunity model, the surface of the membrane facing the mesochannel can be coated with gastrointestinal or respiratory epithelial cells to mimic a portion of a gastrointestinal or respiratory tract, while another surface of the membrane facing the microchannel can be coated with mucosal cells or immune cells such as macrophages and dendritic cells.

In some embodiments, the mucosal immunity model can be used to develop a mucosal vaccine (e.g., a mucosal vaccine to Strep) and/or optimize a vaccine dosage. The regulation of the epithelial layer has been presenting a challenge for mucosal vaccine dosage. For example, if the concentration of a mucosal vaccine is not high enough, the mucosal immunity will not recognize it as a threat and no immunity would develop. Finding the correct concentration has been a challenge and been difficult to measure because the vaccine can be diluted in mucosal secretions, captured in the mucus, attacked by proteases and nucleases, and can be excluded by epithelial barriers. Using the mucosal immunity model developed in one or more embodiments of the device described herein, epithelial cells or differentiated epithelial cells can be pre-exposed to different vaccine test candidates and/or various dosages of the same, and then challenged with a microbe against which is supposed to be vaccinated. By measuring the response of the epithelial cells and/or immune cells to the microbes, efficacy (e.g., immunogenicity), safety and/or optimum dosage of the vaccine test candidates can be determined.

Depending on the administration routes of a vaccine, e.g., but not limited to, intranasal, oral, intramuscular, subcutaneous, or intradermal, the membrane of the device described herein can be coated with different cell types to mimic the microenvironment where the vaccine exerts an effect. For example, as described above, the membrane can be coated with respiratory epithelial cells for development of intranasal vaccines, or gastrointestinal epithelial cells for oral vaccines.

As discussed above, in some embodiments, the devices described herein can be used to model an infectious disease, to determine transmissibility of an infectious pathogen, and/or to identify effective agents (e.g., drugs molecules, and/or vaccine) for therapeutic and/or prophylactic treatments. Various methods can be used to detect the presence or absence of infection in the devices described herein. For example, where fluorescently-labeled (e.g., GFP-expressing) pathogens (e.g., virus or bacteria) are used, normal healthy cells that are infected with the fluorescently-labeled pathogens can be directly followed over time or real-time by fluorescent microscopy. Alternatively or additionally, the infection-suspected cells can be immuno-stained for viral/bacterial proteins and detected by immunofluorescence. In some embodiments where virus or bacteria can produce a cytopathic effect on infected cells, e.g., causing damages to the infected cells' epithelium, the integrity of the infection-suspected cells' epithelium can be examined over time under light or fluorescent microscopy.

Additional methods that can be used to detect the presence or absence of infection in the device described herein can include, e.g., but are not limited to, quantification of pathogen (e.g., virus) replication, which, for example, can be measured by collecting effluent of infection-suspected cells from the mesochannel (termed "apical wash", e.g., using cell culture medium) and/or effluent from the microchannel (termed "basal medium") and then titrating pathogen growth over time in the apical wash and/or basal medium using a plaque assay. Alternatively or additionally, cytokines/chemokines secreted by the infection-suspected cells can be determined by analysis of effluents collected from the mesochannel and/or the microchannel. Some cytokines/chemokines such as CXCL10 or IL-8 can be significantly elevated in the device with the infected cells as compared to non-infected cells. In some embodiments where cellular antiviral proteins such as MX proteins can be up-regulated following infection of the cultures, the cellular antiviral proteins such as MX proteins can be stained in the infection-suspected cells for immunofluorescence detection. In some embodiments, expression analysis of at least one or more genes that are known to be upregulated following pathogen (e.g., viral/bacterial) infection (as compared to non-infected cells) can be performed on the infection-suspected cells, e.g., by microarray and/or quantitative real-time polymerase chain reaction (qRT-PCR).

Without wishing to be limiting, in other embodiments, the device 200 can also be used to examine how nanomaterials or particulates behave with respect to the airway-tissue interface. In particular, nanomaterials (e.g. silica nanoparticles, superparamagnetic nanoparticles, gold nanoparticles, single-walled carbon nanotubes) can be applied to the airway surface of the membrane 208 to investigate potential toxic effects of nanomaterials on airway or endothelial cells grown on the membrane 208, as well as their passage from the airway channel into the blood channel. For instance, sensors 120 can be used to monitor transmigration of nanomaterials through tissue barriers formed on the membrane 208 and nanomaterial-induced changes in barrier functions such as gas exchange and fluid/ion transport.

The device 200 permits direct analysis of a variety of important areas of airway/bronchial biology and physiology including but not limited to gas exchange, fluid/ion transport, inflammation response, infection (e.g., viral or bacterial infection), edema/respiratory distress syndrome, cancer and metastasis development, fungal infection, ciliary clearance of particulates, epithelial differentiation, cytokine production, drug delivery as well as drug screening, biodetection, and pulmonary mechanotransduction. In addition, the device 200 allows for accurately modeling biological tissue-tissue interfaces found in other physiological systems that require taller channel height to support optimal cell culture, form a stratified structure, and/or reduce shear on the cells, including, but not limited to, skin, liver, gut, heart, intestine, choroid plexus, gastrointestinal tract, glomerulus, and cancerous tumor microenvironment. As stated above, more than one device 200 can be multiplexed and automated to provide high-throughput analysis of cell and tissue responses to drugs, chemicals, particulates, toxins, pathogens or other environmental stimuli for drug, toxin and vaccine screening, as well as toxicology and biodetection applications. The device can be used for studying complex tissue and organ physiology in vitro, as well as tissue and organ engineering in vivo with biocompatible or biodegradable devices.

In an embodiment, the device 200 can be used to produce artificial tissue layers therein. In the embodiment, two or more different types of cells are applied on opposing surfaces of the membrane 208 and grown under conditions that mimic the appropriate physiological environments. Additionally or alternatively, a pressure differential can be applied between the central channel and at least one of the operating channels which causes the channel walls to move and thus causes the membrane 208 to undergo expansion/contraction along its plane.

To further demonstrate the device's capabilities to reconstitute the integrated organ-level responses in the airway, a more sophisticated model can be developed that incorporates circulating or static blood-borne immune cells and reproduced the key steps of airway inflammation. Generally, inflammatory responses in the airway involve a highly coordinated multistep cascade of epithelial production and release of early response cytokines, activation of vascular endothelium through upregulation of leukocyte adhesion molecules and subsequent leukocyte infiltration from the pulmonary microcirculation into the airway space. To simulate this process, the apical surface of the airway epithelium can be first stimulated, e.g., with tumor necrosis factor-α (TNF-α), which is a potent pro-inflammatory mediator, and endothelial activation can be examined, e.g., by measuring the expression of intercellular adhesion molecule-1 (ICAM-1). In response to TNF-α stimulation of the airway tissue, the endothelial cells on the opposite side of the membrane can generally increase their surface expression of ICAM-1. Furthermore, the activated endothelium can support capture and firm adhesion of human neutrophils flowing in the vascular microchannel, which did not adhere in the absence of cytokine exposure. Treatment of the epithelial cells with low doses of TNF-α can result in weak activation of the endothelium, which caused captured neutrophils to roll continuously in the direction of flow without being arrested. The transmigrated neutrophils then emigrate onto the apical surface of the airway epithelium preferentially through paracellular junctions and are retained on the epithelial layer in spite of fluid flow and cyclic stretching. These sequential events can replicate the entire process of neutrophil recruitment from the microvasculature to the airway compartment, which is a hallmark of airway inflammation.

In another example, the device 200 utilizes the porous membrane 208, whereby airway or bronchial epithelial cells are grown on one side of the membrane 208 facing the mesochannel 250A and endothelial cells, fibroblasts, smooth muscle cells, and/or pericytes are maintained on the other side of the membrane 208 facing the microchannel 250B. During the operation of the device 200, these two cells layers communicate with each other through passage of chemical and molecular cues through the pores on the membrane 208. This communication can be monitored and analyzed to understand how the cells function differently in a tissue-tissue interface, with or without physiological mechanical simulation, and compared to when grown as single tissue types in isolation as in standard tissue culture systems. By monitoring changes in cell and tissue physiology, as well as passage of chemicals, molecules, particulates and cells across this tissue-tissue interface, information is obtained which can be used to produce more effective drugs or therapies, to identify previously unknown toxicities, and to significantly shorten the timescale of these development processes. In particular, the behavior of cells in such a controlled environment allows researchers to study a variety of physiological phenomena taking place in the systems mentioned above that can not be recreated using conventional in vitro culture techniques. In other words, the device 200 functions to create a monitorable artificial blood or liquid-air barrier outside a patient's body and in a controllable environment that still retains key physiological functions and structures of the airway or bronchus. It should be noted that although the device above is described in terms of mimicking airway or bronchus function, the device can easily be configured to mimic other physiological systems such as peristalsis and absorption in the gastrointestinal tract containing living microbial populations, perfusion and urine production in the kidney, function of the blood-brain barrier, effects of mechanical deformation on skin aging, bone marrow-microvessel interface with hematopoietic stem cell niche, and the like.

In some embodiments, provided herein is an organ mimic device in accordance with an embodiment that contains three or more parallel channels separated by two membranes. The organ mimic device can include at least one mesochannel 250A and at least one microchannel 250B. For example, in one embodiment, one mesochannel 250A can be positioned between two microchannels 250B. In some embodiments, the device can further comprise operating channels as described herein. The overall central channel includes multiple membranes positioned along respective parallel x-y planes which separate the central channel into three distinct central sub-channels (e.g., two microchannels and one mesochannel). The membranes can be permeable and rigid or flexible. Positive and/or negative pressurized media can be applied via operating channels to create a pressure differential to thereby cause the membranes to stretch and retract along their respective planes in parallel.

Details of membrane surface treatment and types of media which can be applied to the membrane and/or through the mesochannel 250A and microchannel 250B in operating the device will now be discussed. The membrane including, e.g., the porous membrane, can be coated with substances such as various cell adhesion promoting substances or ECM proteins, such as fibronectin, laminin, various collagen types, glycoproteins, vitronectin, elastins, fibrin, proteoglycans, heparin sulfate, chondroitin sulfate, keratin sulfate, hyaluronic acid, fibroin, chitosan, or any combinations thereof. In general, one or more cell adhesion molecules is coated on one surface of the membrane 208 whereas another cell adhesion molecule is applied to the opposing surface of the membrane 208, or both surfaces can be coated with the same cell adhesion molecules. In some embodiments, the ECMs, which can be ECMs produced by cells, such as primary cells or embryonic stem cells, and other compositions of matter are produced in a serum-free environment.

In an embodiment, one coats the membrane with a cell adhesion factor and/or a positively-charged molecule that are bound to the membrane to improve cell attachment and stabilize cell growth. The positively charged molecule can be selected from the group consisting of polylysine, chitosan, poly(ethyleneimine) or acrylics polymerized from acrylamide or methacrylamide and incorporating positively-charged groups in the form of primary, secondary or tertiary amines, or quaternary salts. The cell adhesion factor can be added to the membrane and is fibronectin, laminin, various collagen types, glycoproteins, vitronectin, elastins, fibrin, proteoglycans, heparin sulfate, chondroitin sulfate, keratin sulfate, hyaluronic acid, tenascin, antibodies, aptamers, or fragments or analogs having a cell binding domain thereof. The positively-charged molecule and/or the cell adhesion factor can be covalently bound to the membrane. In another embodiment, the positively-charged molecule and/or the cell adhesion factor are covalently bound to one another and either the positively-charged molecule or the cell adhesion factor is covalently bound to the membrane. Also, the positively-charged molecule or the cell adhesion factor or both cam be provided in the form of a stable coating non-covalently bound to the membrane.

In an embodiment, the cell attachment-promoting substances, matrix-forming formulations, and other compositions of matter are sterilized to prevent unwanted contamination. Sterilization can be accomplished, for example, by ultraviolet light, filtration, gas plasma, ozone, ethylene oxide, and/or heat. Antibiotics can also be added, particularly during incubation, to prevent the growth of bacteria, fungi and other undesired micro-organisms. Such antibiotics include, by way of non-limiting example, gentamicin, streptomycin, penicillin, amphotericin and ciprofloxacin.

In some embodiments, the membrane and/or other components of the devices described herein can be treated using gas plasma, charged particles, ultraviolet light, ozone, or any combinations thereof.

Cells:

In another embodiment, at least one side of the membrane is coated or cultured with cell cultures, including without limitation, primary cell cultures, established cell lines, or stem cell cultures, such as ESC, iPSCs attached to ECM substances and/or cell adhesion molecules, if any. Any prokaryotic and eukaryotic cells including, e.g., but not limited to, human cells, animal cells, insect cells, plant cells, bacteria, fungus, and/or parasites, can be used in the devices described herein. In some embodiments, mammalian cells (e.g., a human or an animal) are used in the device described herein. Usually an animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, and avian species, e.g., chicken, emu, ostrich and birds. In some embodiments, the animal cells include cells from fish, reptiles and amphibians. The cells can be derived from a normal healthy subject (e.g., a human or an animal) or a subject (e.g., a human or an animal) determined to have a specific type or stage of a disease or disorder.

In accordance with some embodiments of the invention, cells can be derived from an invertebrate. For example, invertebrates can include, but are not limited to, protozoa, annelids, mollusks, crustaceans, arachnids, echinoderms, and insects.

In some embodiments, insects cells can be used in the devices described herein. In some embodiments, plant cells can be used in the devices described herein. In some embodiments, cells derived from fungi can be used in the devices described herein. Examples of fungi can include, but are not limited to mushrooms, mold, and yeast. In accordance with some embodiments of the invention, cells derived from microorganisms can be used in the devices described herein. Examples of microorganisms can include, but are not limited to, bacteria and viruses.

In an embodiment, the cells attached to either side of the membrane can include epithelial cells, endothelial cells, fibroblasts, smooth muscle cells, basal cells, ciliated cells, columnar cells, goblet cells, muscle cells, immune cells, neural cells, hematopoietic cells, lung cells (e.g., alveolar epithelial cells, airway cells (e.g., small airway cells, and large airway cells), bronchial cells, tracheal cells, and nasal epithelial cells), gut cells, brain cells, stem cells, skin cells, liver cells, heart cells, spleen cells, kidney cells, pancreatic cells, intestinal cells, keratinocytes, dermal keratinocytes, reproductive cells, blood cells (including, e.g., white blood cells, red blood cells, platelets and hematopoietic stem and progenitor cells) and any combinations thereof. In other embodiments, the primary cells or cell lines can be fibroblast cells, which include without limitation, human fetal fibroblast cells. In some embodiments, the stem cells of the stem cell cultures are embryonic stem cells. The source of embryonic stem cells can include without limitation mammals, including non-human primates and humans. Non-limiting examples of human embryonic stem cells include lines BG01, BG02, BG03, BG01v, CHA-hES-1, CHA-hES-2, FCNCBS1, FCNCBS2, FCNCBS3, H1, H7, H9, H13, H14, HSF-1, H9.1, H9.2, HES-1, HES-2, HES-3, HES-4, HES-5, HES-6, hES-1-2, hES-3-0, hES-4-0, hES-5-1, hES-8-1, hES-8-2, hES-9-1, hES-9-2, hES-101, hICM8, hICM9, hICM40, hICM41, hICM42, hICM43, HSF-6, HUES-1, HUES-2, HUES-3, HUES-4 HUES-5, HUES-6, HUES-7 HUES-8, HUES-9, HUES-10, HUES-11, HUES-12, HUES-13, HUES-14, HUESS-15, HUES-16, HUES-17, 13, 14, 16, 13.2, 13.3, 16.2, J3, J3.2, MB01, MB02, MB03, Miz-hES1, RCM-1, RLS ES 05, RLS ES 07, RLS ES 10, RLS ES 13, RLS ES 15, RLS ES 20, RLS ES 21, SA01, SA02, and SA03. In an embodiment, the stem cells of the stem cell cultures are induced pluripotent stem cells.

In an embodiment, the cell cultures can be cell cultures such as primary cell cultures or stem cell cultures which are serum-free. In some these embodiments, a serum-free primary cell ECM is used in conjunction with a primary cell serum-free medium (SFM). Suitable SFM include without limitation (a) EPILIFE® Serum Free Culture Medium supplemented with EPILIFE® Defined Growth Supplement and (b) Defined Keratinocyte-SFM supplemented with Defined Keratinocyte-SFM Growth Supplement, all commercially available from Gibco/Invitrogen (Carlsbad, Calif., US). In some of these embodiments, a serum-free stem cell ECM is used in conjunction with stem cell SFM. Suitable SFM include without limitation STEMPRO® hESC Serum Free Media (SFM) supplemented with basic fibroblast growth factor and .beta.-mercaptoethanol, KNOCKOUT™. D-MEM supplemented with KNOCKOUT™. Serum Replacement (SR), STEMPRO®. MSC SFM and STEMPRO®. NSC SFM, all commercially available from Gibco/Invitrogen (Carlsbad, Calif., US).

In an embodiment, the compositions can also be xeno-free. A composition of matter is said to be "xeno-free" when it is devoid of substances from any animal other than the species of animal from which the cells are derived. In an embodiment, the cell cultures which can be cell cultures such as primary cell cultures or stem cell cultures are xeno-free. In these embodiments, a xeno-free ECM which can be an ECM such as a primary cell ECM or ECM designed specifically to support stem cell growth or differentiation. These matrices can be specifically designed to be xeno-free.

In an embodiment, the cell cultures are primary cells or stem cells cultured in a conditioned culture medium. In other embodiments, the culture medium is an unconditioned culture medium.

In an embodiment, the cell culture conditions are completely defined. In these embodiments, one uses a completely defined cell culture medium in the fluid chambers. Suitable media include without limitation, for primary cells, EPILIFE®. Serum Free Culture Medium supplemented with EPILIFE®. Defined Growth Supplement, and, for stem cells, STEMPRO®. hESC SFM, all commercially available from Gibco/Invitrogen, Carlsbad, Calif., US.

To study the effects of a test agent, e.g., pharmaceuticals, environmental stressors, pathogens, toxins and such, one can add these into the desired cell culture medium suitable for growing the cells attached to the membrane in the channel. Thus, one can introduce pathogens, such as bacteria, viruses, aerosols, various types of nanoparticles, toxins, gaseous substances, and such into the culture medium which flows in the chambers to feed the cells.

A skilled artisan will also be able to control the pH balance of the medium according to the metabolic activity of the cells to maintain the pH in a suitable level for any cell or tissue type in question. Monitors and adjustment systems to monitor and adjust pH can be inserted into the device.

The membrane is preferably coated on one or both sides with cells, molecules or other matter, whereby the device provides a controlled environment to monitor cell behavior along and/or between the mesochannel and the microchannel via the membrane. One can use any cells from a multicellular organism in the device. For example, human body comprises at least 210 known types of cells. A skilled artisan can easily construct useful combinations of the cells in the device. Cell types (e.g., human) which can be used in the devices include, but are not limited to cells of the integumentary system including but not limited to Keratinizing epithelial cells, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell); Wet stratified barrier epithelial cells, such as Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts); Exocrine secretory epithelial cells, such as Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion), Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), pancreatic endocrine cells, Paneth cell of small intestine (lysozyme secretion), intestinal epithelial cells, Types I and II pneumocytes of lung (surfactant secretion), and/or Clara cell of lung.

One can also coat the membrane with Hormone secreting cells, such as endocrine cells of the islet of Langerhands of the pancreas, Anterior pituitary cells, Somatotropes, Lactotropes, Thyrotropes, Gonadotropes, Corticotropes, Intermediate pituitary cell, secreting melanocyte-stimulating hormone; and Magnocellular neurosecretory cells secreting oxytocin or vasopressin; Gut and respiratory tract cells secreting serotonin, endorphin, somatostatin, gastrin, secretin, cholecystokinin, insulin, glucagon, bombesin; Thyroid gland cells such as thyroid epithelial cell, parafollicular cell, Parathyroid gland cells, Parathyroid chief cell, Oxyphil cell, Adrenal gland cells, chromaffin cells secreting steroid hormones (mineralcorticoids and gluco corticoids), Leydig cell of testes secreting testosterone, Theca interna cell of ovarian follicle secreting estrogen, Corpus luteum cell of ruptured ovarian follicle secreting progesterone, Granulosa lutein cells, Theca lutein cells, Juxtaglomerular cell (renin secretion), Macula densa cell of kidney, Peripolar cell of kidney, and/or Mesangial cell of kidney.

Additionally or alternatively, one can treat at least one side of the membrane with Metabolism and storage cells such as Hepatocyte (liver cell), White fat cell, Brown fat cell, Liver lipocyte. One can also use Barrier function cells (Lung, Gut, Exocrine Glands and Urogenital Tract) or Kidney cells such as Kidney glomerulus parietal cell, Kidney glomerulus podocyte, Kidney proximal tubule brush border cell, Loop of Henle thin segment cell, Kidney distal tubule cell, and/or Kidney collecting duct cell.

Other cells that can be used in the device include Type I pneumocyte (lining air space of lung), Pancreatic duct cell (centroacinar cell), Nonstriated duct cell (of sweat gland, salivary gland, mammary gland, etc.), principal cell, Intercalated cell, Duct cell (of seminal vesicle, prostate gland, etc.), Intestinal brush border cell (with microvilli), Exocrine gland striated duct cell, Gall bladder epithelial cell, Ductulus efferens nonciliated cell, Epididymal principal cell, and/or Epididymal basal cell.

One can also use Epithelial cells lining closed internal body cavities such as Synovial cell (lining joint cavities, hyaluronic acid secretion), Serosal cell (lining peritoneal, pleural, and pericardial cavities), Squamous cell (lining perilymphatic space of ear), Squamous cell (lining endolymphatic space of ear), Columnar cell of endolymphatic sac with microvilli (lining endolymphatic space of ear), Columnar cell of endolymphatic sac without microvilli (lining endolymphatic space of ear), Dark cell (lining endolymphatic space of ear), Vestibular membrane cell (lining endolymphatic space of ear), Stria vascularis basal cell (lining endolymphatic space of ear), Stria vascularis marginal cell (lining endolymphatic space of ear), Cell of Claudius (lining endolymphatic space of ear), Cell of Boettcher (lining endolymphatic space of ear), Choroid plexus cell (cerebrospinal fluid secretion), Pia-arachnoid squamous cell, Pigmented ciliary epithelium cell of eye, Nonpigmented ciliary epithelium cell of eye.

The following cells can be used in the device by adding them to the surface of the membrane in culture medium. These cells include cells such as Ciliated cells with propulsive function such as Respiratory tract ciliated cell, Oviduct ciliated cell (in female), Uterine endometrial ciliated cell (in female), Rete testis ciliated cell (in male), Ductulus efferens ciliated cell (in male), and/or Ciliated ependymal cell of central nervous system (lining brain cavities).

One can also plate cells that secrete specialized ECMs, such as Ameloblast epithelial cell (tooth enamel secretion), Planum semilunatum epithelial cell of vestibular apparatus of ear (proteoglycan secretion), Organ of Corti interdental epithelial cell (secreting tectorial membrane covering hair cells), Loose connective tissue fibroblasts, Corneal fibroblasts (corneal keratocytes), Tendon fibroblasts, Bone marrow reticular tissue fibroblasts, Other nonepithelial fibroblasts, Pericyte, Nucleus pulposus cell of intervertebral disc, Cementoblast/cementocyte (tooth root bonelike cementum secretion), Odontoblast/odontocyte (tooth dentin secretion), Hyaline cartilage chondrocyte, Fibrocartilage chondrocyte, Elastic cartilage chondrocyte, Osteoblast/osteocyte, Osteoprogenitor cell (stem cell of osteoblasts), Hyalocyte of vitreous body of eye, Stellate cell of perilymphatic space of ear, Hepatic stellate cell (Ito cell), and/or Pancreatic stellate cell.

Additionally or alternatively, contractile cells, such as Skeletal muscle cells, Red skeletal muscle cell (slow), White skeletal muscle cell (fast), Intermediate skeletal muscle cell, nuclear bag cell of muscle spindle, nuclear chain cell of muscle spindle, Satellite cell (stem cell), Heart muscle cells, Ordinary heart muscle cell, Nodal heart muscle cell, Purkinje fiber cell, Smooth muscle cell (various types), Myoepithelial cell of iris, Myoepithelial cell of exocrine glands can be used in the present device.

The following cells can also be used in the present device: Blood and immune system cells, such as Erythrocyte (red blood cell), Megakaryocyte (platelet precursor), Monocyte, Connective tissue macrophage (various types), Epidermal Langerhans cell, Osteoclast (in bone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types). One can use these cells as single cell types or in mixtures to determine effects of the immune cells in the tissue culture system.

One can also treat the membranes with one or more Nervous system cells, Sensory transducer cells such as Auditory inner hair cell of organ of Corti, Auditory outer hair cell of organ of Corti, Basal cell of olfactory epithelium (stem cell for olfactory neurons), Cold-sensitive primary sensory neurons, Heat-sensitive primary sensory neurons, Merkel cell of epidermis (touch sensor), Olfactory receptor neuron, Pain-sensitive primary sensory neurons (various types); Photoreceptor cells of retina in eye including Photoreceptor rod cells, Photoreceptor blue-sensitive cone cell of eye, Photoreceptor green-sensitive cone cell of eye, Photoreceptor red-sensitive cone cell of eye, Proprioceptive primary sensory neurons (various types); Touch-sensitive primary sensory neurons (various types); Type I carotid body cell (blood pH sensor); Type II carotid body cell (blood pH sensor); Type I hair cell of vestibular apparatus of ear (acceleration and gravity); Type II hair cell of vestibular apparatus of ear (acceleration and gravity); and/or Type I taste bud cell.

One can further use Autonomic neuron cells such as Cholinergic neural cell (various types), Adrenergic neural cell (various types), Peptidergic neural cell (various types) in the present device. Further, sense organ and peripheral neuron supporting cells can also be used. These include, for example, Inner pillar cell of organ of Corti, Outer pillar cell of organ of Corti, Inner phalangeal cell of organ of Corti, Outer phalangeal cell of organ of Corti, Border cell of organ of Corti, Hensen cell of organ of Corti, Vestibular apparatus supporting cell. Type I taste bud supporting cell, Olfactory epithelium supporting cell, Schwann cell, Satellite cell (encapsulating peripheral nerve cell bodies) and/or Enteric glial cell. In some embodiments, one can also use central nervous system neurons and glial cells such as Astrocyte (various types), Neuron cells (large variety of types, still poorly classified), Oligodendrocyte, and Spindle neuron.

Lens cells such as Anterior lens epithelial cell and Crystallin-containing lens fiber cell can also be used in the present device. Additionally, one can use pigment cells such as melanocytes and retinal pigmented epithelial cells; and germ cells, such as Oogonium/Oocyte, Spermatid, Spermatocyte, Spermatogonium cell (stem cell for spermatocyte), and Spermatozoon.

In some embodiments one can add to the membrane nurse cells Ovarian follicle cell, Sertoli cell (in testis), Thymus epithelial cell. One can also use interstitial cells such as interstitial kidney cells.

In an embodiment, one can coat at least one side of the membrane with epithelial cells. Epithelium is a tissue composed of cells that line the cavities and surfaces of structures throughout the body. Many glands are also formed from epithelial tissue. It lies on top of connective tissue, and the two layers are separated by a basement membrane. In humans, epithelium is classified as a primary body tissue, the other ones being connective tissue, muscle tissue and nervous tissue. Epithelium is often defined by the expression of the adhesion molecule e-cadherin (as opposed to n-cadherin, which is used by neurons and cells of the connective tissue).

Functions of epithelial cells include secretion, selective absorption, protection, transcellular transport and detection of sensation and they commonly as a result present extensive apical-basolateral polarity (e.g. different membrane proteins expressed) and specialization. Examples of epithelial cells include squamous cells that have the appearance of thin, flat plates. They fit closely together in tissues; providing a smooth, low-friction surface over which fluids can move easily. The shape of the nucleus usually corresponds to the cell form and helps to identify the type of epithelium. Squamous cells tend to have horizontally flattened, elliptical nuclei because of the thin flattened form of the cell. Classically, squamous epithelia are found lining surfaces utilizing simple passive diffusion such as the alveolar epithelium in the lungs. Specialized squamous epithelia also form the lining of cavities such as the blood vessels (endothelium) and heart (mesothelium) and the major cavities found within the body.

Another example of epithelial cells is cuboidal cells. Cuboidal cells are roughly cuboidal in shape, appearing square in cross section. Each cell has a spherical nucleus in the centre. Cuboidal epithelium is commonly found in secretive or absorptive tissue: for example the (secretive) exocrine gland the pancreas and the (absorptive) lining of the kidney tubules as well as in the ducts of the glands. They also constitute the germinal epithelium which produces the egg cells in the female ovary and the sperm cells in the male testes.

Yet another type of epithelial cells are columnar epithelial cells that are elongated and column-shaped. Their nuclei are elongated and are usually located near the base of the cells. Columnar epithelium forms the lining of the stomach and intestines. Some columnar cells are specialised for sensory reception such as in the nose, ears and the taste buds of the tongue. Goblet cells (unicellular glands) are found between the columnar epithelial cells of the duodenum. They secrete mucus, which acts as a lubricant.

Still another example of the epithelial cells are pseudostratified cells. These are simple columnar epithelial cells whose nuclei appear at different heights, giving the misleading (hence "pseudo") impression that the epithelium is stratified when the cells are viewed in cross section. Pseudostratified epithelium can also possess fine hair-like extensions of their apical (luminal) membrane called cilia. In this case, the epithelium is described as "ciliated" pseudostratified epithelium. Cilia are capable of energy dependent pulsatile beating in a certain direction through interaction of cytoskeletal microtubules and connecting structural proteins and enzymes. The wafting effect produced causes mucus secreted locally by the goblet cells (to lubricate and to trap pathogens and particles) to flow in that direction (typically out of the body). Ciliated epithelium is found in the airways (nose, bronchi), but is also found in the uterus and Fallopian tubes of females, where the cilia propel the ovum to the uterus.

Epithelium lines both the outside (skin) and the inside cavities and lumen of bodies. The outermost layer of our skin is composed of dead stratified squamous, keratinised epithelial cells.

Tissues that line the inside of the mouth, the oesophagus and part of the rectum are composed of nonkeratinized stratified squamous epithelium. Other surfaces that separate body cavities from the outside environment are lined by simple squamous, columnar, or pseudostratified epithelial cells. Other epithelial cells line the insides of the lungs, the gastrointestinal tract, the reproductive and urinary tracts, and make up the exocrine and endocrine glands. The outer surface of the cornea is covered with fast-growing, easily-regenerated epithelial cells. Endothelium (the inner lining of blood vessels, the heart, and lymphatic vessels) is a specialized form of epithelium. Another type, mesothelium, forms the walls of the pericardium, pleurae, and peritoneum.

Accordingly, one can recreate any of these tissues in the cell culture device as described by plating applicable cell types on the membranes and/or applying applicable mechanical modulation of the membrane to provide physiological or artificial mechanical force on the cells to mimic physiological forces, such as tension on skin or mechanical strain on lung. In an embodiment, one side of the membrane is coated with epithelial cells and the other side is coated with endothelial cells. Examples of endothelial cells include, but are not limited to, blood vessel and lymphatic vascular endothelial fenestrated cell, blood vessel and lymphatic vascular endothelial continuous cell, blood vessel and lymphatic vascular endothelial splenic cell, corneal endothelial cell, and any combinations thereof.

The endothelium is the thin layer of cells that line the interior surface of blood vessels and lymphatic vessels, forming an interface between circulating blood or lymph in the lumen and the rest of the vessel wall. Endothelial cells in direct contact with blood are vascular endothelial cells, whereas those in direct contact with lymph are known as lymphatic endothelial cells. Endothelial cells line the entire circulatory system, from the heart to the smallest capillary. These cells reduce turbulence of the flow of blood allowing the fluid to be pumped farther.

The foundational model of anatomy makes a distinction between endothelial cells and epithelial cells on the basis of which tissues they develop from and states that the presence of vimentin rather than keratin filaments separate these from epithelial cells. Endothelium of the interior surfaces of the heart chambers are called endocardium. Both blood and lymphatic capillaries are composed of a single layer of endothelial cells called a monolayer. Endothelial cells are involved in many aspects of vascular biology, including: vasoconstriction and vasodilation, and hence the control of blood pressure; blood clotting (thrombosis & fibrinolysis); atherosclerosis; formation of new blood vessels (angiogenesis); inflammation and barrier function—the endothelium acts as a selective barrier between the vessel lumen and surrounding tissue, controlling the passage of materials and the transit of white blood cells into and out of the bloodstream. Excessive or prolonged increases in permeability of the endothelial monolayer, as in cases of chronic inflammation, can lead to tissue edema/swelling. In some organs, there are highly differentiated endothelial cells to perform specialized 'filtering' functions. Examples of such unique endothelial structures include the renal glomerulus and the blood-brain barrier.

In an embodiment, the membrane side that contains cultured endothelial cells can be exposed to various test substances and also white blood cells or specific immune system cells flowing in the bottom microchannel to study effects of the test agents on the function of the immune system cells at the tissue level.

The devices described herein can be provided with pre-seeded cells or a pre-formed tissue structure, or without pre-seeded cells.

Using the organ mimic device described herein, one can study biotransformation, absorption, clearance, metabolism, and activation of xenobiotics, as well as drug delivery. The bioavailability and transport of chemical and biological agents across epithelial layers as in the intestine, endothelial layers as in blood vessels, and across the blood-brain barrier can also be studied. The acute basal toxicity, acute local toxicity or acute organ-specific toxicity, teratogenicity, genotoxicity, carcinogenicity, and mutagenicity, of chemical agents can also be studied. Effects of infectious biological agents, biological weapons, harmful chemical agents and chemical weapons can also be detected and studied. Infectious diseases and the efficacy of chemical and biological agents to treat these diseases, as well as optimal dosage ranges for these agents, can be studied. The response of organs in vivo to chemical and biological agents, and the pharmacokinetics and pharmacodynamics of these agents can be detected and studied using the present device. The impact of genetic content on response to the agents can be studied. The amount of protein and gene expression in response to chemical or biological agents can be determined. Changes in metabolism in response to chemical or biological agents can be studied as well using the present device.

The advantages of the organ mimic device, as opposed to conventional cell cultures or tissue cultures are numerous. For instance, when cells are placed in the organ mimic device, fibroblast, SMC (smooth muscle cell), endothelial cells, and/or epithelial cell differentiation can occur that reestablishes a defined three-dimensional architectural tissue-tissue relationships that are close to the in vivo situation, and cell functions and responses to pharmacological agents or active substances or products can be investigated at the tissue and organ levels.

In addition, many cellular or tissue activities are amenable to detection in the organ mimic device, including, but not limited to, diffusion rate of the drugs into and through the layered tissues in transported flow channel; cell morphology, differentiation and secretion changes at different layers; cell locomotion, growth, apoptosis, and the like. Further, the effect of various drugs on different types of cells located at different layers of the system can be assessed easily.

For drug discovery, for example, there can be two advantages for using the organ mimic device described herein: (1) the organ mimic device is better able to mimic in vivo layered architecture of tissues and therefore allow one to study drug effect at the organ level in addition to at the cellular and tissue levels; and (2) the organ mimic device decreases the use of in vivo tissue models and the use of animals for drug selection and toxicology studies.

In addition to drug discovery and development, the organ mimic device described herein can be also useful in basic and clinical research. For example, the organ mimic device can be used to research the mechanism of tumorigenesis. It is well established that in vivo cancer progression is modulated by the host and the tumor micro-environment, including the stromal cells and extracellular matrix (ECM). For example, stromal cells were found being able to convert benign epithelial cells to malignant cells, thereby ECM was found to affect the tumor formation. There is growing evidence that cells growing in defined architecture are more resistant to cytotoxic agents than cells in mono layers. Therefore, an organ mimic device is a better means for simulating the original growth characteristics of cancer cells and thereby better reflects the real drug's sensitivity of in vivo tumors.

The organ mimic device can be employed in engineering a variety of tissues including, but not limited to, the cardiovascular system, lung, intestine, kidney, brain, bone marrow, bones, teeth, and skin. If the device is fabricated with a suitable biocompatible and/or biodegradable material, such as poly-lactide-co-glycolide acid (PLGA), the organ mimic device can be used for transplantation or implantation in vivo. Moreover, the ability to spatially localize and control interactions of several cell types presents an opportunity to engineer hierarchically, and to create more physiologically correct tissue and organ analogs. The arrangement of multiple cell types in defined arrangement has beneficial effects on cell differentiation, maintenance, and functional longevity.

The organ mimic device can also allow different growth factors, chemicals, gases and nutrients to be added to different cell types according to the needs of cells and their existence in vivo. Controlling the location of those factors or proteins can direct the process of specific cell remodeling and functioning, and also can provide the molecular cues to the whole system, resulting in such beneficial developments as neotissue, cell remodeling, enhanced secretion, and the like.

In yet another aspect, the organ mimic device can be utilized as multi cell type cellular microarrays, such as microfluidic devices. Using the organ mimic device, pattern integrity of cellular arrays can be maintained. These cellular microarrays can constitute the future "lab-on-a-chip", particularly when multiplexed and automated. These miniaturized multi cell type cultures will facilitate the observation of cell dynamics with faster, less noisy assays, having built-in complexity that will allow cells to exhibit in vivo-like responses to the array.

In yet another aspect, the organ mimic device can be utilized as biological sensors. Cell-based biosensors can provide more information than other biosensors because cells often have multifaceted physiological responses to stimuli, as well as novel mechanisms to amplify these responses. All cell types in the organ mimic device can be used to monitor different aspects of an analyte at the same time; different cell type in the organ mimic device can be used to monitor different analytes at the same time; or a mixture of both types of monitoring. Cells ranging from *E. coli* to cells of mammalian lines have been used as sensors for applications in environmental monitoring, toxin detection, and physiological monitoring.

In yet another aspect, the organ mimic device can be used in understanding fundamental processes in cell biology and cell-ECM interactions. The in vivo remodeling process is a complicated, dynamic, reciprocal process between cells and ECMs. The organ mimic device would be able to capture the complexity of these biological systems, rendering these systems amenable to investigation and beneficial manipulation. Furthermore, coupled with imaging tools, such as fluorescence microscopy, microfluorimetry or optical coherence tomography (OCT), real-time analysis of cellular behavior in the multilayered tissues is expected using the device. Examples of cell and tissue studies amenable to real-time analysis include cell secretion and signaling, cell-cell interactions, tissue-tissue interactions, dynamic engineered tissue construction and monitoring, structure-function investigations in tissue engineering, and the process of cell remodeling matrices in vitro.

Another example of the use of this device is to induce tissue-tissue interfaces and complex organ structures to form within the device by implanting it in vivo within the body of a living animal, and allowing cells and tissues to impregnate the device and establish normal tissue-tissue interfaces. Then the whole device and contained cells and tissues is surgically removed while perfusing it through one or more of the fluid channels with medium and gases necessary for cell survival. This complex organ mimic can then be maintained viable in vitro through continuous perfusion and used to study highly complex cell and tissue functions in their normal 3D context with a level of complexity not possible using any existing in vitro model system.

In particular, a microchannel device can be implanted subcutaneously in vivo into an animal in which the device contains bone-inducing materials, such as demineralized bone powder or bone morphogenic proteins (BMPs), in a channel that has one or more corresponding ports open to the surrounding tissue space. The second channel would be closed during implantation by closing its end ports or filling it with a solid removable material, such as a solid rod. As a result of wound healing, connective tissues containing microcapillaries and mesenchymal stem cells would grow into the open channels of the device and, due to the presence of the bone-inducing material, will form bone with spaces that recruit circulating hematopoietic precursor cells to form fully functional bone marrow, as shown in past studies.

Once this process is complete, the surgical site would be reopened, and the second channel would be reopened by removing the rod or plugs and would then be connected with catheters linked to a fluid reservoir so that culture medium containing nutrients and gases necessary for cell survival could be pumped through the second channel and passed through the pores of the membrane into the first channel containing the formed bone marrow. The entire microchannel device could then be cut free from the surrounding tissue, and with the medium flowing continuously into the device, would be removed from the animal and passed to a tissue culture incubator and maintained in culture with continuous fluid flow through the second channel, and additional flow can be added to the first channel as well if desired by connecting to their inlet and outlet ports. The microchannel device would then be used to study intact bone marrow function in vitro as in a controlled environment.

Both biocompatible and biodegradable materials can be used in the present device to facilitate in vivo implantation of the present device. One can also use biocompatible and biodegradable coatings. For example, one can use ceramic coatings on a metallic substrate. But any type of coating material and the coating can be made of different types of materials: metals, ceramics, polymers, hydrogels or a combination of any of these materials.

Biocompatible materials include, but are not limited to an oxide, a phosphate, a carbonate, a nitride or a carbonitride. Among the oxide the following ones are preferred: tantalum oxide, aluminum oxide, iridium oxide, zirconium oxide or titanium oxide. In some cases the coating can also be made of a biodegradable material that will dissolve over time and can be replaced by the living tissue. Substrates are made of materials such as metals, ceramics, polymers or a combination of any of these. Metals such as stainless steel, Nitinol, titanium, titanium alloys, or aluminum and ceramics such as zirconia, alumina, or calcium phosphate are of particular interest.

The biocompatible material can also be biodegradable in that it will dissolve over time and can be replaced by the living tissue. Such biodegradable materials include, but are not limited to, poly(lactic acid-co-glycolic acid), polylactic acid, polyglycolic acid (PGA), collagen or other ECM molecules, other connective tissue proteins, magnesium alloys, polycaprolactone, hyaluric acid, adhesive proteins, biodegradable polymers, synthetic, biocompatible and biodegradable material, such as biopolymers, bioglasses, bioceramics, calcium sulfate, calcium phosphate such as, for example, monocalcium phosphate monohydrate, monocalcium phosphate anhydrous, dicalcium phosphate dihydrate, dicalcium phosphate anhydrous, tetracalcium phosphate, calcium orthophosphate phosphate, calcium pyrophosphate, alpha-tricalcium phosphate, beta-tricalcium phosphate, apatite such as hydroxyapatite, or polymers such as, for example, poly(alpha-hydroxyesters), poly(ortho esters), poly(ether esters), polyanhydrides, poly(phosphazenes), poly(propylene fumarates), poly(ester amides), poly(ethylene fumarates), poly(amino acids), polysaccharides, polypeptides, poly(hydroxy butyrates), poly(hydroxy valerates), polyurethanes, poly(malic acid), polylactides, polyglycolides, polycaprolactones, poly(glycolide-co-trimethylene carbonates), polydioxanones, or copolymers, terpolymers thereof or blends of those polymers, or a combination of biocompatible and biodegradable materials. One can also use biodegradable glass and bioactive glass self-reinforced and ultrahigh strength bioabsorbable composites assembled from partially crystalline bioabsorbable polymers, like polyglycolides, polylactides and/or glycolide/lactide copolymers.

These materials preferably have high initial strength, appropriate modulus and strength retention time from 4 weeks up to 1 year in vivo, depending on the implant geometry. Reinforcing elements such as fibers of crystalline polymers, fibers of carbon in polymeric resins, and particulate fillers, e.g., hydroxyapatite, can also be used to provide the dimensional stability and mechanical properties of biodegradable devices. The use of interpenetrating networks (IPN) in biodegradable material construction has been demonstrated as a means to improve mechanical strength. To further improve the mechanical properties of IPN-reinforced biodegradable materials, the present device can be prepared as semi-interpenetrating networks (SIPN) of crosslinked polypropylene fumarate within a host matrix of poly(lactide-co-glycolide) 85:15 (PLGA) or poly(l-lactide-co-d,l-lactide) 70:30 (PLA) using different crosslinking agents. One can also use natural poly(hydroxybutyrate-co-9% hydroxyvalerate) copolyester membranes as described in Charles-Hilaire Rivard et al. (Journal of Applied Biomaterials, Volume 6 Issue 1, Pages 65-68, 1 Sep. 2004). A skilled artisan will be able to also select other biodegradable materials suitable for any specific purposes and cell and tissue types according to the applications in which the device is used.

The device as described can also be used as therapeutic devices, when placed in vivo. One can re-create organ mimics, such as bone marrow or lymph nodes by placing the devices in, for example an animal model allowing the device to be inhabited by living cells and tissues, and then removing the entire device with living cells while perfusing the vascular channel with medium. The device can then be removed and kept alive ex vivo for in vitro or ex vivo studies. In particular, the membrane can be coated with one or more cell layers on at least one side of the membrane in vitro. In this embodiment, the cells are plated outside an organism. In an embodiment, the membrane is coated with one or more cell layers on at least one side of the membrane in vivo. One can treat one side of the membrane in vitro and the other side in vivo. One can also have one or both sides initially coated with one cell type in vitro and then implant the device to attract additional cell layers in vivo.

Additional Examples of Tissue/Organ-Mimic Devices

In some embodiments, the devices described herein can be adapted to model at least a portion of a tissue or organ that requires a taller channel to accommodate formation of a stratified, pesudostratified or three-dimensional structure, and/or provide sufficient overhead space to permit low shear stress produced by air and/or liquid flow over the cells in order to simulate a native physiological environment. Without wishing to be limiting, one of skill in the art will readily appreciate that the devices described herein can also be used to model at least a portion of a tissue or organ that does not necessarily require such additional space for optimum cell growth and/or fluid flow. In these embodiments, the air/fluid flow can be adjusted to account for an increased overhead space over the cells in order to maintain a physiologically-relevant shear level subjected to the cells.

In some embodiments, the devices described herein can be used to model at least a portion of a skin tissue or organ, which can be in turn used to study or mimic a skin-related physiologically-relevant condition (e.g., a normal and/or pathological condition) for various applications described herein. The taller mesochannel can be used to provide more space for multiple layers of cells and/or structures as they mature or differentiate. Examples of a skin-related disease or disorder that can be modeled using the devices described herein include, but are not limited to, aging, atopic dermatitis, contact dermatitis (allergy or irritant), eczema, psoriasis, acne, epidermal hyperkeratosis, acanthosis, epidermal inflammation, dermal inflammation or pruritus, rosacea, netherton syndrome, peeling skin syndrome type A and B, hereditary ichtyosis, hidradenitis suppurativa, erythroderma (generalized exfoliative dermatitis), skin cancer, and any combinations thereof. This can also be used to study absorption, efficacy and/or toxicity of topically applied cosmetics or consumer products. In some embodiments, the devices described herein can be used to model an aging skin. This can also be used to study transdermal drug delivery.

A mammalian skin is generally composed of two primary layers: the epidermis, which provides a protective barrier; and the dermis, which is the layer of skin beneath the epidermis. The epidermis is a stratified squamous epithelium comprising multiple cell layers, namely (beginning with the outermost layer), stratum corneum, stratum lucidum (primarily in palms and soles), stratum granulosum, stratum spinosum, stratum germinativum (also known as stratum basale). Keratinocytes constitute a majority of the epidermis, while Merkel cells, melanocytes, and Langerhans cells are also present.

The dermis layer is primarily composed of connective tissue and extracelluar matrix (e.g., collagen fibrils, microfibrils, and elastic fibers) which provide tensile strength and elasticity to the skin. The dermis layer also harbors many mechanoreceptors (e.g., nerve endings) that provide sense of touch and heat. It also contains hair follicles, sweat glands, sebaceous glands, apocrine glands, lymphatic vessels and blood vessels. The blood vessels in the dermis can provide nourishment and/or waste removal from its own cells as well as for the epidermis.

The dermis is connected to the epidermis through a basement membrane and is structurally divided into two areas: a superficial area adjacent to the epidermis, called the papillary region, and a deep thicker area known as the reticular region. The papillary region contains loose areolar connective tissue and fingerlike projections (known as papillae) that extend toward the epidermis. The papillae provide the dermis with a "bumpy" surface that interdigitates with the epidermis, strengthening the connection between the two layers of skin. The reticular region lies deep in the papillary region and is usually much thicker. The reticular region contains dense irregular connective tissue, and a dense concentration of collagenous, elastic, and reticular fibers that weave throughout it. These protein fibers give the dermis its properties of strength, extensibility, and elasticity. The other component of the dermis that can be critical for skin physiology and/or pathophysiology includes the vasculature.

Accordingly, the mesochannel 250A can have a height dimension configured to permit formation of a skin equivalent that mimics the skin of a human or an animal. In some embodiments, the membrane of the device can be used as a basement separating the epidermis layer and dermis layer. For example, the surface of the membrane facing the mesochannel can be coated with keratinocytes (and optionally other cells that are typically present in an epidermis such as Merkel cells, melanocytes, and Langerhans cells). The keratinocytes on the membrane can be cultured at an air-liquid interface (in a similar setup as shown in the "small airway" example) to induce cell differentiation for formation of the stratified epidermis layer. During the differentiation process, the keratinocytes can become highly organized, form cellular junctions (to mimic desmosomes) between each other and/or secrete keratin proteins and/or lipids which can contribute to the formation of an extracellular matrix and provide mechanical strength. In some embodiments, keratinocytes from the outermost stratified layer can eventually shed from the epidermis, as keratinocytes shed from the stratum corneum in vivo.

While in some embodiments, the epidermis layer and dermis layer can be formed in the mesochannel and microchannel, respectively, in some embodiments, both the epidermis layer and dermis layer can be formed in the mesochannel.

The other surface of the membrane facing the microchannel can be coated with or without cells. In some embodiments, the surface of the membrane facing the microchannel can be coated with cells selected from the group consisting of cell types that are typically present in a dermis layer (e.g., fibroblasts), hypodermis-associated cells (e.g., fibroblasts, macrophages, and/or adipocytes), blood vessel-associated cells as described herein, and any combinations thereof.

In some embodiments where the surface of the membrane facing the microchannel is used to model a dermis layer, the other surface of the membrane facing the mesochannel can be coated with or without epidermis-associated cells. In these embodiments, the membrane of the device can be used as a protective barrier as the epidermis layer.

In some embodiments, microorganisms typically present on a skin surface, e.g., *Staphylococcus epidermis*, can be cultured with the epidermis layer formed in the mesochannel.

In some embodiments, the membrane used in the device for modeling a skin tissue can be porous and flexible. In some embodiments, the membrane can be mechanically modulated by a pneumatic mechanism and/or mechanical means as described herein, for example, to mimic a mechanical static strain typically experienced by skin cells in vivo.

In some embodiments, the devices described herein can be used to model at least a portion of a heart. In accordance with some embodiments of the invention, the heart-mimic device can be used to study or mimic a heart-related physiologically-relevant condition (e.g., a normal and/or pathological condition) for various applications described herein. Examples of a heart-related disease or disorder that can be modeled using the devices described herein include, but are not limited to, coronary heart disease (also ischemic heart disease or coronary artery disease), cardiomyopathy, hypertensive heart disease, heart failure, cor pulmonale, cardiac dysrhythmias, inflammatory heart disease (e.g., endocarditis, inflammatory cardiomegaly, and myocarditis), valvular heart disease, congenital heart disease, rheumatic heart disease, atherosclerosis, and any combinations thereof. It can also be used to study effects of drugs or toxins on normal heart viability and/or function.

For example, in some embodiments, the surface of the membrane facing the mesochannel can be coated with thin films of functional heart tissues, while the other surface facing the microchannel can be coated with or without blood vessel-associated cells as described herein. In some embodiments, thin films of functional heart tissues can be fabricated first and then placed on the membrane facing the mesochannel. For example, thin films of functional heart tissues can be fabricated by culturing cardiomyocytes (e.g., ventricular cardiomyocytes) on elastomeric polymer thin films micropatterned with cell adhesion proteins (e.g., extracellular matrix proteins) to promote spatially ordered, two-dimensional myogenesis and thus create "muscular thin films" (MTFs) as previously described, e.g., in Grosberg A. et al. "Ensembles of engineered cardiac tissues for physiological and pharmacological study: Heart on a chip" Lab on a chip (2011) 11: 4165, as well as the International Application Nos. WO 2008/051265, and WO2010/042856, the contents of which are incorporated herein by reference. These muscular thin films can be electrically functional and actively contractile, generating stresses comparable to those produced by whole papillary muscle. For example, the cardiomyocytes on the muscular thin films can contract, causing the elastomeric polymer thin films to bend and form a three-dimensional (3D) structure. Accordingly, in some embodiments, the mesochannel 250A can have a height dimension sufficient to accommodate the height of the muscular thin films as they bend and form a 3D structure.

In some embodiments, contractile heart muscle cells (e.g., cardiomyocytes) can be grown on a surface of a flexible and porous membrane facing the mesochannel, while the other surface facing the microchannel can be coated with or without blood vessel-associated cells as described herein. As the heart muscle cells contract, the pore apertures on the membrane can deform due to cell contraction. By way of example only, the pore apertures can remain as a circle when the heart muscle cells are in a relaxed state, but the circular pore apertures become deformed, e.g., becoming an oval, or an ellipse, due to muscle cell contraction. See, e.g., International Patent Application: PCT/US12/68766 filed Dec. 10, 2012, the content of which is incorporated herein by reference. In this embodiment, a taller mesochannel can provide low shear stress to heart muscle cells as in a native physiological microenvironment.

In some embodiments, myoblasts can be grown on the membrane facing the mesochannel (with or without mechanical modulation of the membrane) to induce differentiation of the myoblasts to form myocytes or cardiomyocytes.

In some embodiments, the devices described herein can be used to model at least a portion of an eye, which can be in turn used to study or mimic an ocular condition (e.g., a normal and/or pathological condition) for various applications described herein. The taller mesochannel can provide low shear stress to the delicate ocular cells as in a native physiological microenvironment. Examples of an ocular disease or disorder associated with the front and/or back of an eye that can be modeled using the devices described herein include, but are not limited to, age-related macular degeneration, choroidal neovascularization, diabetic macular edema, acute and chronic macular neuroretinopathy, central serous chorioretinopathy, macular edema, acute multifocal placoid pigment epitheliopathy, Behcet's disease, birdshot retinochoroidopathy, posterior uveitis, posterior scleritis, serpignous choroiditis, subretinal fibrosis, uveitis syndrome, Vogt-Koyanagi-Harada syndrome, retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, carotid artery disease (CAD), frosted branch angitis, sickle cell retinopathy, angioid streaks, familial exudative vitreoretinopathy, Eales disease, proliferative vitreal retinopathy, diabetic retinopathy, retinal disease associated with tumors, congenital hypertrophy of the retinal pigment epithelium (RPE), posterior uveal melanoma, choroidal hemangioma, choroidal osteoma, choroid metastasis, combined hamartoma of the retina and retinal pigmented epithelium, retinoblastoma, vasoproliferative tumors of the ocular fundus, retinal astrocytoma, intraocular lymphoid tumors, myopic retinal degeneration, acute retinal pigment epithelitis, glaucoma, endophthalmitis, cytomegalovirus retinitis, retinal cancers, and any combinations thereof. This can also be used to study ocular drug delivery.

In some embodiments, the devices described herein can be used to model at least a front portion of an eye. For example, in some embodiments, the surface of the membrane facing the mesochannel can be coated with cornea-associated cells (e.g., but not limited to, corneal epithelial cells, corneal keratocytes, and/or corneal nerve cells), while the other surface of the membrane can be optionally lined by corneal endothelial cells, with or without corneal fibroblasts included as an intervening layer. A liquid fluid with a similar viscosity as aqueous humor can flow through the microchannel to provide nutrients to the cells in the mesochannel, while the cells are cultured at an air-liquid interface (in a similar setup as in the "small airway" example). This model can be used to study immune response of the cornea.

In some embodiments, the devices described herein can be used to model at least a back portion of an eye, e.g., a portion of a retina. Retina is a light-sensitive layered structure with several layers of neurons, a photoreceptor layer (e.g., comprising rod and/or cone cells) and a retinal pigment epithelium (e.g., comprising cuboidal cells). Accordingly, in some embodiments, the surface of the membrane facing the mesochannel can be coated with at least one or more layers (including, e.g., at least two or more layers) of retina-associated cells. For example, in one embodiment, the surface of the membrane facing the mesochannel can be coated with a bottom layer of retinal epithelial cells overlaid with at least one cell layer comprising photoreceptor cells (e.g., rod and/or cone cells). The other surface of the membrane facing the microchannel can be coated with or without blood vessel-associated cells as described herein.

In some embodiments, a liquid fluid with a viscosity as vitreous humor can flow through the mesochannel, while a liquid fluid, e.g., cell culture medium and/or blood, can flow through the microchannel.

The retina tissue-mimic device can be used to model a retina-associated disease, including, e.g., but not limited to, retinitis pigmentosa, macular degeneration, cone-rod dystrophy (CORD), hypertensive retinopathy, diabetic retinopathy, retinoblastoma, retinal dysplasia, progressive retinal atrophy, and any combinations thereof.

In some embodiments, the membrane used in the device to model a front or back portion of a tissue can be porous and rigid or flexible.

In addition to modeling a portion of an intestine (e.g., a small or large intestine) as described earlier, in some embodiments, the devices described herein can be used to model at least a portion of an organ associated with a gastrointestinal tract or a digestive system, including, e.g., but not limited to, oropharynx, stomach, esophagus, pancreas, rectum and anus. In some embodiments, the devices described herein can be used to model at least a portion of a pancreatic tissue, which can be in turn used to study or mimic a pancreas-related physiologically-relevant condition (e.g., a normal and/or pathological condition) for various applications described herein. The taller mesochannel can provide low shear stress to pancreas-associated cells, such as endocrine islet beta cells or exocrine acinar cells, as in a native physiological environment, optionally along with vascular endothelial cells lining the opposite side of the porous membrane under normal hemodynamic flow conditions. Examples of a pancreas-related disease or disorder that can be modeled using the devices described herein include, but are not limited to, diabetes, pancreatitis, cystic fibrosis, pancreatic cancer, and any combinations thereof.

In some embodiments, the surface of the membrane facing the mesochannel can be coated with pancreas-associated cells (e.g., islets of Langerhans or endocrine cells and/or acinar cells), while the other surface of the membrane facing the microchannel can be coated with or without blood vessel-associated cells.

In some embodiments, the membrane used in the device to model a pancreatic tissue can be porous and rigid or flexible.

Use of the devices described herein to model various specific tissues are provided herein as illustrative examples and are not intended to be in any way limiting. Those of skill in the art will realize that the devices described herein can be adapted to mimic function of any portion of a tissue or organ in any living organisms, e.g., vertebrates (e.g., but not limited to, human subjects or animals such as fish, birds, reptiles, and amphibians), invertebrates (e.g., but not limited to, protozoa, annelids, mollusks, crustaceans, arachnids, echinoderms and insects), plants, fungi (e.g., but not limited to mushrooms, mold, and yeast), and microorganisms (e.g., but not limited to bacteria and viruses) in view of the specification and examples provided herein. Further, a skilled artisan can adapt methods of uses described herein for various applications of different tissue-mimic devices.

In accordance with some embodiments of the invention, the devices described herein can be used to mimic function of a blood-brain barrier. For example, brain cells (e.g., neurons, and/or astrocytes) can be cultured on one surface of the membrane and blood vessel-associated cells (e.g., endothelial cells, fibroblasts, smooth muscle cells, pericytes, and/or any combinations thereof) on another surface of the membrane. It is commonly believed that the native brain cells are usually exposed to a high shear stress. Accordingly, in some embodiments, application of a mechanical strain/stress to the brain cells can be used instead in place of a high-shear flow.

Methods of Making a Device Described Herein

Figure 3A:
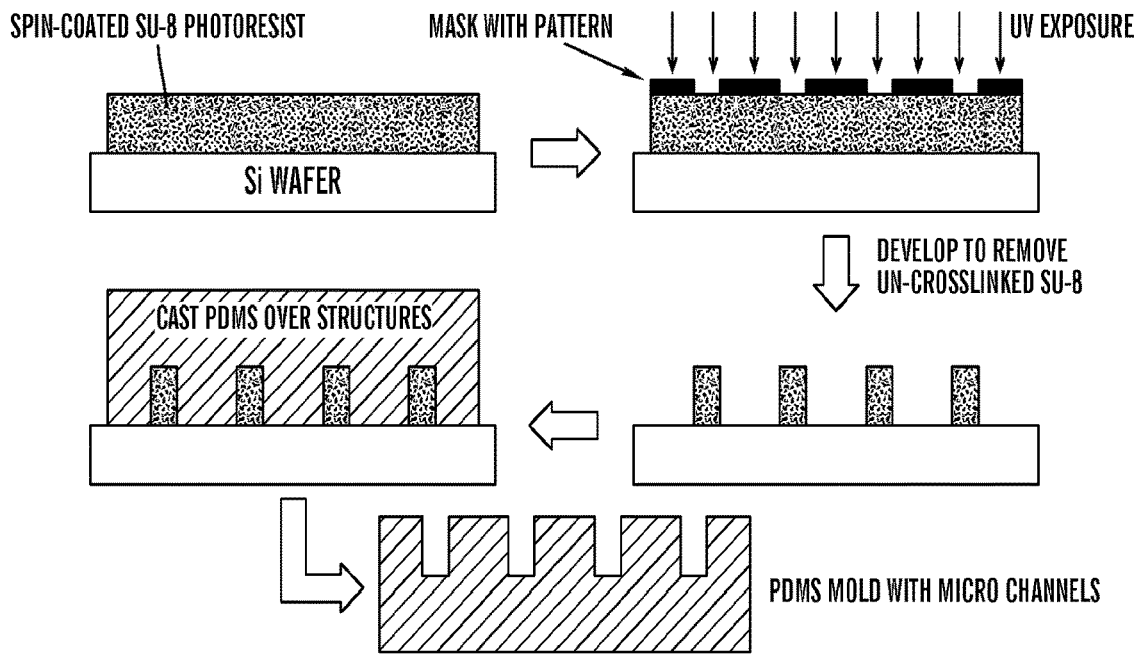
FIG. 3A is a schematic of a photolithography process used to fabricate a bottom body portion of the device comprising a microchannel in accordance with an embodiment.

Details on how the device 200 is formed will now be discussed in accordance with an embodiment. Embodiments of various devices described herein enables us to leverage the control of microfluidic technology and reconstitute the organ level function associated with the primary cell type, e.g., breathing/strain of airway epithelial cells while for the first time offering a reduced stress environment and increased overhead space for growth, only feasible in a larger meso-scale channel. In some embodiments, two technologies are used to fabricate the devices described herein. The bottom microchannel, which, in one embodiment, is approximately 100 μm tall, can be manufactured using any conventional fabrication methods, including, e.g., injection molding, embossing, etching, casting, machining, stamping, lamination, photolithography, or any combinations thereof. In one embodiment, the bottom microchannel is manufactured by a process comprising traditional photolithography, a technique useful for creating fluidic features of the order ten to several hundred microns. As seen in FIG. 3A, the end result of photolithography is a silicon wafer with the design of microchannels raised to a pre-determined height (e.g., about 25 μm to about 1000 μm). In one embodiment, the bottom microchannel is manufactured by a process comprising soft lithography techniques, the details of which are described in "Soft Lithography in Biology and Biochemistry," by Whitesides, et al., published Annual Review, Biomed Engineering, 3.335-3.373 (2001), as well as "An Ultra-Thin PDMS Membrane As A Bio/Micro-Nano Interface: Fabrication And Characterization", by Thangawng et al., Biomed Microdevices, vol. 9, num. 4, 2007, p. 587-95, both of which are hereby incorporated by reference. After the wafer with the design of raised features is made, a curable biocompatible polymer, e.g., but not limited to, PDMS, polyurethane, SEBS, polypropylene, and any combinations thereof, can be casted into the mold, which then forms the microchannel. In some embodiments, the bottom microchannel can be fabricated using a combination of two or more techniques described herein.

Figure 3B:
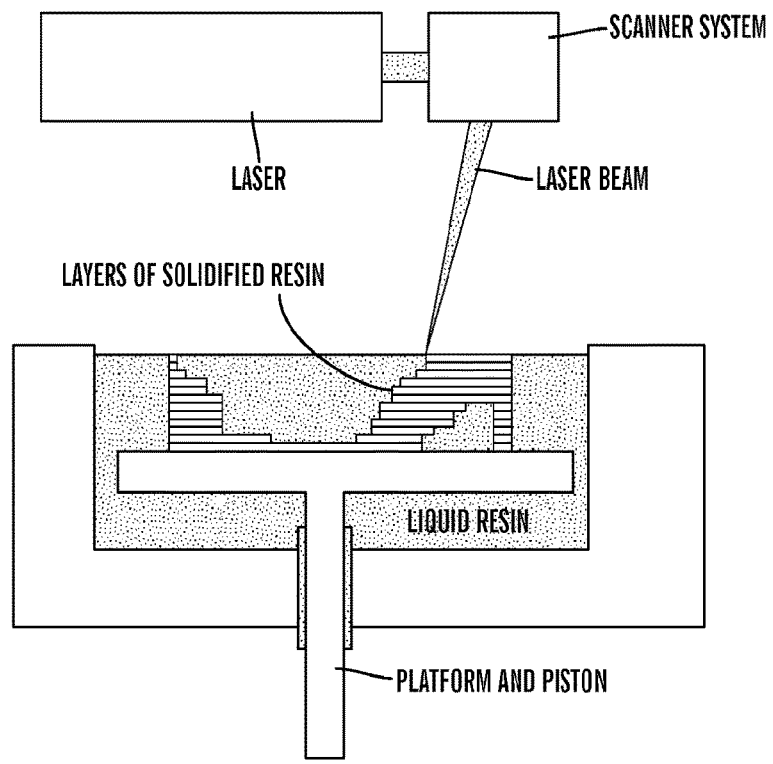
FIG. 3B is a schematic of a stereolithographic process used to fabricate a top body portion of the device comprising a mesochannel in accordance with an embodiment.

The top mesochannel, which, in one embodiment, is approximately 1 mm tall, can be can be manufactured using any conventional fabrication methods, including, e.g., injection molding, embossing, etching, casting, machining, stamping, lamination, photolithography, or any combinations thereof. In some embodiments, the top mesochannel can be less desirable to be made using photolithography because SU-8 structures of larger size (e.g., in millimeter range) can have material defects. In some embodiments, the solid free-form fabrication technology such as stereo-lithography can be used to make a mold for the mesochannel, due to its superior surface finish and resolution. Generally, stereo-lithography can be used to make a mold with features having a minimum dimension of at least about 20 μm to about 50 μm, depending on the machine. An example schematic diagram of the stereo-lithography procedure is shown in FIG. 3B. In this process, the silicon wafer used in photolithography is being replaced by a layer of solidified resin. As the process continues, the features of the channels are etched by the laser and thus solidified, and the result is a wafer-like device made entirely of thermoplastic resin.

Figure 3C:
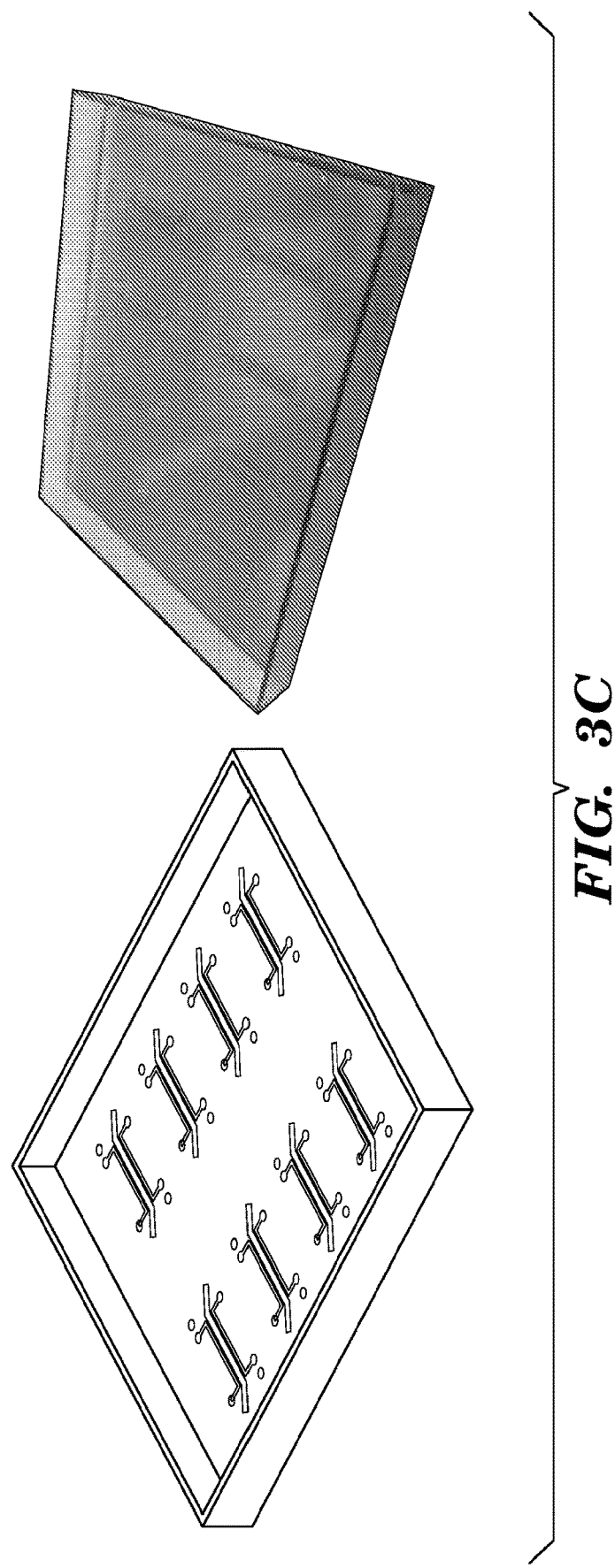
FIG. 3C is a set of images showing a CAD model of tall channel "wafer" (left panel) and a stereolithographic thermoplastic reconstruction (right panel).

The design of the device described herein can be drawn in 3D CAD design software, e.g., SolidWorks, which is then read by a stereolithography machine and drawn in thermoset resin with an ultraviolet laser. The drawing and final mold are shown in FIG. 3C.

In some embodiments where the height of the operating channel(s) is much smaller than the height of the mesochannel (e.g., by a factor of 2 or higher, such as a factor of 2, 3, 4, 5, 6, 7, 8, 9, 10, or higher), the inventors have surprisingly discovered that stereo-lithography can be used to produce a mold with features of different scales (e.g., mesochannel vs. operating channels).

Similar to the silicon wafer with microstructures, which PDMS is then cast upon, the PDMS is cast into the entire thermoplastic mold which then forms the mesochannels. In addition to PDMS, other materials such as polyurethanes (e.g., see PCT/US12/36920 for use of polyurethane materials to produce microfluidic devices), styrene-ethylene-butylene-styrene (SEBS) (e.g., see, US2011/0085949 for use of thermoplastic elastomers to produce microfluidic devices), polypropylene, silicon, or any combinations thereof. The content of the patent applications are incorporated herein by reference.

Without wishing to be limiting, in some embodiments, the devices described herein can be produced as a monolithic device or as individual components (e.g., a first portion of the body comprising a mesochannel, a second portion of the body comprising a microchannel, and a membrane), which can then be assembled together to form a device described herein. Each individual component can be produced by a conventional manufacturing method such as injection molding, extrusion, casting, lamination, embossing, compression molding, solvent casting, an additive manufacturing method (e.g., 3D printing), or any combinations thereof.

The top outer body portion 204 can have a thickness of any dimension, depending, in part, on the height of the mesochannel 250A. In some embodiments, the thickness of the top outer body portion 204 can be about 1 mm to about 100 mm, or about 2 mm to about 75 mm, or about 3 mm to about 50 mm, or about 3 mm to about 25 mm. In one embodiment, the thickness of the top outer body portion 204 can be about 4.8 mm.

The bottom outer body portion 206 can have a thickness of any dimension, depending, in part, on the height of the microchannel 250B. In some embodiments, the thickness of the bottom outer body portion 206 can be about 50 μm to about 10 mm, or about 75 μm to about 8 mm, or about 100 μm to about 5 mm, or about 200 μm to about 2.5 mm. In one embodiment, the thickness of the bottom outer body portion 206 can be about 1 mm to about 1.5 mm. In one embodiment, the thickness of the bottom outer body portion 206 can be about 0.2 mm to about 0.5 mm.

Once the top and bottom outer body portions 204, 206 are formed and removed from their respective molds, the access ports can be made to access the channels. In one embodiment, the ports are created using a 0.5 mm biopsy punch at 90° (FIG. 2C, top panels). This sharp redirection of flow can create forces that can cause undesirable effects on the cells, local pressure variations and cell aggregation. An alternative design is for the punch to be used at a lower angle (FIG. 2C, bottom panels). This can mitigate the problems associated with the purely vertical punch. In this embodiment, the access ports (e.g., for inlets and outlets) are positioned on the lateral sides of the devices described herein such that the inlet channels and outlet channels can be angled at an angle smaller than 90 degrees, e.g., ranging from about 15 degrees to about 45 degrees. In one embodiment, the inlet channels and outlet channels can be angled at an angle of about 25 degrees.

The membrane 208 can be engineered for a variety of purposes, some discussed above. For example, the pores on the membrane 208 can be coated or filled with ECM molecules or gels, such as MATRIGEL, laminin, collagen, fibronectin, fibrin, elastin, etc., which are known to those skilled in the art. The tissue-tissue interface can be coated by culturing different types of cells on each side of the membrane 208, as shown in FIG. 2D. In particular, as shown in FIG. 2D, one type of cells are coated on one side of the membrane 208 whereas another type of cells are coated on the opposing side of the membrane 208.

As described earlier, the membrane 208 can be rigid or flexible. In some embodiments, the membrane 208 can be rigid, e.g., a polycarbonate or polyester membrane. In some embodiments, the membrane 208 can be flexible, e.g., a PDMS membrane.

In general, the membrane 208 is sandwiched between the top outer body portion 204 comprising a mesochannel 250A and the bottom outer body portion 206 comprising a microchannel 250B, whereby the channel walls 234, 244 as well as the outside walls 238, 248 are aligned using appropriate manufacturing equipment and techniques. Thereafter, the membrane 208 is fastened to the channel walls 234, 244 and optional outside walls 238, 248 using an appropriate adhesive or epoxy, physical clamping and/or plasma bond between the two PDMS surfaces, in order to form a fluidic seal between the membrane and the top body portion 204 and the bottom body portion 206.

For example, a fluidic seal can be formed by a chemical bond between the membrane and the top body portion and the bottom body portion. In one embodiment, the chemical bond can be created with an adhesive chemical coating, e.g., 3-Aminopropyl-triethoxysilane (APTES), which can create an irreversible bond between the polycarbonate or polyester membrane, and the top body portion and the bottom body portion. See, e.g., Aran et al. "Irreversible, direct bonding of nanoporous polymer membranes to PDMS or glass microdevices." Lab Chip. 2010 Mar. 7; 10(5):548-52, for use of 3-aminopropyltriethoxysilane as a chemical crosslinking agent to integrate polymer membranes such as polyethersulfone and polyethylene terephthalate, with PDMS and glass microfluidic channels. The APTES procedure is described in FIG. 4A.

Figure 4B:
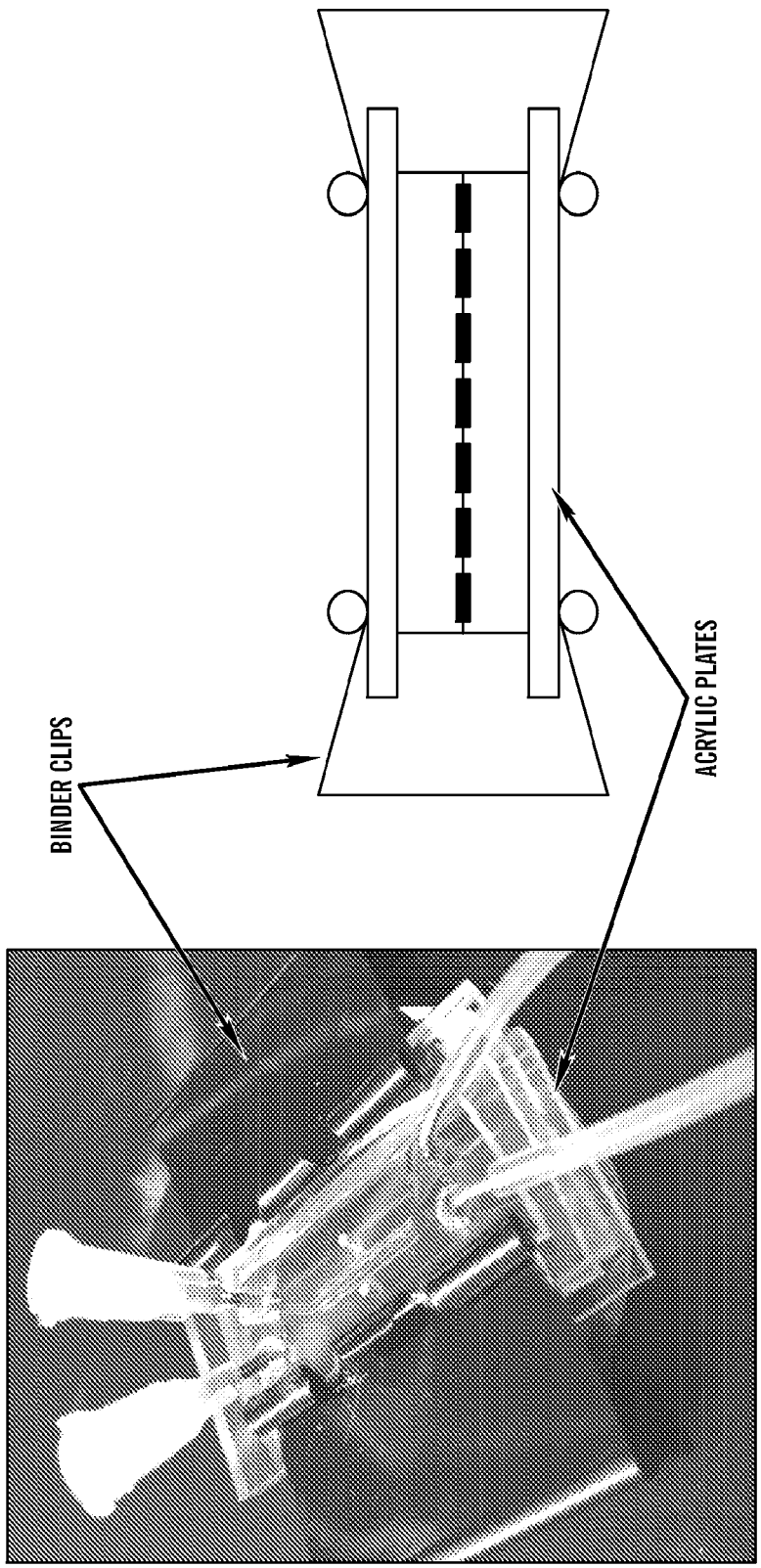

In some embodiments, a fluidic seal can be formed by clamping the membrane between the top and bottom body portions 204, 206 (e.g., PDMS portions) utilizing all membrane-PDMS surface area. Clamping the membrane between the top and bottom body portions 204, 206 can be achieved by placing the device between two plates, e.g., acrylic plates. The plates (e.g., acrylic plates) can then be clamped together either with screws or clips as seen in FIG. 4B. This method can allow the user to access the membrane after the experiment with minimal damage to the cells on the membrane, yielding a higher quality images.

Figure 4C:
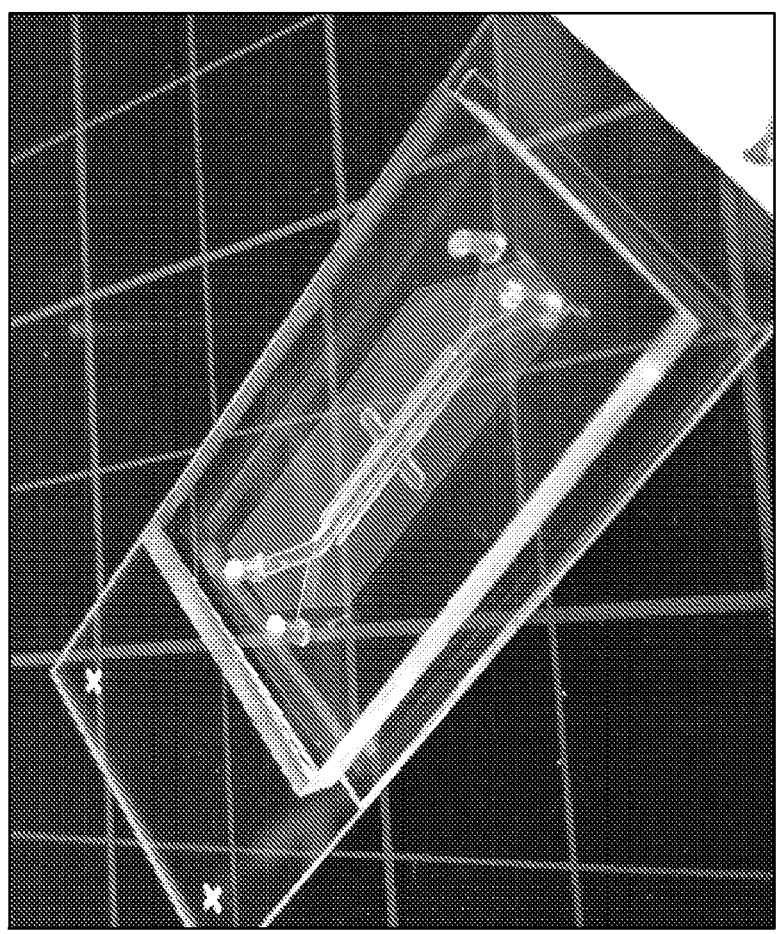

In some embodiments where the top and bottom body portions are made of PDMS, a fluidic seal can be formed by cutting a membrane smaller than the PDMS surface area and plasma bonding the PDMS together around the membrane, e.g., as shown in FIG. 4C. This method can allow the user to access the membrane after the experiment with minimal damage to the cells on the membrane, yielding a higher quality images.

Figure 20:
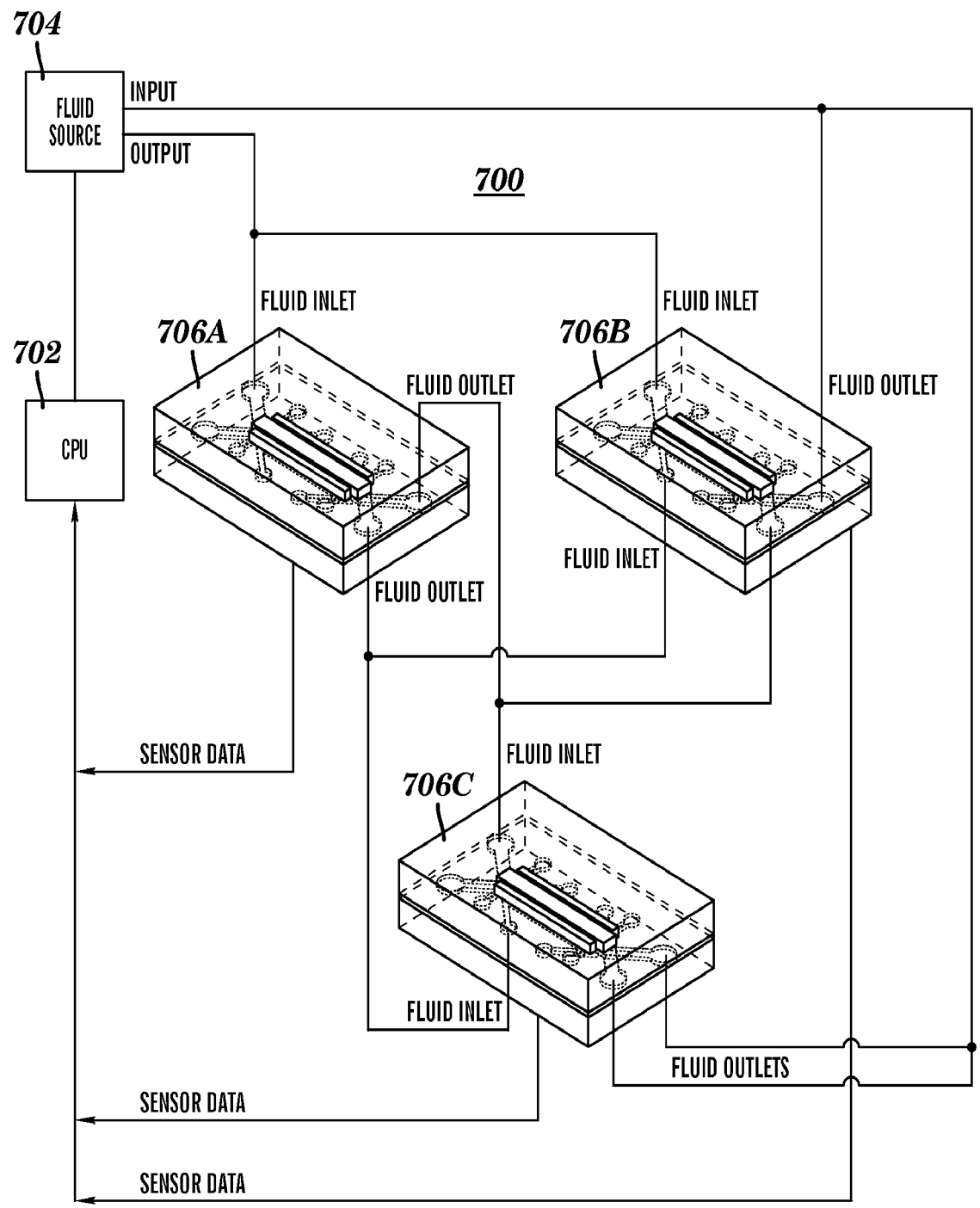
FIG. 20 illustrates a system diagram employing more than one devices described herein, which are fluidically connected to each other and/or to fluid sources.

FIG. 20 illustrates a schematic of a system having multiple devices in accordance with an embodiment. In particular, as shown in FIG. 20, the system 700 includes one or more CPUs 702 coupled to one or more fluid sources 704 and external force sources (e.g., pressure sources) (not shown), whereby the preceding are coupled to three devices 706A, 706B, and 706C. It should be noted that although three devices 706 are shown in this embodiment, fewer or greater than three devices 706 can be used. In the system 700, two of the three devices (i.e. 706A and 706B) are connected in parallel with respect to the fluid source 704 and devices 706A and 706C are connected in serial fashion with respect to the fluid source 704. It should be noted that the shown configuration is only one example and any other types of connection patterns can be utilized depending on the application. In some embodiments, a system can be the one described in the International Patent Application No. PCT/US12/68725, entitled "Integrated human organ-on-chip microphysiological systems," where one or more devices described herein can be fluidically connected to form the system. For example, as shown in FIG. 19, about 8-16 devices described herein can be fluidically connected to form one or more systems maintained in an incubator.

In the example shown, fluid from the fluid source 704 is provided directly to the fluid inlets of devices 706A and 706B. As the fluid passes through device 706A, it is output directly into the fluid inlet port of devices 706B and 706C. Additionally, the fluid outlet from device 706B is combined with the output from device 706A into device 706C. With multiple devices operating, it is possible to monitor, using sensor data, how the cells in the fluid or membrane behave after the fluid has been passed through another controlled environment. This system thus allows multiple independent "stages" to be set up, where cell behavior in each stage can be monitored under simulated physiological conditions and controlled using the devices 706. One or more devices are connected serially can provide use in studying chemical communication between cells. For example, one cell type can secrete protein A in response to being exposed to a particular fluid, whereby the fluid, containing the secreted protein A, exits one device and then is exposed to another cell type specifically patterned in another device, whereby the interaction of the fluid with protein A with the other cells in the other device can be monitored (e.g. paracrine signaling). For the parallel configuration, one or more devices connected in parallel can be advantageous in increasing the efficiency of analyzing cell behavior across multiple devices at once instead of analyzing the cell behavior through individual devices separately.

Additional Examples of Cytokines

As used herein, the term "cytokine" refers to an agent that can stimulate, inhibit, and/or mediate a cellular process, including, e.g., but not limited to, proliferation, differentiation, inflammation, apoptosis, cellular metabolism, cytoskeletal regulation, cell adhesion, cell migration, angiogenesis, DNA repair, protein synthesis, and any combinations thereof. A "cytokine" can be or include a small molecule, a biological molecule (e.g., but not limited to, a protein, peptide, nucleic acid, lipid, carbohydrate, glycoprotein, glycolipid, proteoglycan, lipoprotein), an antibody, oligonucleotide, a metal, a vitamin, or any combinations thereof. For example, a cytokine can include, but are not limited to, a growth-promoting agent, a cell differentiation agent, an anti-inflammatory agent, a pro-inflammatory agent, an apoptosis-inducing agent, an anti-apoptotic agent, a pro-angiogenic agent, an anti-angiogenic agent, or any combinations thereof.

In some embodiments, the cytokine can include a pro-inflammatory agent. As used herein, the term "pro-inflammatory agent" refers to an agent that can directly or indirectly induce or mediate an inflammatory response in cells, or is directly or indirectly involved in production of a mediator of inflammation. A variety of proinflammatory agents are known to those skilled in the art. Illustratively, pro-inflammatory agents include, without limitation, eicosanoids such as, for example, prostaglandins (e.g., PGE2) and leukotrienes (e.g., LTB4); gases (e.g., nitric oxide (NO)); enzymes (e.g., phospholipases, inducible nitric oxide synthase (iNOS), COX-1 and COX-2); and cytokines such as, for example, interleukins (e.g., IL-1α, IL-β, IL-2, IL-3, IL-4, IL-5, IL-6, IL-8, IL-10, IL-12 and IL-18), members of the tumor necrosis factor family (e.g., TNF-α, TNF-β and lymphotoxin β), interferons (e.g., IFN-β and IFN-γ), granulocyte/macrophage colony-stimulating factor (GM-CSF), transforming growth factors (e.g., TGF-β1, TGF-β2 and TGF-β3, leukemia inhibitory factor (LTF), ciliary neurotrophic factor (CNTF), migration inhibitory factor (MTF), monocyte chemoattractant protein (MCP-I), macrophage inflammatory proteins (e.g., MIP-1α, MIP-1β and MIP-2), and RANTES, as well as environmental or physical agents such as silica micro- and nano-particles and pathogens. In some embodiments, at least one or more of these pro-inflammatory agents can be added to a cell culture medium, e.g., to stimulate or challenge tissue-specific cells and/or immune cells within the device to simulate an inflammatory response or an inflammation-associated disease, disorder, or injury in vivo.

In some embodiments, the cytokine can include an anti-inflammatory agent. The term "anti-inflammatory agent," as used herein, refers to an agent capable of counteracting the effects of pro-inflammatory and/or inflammatory agents and other agents that mediate an inflammatory condition or reaction. Examples of an anti-inflammatory agent can include, but are not limited to, inhibitors of any pro-inflammatory agents as described above, e.g., in a form of soluble receptors, receptor antagonists, aptamers, antibodies, or any combinations thereof; and/or an agent that can mediate an inflammatory pathway in a cell, e.g., in a form of soluble proteins, antisense oligonucleotides, siRNA, shRNA, vectors, or any combinations thereof. For example, an anti-inflammatory agent can include an agent that can inhibit a particular protein function and/or silence a specific gene that induces inflammation; or an agent that can promote a particular protein function and/or express a specific gene that inhibits inflammation. In some embodiments, an anti-inflammatory agent can be or include a steroid, a nonsteroidal anti-inflammatory drug, an analgesic, an inhibitor of at least one or more chemokines (e.g., but not limited to, CXCL-8, CCL2, CCL3, CCL4, CCL5, CCL11, and CXCL10) and/or a COX-2 inhibitor. A variety of anti-inflammatory agents are known to those skilled in the art, e.g., as described in International Patent App. NO. WO 2004/082588, the content of which is incorporated herein by reference, and can be added to a cell culture medium and/or used to stimulate or challenge tissue-specific cells and/or immune cells within the device to provoke an anti-inflammatory response.

In some embodiments, the cytokine can include a growth-promoting agent. As used herein, the term "growth-promoting agent" refers to an agent that stimulates cell proliferation. Examples of a growth-promoting agent can include but are not limited to any art-recognized growth factors such as Bone morphogenetic proteins (BMPs); Brain-derived neurotrophic factor (BDNF); Epidermal growth factor (EGF); Erythropoietin (EPO); Fibroblast growth factor (FGF); Glial cell line-derived neurotrophic factor (GDNF); Granulocyte colony-stimulating factor (G-CSF); Granulocyte macrophage colony-stimulating factor (GM-CSF); Hepatocyte growth factor (HGF); Hepatoma-derived growth factor (HDGF); Insulin-like growth factor (IGF); Myostatin (GDF-8); Nerve growth factor (NGF) and other neurotrophins; Platelet-derived growth factor (PDGF); Thrombopoietin (TPO); Transforming growth factor alpha (TGF-α); Transforming growth factor beta (TGF-β); Vascular endothelial growth factor (VEGF); Placental growth factor (PlGF); hormones, steroid hormones, and any combinations thereof.

In some embodiments, the cytokine can include a differentiation agent as described earlier. Appropriate differentiation agent(s) can be selected based on different cell types, including, e.g., stem cells, and undifferentiated or partially differentiated cells.

In some embodiments, the cytokine can include an apoptosis modulating agent. The term "apoptosis modulating agents," as used herein, refers to agents which are involved in modulating (e.g., inhibiting, decreasing, increasing, promoting) apoptosis. Apoptosis is generally known as a process of programmed cell death. Examples of apoptosis modulating agents include, but are not limited to, Fas/CD95, TRAMP, TNF RI, DR1, DR2, DR3, DR4, DR5, DR6, FADD, RIP, TNFα, Fas ligand, antibodies to Fas/CD95 and other TNF family receptors, TRAIL, antibodies to TRAIL-R1 or TRAIL-R2, Bcl-2, p53, BAX, BID, BAD, BAK, Akt, CAD, PI3 kinase, PPI, and caspase proteins. Modulating agents broadly include agonists and antagonists of TNF family receptors and TNF family ligands. Apoptosis modulating agents can be soluble or membrane bound (e.g. ligand or receptor).

In some embodiments, the cytokine can include a pro-angiogenic agent. As used herein, the term "pro-angiogenic agent" is intended to mean an agent that directly or indirectly stimulates, enhances and/or stabilizes angiogenesis. Exemplary pro-angiogenic agents include, but are not limited to, VEGF, FGF, Ang1, Ang2, PDGF-BB, and any combinations thereof.

In some embodiments, the cytokine can include an anti-angiogenic agent. As used herein, the term "anti-angiogenic agent" refers to an agent that directly or indirectly reduces or inhibits formation of new blood vessels, and/or destabilizes the formed blood vessels. Examples of anti-angiogenic agents include, but are not limited to, inhibitors and/or antagonists of the pro-angiogenic agents as described above, soluble VEGF receptors, angiopoietin 2, TSP-1, TSP-2, angiostatin, endostatin, vasostatin, platelet factor-4, and any combinations thereof.

Embodiments of Various Aspects Described Herein can be Defined in any of the Following Numbered Paragraphs:
1. A device comprising:
   a. a body comprising a central channel therein; and
   b. a membrane positioned within the central channel and along a plane, the membrane configured to separate the central channel to form at least one microchannel and at least one mesochannel, wherein the height of the mesochannel is substantially greater than the height of the microchannel.
2. The device of paragraph 1, wherein the height ratio of the mesochannel to the microchannel ranges from about 2.5:1 to about 50:1.
3. The device of paragraph 1 or 2, wherein the height ratio of the mesochannel to the microchannel ranges from about 5:1 to about 25:1.
4. The device of any of paragraphs 1-3, wherein the membrane is rigid.
5. The device of any of paragraphs 1-3, wherein the membrane is at least partially flexible.
6. The device of any of paragraphs 1-5, wherein the membrane has a thickness of about 1 μm to about 100 μm.

7. The device of any of paragraphs 1-5, wherein the membrane has a thickness of about 100 nm to about 50 μm.
8. The device of any of paragraphs 1-7, wherein the membrane is non-porous.
9. The device of any of paragraphs 1-8, wherein the membrane is at least partially porous.
10. The device of paragraph 9, wherein pores of the membrane has a diameter of about 0.1 μm to about 15 μm.
11. The device of paragraph 9 or 10, wherein center-to-center pore spacing ranges from about 1 μm to about 100 μm.
12. The device of any of paragraphs 1-11, wherein one end of the mesochannel is adapted to engage to a gas-flow modulation device.
13. The device of paragraph 12, wherein the gas-flow modulation device is adapted to provide a uni-directional or bi-directional flow of gas.
14. The device of paragraph 12 or 13, wherein the gas-flow modulation device comprises a gas-receiving chamber having at least one end enclosed by a flexible diaphragm.
15. The device of paragraph 14, wherein the gas-receiving chamber expands or contracts as the flexible diaphragm moves.
16. The device of any of paragraphs 1-15, wherein another end of the mesochannel is adapted to engage to a gas-flow generator.
17. The device of any of paragraphs 1-16, wherein the body is further adapted to provide mechanical modulation of the membrane within the central channel.
18. The device of paragraph 17, wherein the body further comprises a first operating channel separated from the microchannel and the mesochannel by a first channel wall, wherein a first edge of the membrane is fastened to the first channel wall and a second edge of the membrane is fastened to an opposite wall of the central channel; and wherein the first operating channel is positioned around the membrane such that a pressure differential applied between the first operating channel and the central channel causes the membrane to stretch or retract in a first desired direction along the plane within the central channel.
19. The device of paragraph 18, wherein the body further comprises a second operating channel separated from the microchannel and the mesochannel by a second channel wall, wherein the second edge of the membrane is fastened to the second channel wall; and wherein the second operating channel is positioned around the membrane such that the pressure differential applied between the second operating channel and the central channel causes the membrane to stretch or retract in a second desired direction along the plane within the central channel.
20. The device of paragraph 18 or 19, wherein a first height of the first operating channel and a second height of the second operating channel are smaller than the height of the central channel.
21. The device of any of paragraphs 18-20, wherein at least one or both of the first operating channel and the second operating channel are symmetrically arranged around the membrane.
22. The device of any of paragraphs 1-21, wherein the height of the microchannel ranges from about 20 μm to about 1 mm.
23. The device of any of paragraphs 1-21, wherein the height of the microchannel ranges from about 50 μm to about 200 μm.
24. The device of any of paragraphs 1-23, wherein the dimensions of the mesochannel are configured to provide a fluid shear stress appropriate for cell growth and/or cell differentiation.
25. The device of any of paragraphs 1-24, wherein the height of the mesochannel is sufficient for formation of a stratified or three-dimensional tissue.
26. The device of any of paragraphs 1-25, wherein an aspect ratio of the height of the mesochannel to the width of the central channel ranges from about 1:5 to about 25:1.
27. The device of any of paragraphs 1-26, wherein the height of the mesochannel ranges from about 100 μm to about 50 mm.
28. The device of any of paragraphs 1-27, wherein the width of the central channel ranges from about 200 μm to about 10 mm.
29. The device of any of paragraphs 1-28, wherein at least one surface of the membrane comprises cells adhered thereto.
30. The device of paragraph 29, wherein the cells form one or more cell layers.
31. The device of paragraph 29 or 30, wherein the cells are selected from the group consisting of mammalian cells, plant cells, insect cells, and any combinations thereof
32. The device of paragraph 31, wherein the mammalian cells comprise human cells.
33. The device of paragraph 31, wherein the mammalian cells comprise animal cells.
34. The device of any of paragraphs 29-33, wherein the cells display at least one characteristic corresponding to a pre-determined physiological endpoint.
35. The device of paragraph 34, wherein the pre-determined physiological endpoint is selected from the group consisting of a mature state, a differentiated state, a precursor state, a stratified state, a pseudo-stratified state, a confluency state, an inflamed state, an infected state, a stimulated state, an activated state, an inhibitory state, a normal healthy state, a disease-specific state, a growth state, a migratory state, a metamorphosing state, or any combinations thereof
36. The device of paragraph 35, wherein the disease-specific state is a specific stage of a disease, disorder or injury.
37. The device of paragraph 35 or 36, wherein the disease-specific state comprises a cancerous state.
38. The device of any of paragraphs 35-37, wherein the disease-specific state is associated with an intestinal disease selected from the group consisting of inflammatory bowel disease, Crohn's disease, ulcerative colitis, celiac disease, angiodysplasia, appendicitis, bowel twist, chronic functional abdominal pain, coeliac disease, colorectal cancer, diverticular disease, endometriosis, enteroviruses, gastroenteritis, Hirschsprung's disease, ileitis, irritable bowel syndrome, polyp, pseudomembranous colitis, or any combinations thereof.
39. The device of any of paragraphs 35-37, wherein the disease-specific state is associated with a lung disease selected from the group consisting of asthma, chronic obstructive pulmonary disease (COPD), pulmonary hypertension, radiation induced injury, cystic fibrosis, or any combination thereof.
40. The device of any of paragraphs 35-37, wherein the disease-specific state is associated with an airborne disease.
41. The device of paragraph 40, wherein the airborne disease is a bacterial infection or a viral infection.
42. The device of any of paragraphs 29-41, wherein at least a portion of the cells are selected from the group consisting of epithelial cells, endothelial cells, fibroblasts, smooth muscle cells, basal cells, ciliated cells, mucus-secreting cells, columnar cells, goblet cells, muscle cells, immune cells, neural cells, hematopoietic cells, lung cells (e.g., alveolar epithelial cells, airway cells, bronchial cells, tracheal cells, and nasal epithelial cells), gut cells, intestinal cells, brain cells, stem cells, skin cells, liver cells, heart cells, spleen cells, kidney cells, pancreatic cells, reproductive cells, blood cells (including, e.g., white blood cells, red blood cells, platelets, and hematopoietic stem cells and progenitor cells) and any combinations thereof 43. The device of any of paragraphs 29-42, wherein the cells are selected to create an in vitro model that mimics cell behavior of at least a portion of a tissue.
44. The device of paragraph 43, wherein the tissue is selected from the group consisting of airway, bronchus, gut, skin, choroid plexus, liver, heart, and gastrointestinal tract.
45. The device of any of paragraphs 29-44, wherein a first surface of the membrane facing the mesochannel comprises tissue-specific cells requiring low shear and/or space to form a stratified tissue.
46. The device of paragraph 45, wherein the tissue-specific cells comprise epithelial cells, basal cells, ciliated cells, columnar cells, goblet cells, fibroblasts, smooth muscle cells, or any combinations thereof
47. The device of paragraph 45 or 46, wherein the tissue-specific cells selected to create the in vitro model that mimics cell behavior of at least a portion of an airway comprises airway epithelial cells, bronchial epithelial cells, nasal epithelial cells, or any combinations thereof.
48. The device of any of paragraphs 29-47, wherein a second surface of the membrane facing the microchannel comprises blood vessel-associated cells.
49. The device of paragraph 48, wherein the blood vessel-associated cells comprise endothelial cells, fibroblasts, smooth muscle cells, pericytes, or any combinations thereof
50. The device of any of paragraphs 1-49, wherein the membrane is coated with at least one cell adhesion agent.
51. The device of paragraph 50, wherein said at least one cell adhesion agent comprises an extracellular matrix molecule.
52. The device of paragraph 51, wherein the extracellular matrix molecule comprises glycoproteins, collagen, fibronectin, laminin, vitronectin, elastins, fibrin, proteoglycans, heparin sulfate, chondroitin sulfate, keratan sulfate, hyaluronic acid, fibroin, chitosan, or any combinations thereof
53. The device of any of paragraphs 1-52, wherein the body of the device and/or the membrane comprises a biocompatible polymer.
54. The device of paragraph 53, wherein the biocompatible polymer comprises polydimethylsiloxane (PDMS), polyurethane, styrene-ethylene-butylene-styrene (SEBS), polypropylene, polycarbonate, polyester, polypropylene, silicon, or any combinations thereof.
55. The device of any of paragraphs 1-54, wherein the body of the device and/or the membrane comprises an extracellular matrix polymer, gel, or scaffold.
56. The device of any of paragraphs 1-55, wherein the central channel is linear.
57. The device of any of paragraphs 1-55, wherein the central channel comprise a non-linear portion.
58. The device of any of paragraphs 1-57, wherein the height of the first and/or second operating channel is larger than the height of the central channel.
59. The device of any of paragraphs 1-57, wherein the height of the first and/or second operating channels is substantially the same as or smaller than the height of the central channel.
60. A method comprising:
    providing at least one device comprising:
        a. a body comprising a central channel therein; and
        b. an at least partially porous membrane positioned within the central channel and along a plane, the membrane configured to separate the central channel to form a first sub-channel and a second sub-channel, wherein at least the first sub-channel has a height sufficient to form a stratified structure;
    seeding tissue-specific cells on a first surface of the membrane facing the first sub-channel; and
    culturing the tissue-specific cells on the first surface at a gas-liquid interface.
61. The method of paragraph 60, wherein the tissue-specific cells form a first cell monolayer prior to said culturing at the gas-liquid interface.
62. The method of paragraph 61, wherein the first cell monolayer is formed by culturing the tissue-specific cells submerged in a first liquid fluid within the first sub-channel.
63. The method of any of paragraphs 60-62, wherein the gas-liquid interface is formed by having a gaseous fluid in the first sub-channel and a second liquid fluid in the second sub-channel.
64. The method of paragraph 63, wherein the second liquid fluid comprises at least one differentiation-inducing agent.
65. The method of any of paragraphs 60-64, wherein at least a portion of the tissue-specific cells reach a pre-determined physiological endpoint upon said culturing at the gas-liquid interface for a period of time.
66. The method of any of paragraphs 60-65, further comprising flowing a gaseous fluid through the first sub-channel.
67. The method of any of paragraphs 60-66, further comprising flowing a liquid fluid through the second sub-channel.
68. A method comprising:
    providing at least one device comprising:
        a. a body comprising a central channel therein; and
        b. an at least partially porous membrane positioned within the central channel and along a plane, the membrane configured to separate the central channel to form a first sub-channel and a second sub-channel, wherein at least the first sub-channel has a height sufficient to form a stratified structure; and
        c. tissue-specific cells on a first surface of the membrane facing the first sub-channel, wherein the cells display at least one characteristic corresponding to a pre-determined physiological endpoint.
    flowing a gaseous fluid through the first sub-channel; and
    flowing a liquid fluid through the second sub-channel.
69. The method of any of paragraphs 66-68, wherein the gaseous fluid is maintained at a static flow.
70. The method of any of paragraphs 66-68, wherein the gaseous fluid is continuously flowed through the first sub-channel.
71. The method of any of paragraphs 66-68, wherein the gaseous fluid is intermittently or cyclically flowed through the first sub-channel.

72. The method of any of paragraphs 60-71, wherein the height of the first sub-channel is configured to provide an air shear stress appropriate for cell growth and/or cell differentiation.
73. The method of paragraph 72, wherein the air shear stress ranges from about 0.01 dynes/cm$^2$ to about 2000 dynes/cm$^2$.
74. The method of any of paragraphs 60-73, wherein the height of the first sub-channel is at least about 100 µm or about 500 µm.
75. The method of any of paragraphs 60-74, wherein the second sub-channel has a height that is substantially smaller than the height of the first sub-channel.
76. The method of paragraph 75, wherein the second sub-channel has a height of about 20 µm to about 1 mm or about 50 µm to about 200 µm.
77. The method of any of paragraphs 60-76, wherein the height of the second sub-channel is substantially same as the height of the first sub-channel.
78. The method of any of paragraphs 60-77, wherein the pre-determined physiological endpoint is selected from the group consisting of a mature state, a differentiated state, a precursor state, a stratified state, a pseudo-stratified state, a confluency state, an inflamed states, an infected state, a stimulated state, an activated state, an inhibitory state, a normal healthy state, a disease-specific state, a growth state, a migratory state, a metamorphosing state, or any combinations thereof
79. The method of paragraph 78, wherein the disease-specific state is a specific stage of a disease, disorder or injury.
80. The method of paragraph 78 or 79, wherein the disease-specific state comprises a cancerous state.
81. The method of any of paragraphs 65-80, wherein the pre-determined physiological endpoint is detected by the presence of at least one marker associated with the pre-determined physiological endpoint.
82. The method of any of paragraphs 60-81, wherein the tissue-specific cells comprise mammalian cells.
83. The method of any of paragraphs 60-82, wherein the tissue-specific cells comprise airway, bronchial, and/or nasal epithelial cells.
84. The method of paragraph 83, wherein the physiological endpoint of the airway or bronchial epithelial cells is differentiation of the airway or bronchial epithelial cells to ciliated cells and/or mucus-secreting cells.
85. The method of paragraph 84, wherein the differentiated state is detected by the presence of at least one of the cilia-associated markers, goblet cell-associated markers, and tight junction-associated markers.
86. The method of any of paragraphs 60-85, further comprising treating differentiated cells with retinoic acid.
87. The method of paragraph 86, wherein the retinoic acid reverses squamous phenotype.
88. The method of any of paragraphs 60-87, wherein one end of the first sub-channel is adapted to engage to a gas-flow modulation device.
89. The method of paragraph 88, wherein gas-flow modulation device is adapted to provide a unidirectional and/or a bidirectional flow of the gaseous fluid.
90. The method of paragraph 89, wherein the bidirectional flow of the gaseous fluid simulates air flow during respiration.
91. The method of any of paragraphs 88-90, wherein the gas-flow modulation device comprises a gas-receiving chamber having at least one end enclosed by a flexible diaphragm.
92. The method of paragraph 91, wherein the gas-receiving chamber expands or contracts as the flexible diaphragm moves.
93. The method of any of paragraphs 60-92, further comprising determining ciliary clearance of a particle flowing through the first sub-channel.
94. The method of any of paragraphs 60-93, further comprising forming a second cell layer on a second surface of the membrane facing the second sub-channel.
95. The method of paragraph 94, wherein the second cell layer comprises blood vessel-associated cells.
96. The method of paragraph 95, wherein the blood vessel-associated cells comprise endothelial cells, fibroblasts, smooth muscle cells, pericytes, or any combinations thereof
97. The method of any of paragraphs 60-96, further comprising creating within the central channel an in vitro model that mimics a tissue-specific condition (e.g., in a normal healthy state or in a disease-specific state).
98. The method of paragraph 97, wherein the tissue-specific cells are adapted to display at least one characteristic associated with the tissue-specific condition in a disease-specific state.
99. The method of paragraph 98, wherein the tissue-specific cells are disease-specific cells isolated from at least one subject.
100. The method of paragraph 98, wherein the tissue-specific cells are contacted with a condition-inducing agent that is capable of inducing the tissue-specific cells to acquire at least one characteristic associated with the disease-specific state.
101. The method of paragraph 100, wherein the condition-inducing agent comprises a physical agent or an environmental stimulus (e.g., radiation or air flow rhythm).
102. The method of paragraph 100 or 101, wherein the condition-inducing agent comprises a chemical and/or biological agent (e.g., pathogens, and/or pro-inflammatory agents).
103. The method of any of paragraphs 97-102, wherein the tissue-specific condition is associated with a lung disease, disorder and/or injury or an airborne disease.
104. The method of paragraph 103, wherein the tissue-specific cells selected to mimic the condition associated with the lung disease, disorder and/or injury or the airborne disease comprise airway epithelial cells, bronchial epithelial cells, and/or nasal epithelial cells.
105. The method of paragraph 103 or 104, wherein the lung disease, disorder and/or injury is selected from the group consisting of acute lung injuries, chronic lung disorders, lung infections, and lung cancer.
106. The method of paragraph 103, wherein the airborne disease is a viral infection or a bacterial infection.
107. The method of paragraph 105, wherein the acute lung injuries comprise lung injuries resulting from bacterial sepsis, hemorrhagic shock, toxic inhalation, a drug-induced lung injury (e.g., bleomycin-induced lung injury), or any combinations thereof
108. The method of paragraph 105, wherein the chronic lung disorders comprises chronic obstructive pulmonary disorder (COPD), asthma, cystic fibrosis, fibrotic conditions, sarcoidosis, idiopathic lung fibrosis.
109. The method of any of paragraphs 97-102, wherein the tissue-specific condition is associated with an intestinal disease or disorder.
110. The method of paragraph 109, wherein the tissue-specific cells selected to mimic the condition associated with the intestinal disease or disorder comprise intestinal cells, colon cells, appendix cells, ileum cells, caecum cells, duodenum cells, jejunum cells, or any combinations thereof 111. The method of paragraph 109 or 110, wherein the intestinal disease, disorder and/or injury is selected from the group consisting of inflammatory bowel disease, Crohn's disease, ulcerative colitis, celiac disease, angiodysplasia, appendicitis, bowel twist, chronic functional abdominal pain, coeliac disease, colorectal cancer, diverticular disease, endometriosis, enteroviruses, gastroenteritis, Hirschsprung's disease, ileitis, irritable bowel syndrome, polyp, pseudomembranous colitis, or any combinations thereof.

112. The method of any of paragraphs 60-111, further comprising contacting the tissue-specific cells with a test agent.

113. The method of paragraph 112, wherein the tissue-specific cells are contacted with the test agent by delivery as an aerosol or liquid through the first sub-channel and/or via diffusion from the second sub-channel.

114. The method of paragraph 112 or 113, wherein the test agent is selected from the group consisting of proteins, peptides, nucleic acids, antigens, nanoparticles, environmental toxins or pollutant, cigarette smoke, chemicals or particles used in cosmetic products, small molecules, drugs or drug candidates, vaccine or vaccine candidates, aerosols, pro-inflammatory agents, naturally occurring particles including pollen, chemical weapons, viruses, bacteria, unicellular organisms, cytokines, and any combinations thereof.

115. The method of any of paragraphs 112-114, further comprising performing a pharmacokinetic, a pharmacodynamics, or a pharmacokinetic-pharmacodynamic (PK-PD) assay and/or analysis of an effect of the test agent on the cells, thereby determining an in vitro pharmacokinetic and/or pharmacodynamics effect of the test agent on the cells.

116. The method of any of paragraphs 112-115, further comprising measuring response of the cells on at least one side of the membrane to the test agent, the gaseous fluid exiting the first sub-channel, the liquid fluid exiting the second sub-channel, or any combinations thereof.

117. The method of paragraph 116, wherein said measuring the response of the cells comprises measuring adhesion of immune cells that are flowing through the second sub-channel, cell labeling, immunostaining, optical or microscopic imaging (e.g., immunofluorescence microscopy and/or scanning electron microscopy), gene expression analysis, cytokine/chemokine secretion analysis, metabolite analysis, polymerase chain reaction, immunoassays, ELISA, gene arrays, or any combinations thereof 118. The method of paragraph 116 or 117, wherein measurement of the response of the cells or at least one component present in a fluid within the device or present in an output fluid from the device after exposure to the test agent determines an effect of the test agent on the cells.

119. The method of paragraph 118, wherein the effect comprises ciliary clearance, cell viability, permeability of a cell layer, cell morphology, protein expression, gene expression, cell adhesion, adhesiveness of immune cells, cell differentiation, cytokine or chemokine production, inflammation, or any combinations thereof.

120. The method of paragraph 116 or 117, wherein measurement of the response of the cells or at least one component present in a fluid within the device or present in an output fluid from the device after exposure to the test agent determines an efficacy of the test agent.

121. The method of paragraph 116 or 117, wherein measurement of the response of the cells or at least one component present in a fluid within the device or present in an output fluid from the device after exposure to the test agent determines toxicity of the test agent.

122. The method of paragraph 116 or 117, wherein measurement of the response of the cells or at least one component present in a fluid within the device or present in an output fluid from the device after exposure to the test agent determines a mechanism of efficacy or toxicity of the test agent.

123. The method of paragraph 116 or 117, wherein measurement of the response of the cells or at least one component present in a fluid within the device or present in an output fluid from the device after exposure to the test agent determines physical-chemical, pharmacokinetic or pharmacodynamic parameters.

124. The method of any of paragraph 112-123, wherein when the tissue-specific cells are adapted to be condition-specific, said determination of the effect of the test agent identifies a therapeutic agent for treatment of the condition.

125. The method of any of paragraphs 112-123, wherein when the tissue-specific cells are patient-specific, said determination of the effect of the test agent identifies a personalized treatment for a subject.

126. The method of any of paragraphs 112-123, wherein when the tissue-specific cells are patient population-specific, said determination of the effect of the test agent identifies a treatment specified for that particular patient subpopulation.

127. The method of any of paragraphs 60-126, further comprising flowing immune cells through the second sub-channel.

128. The method of paragraph 127, wherein the tissue-specific cells in the first sub-channel and the immune cells flowing in the second sub-channel form an in vitro mucosal immunity model.

129. The method of paragraph 128, wherein the mucosal immunity model is adapted to determine efficacy or immunogenicity of a vaccine.

130. The method of any of paragraphs 127-129, further comprising measuring response of the immune cells.

131. The method of paragraph 130, wherein the response of the immune cells comprises trans-epithelial migration, maturation, activation, cell killing, and/or drainage.

132. The method of any of paragraphs 60-131, further comprising connecting said at least one device to a second device comprising:
   a second body comprising a second central channel therein; and
   a second membrane positioned within the second central channel and along a second plane, the second membrane configured to separate the second central channel to form a first sub-channel and a second sub-channel, wherein at least the first sub-channel has a height sufficient to form a stratified structure; and
   second tissue-specific cells on a first surface of the second membrane facing the first sub-channel, wherein the second tissue-specific cells display at least one characteristic corresponding to a second pre-determined physiological endpoint.

133. The method of paragraph 132, further comprising directing an air flow from the first sub-channel of said at least one device to the first sub-channel of the second device.

134. The method of paragraph 132 or 133, wherein the tissue-specific cells in said at least one device comprise pathogen-infected cells and the second tissue-specific cells in the second device are normal healthy cells.

135. The method of any of paragraphs 132-134, further comprising measuring response of the pathogen-infected cells upon exposure of the air flow.

136. The method of any of paragraphs 132-135, further comprising measuring response of the normal healthy cells upon exposure to the air flow from the first sub-channel of said at least one device.

137. The method of paragraph 136, wherein the measured response of the normal healthy cells determines transmissibility of airborne pathogens.

138. The method of any of paragraphs 60-137, wherein the membrane is rigid.

139. The method of any of paragraphs 60-137, wherein the membrane is at least partially flexible.
140. The method of any of paragraphs 60-139, further comprising mechanically modulating the membrane to move or deform within the central channel.
141. The method of paragraph 140, wherein the mechanical modulation of the membrane simulates a physiological strain.
142. The method of paragraph 141, wherein the simulated physiological strain is substantially the same as the strain produced by motion associated with breathing, peristalsis, or heart beating.
143. The method of any of paragraphs 140-142, wherein the membrane is mechanically modulated by a pneumatic mechanism.
144. The method of paragraph 143, wherein the device further comprises a first operating channel separated from the second sub-channel and the first sub-channel by a first channel wall, wherein a first edge of the membrane is fastened to the first channel wall and a second edge of the membrane is fastened to an opposite wall of the central channel; and wherein the first operating channel has a first height smaller than the height of the central channel.
145. The method of paragraph 144, wherein the device further comprises a second operating channel separated from the second sub-channel and the first sub-channel by a second channel wall, wherein the second edge of the membrane is fastened to the second channel wall; and wherein the second operating channel has a second height smaller than the height of the central channel.
146. The method of paragraph 144 or 145, further comprising applying a first pressure differential between the first operating channel and the central channel to cause the membrane to stretch or retract along the plane within the central channel.
147. The method of any of paragraphs 145-146, further comprising applying a second pressure differential between the second operating channel and the central channel to cause the membrane to stretch or retract along the plane within the central channel.
148. The method of paragraph 146 or 147, wherein said applying the first or second pressure differential comprises applying a cyclic pressure inside the first operating channel or the second operating channel such that the first edge of the membrane fastened to the first channel wall and/or the second edge of the membrane fastened to the second channel wall stretches or retracts along the plane within the central channel.
149. The method of paragraphs 60-148, wherein the liquid fluid in the second sub-channel comprises a cell culture medium and/or a biological fluid.
150. The method of paragraph 149, wherein the biological fluid comprises blood.
151. A method of making a microfluidic device comprising a microstructure and a mesostructure, wherein a dimension of the mesostructure is substantially greater than a dimension of the microstructure, the method comprising:
generating, by photolithography, a semiconductor wafer mold having a raised feature of the microstructure; and
generating, by stereo-lithography, a thermoplastic mold having a raised feature of the mesostructure.
152. The method of paragraph 151, wherein the dimensions of the mesostructure and the microstructure are differed by a factor of at least 2.
153. The method of paragraph 151 or 152, further comprising forming the microstructure by casting in the semiconductor wafer mold.
154. The method of any of paragraphs 151-153, further comprising forming the mesostructure by casting in the thermoplastic mold.
155. The method of paragraph 154, wherein the formed mesostructure has a smooth surface finish.
156. The method of paragraph 155, wherein the smooth surface finish of the mesostructure facilitates bonding to the microstructure.
157. The method of any of paragraphs 151-156, wherein the mesostructure is a mesochannel disposed in a bottom surface of a first substrate.
158. The method of any of paragraphs 151-157, wherein the microstructure is a microchannel disposed in a top surface of a second substrate.
159. The method of paragraph 157 or 158, further comprising placing an at least partially porous membrane between the top surface of the microchannel and the bottom surface of the mesochannel; and forming a fluidic seal between the membrane and the first substrate and the second substrate, thereby forming a body of the device having a central channel therein, wherein the central channel comprises the microchannel and the mesochannel separated by the membrane.
160. The method of paragraph 159, wherein said forming the fluidic seal comprises forming a chemical bond between the membrane and the first substrate and the second substrate.
161. The method of paragraph 160, wherein the chemical bond is formed by using an adhesive chemical coating to covalently bond the membrane to the bottom surface of first substrate and the top surface of the second substrate.
162. The method of paragraph 161, wherein the adhesive chemical coating comprises (3-aminopropyl)triethoxysilane (APTES).
163. The method of any of paragraphs 159-162, wherein the fluidic seal is reversible such that the membrane is capable of being removed from the device for examination.
164. The method of paragraph 163, wherein said forming the fluidic seal comprises clamping the membrane between the first substrate and the second substrate together.
165. The method of paragraph 159-164, wherein said forming the fluidic seal comprises forming a plasma bond between the top surface of the first substrate and the bottom surface of the second substrate.
166. The method of any of paragraphs 157-165, wherein the first substrate, the second substrate, and/or the membrane comprise polydimethylsiloxane, polyurethanes, styrene-ethylene-butylene-styrene (SEBS), polypropylene, polycarbonate, polyester, silicon, or any combinations thereof 167. A method of developing a vaccine comprising:
  providing at least one device comprising:
    a. a body comprising a central channel therein; and
    b. an at least partially porous membrane positioned within the central channel and along a plane, the membrane configured to separate the central channel to form a first sub-channel and a second sub-channel, wherein at least the first sub-channel has a height sufficient to form a stratified structure; and
    c. tissue-specific epithelial cells on a first surface of the membrane facing the first sub-channel.
  flowing a gaseous fluid through the first sub-channel;
  flowing a liquid fluid comprising immune cells through the second sub-channel;
  contacting the tissue-specific epithelial cells with a vaccine candidate;
  contacting with the vaccinated tissue-specific epithelial cells with a microbe;
  measuring response of the tissue-specific epithelial cells to the microbe, thereby determining efficacy of the vaccine candidate against the microbe.
168. The method of paragraph 167, wherein the tissue-specific epithelial cells are contacted with the vaccine candidate at different dosages, thereby determining an optimum dosage of the vaccine candidate against the microbe.
169. The method of paragraph 167 or 168, further comprising measuring response of the immune cells.
170. The method of paragraph 169, wherein the response of the immune cells comprises trans-epithelial migration, maturation, activation, cell killing, and/or drainage.
171. The method of any of paragraphs 60-170, wherein the central channel is linear.
172. The method of any of paragraphs 60-170, wherein the central channel comprise a non-linear portion.
173. The method of any of paragraphs 144-148, wherein the height of the first and/or second operating channel is larger than the height of the central channel.
174. The method of any of paragraphs 144-148, wherein the height of the first and/or second operating channels is substantially the same as or smaller than the height of the central channel.

Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±5%.

In one aspect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1. Differentiation of Human Primary Airway (e.g., Small Airway) Epithelial Cells into Ciliated, Mucous-Secreting and Clara Cells Methods of differentiating airway epithelial cells in transwell systems has been previously described (Villenave et al., PNAS 2012, 109 (13) 5040-5045; and Villenave et al., J. Virol., 2010, 84 (22) 11718-11728). However, technologies and methods for differentiating primary human airway epithelial cells in microfluidic setting have not yet existed. Presented below is an example protocol to differentiate human primary airway epithelial cells (e.g., primary small airway epithelial cells).

Medium #1
  Bronchial Epithelial cell Basal Medium (BEBM) 500 ml (Lonza; Cat # CC-3171) plus BEGM SingleQuot Kit Suppl. & Growth Factors (Lonza; Cat # CC-4175); these supplements are shown as follows:
    1. BPE, ~2 ml
    2. Hydrocortisone, ~0.5 ml
    3. hEGF (human epidermal growth factor), 0.5 ml
    4. Epinephrine, ~0.5 ml
    5. Transferrin, ~0.5 ml
    6. Insulin, ~0.5 ml
    7. Retinoic Acid, ~0.5 ml
    8. Triiodothyronine (T3), ~0.5 ml
    9. GA-1000 (gentamicin), ~0.5 ml
Medium #2
  BEBM 250 ml (Lonza; Cat # CC-3171) plus DMEM 250 ml (Life Technologies, Cat #11885-092)—supplemented with 1% v/v penicillin/streptomycin, plus the following supplements & growth factors:
    1. BPE, ~2 ml
    2. Hydrocortisone, ~0.5 ml
    3. hEGF (human epidermal growth factor), ~0.5 ml 4. Epinephrine, ~0.5 ml
5. Transferrin, ~0.5 ml
6. Insulin, ~0.5 ml
7. BSA (bovine serum albumin), ~1 ml of ~1.5 mg/ml per ~500 ml BEBM/DMEM mixed medium
8. Retinoic Acid, ~0.5 ml of ~0.015 mg/ml per ~500 ml BEBM/DMEM mixed medium Items 1-6 were obtained from BEGM SingleQuot Kit Suppl. & Growth Factors (Lonza; Cat # CC-4175). Item 7 was purchased from Sigma, Cat # A9576, and diluted in Medium #1. Item 8 was purchased from Sigma, Cat # R2625, and diluted in DMSO Medium #3

BEBM 250 ml (Lonza; Cat # CC-3171) plus DMEM 250 ml (Life Technologies, Cat #11885-092) plus the following supplements & growth factors:
1. BPE, ~2 ml
2. Hydrocortisone, ~0.5 ml
3. hEGF (human epidermal growth factor), ~0.5 ml
4. Epinephrine, ~0.5 ml
5. Transferrin, ~0.5 ml
6. Insulin, ~0.5 ml
7. BSA (bovine serum albumin), ~1 ml of ~1.5 mg/ml per ~500 ml BEBM/DMEM mixed medium
8. Retinoic Acid, ~0.5 ml of ~3 mg/ml per ~500 ml BEBM/DMEM mixed medium Items 1-6 were obtained from BEGM SingleQuot Kit Suppl. & Growth Factors (Lonza; Cat # CC-4175). Item 7 was purchased from Sigma, Cat # A9576, and diluted in Medium #1. Item 8 was purchased from Sigma, Cat # R2625, and diluted in DMSO.

Differentiation Procedure

About $2\times10^5$ primary airway epithelial cells (e.g., primary small airway epithelial cells) re-suspended in about 20-40 µl of medium #2 is added through inlet or outlet of "airway lumen" channel into the device according to one embodiment as shown in FIG. 2G;

Cells are incubated for at least about 3 hours at 37° C., 5% $CO_2$ to allow adhesion to the membrane (e.g., the rigid polyester or polycarbonate membrane or flexible PDMS membrane);

Device is connected to medium flow on both top mesochannel and bottom microchannel at about 30 µl/h using syringe pumps or about 61 µl/h using peristaltic pump;

Medium #2 is used for culture under submerged condition

About 4-5 days post-culture when cells reach full confluence, an air-liquid interface (ALI) is generated by removing the apical medium slowly through the outlet of the "airway lumen" channel;

Medium #3 is used for culture during ALI;

Cells are kept in culture for about 3-4 weeks with periodic replenishment of fresh medium (e.g., freshly prepared media is added to a reservoir every 5-7 days);

The quality of differentiated chips is assessed regularly by microscopic imaging. In some embodiments, the device can be disconnected from the flow. About ~400-200 µl medium #3 is added into the "airway lumen" channel and the device is visualized under a microscope—after examination, the apical medium (in the "airway lumen" channel) is removed to restore ALI until the cells become fully differentiated.

Figure 5E:
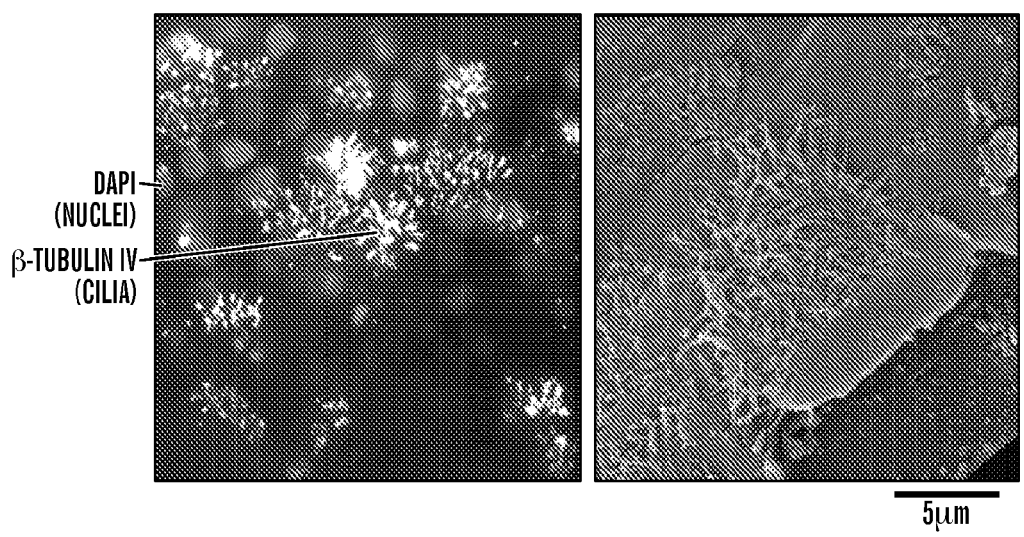
Figure 5F:
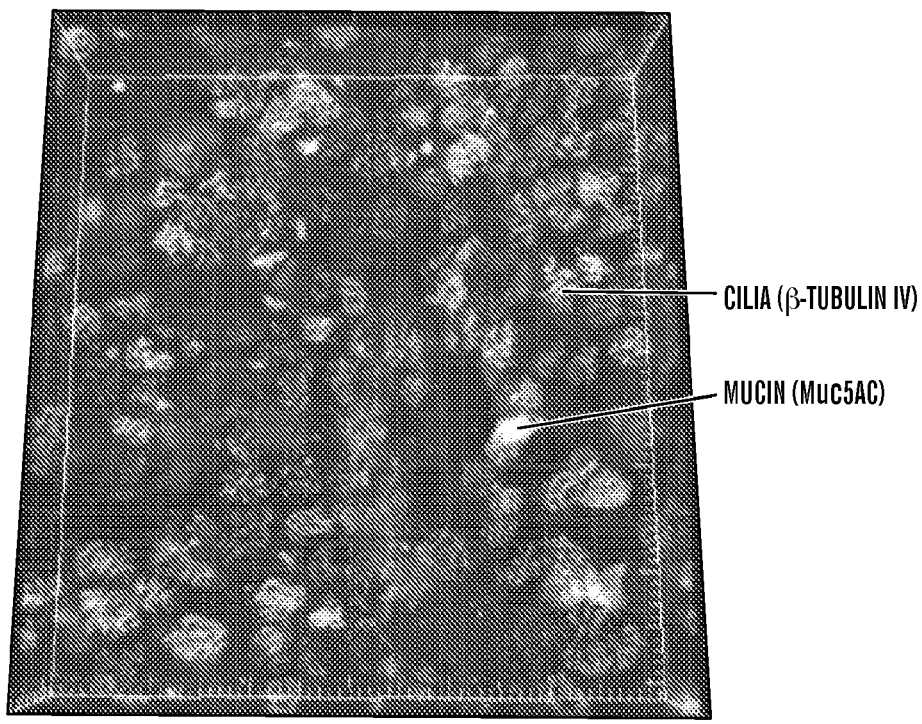
Figure 5G:
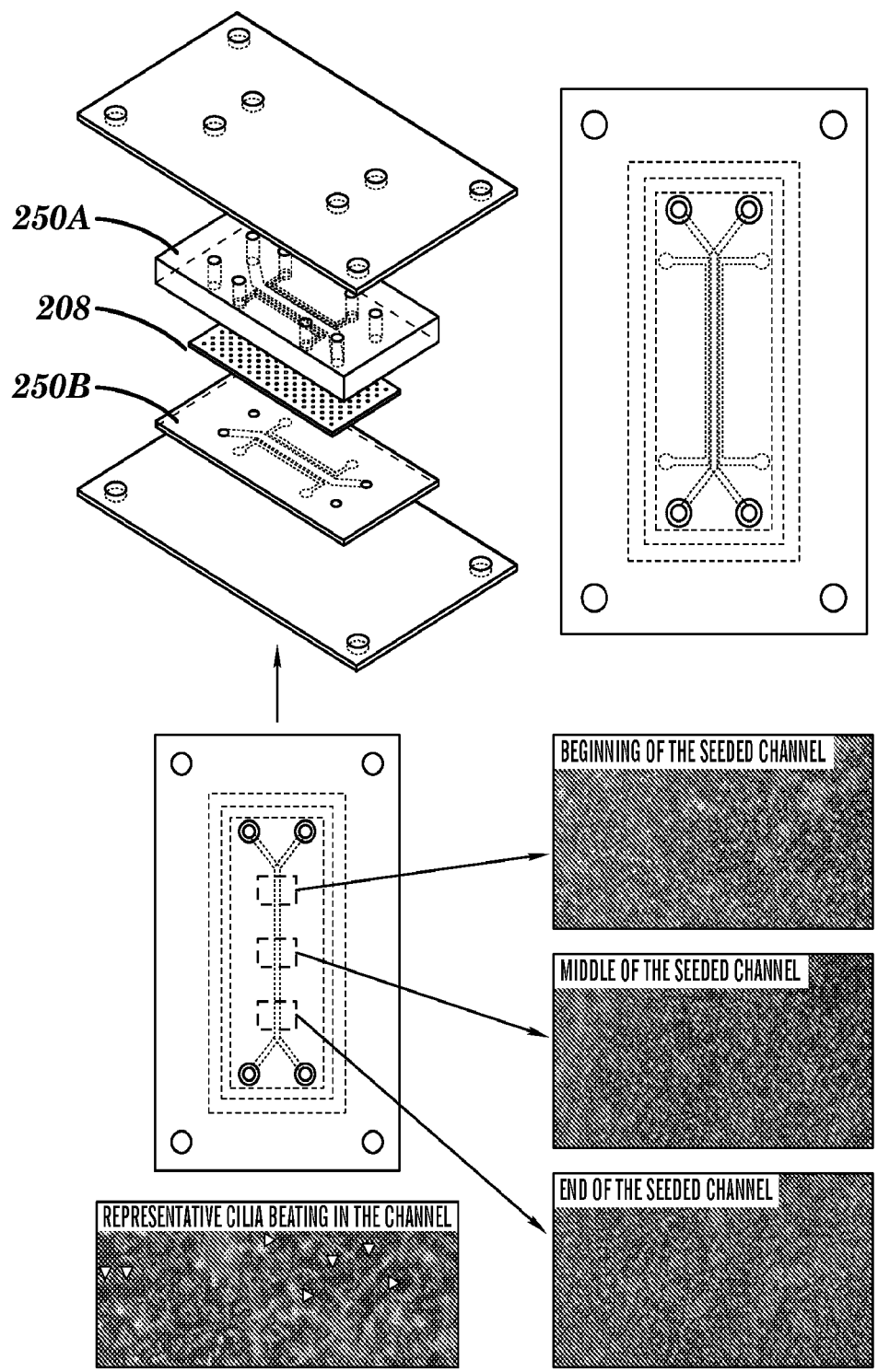
Figure 6A:
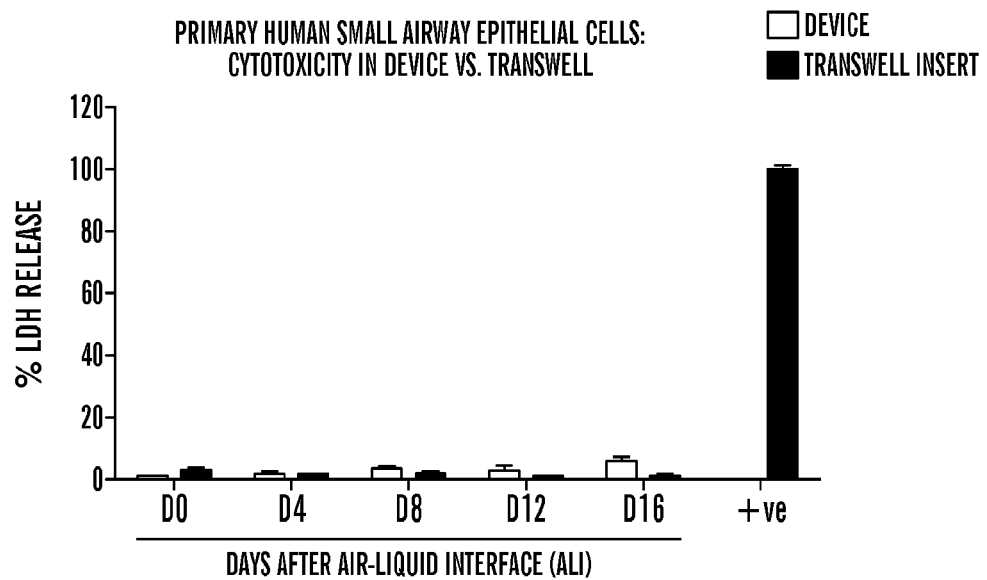
FIGS. 6A-6B show cell viability data directed to cultures of primary human small airway epithelial cells in a device according to an embodiment and in a transwell.
Figure 6B:
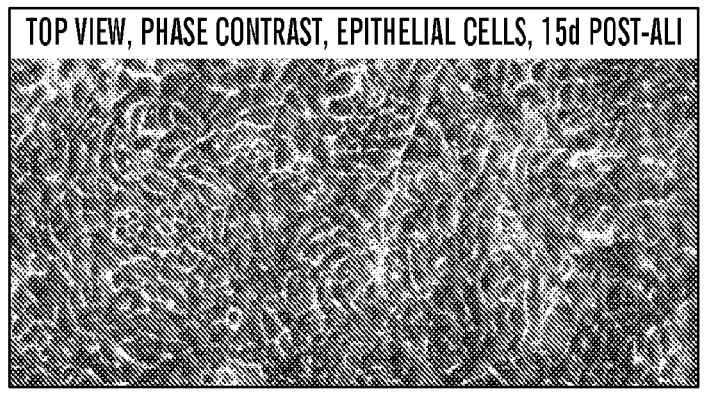

The differentiated state of the cells can be determined by detecting the presence of cilia-associated markers, globet cell-associated markers, and/or tight junction-associated markers. For example, FIG. 5D is a set of immunofluorescence images showing formation of a primary small airway epithelium on the membrane. Tight junction proteins (e.g., TJP-1 and/or ZO-1) were detected to indicate a functional tight junction barrier formed by the formed epithelium. FIG. 5E is a set of immunofluorescence and SEM images showing differentiation of the airway epithelial cells to ciliated cells. FIG. 5F shows a 3D view of differentiated epithelial primary cells (cilia beating: detected by beta-tubulin IC; and mucus secretion: detected by Muc5AC) in the device described herein. FIG. 5G shows representative images of ciliated cells along the length of the mesochannel of the device described herein. A uniform distribution of abundant cilia beating after about 3 weeks of culturing at an air-liquid interface is a hallmark of epithelial differentiation in vivo.

Figure 29A:
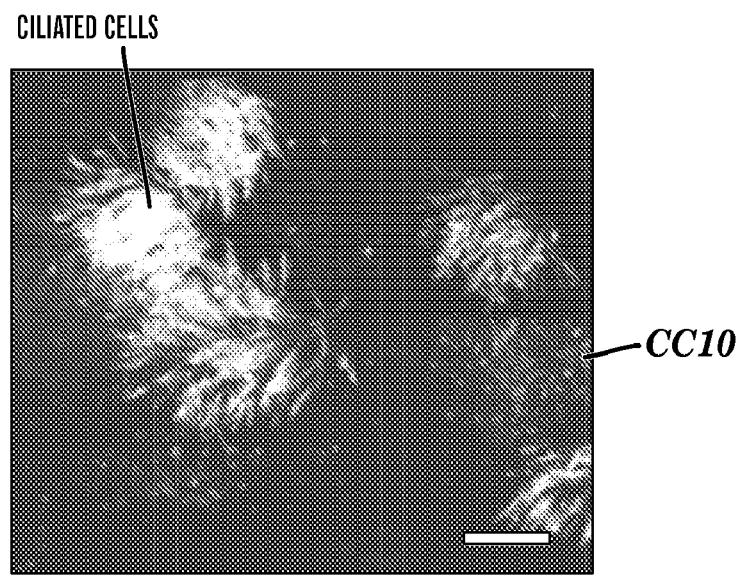
FIGS. 29A-29B are images showing human airway epithelial cells differentiated into Clara cells in one or more embodiments of the devices described herein.
Figure 29B:
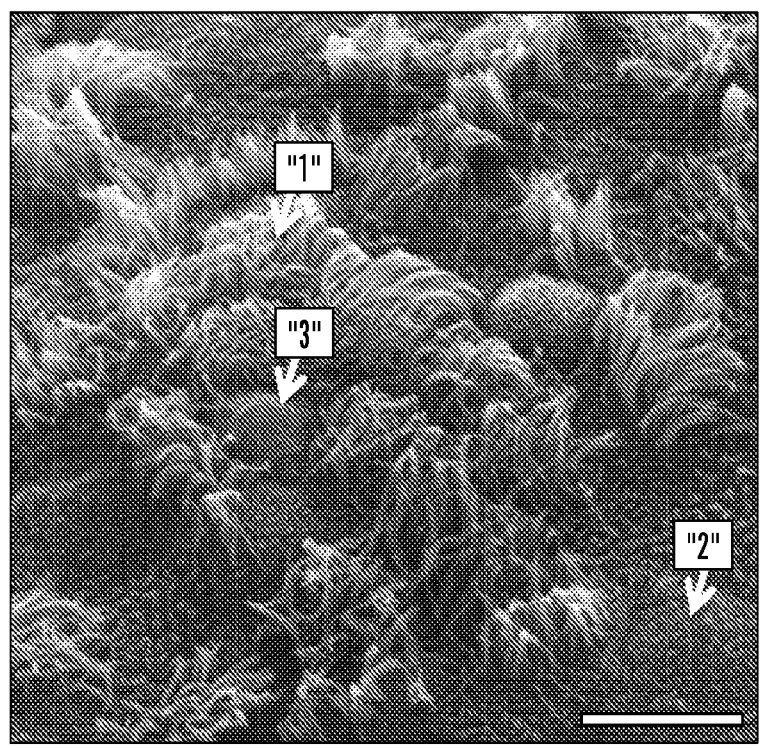

Using the devices described herein, the small airway human epithelial (bronchiolar) cells can also be differentiated into Clara cells. These cells are apically dome-shaped cells that contain drug-metabolizing enzymes like p450 and secrete proteins like CC10 (Clara cell secretory protein 10). An antibody against CC10 was used to identify these cells in the device. FIG. 29A is a confocal microscopic top view image of Clara cells stained for CC10 and ciliated cells labeled with β-tubulin IV following well-differentiation of bronchiolar cells in the device. The Clara cells were also imaged with scanning electron microscopy. FIG. 29B is a scanning electron micrograph of differentiated bronchiolar cells grown in the device, showing the extensive ciliated cells coverage ("1" arrow), microvilli ("2" arrow) that normally indicates apical membrane of mucous-producing goblet cells, and some dome-shaped structures that indicate Clara cells ("3" arrow).

Example 2. Uses of the Devices Described Herein to Mimic Effects of Chronic Obstructive Pulmonary Disease (COPD)

Figures 25A, 25B:
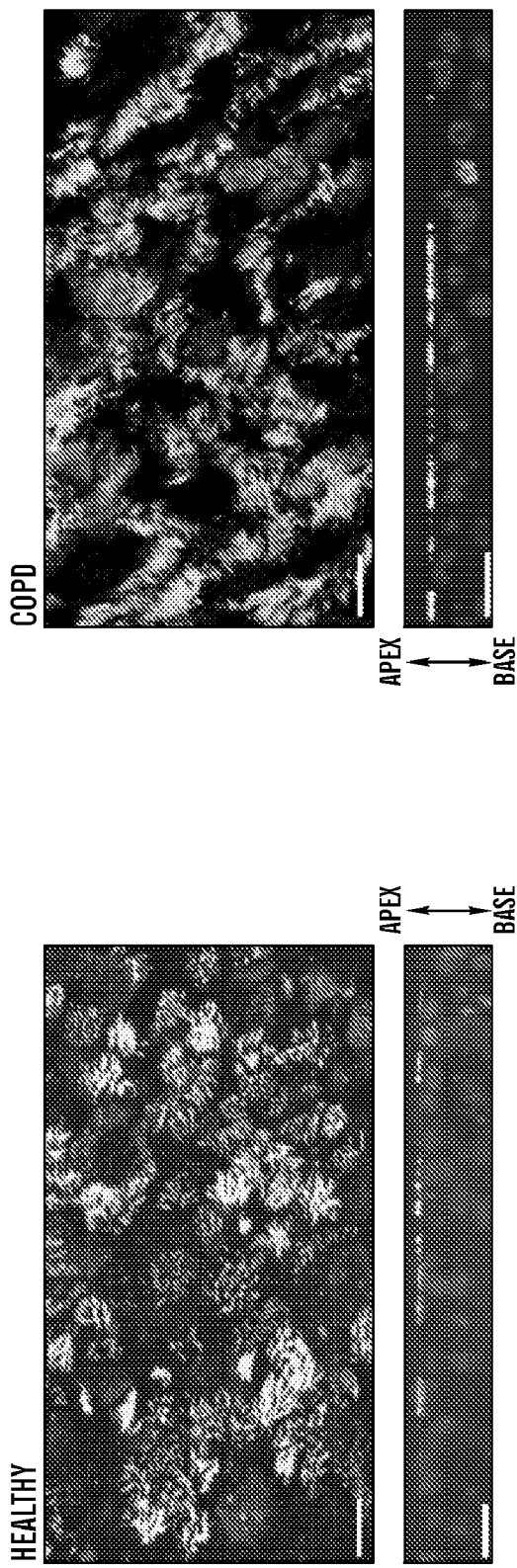
FIGS. 25A-25B are confocal images of well-differentiated normal and chronic obstructive pulmonary disease (COPD) epithelia following air-liquid interface (ALI) induction in the device according to one or more embodiments described herein.

Similar differentiation protocol as described in Example 1 above can be used to culture airway epithelial cells obtained from both healthy normal and chronic obstructive pulmonary disease (COPD) airways and induce the cells to differentiate into pseudostratified mucociliary epithelium in the devices described herein. FIGS. 25A-25B are confocal images of well-differentiated normal and COPD epithelia following air-liquid interface (ALI) induction in the devices described herein.

To determine if the COPD disease phenotypes were established in the devices described herein, the differentiated cells were stimulated, e.g., with a pro-inflammatory agent (e.g., a pathogen or fragments thereof such as lipopolysaccharides) and gene expression levels of Toll-like receptor 4 (TLR4) and TLR3 were then measured and compared to the levels in the normal cells.

Figure 26A:
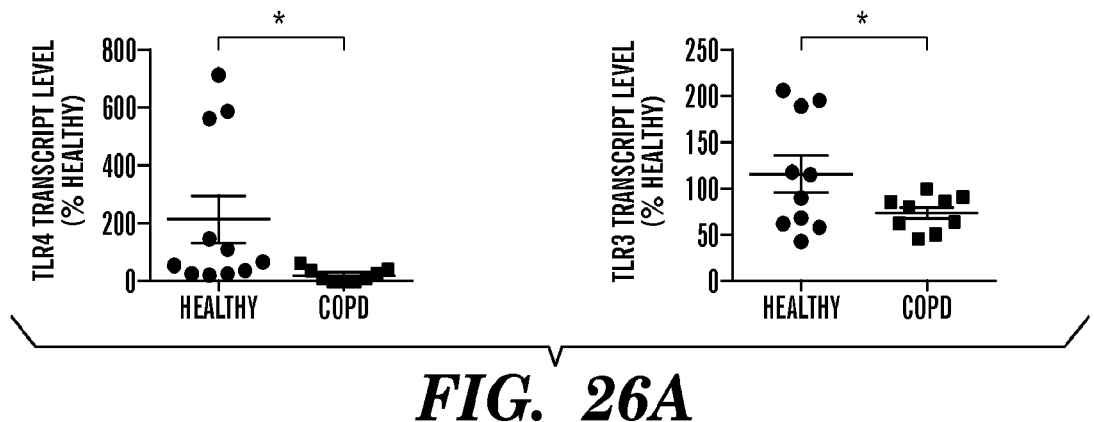
FIGS. 26A-26E are data graphs showing COPD disease phenotype can be established in the device according to one or more embodiments described herein.

TLRs, e.g., TLR3 and TLR4, are molecules that mediate recognition and response to stimulants (e.g., pathogens or fragments thereof such as lipopolysaccharides) in airway epithelial cells. A quantitative assay (e.g., real-time polymerase chain reaction (qPCR)) was performed to identify and determine difference in mRNA levels of TLR4 and TLR3 expression between normal/healthy and COPD-derived epithelial cells that were grown in the devices described herein. FIG. 26A shows that COPD devices (i.e., devices with COPD-derived cells) exhibited lower TLR3 and TLR4 mRNA levels than healthy devices (i.e., devices with healthy cells). The difference in TLR4 mRNA levels detected between the COPD devices and healthy devices is consistent with what is generally observed between COPD and healthy patients.

Figures 26B, 26C:
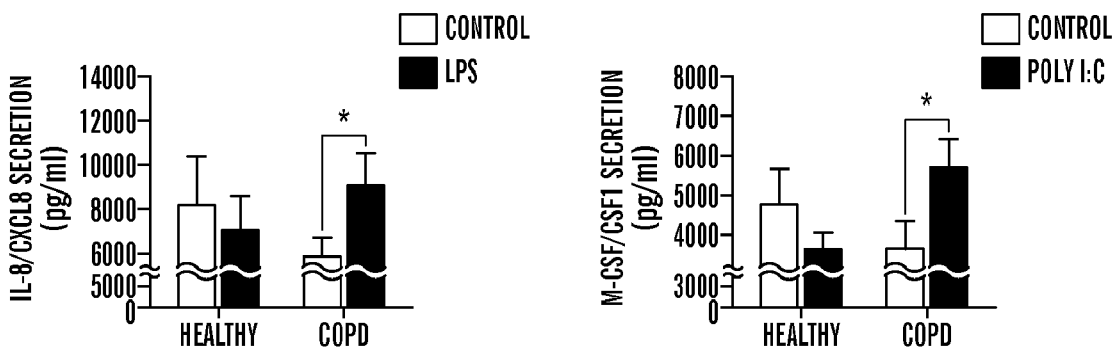
Figures 26D, 26E:
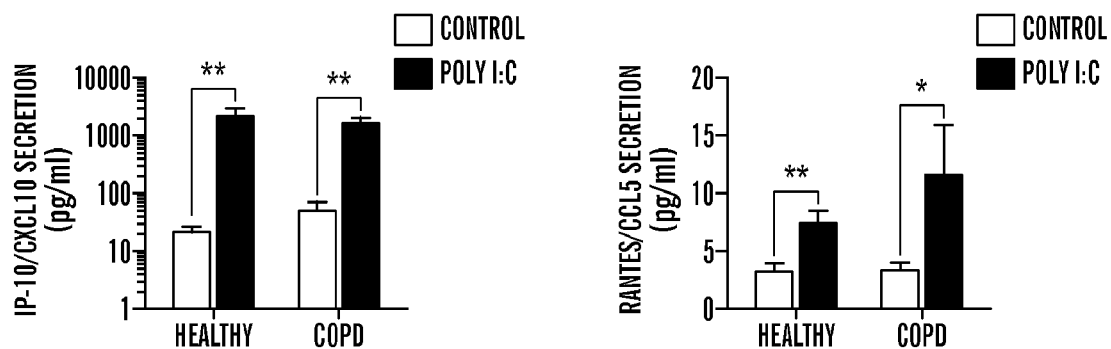

It was next sought to determine cytokine production in response to TLR stimulation. Cytokines are molecules that are involved in inflammation and their generation can be modulated by TLR activation. After the well-differentiated (i.e. mucociliary) epithelium (normal and COPD-derived) was stimulated with lipopolysaccharides (LPS), a qPCR was performed on the cells to compare inflammatory response between COPD and healthy epithelia in the devices described herein. LPS is a bacterial derived molecule that stimulates TLR4. It was found that LPS selectively induced IL8 secretion from COPD epithelial cells without increasing IL8 in healthy epithelial cells (FIG. 26B). This is in line with clinical reports and other ex vivo observations that COPD patients are hyper-reactive inflammation-wise and produce more pro-inflammatory mediators. Similarly, when the differentiated (i.e. mucociliary) epithelium (normal and COPD-derived) was stimulated with poly (I:C) (polyinosinic:polycytidylic acid—a synthetic analogue of the double-stranded RNA that mimic viral infection and stimulates TLR3), poly(I:C) selectively up-regulated M-CSF in COPD epithelial cells while there was no significant change in healthy epithelial cells (FIG. 26C). M-CSF is a cytokine that promotes survival and differentiations of a subset of immune cells, e.g., macrophages, in our bodies. This agrees with general observations that in the lungs of COPD patients there is generally an increased number of macrophages as compared to the number of macrophages in healthy individuals. The expression of two other cytokines (IP-10 and RANTES) was induced in both healthy donor and COPD epithelial cells by poly (I:C) (FIGS. 26D-26E).

Figure 27A:
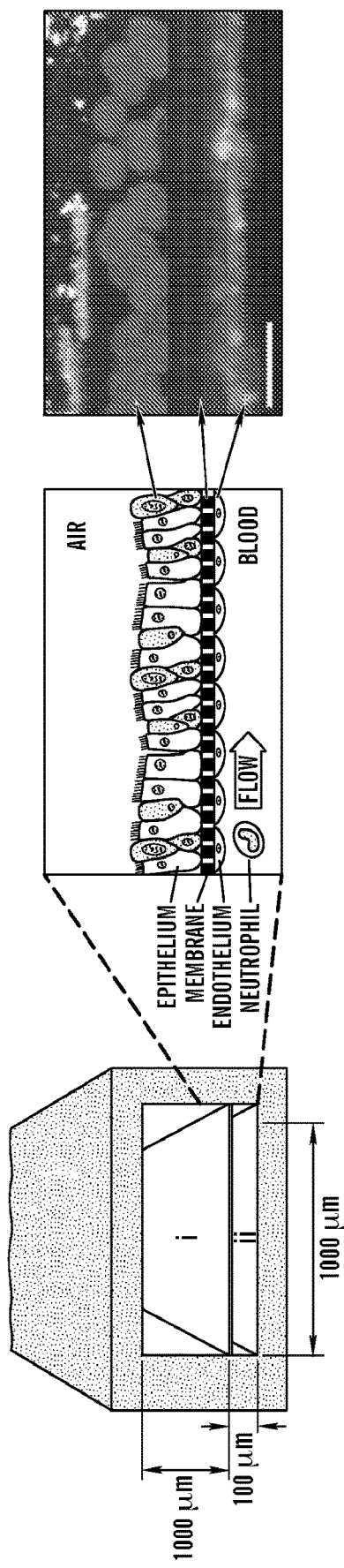
FIGS. 27A-27C show establishment of a three-cell type microfluidic co-culture system comprising ciliated epithelium, endothelium and circulating leukocytes.

Example 3. Establishment of a Complex 3-Cell Type Microfluidic Co-Culture System Any embodiment of the devices described herein can be used to establish a 3-cell type microfluidic co-culture system as described below. The 3-cell type microfluidic co-culture system comprises ciliated epithelium, endothelium and circulating leukocytes. By way of example only, FIG. 27A shows one embodiment of the devices that was used in this Example. The device comprised two parallel channels separated by an ECM-coated porous membrane: (i) a top mesochannel ("airway lumen" channel) with height corresponding to radius of a human lung small airway (1000 µm) and (ii) a bottom microchannel ("microvascular" channel) (100 µm deep) to re-create post-capillary venules (major sites of leukocyte recruitment and adhesion in vivo). The epithelium was cultured on one side of the membrane facing the mesochannel, while the endothelium was cultured on another side of the membrane facing the microchannel. Neurophils, a subset of circulating immune cells important in infection and inflammation and accumulate in and contribute to lung pathology in many diseases including COPD, were then introduced into the "microvascular" channel.

Figure 27B:
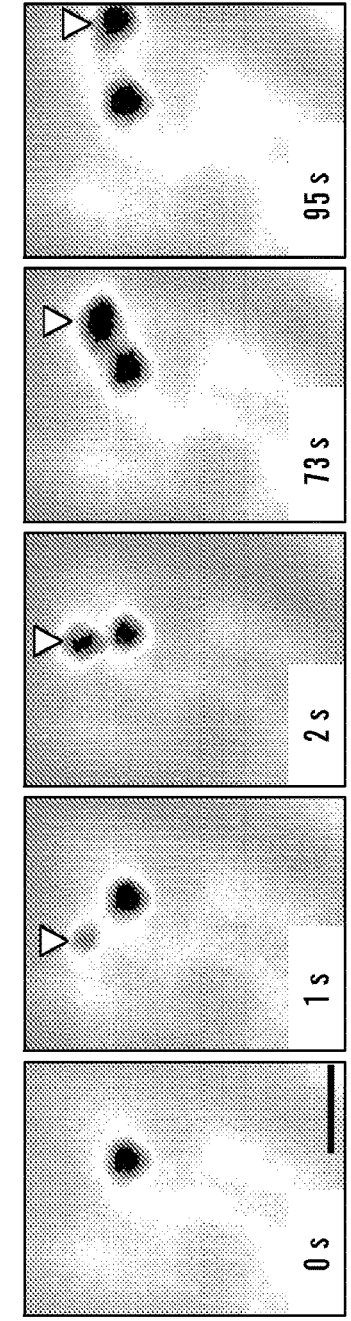

To visualize endothelium-leukocyte interactions, differentiated airway epithelial cells were stimulated in the device with poly (I:C) 10 µg/ml for 6 h to mimic inflammation phenotype by TLR3 pathway stimulation. Freshly isolated blood neutrophils were then flowed over an endothelial layer (activated by the stimulation of the airway epithelial cells with poly (I:C)) through "microvascular" channel to generate physiological wall shear stress of 1 dyne/cm$^2$. A series of time-lapse microscopic images (FIG. 27B) showed capture of a flowing neutrophil (not visible in the first panel from left but appears in the second panel; shown by the arrow head) to endothelium adjacent to a pre-adhered neutrophil (circles). Following initial attachment the neutrophil crawled over apical surface of activated endothelium and then firmly adhered (times indicated in seconds). The shadows in background are weak endothelial florescence signals bleeding into neutrophil channel during live high-speed multichannel image acquisition.

Figure 27C:
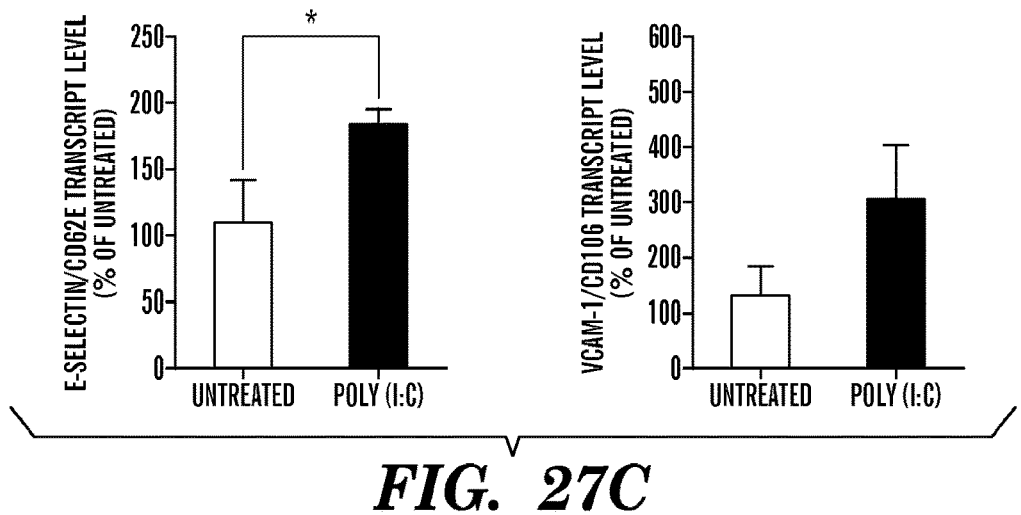

To analyze cell adhesion molecules gene expression, fully differentiated epithelial cells were co-cultured in the device with pulmonary microvascular endothelial cells, stimulated apically with poly (I:C) 10 µg/ml for 6 h and endothelial cells were then lysed to determine E-selectin and VCAM1 mRNA levels. E-selectin (endothelial selectin) is a cell adhesion molecule expressed on endothelial cells and up-regulated during inflammation. VCAM1 (vascular cell adhesion molecule 1) is another cell adhesion molecule that endothelial cells express. Both of these molecules are important for capture and adhesion of leukocytes from circulation. As shown in FIG. 27C, epithelial challenge with poly (I:C) induced a significant up-regulation of E-selectin gene expression and a higher, but not statistically significant, VCAM-1 transcript levels in endothelial cells, as compared to the cells without the poly (I:C) challenge.

Figure 28A:
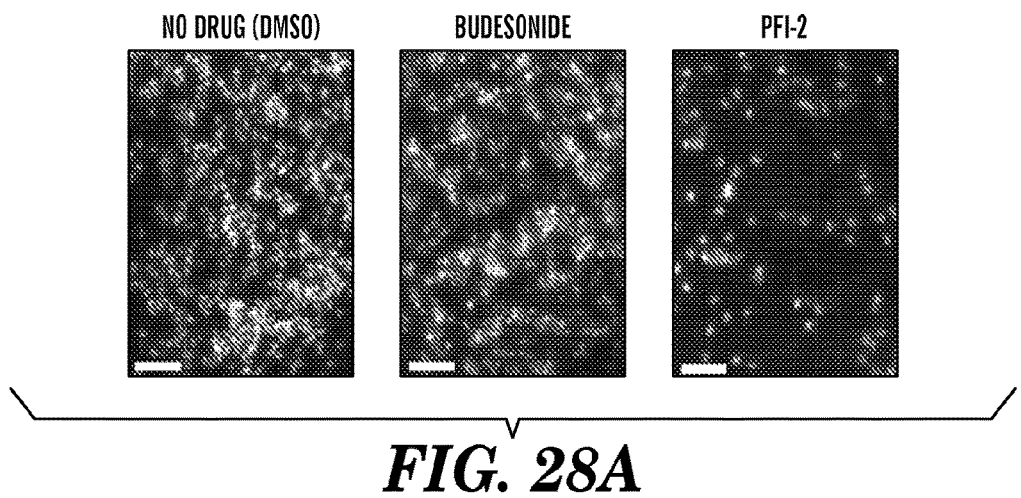
FIGS. 28A-28C show capability of determining drug efficacy on neutrophil capture and adhesion and inflammation suppression in a small airway mimicking device according to one or more embodiments described herein.

Example 4. Comparing Drug Efficacy on Neutrophil Capture and Adhesion and Inflammation Suppression in a Small Airway Mimicking Device COPD epithelium-microvascular endothelium co-culture devices were established, e.g., as described in Example 1 or 2, and then were either treated with the corticosteroid drug budesonide (10 nM) or PFI-2 (a bromodomain-containing protein 4 (BRD4) inhibitor drug; 500 nM), or left untreated. The COPD epithelium was then stimulated with poly (I:C) 10 µg/ml via the "airway lumen" channel for 6 h and then examined for adhesion of recruited neutrophils. Neutrophils were stained with Hoechst immediately prior to experiment to allow visualization and quantification. Representative immunofluorescence images of the three conditions are illustrated in FIG. 28A.

Figure 28B:
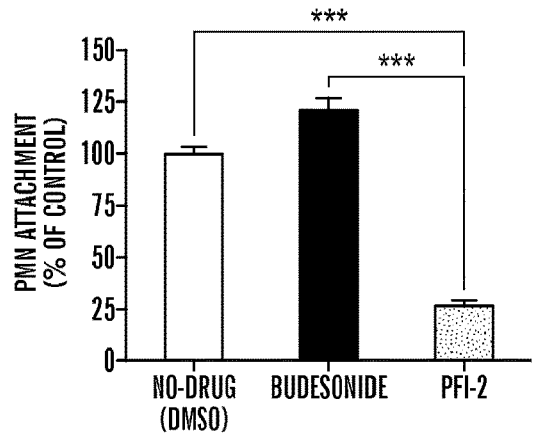

Effects of budesonide and PFI-2 on neutrophil adhesion were quantified. PFI-2 significantly lowered neutrophil recruitment compared with no treatment and budesonide, whereas the effect of budesonide was not significant (FIG. 28B).

Figure 28C:
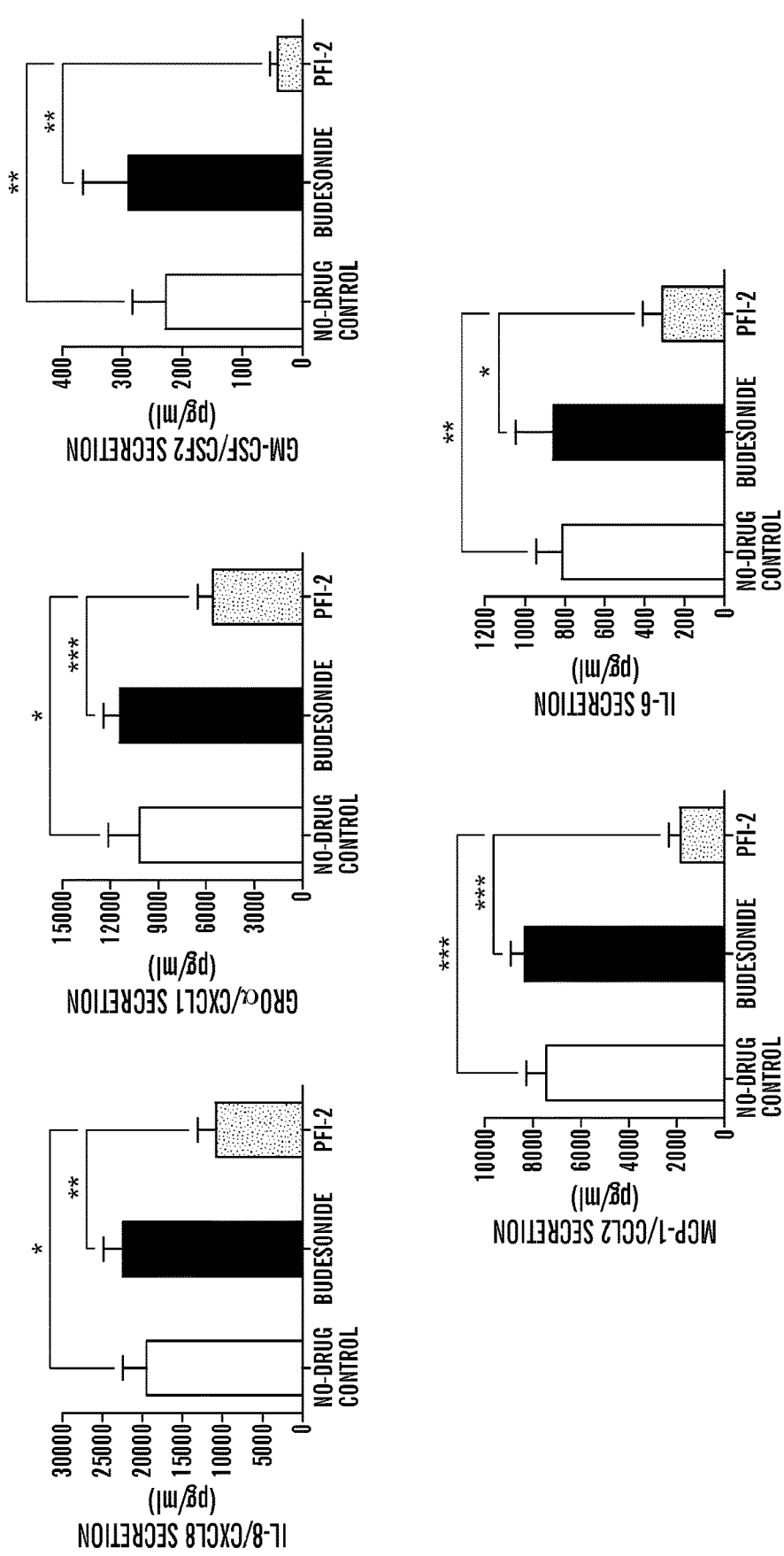

To compare the ability of budesonide and PFI-2 in suppressing inflammatory cytokine secretion, secreted cytokines from the "microvascular" channel of the co-culture devices were also analyzed by Multiplex Cytokine Detection System prior to neutrophil recruitment assay. FIG. 28C shows that PFI-2, unlike budesonide, significantly lowered secretion of neutrophil-chemoattractants IL-8, GROα and GM-CSF, monocyte-chemoattractant MCP-1, and acute inflammation associated cytokine IL-6.

Figure 30A:
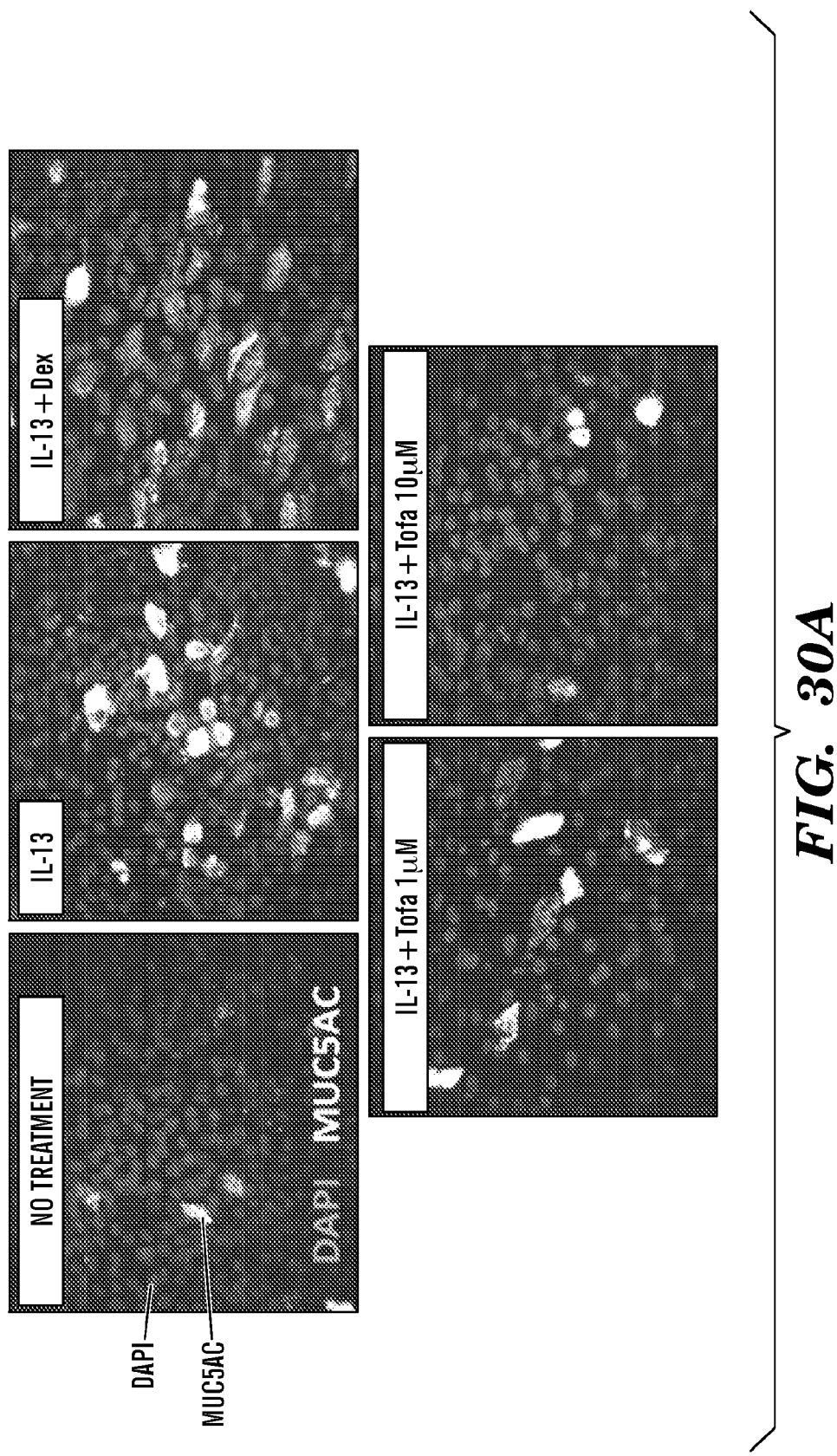
FIGS. 30A-30D show induction of asthma-like phenotype in the airway-on-a-chip for assessment of drug efficacy.
Figure 30B:
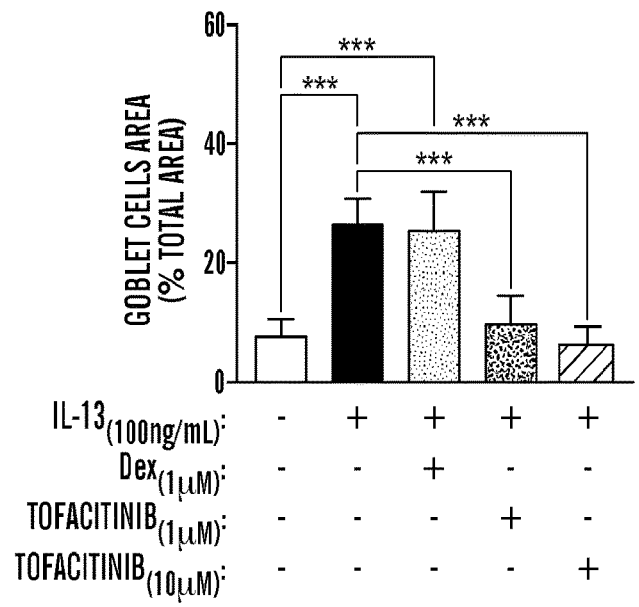

Example 5. Induction of Asthma-Like Phenotype in the Airway-On-A-Chip for Assessment of Drug Efficacy To develop asthma-like phenotype in the devices described herein, airway cells were differentiated in the devices, e.g., using the methods as described in Example 1 or 2, and then stimulated with IL-13 to induce asthma-like phenotype in the devices. IL-13 is a protein secreted by immune cells which is found in high quantities in lungs of asthmatics. The cells in the devices stimulated with IL-13 reproduced at least few hallmarks of asthma, e.g., with a higher number of goblet cells (cells that produce mucus) (FIGS. 30A and 30B), lower cilia beating frequency (FIG.

Figure 30C:
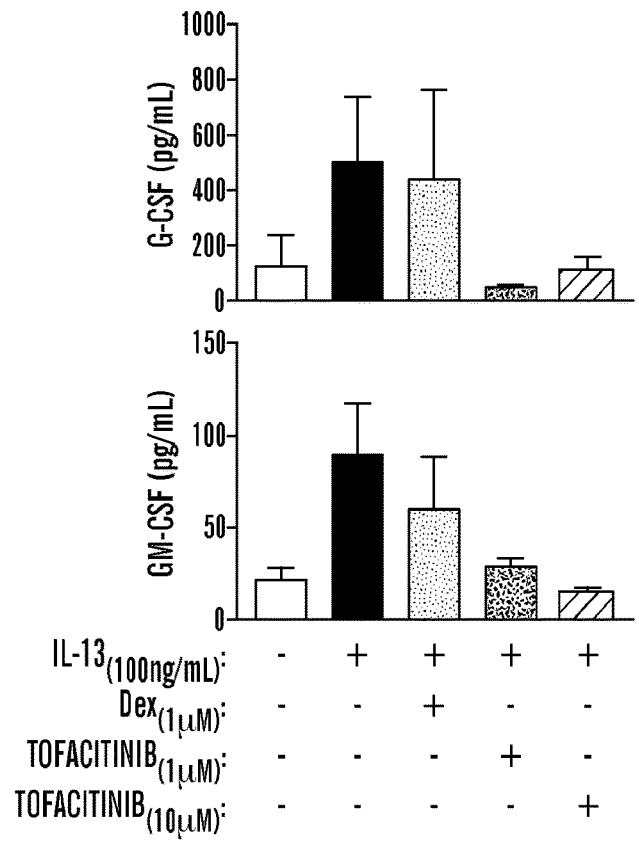

30D) and higher secretion of G-CSF and GM-CSF (FIG. 30C), as compared to cells without IL-13 stimulation.

Figure 30D:
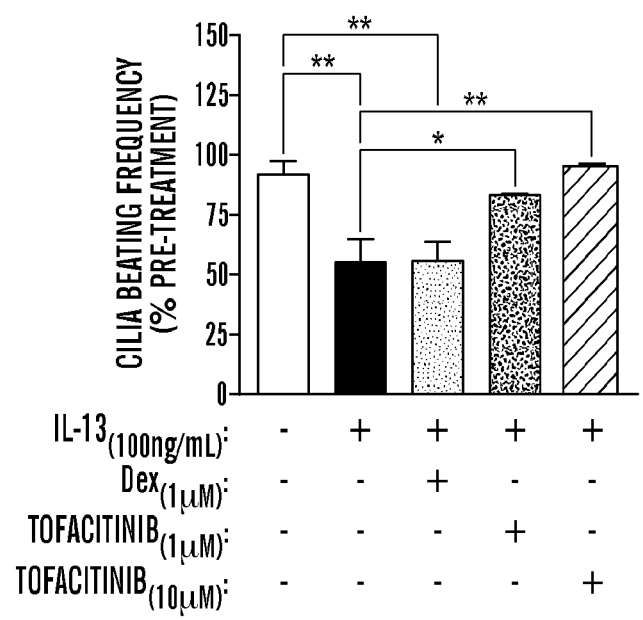

The "airway" devices were then used to assess the drug efficacy of Tofacitinib, a JAK inhibitor. The IL-13 stimulated cells were treated with Tofacitinib and it was found that the drug was able to reverse phenotypes associated with asthma in the IL-13 stimulated cultures. For example, the drug was able to decrease the number of goblet cells (FIGS. 30A-30B), to decrease GM-CSF and G-CSF secretion (FIG. 30C), and/or also to increase cilia beating frequency (FIG. 30D), in IL-13 stimulated cultures to healthy levels.

What is claimed is:

1. A method for culturing chronic obstructive pulmonary disease (COPD) cells comprising:
   1) providing a microfluidic device comprising:
      a) a body comprising a central channel therein; and
      b) an at least partially porous membrane positioned within the central channel, wherein the at least partially porous membrane separates at least one microchannel and at least one mesochannel,
      wherein a height ratio of the at least one mesochannel to the at least one microchannel ranges from about 1.1:1 to about 50:1,
      wherein said at least one mesochannel comprises a liquid;
   2) seeding human epithelial cells from a COPD patient on said membrane facing the at least one mesochannel;
   3) culturing the seeded human cells from step 2) on said membrane submerged within a first liquid;
   4) removing the first liquid from the at least one mesochannel, such that a gas-liquid interface is established, whereby said human cells are induced to differentiate into pseudostratified epithelial cells.

2. The method of claim 1, wherein the human epithelial cells are primary cells.

3. The method of claim 1, wherein the COPD epithelial cells are selected from the group consisting of airway cells, bronchial cells, and nasal epithelial cells.

4. The method of claim 1, wherein the cells are from a patient and the patient has a disease selected from the group consisting of asthma, cystic fibrosis, sarcoidosis, and idiopathic lung fibrosis.

5. The method of claim 1, wherein the at least partially porous membrane is positioned along a plane and is configured to separate the central channel to form a first channel and a second channel, and at least the first channel has a height sufficient to form a stratified structure.

6. A device comprising:
   a) a body comprising a central channel therein; and
   b) an at least partially porous membrane positioned within the central channel, the membrane configured to separate the central channel to form at least one microchannel and at least one mesochannel, wherein a height ratio of the at least one mesochannel to the at least one microchannel ranges from about 1.1:1 to about 50:1.

7. The device of claim 6, wherein the height ratio of the mesochannel to the microchannel ranges from about 2.5:1 to about 50:1.

8. The device of claim 6, wherein the height ratio of the mesochannel to the microchannel ranges from about 5:1 to about 25:1.

9. The device of claim 6, wherein the membrane is rigid.

10. The device of claim 6, wherein the membrane is at least partially flexible.

11. The device of claim 6, wherein the membrane has a thickness of about 100 nm to about 50 μm.

12. The device of claim 6, wherein said pores of the membrane has a diameter of about 0.1 μm to about 15 μm.

13. The device of claim 6, wherein center-to-center spacing between said pores ranges from about 1 μm to about 100 μm.

14. The device of claim 6, wherein at least one surface of the membrane comprises cells adhered to thereto.

* * * * *